US012509451B2

(12) United States Patent
Volkmann et al.

(10) Patent No.: US 12,509,451 B2

(45) Date of Patent: Dec. 30, 2025

(54) HETEROARYL AMIDE INHIBITORS OF CD38

(71) Applicants: NAPA THERAPEUTICS LTD., Tortola (VG); BUCK INSTITUTE FOR RESEARCH ON AGING, Novato, CA (US)

(72) Inventors: Robert A. Volkmann, Mystic, CT (US); Jotham W. Coe, Niantic, CT (US); Eric Verdin, Mill Valley, CA (US); Rosalba Perrone, San Francisco, CA (US); Margaret Jackson, Sudbury, MA (US); Frederick R. Nelson, Groton, CT (US); Elena Silva, Novato, CA (US); Steve Felstead, Earlston (GB)

(73) Assignees: NAPA THERAPEUTICS LIMITED, Ramsey (IM); BUCK INSTITUTE FOR RESEARCH ON AGING, Novato, CA (US)

( * ) Notice: Subject to any disclaimer, the term of this patent is extended or adjusted under 35 U.S.C. 154(b) by 445 days.

(21) Appl. No.: 18/248,325

(22) PCT Filed: Oct. 8, 2021

(86) PCT No.: PCT/US2021/071805

§ 371 (c)(1),
(2) Date: Apr. 7, 2023

(87) PCT Pub. No.: WO2022/077034

PCT Pub. Date: Apr. 14, 2022

(65) Prior Publication Data

US 2023/0382901 A1 Nov. 30, 2023

Related U.S. Application Data

(60) Provisional application No. 63/089,818, filed on Oct. 9, 2020.

(51) Int. Cl.

| | |
|---|---|
| ***C07D 405/14*** | (2006.01) |
| ***C07D 401/14*** | (2006.01) |
| ***C07D 487/04*** | (2006.01) |

(52) U.S. Cl.

CPC ......... *C07D 405/14* (2013.01); *C07D 401/14* (2013.01); *C07D 487/04* (2013.01)

(58) Field of Classification Search

CPC ... C07D 405/14; C07D 401/14; C07D 487/04

See application file for complete search history.

(56) References Cited

U.S. PATENT DOCUMENTS

| | | | | |
|---|---|---|---|---|
| 2004/0106616 | A1* | 6/2004 | Bakthavatchalam | ... A61P 25/06 544/405 |
| 2007/0149547 | A1 | 6/2007 | Bonnefous et al. | |
| 2014/0249135 | A1 | 9/2014 | Burger et al. | |
| 2021/0032251 | A1* | 2/2021 | Schenkel | ............ C07D 403/04 |

FOREIGN PATENT DOCUMENTS

| | | | |
|---|---|---|---|
| JP | 2007-524682 | A | 8/2007 |
| WO | WO 2015/187499 | | 12/2015 |
| WO | 2018/090869 | A1 | 5/2018 |
| WO | 2019/014460 | A1 | 1/2019 |
| WO | WO 2019/227059 | | 11/2019 |

OTHER PUBLICATIONS

Extended European Search Report for Application No. 21878737.2 dated Oct. 29, 2024 (8 pages).

International Search Report and Written Opinion for PCT/US2021/071805 mailed Feb. 1, 2022 (4 pages).

Written Opinion of the International Searching Authority for PCT/US2021/071805 mailed Feb. 1, 2022 (7 pages).

* cited by examiner

*Primary Examiner* — Joseph K McKane

*Assistant Examiner* — Jalisa Holmes Ferguson

(74) *Attorney, Agent, or Firm* — Debora Plehn-Dujowich; Eckert Seamans Cherin & Mellott, LLC

(57) ABSTRACT

Disclosed are heteroaryl amide inhibitors of CD38 and methods of making and using the same in disease and disorder treatment.

24 Claims, 42 Drawing Sheets

HETEROARYL AMIDE INHIBITORS OF CD38

RELATED APPLICATION

This application is a national stage filing under 35 U.S.C. § 371 of International Application No. PCT/US2021/071805, filed on Oct. 8, 2021, which claims the benefit of U.S. Provisional Application No. 63/089,818, filed Oct. 9, 2020, all of which are incorporated herein by reference in their entirety.

FIELD OF THE INVENTION

The present disclosure relates to biochemistry, and medicine. More specifically, this disclosure relates to novel compounds, processes for their preparation, and pharmaceutical formulations and methods of treating diseases by modulating the level of cellular NAD+ and related metabolites thereof through the inhibition of the CD38 enzyme.

BACKGROUND

Nicotinamide Adenine Dinucleotide (NAD+) is a biochemical that is found in all cells performing its critical role in oxidoreductase reactions. NAD+ and its related pyridine nucleotides NADH, nicotinamide adenine dinucleotide phosphate (NADP+), and NADPH are recognized as major redox carriers in all organisms. These pyridine dinucleotides regulate the cytosolic and mitochondrial redox state and are key participants monitoring the metabolic status of the cell (Houtkooper et al. (2010) *Endo. Rev.* 31(2):194-223); Koch-Nolte et al. (2009) Sci. Signal. 2(57); Houtkooper et al. (2012) *J. Cell Biol.*) 199(2):205-209).

In addition to its role as a cofactor for oxidoreductases, NAD+ is also a substrate for various enzymes, where it is consumed in the process of donating its adenosine diphosphate (ADP) ribose to acceptor molecules or in the process of hydrolysis or cyclization. The enzymes that are the major consumers of NAD+ are the ADP ribosyl transferases (i.e., poly(ADP-ribose) polymerase (PARP) and ADP-ribosyltransferase (ART) family of enzymes), the sirtuins (Sirt1-7), and the ADP ribosyl cyclases/hydrolases (CD38/CD157). These enzymes are involved in pathways that regulate Ca2+ signalling, gene transcription, DNA repair, cell survival, energy metabolism, and oxidative stress. Thus, NAD+ and its phosphorylated relatives NADP and nicotine acid adenine dinucleotide phosphate (NAADP), both of which are derived from NAD+, also act as signalling molecules. NAD+ is also a component of the circadian cycle with daily oscillations that tie cellular metabolism to chromatin remodelling and gene transcription. It is known that exercise and caloric restriction elevate NAD+ levels while aging and obesity decrease cellular NAD+ levels.

Cellular NAD+ is produced by either the de novo synthesis pathway from tryptophan or by the Preiss-Handler and/or the salvage synthesis pathways from precursors such as nicotinic acid (niacin), nicotinamide (NAM), nicotinamide riboside (NR), and nicotinamide mononuscleotide (NMN), which are imported into the cells. The modulation of cellular NAD+ levels can be achieved by blocking the consumption of NAD+ by inhibiting enzymes that consume NAD+. CD38 is one of such NAD+ consuming enzymes and reported to be the main cellular NAD+ consumer. Also known as ADP ribosyl cyclase, CD38 is a type II membrane-anchored enzyme. It efficiently catalyzes the breakdown of NAD+ to nicotinamide (NAM) and ADP ribose (ADPR) and hydrolyzes NAADP to ADPR phosphate (ADPRP). CD38 acts as a cyclase converting NAD+ to cyclic ADPR (cADPR). Finally, ADPR is also a breakdown product of cADPR hydrolysis mediated by CD38.

ADP ribose (ADPR) and cyclic ADPR (cADPR) are metabolites of NAD+ generated by CD38-mediated hydrolysis or cyclization and they play a key role as intracellular Ca2+ mobilizing second messengers. cADPR is mainly involved stimulating Ca2+ release from the endoplasmic reticulum via ryanodine receptors, whereas ADPR activates the plasma membrane cation channel TRPM2 (Transient receptor potential melastatin 2) facilitating calcium entry into the cells. Aberrant TRPM2 activation has been shown to induce abnormal intracellular Ca2+ accumulation and cell death in a variety of cell types, including neurons, and is implicated in several neurological disorders. In particular, the activation of TRPM2 has been linked to diseases such as ischemia-reperfusion injury, bipolar disorder, Alzheimer's disease, neuropathic pain, and Parkinson's disease.

Nicotinamide (NAM) is a precursor for $NAD^+$ and is a key molecule involved in energy metabolism. NAM is converted into nicotinamide mononucleotide (NMN) by the enzyme nicotinamide phosphoribosyltransferase (NAMPT). Alternatively, NAM can be irreversibly methylated by Nicotinamide N-methyltransferase (NNMT) enzyme and excreted from the body. The methylated form of NAM (i.e., N1-methylnicotinamide (MNAM)) has been shown to be associate with coronary artery disease (CAD), obesity, type-2 diabetes, hepatotoxicity, Parkinson's disease, and cancers.

Although NAM supplementation has shown positive effects, high levels of NAM can exert negative effects through multiple routes, including inhibition of PARPs and sirtuins and alteration of methyl metabolism. NAM supplementation has shown to cause a significant decrease of insulin sensitivity in human subjects, neurotoxicity and hepatotoxicity.

Certain heteroaryl amides are known such as N-(3-chloro-2-methylpyridin-4-yl)-6-imidazol-1-ylpyridine-2-carboxamide, pubchem.ncbi.nlm.nih.gov/compound/99607495, however, no biological data for the compound is reported. Int. Patent Pub. WO 2015/187499 refers to certain unrelated reverse amides as ASK1 inhibitors. Int. Patent Pub. WO 2009/014637 refers to certain benzimidazolylpyridines as protein kinase inhibitors. U.S. Pat. No. 7,919,487 refers to certain heteroaryl hydrazones.

Accordingly, there is still a need for novel inhibitors of CD38 and treatments of diseases or disorders that benefit from the modulation of the level of cellular NAD+ and related metabolites thereof.

SUMMARY

The present disclosure provides novel compounds, processes for their preparation, and pharmaceutical formulations and methods of treating diseases by modulating the level of cellular NAD+ and related metabolites thereof through the inhibition of the CD38 enzyme This disclosure pertains to a compound of Formula I or a pharmaceutically acceptable salt, ester, or prodrug thereof

I (II)

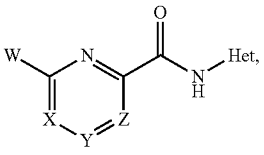

or a compound of Formula I* or a pharmaceutically acceptable salt, ester, or prodrug thereof, (I*)

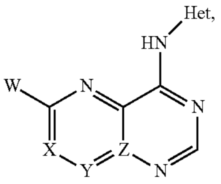

wherein:

—X—Y—Z— is =CR$^1$—CR$^2$=CR$^3$—, =N—CR$^2$=CR$^3$—, =CR$^1$—N=CR$^3$— or =CR$^1$—CR$^2$=N— if the compound is of Formula I;

X—Y—Z— is CR$^1$—CR$^2$=C, N—CR$^2$=C, or CR$^1$—N=C if the compound is of Formula I*;

$R^1$ is selected from the group consisting of H, halo, —CN, $(C_1$-$C_6)$alkyl, $(C_1$-$C_6)$alkoxy, and perfluoro$(C_1$-$C_6)$alkoxy-; wherein $(C_1$-$C_6)$alkyl is optionally substituted with 1-3 substituents independently selected from the group consisting of H, halo, —CN, $(C_1$-$C_3)$alkyl, —$NH_2$, $(C_1$-$C_3)$alkyl-(NH)—, $((C_1$-$C_3)alkyl)_2N$—, —$CF_3$, —$OCH_3$ and —$OCF_3$;

$R^2$ is H, halo, —CN, $(C_1$-$C_6)$alkyl, $(C_1$-$C_6)$alkoxy, perfluoro$(C_1$-$C_6)$alkyl, perfluoro$(C_1$-$C_6)$alkoxy-, cycloalkyl, cycloalkyl-O—, heterocycloalkyl, heterocycloalkyl-O—, aryl, aryl-O—, $R^5$—$(C(R^4)_2)_n$—O— or $(R^6)_2$N—; wherein $(C_1$-$C_6)$alkyl, cycloalkyl, heterocycloalkyl, and aryl are each optionally substituted with 1-3 substituents independently selected from the group consisting of H, halo, —CN, $(C_1$-$C_3)$alkyl, —$NH_2$, $(C_1$-$C_3)$alkyl-(NH)—, $((C_1$-$C_3)alkyl)_2N$—, —$CF_3$, —$OCH_3$ and —$OCF_3$;

$R^3$ is H, halo, $(C_1$-$C_3)$alkyl, —$CF_3$, $(C_1$-$C_3)$alkoxy, —$OCF_3$ or $(R^7)_2N$—; wherein $R^7$ is H or $(C_1$-$C_3)$alkyl;

each $R^4$ is independently H or $(C_1$-$C_3)$alkyl; wherein $(C_1$-$C_3)$alkyl is optionally substituted with 1-3 substituents independently selected from the group consisting of H, halo, —CN, $(C_1$-$C_3)$alkyl, —$NH_2$, $(C_1$-$C_3)$alkyl-(NH)—, $((C_1$-$C_3)alkyl)_2N$—, —$CF_3$, —$OCH_3$ and —$OCF_3$;

$R^5$ is selected from the group consisting of $(C_1$-$C_3)$alkyl, perfluoro$(C_1$-$C_3)$alkyl, HO—$(C_2$-$C_4)$alkyl-, cycloalkyl, heterocycloalkyl, and aryl; wherein $(C_1$-$C_3)$alkyl, cycloalkyl, heterocycloalkyl, and aryl are each optionally substituted with 1-3 substituents independently selected from the group consisting of H, halo, —CN, $(C_1$-$C_3)$alkyl, —$NH_2$, $(C_1$-$C_3)$alkyl-(NH)—, $((C_1$-$C_3)alkyl)_2N$—, —$CF_3$, —$OCH_3$ and —$OCF_3$;

$R^6$ is independently H or $(C_1$-$C_3)$alkyl; wherein $(C_1$-$C_3)$alkyl is optionally substituted with 1-3 substituents independently selected from the group consisting of H, halo, —CN, $(C_1$-$C_3)$alkyl, —$NH_2$, $(C_1$-$C_3)$alkyl-(NH)—, $((C_1$-$C_3)alkyl)_2N$—, —$CF_3$, —$OCH_3$ and —$OCF_3$;

n is an integer from one to three;

W is (a)

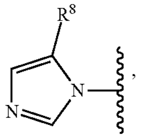

(b)

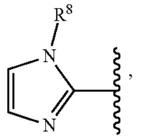

(c)

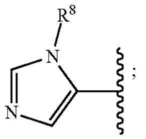

(d)

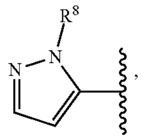

(e)

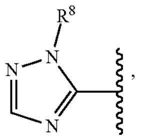

or (f)

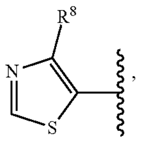

$R^8$ is H, —$CH_3$ or —$CF_3$;

Het is a heterocycle of the formula i

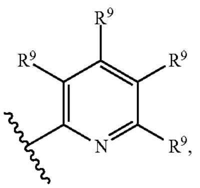

-continued ii

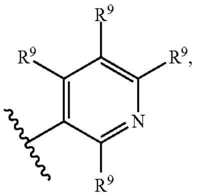

iii

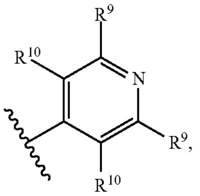

iv

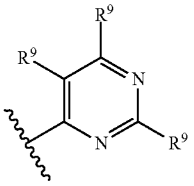

v

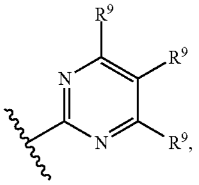

vi

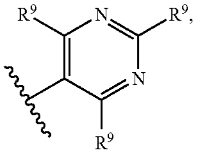

vii

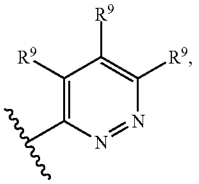

viii

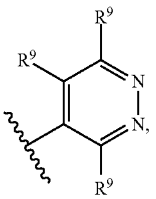

or ix

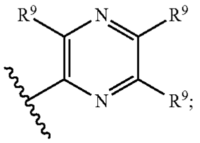

each $R^9$ is independently selected from H, halo, $(C_1\text{-}C_6)$alkyl, —$CF_3$, $(C_1\text{-}C_6)$alkoxy, —$OCF_3$, —CN, $(R^{11})_2N$—, $R^{12}(O)(C{=}O)$—, $R^{12}O((C_1\text{-}C_3)\text{alkyl})\text{-}(NR^{11})$—, $R^{13}$—(C═O)—$(NR^{11})$— and $(R^{11})_2N$—(C═O)—;

each $R^{10}$ is independently selected from H, $(C_1\text{-}C_3)$alkyl, —$CF_3$, —$OCH_3$, —$OCF_3$, —CN, $(R^{11})_2N$—, $R^{12}(O)(C{=}O)$—, $R^{12}O$—$((C_1\text{-}C_3)\text{alkyl})\text{-}(NR^{11})$—, $R^{13}$—(C═O)—$(NR^{11})$—, and $(R^{11})_2N$—(C═O);

$R^{11}$ is independently H or $(C_1\text{-}C_3)$alkyl;

$R^{12}$ is H or $(C_1\text{-}C_3)$alkyl; and $R^{13}$ is $(C_1\text{-}C_3)$alkyl.

In some embodiments of the compounds of Formula I and I*, Het is a ring of the

Formula i:

i

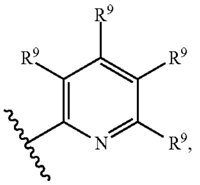

Formula ii:

ii

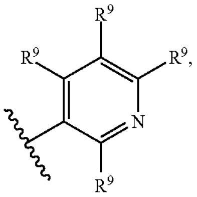

Formula iii:

iii

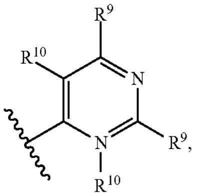

Formula iv:

iv

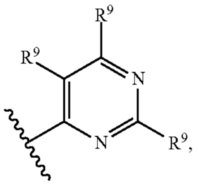

Formula v:

v

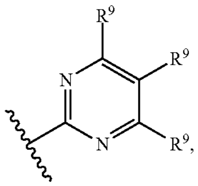

-continued

Formula vi:

vi

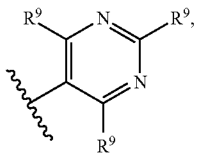

Formula vii:

vii

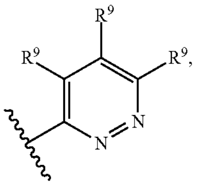

Formula viii:

viii

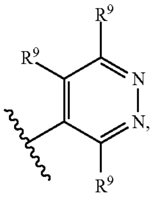

or

Formula ix:

ix

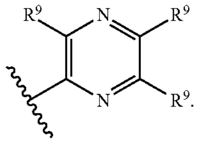

In particular embodiments of the compounds of Formula I and I*, including any of the compounds recited supra, $R^8$ is —$CH_3$ or —$CF_3$; and W is a compound of Formula (a):

(a)

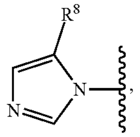

Formula (b):

(b)

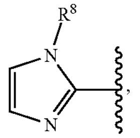

Formula (c):

(c)

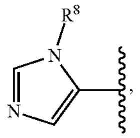

-continued

Formula (d):

(d)

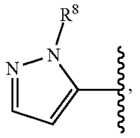

Formula (e):

(e)

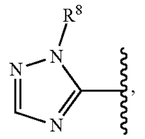

or

Formula (f):

(f)

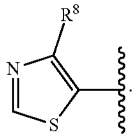

In some embodiments of the compounds of Formula I and I*, including any of the compounds recited supra, $R^1$ is selected from the group consisting of H, halo, —CN, $(C_1\text{-}C_3)$alkyl, —$OCH_3$, and —$OCF_3$.

In certain embodiments, in the compounds of Formula I and I*, including any of the compounds recited supra:

$R^2$ is selected from the group consisting of H, $(C_1\text{-}C_6)$alkyl, $(C_1\text{-}C_6)$alkoxy-, perfluoro$(C_1\text{-}C_6)$alkyl, perfluoro$(C_1\text{-}C_6)$alkoxy-, cycloalkyl, cycloalkyl-O—, heterocycloalkyl, aryl, $R^5$—$(C(R^4)_2)_n$—O— or $(R^6)_2N$—; wherein $(C_1\text{-}C_6)$alkyl, cycloalkyl, heterocycloalkyl and aryl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)\text{alkyl})_2N$—, —$CF_3$, —$OCH_3$ and —$OCF_3$;

each $R^4$ is independently H or $(C_1\text{-}C_3)$alkyl optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)\text{alkyl})_2N$—, —$CF_3$, —$OCH_3$ and —$OCF_3$;

$R^5$ is selected from the group consisting of $(C_1\text{-}C_3)$alkyl, cycloalkyl, heterocycloalkyl, and aryl; wherein $(C_1\text{-}C_6)$alkyl, cycloalkyl, heterocycloalkyl and aryl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)\text{alkyl})_2N$—, —$CF_3$, —$OCH_3$, and —$OCF_3$; and $R^6$ is independently H or $(C_1\text{-}C_3)$alkyl optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)\text{alkyl})_2N$—, —$CF_3$, —$OCH_3$, and —$OCF_3$.

In some embodiments of the compound of Formula 1, including any of the compounds recited supra, $R^3$ is selected from the group consisting of H, halo, $(C_1\text{-}C_3)$alkyl, —$CF_3$, —$OCH_3$, —$OCF_3$, and $(R^7)_2N$—; and wherein $R^7$ is H or $(C_1\text{-}C_3)$alkyl.

In particular embodiments, $R^1$ is selected from the group consisting of H, F, —$CH_3$, and —$OCH_3$.

In some embodiments of the compounds of Formula I and I*, including any of the compounds recited above, $R^1$ is H.

In certain embodiments of the compounds of Formula I and I*, including any of the compounds recited above, $R^2$ is selected from the group consisting of H, $(C_1\text{-}C_3)$alkyl, $(C_1\text{-}C_3)$alkoxy-, perfluoro$(C_1\text{-}C_3)$alkyl, perfluoro$(C_1\text{-}C_3)$alkoxy-, 3- to 10-membered cycloalkyl, 3- to 10-membered cycloalkyl-O—, 5- to 10-membered heterocycloalkyl, 6- to 10-membered aryl, $R^5$—$(C(R^4)_2)_n$—O— or $(R^6)_2N$—; wherein $(C_1\text{-}C_3)$alkyl, 3- to 10-membered cycloalkyl, 3- to 10-membered cycloalkyl-O—, 5- to 10-membered heterocycloalkyl, 6- to 10-membered aryl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$; each $R^4$ is independently H or $(C_1\text{-}C_3)$alkyl optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$; $R^5$ is selected from $(C_1\text{-}C_3)$alkyl, 3- to 10-membered cycloalkyl, 3- to 10-membered heterocycloalkyl, and 6- to 10-membered aryl; wherein $(C_1\text{-}C_3)$alkyl, 3- to 10-membered cycloalkyl, 3- to 10-membered heterocycloalkyl, and 6- to 10-membered aryl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$; and $R^6$ is independently H or $(C_1\text{-}C_3)$alkyl optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$.

In specific embodiments of the compounds of Formula I and I*, including any of the compounds recited above, $R^2$ is selected from the group consisting of methoxy-, cyclopropoxy- or $R^5$—$(C(R^4)_2)$—O—; and each $R^4$ is H; wherein $R^5$ is selected from the group consisting of $C_1$-alkyl and tetrahydropyran, and wherein said $C_1$-alkyl is substituted with —$OCH_3$.

In some embodiments of the compounds of Formula I and I*, including any of the compounds recited above, $R^3$ is selected from the group consisting of H, F, —$CH_3$, —$OCH_3$, or $H_2N$—. In certain embodiments, $R^3$ is H.

In some embodiments of the compounds of Formula I and I*, including any of the compounds recited above, $R^9$ is selected from the group consisting of H, halo, $(C_1\text{-}C_3)$alkyl, —$CF_3$, —$OCH_3$, —$OCF_3$, —CN, $R^{12}O((C_1\text{-}C_3)alkyl)$-$(NR^{11})$—, —$CO_2R^{12}$, and $(R^{11})_2N$—(C═O)—; and each $R^{11}$ is independently selected from H, $(C_1\text{-}C_3)$alkyl; $R^{12}$ is H or $(C_1\text{-}C_3)$alkyl.

In certain embodiments, at least one $R^9$ is selected from the group consisting of F, $(C_1\text{-}C_3)$alkyl, —$CF_3$, —$OCH_3$, —$OCF_3$, —CN, and in a specific embodiment, at least one $R^9$ is —CF.

In some embodiments of the compounds of Formula I and I*, including any of the compounds of Formula (iii) and Formulae (a)-(f), at least one $R^{10}$ is H, and in certain embodiments, $R^{10}$ is H.

In certain embodiments of the compounds of Formula I and I*, including any of the compounds recited above, Het is a ring of the Formula iii:

iii

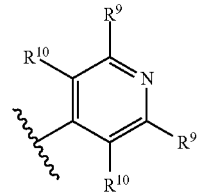

wherein: one $R^9$ is H, and the other $R^9$ is —$CF_3$, and $R^{10}$ is H.

In some embodiments of the compounds of Formula I and I*, including any of the compounds recited above, $R^8$ is H.

In some embodiments of the compounds of Formula I and I*, including any of the compounds recited above, —X—Y—Z— is ═$CR^1$—$CR^2$═$CR^3$— or ═N—$CR^2$═$CR^3$—, and in a particular embodiment, —X—Y—Z— is ═$CR^1$—$CR^2$═$CR^3$—.

In some embodiments of the compounds of Formula I, including any of the compounds recited in any of the compounds of Formula (iii) and Formula (a), the compound is a compound of Formula 1A or a pharmaceutically acceptable salt, ester, or prodrug thereof:

(IA)

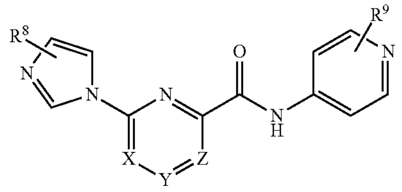

and the compound of Formula I* is a compound of Formula I* A or a pharmaceutically acceptable salt, ester, or prodrug thereof (I*A)

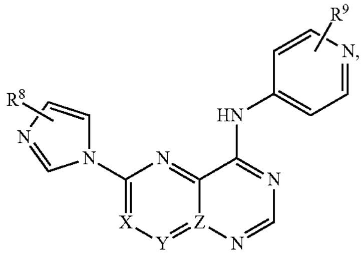

wherein:

—X—Y—Z— of the Formula IA is ═$CR^1$—$CR^2$═$CR^3$— or ═N—$CR^2$═$CR^3$—;

—X—Y—Z— of the Formula I* A is $CR^1$—$CR^2$═C or ═N—$CR^2$═C;

$R^1$ is selected from the group consisting of H, halo, —CN, $(C_1\text{-}C_3)$alkyl, —$OCH_3$, and —$OCF_3$;

$R^2$ is H, $(C_1\text{-}C_6)$alkyl, $(C_1\text{-}C_6)$alkoxy-, perfluoro$(C_1\text{-}C_6)$alkyl, perfluoro$(C_1\text{-}C_6)$alkoxy-, cycloalkyl, cycloalkyl-O, heterocycloalkyl, aryl, $R^5$—$(C(R^4)_2)_n$—O— or $(R^6)_2$ N—, wherein $(C_1\text{-}C_6)$alkyl, cycloalkyl, cycloalkyl-O, heterocycloalkyl and aryl are optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$, and —$OCF_3$;

n is an integer from one to three;

each $R^4$ is independently H or $(C_1\text{-}C_3)$alkyl;

$R^5$ is selected from the group consisting of $(C_1\text{-}C_3)$alkyl, cycloalkyl, heterocycloalkyl, and aryl, wherein $(C_1\text{-}C_3)$ alkyl, cycloalkyl, heterocycloalkyl and aryl are optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)$ $alkyl)_2N$—, —$CF_3$, —$OCH_3$. and —$OCF_3$;

$R^6$ is independently H or $(C_1\text{-}C_3)$alkyl; wherein $(C_1\text{-}C_3)$ alkyl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$;

$R^3$ is H, halo, $(C_1\text{-}C_3)$alkyl, —$CF_3$, —$OCH_3$, —$OCF_3$ or $(R^7)_2N$—;

$R^7$ is H or $(C_1\text{-}C_3)$alkyl;

$R^8$ is H, —$CH_3$ or —$CF_3$;

$R^9$ is selected from H, halo, $(C_1\text{-}C_3)$alkyl, —$CF_3$, —$OCH_3$, —$OCF_3$, —CN, $R^{12}O((C_1\text{-}C_3)alkyl)$-$(NR^{11})$—, —$CO_2R^{12}$, and $(R^{11})_2N$—(C═O)—;

each $R^{11}$ is independently selected from the group consisting of H and $(C_1\text{-}C_3)$alkyl; and $R^{12}$ is H or $(C_1\text{-}C_3)$alkyl.

In some embodiments of the compound of Formula I, including any of the compounds of Formula (ii) and Formula (a), the compound is a compound of Formula 1B, or a pharmaceutically acceptable salt, ester, or prodrug thereof:

(IB)

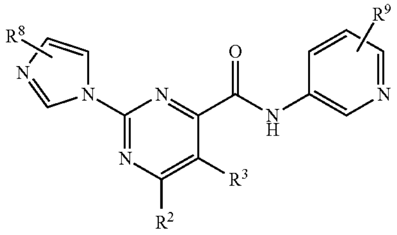

and the compound of Formula I* is a compound of Formula I* B, or a pharmaceutically acceptable salt, ester, or prodrug thereof (I*B)

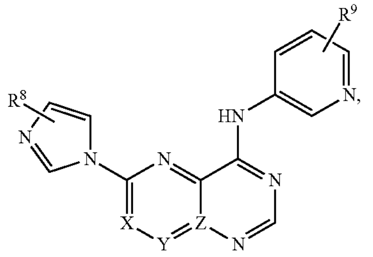

wherein:

—X—Y—Z— of the Formula I* B is CH—$CR^2$═C or N—$CR^2$═C; $R^2$ is H, $(C_1\text{-}C_3)$alkyl, $(C_1\text{-}C_3)$alkoxy-, perfluoro$(C_1\text{-}C_3)$alkyl, perfluoro$(C_1\text{-}C_3)$alkoxy-, cycloalkyl, heterocycloalkyl, aryl, $R^5$—$(C(R^4)_2)_n$—O—, or $(R^6)_2N$—; wherein $(C_1\text{-}C_3)$alkyl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)$ $alkyl)_2N$—, —$CF_3$, —$OCH_3$, and —$OCF_3$;

n is an integer from one to three;

each $R^4$ is independently H or $(C_1\text{-}C_3)$alkyl, wherein $(C_1\text{-}C_3)$alkyl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$, and —$OCF_3$;

$R^5$ is selected from the group consisting of $(C_1\text{-}C_3)$alkyl, cycloalkyl, heterocycloalkyl, and aryl; wherein $(C_1\text{-}C_3)$ alkyl, cycloalkyl, heterocycloalkyl and aryl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)$ $alkyl)_2N$—, —$CF_3$, —$OCH_3$, and —$OCF_3$;

$R^6$ is independently H or $(C_1\text{-}C_3)$alkyl; wherein $(C_1\text{-}C_3)$ alkyl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$;

$R^3$ is H, halo, $(C_1\text{-}C_3)$alkyl, —$CF_3$, —$OCH_3$, —$OCF_3$ or $(R^7)_2N$—, wherein $R^7$ is H or $(C_1\text{-}C_3)$alkyl;

$R^8$ is H, —$CH_3$ or —$CF_3$; and $R^9$ is selected from the group consisting of H, halo, $(C_1\text{-}C_3)$alkyl, —$CF_3$, —$OCH_3$, —$OCF_3$, —CN, —$(NR^{10})$—$((C_1\text{-}C_3)alkyl)$-$OR^{11}$, —$CO_2R^{11}$, and —(C═O)—$N(R^{10})_2$, wherein $R^{10}$ is H or $(C_1\text{-}C_3)$alkyl; and $R^{11}$ is $(C_1\text{-}C_3)$alkyl.

In certain embodiments, the compound of is selected from the group consisting of 6-(1H-imidazol-1-yl)-4-((tetrahydro-2H-pyran-4-yl)methoxy)-N-(2-(trifluoromethyl)pyridin-4-yl)picolinamide, 6-(1H-imidazol-1-yl)-4-methoxy-N-(2-(trifluoromethyl)pyridin-4-yl)picolinamide, 2-(1H-imidazol-1-yl)-6-(2-methoxyethoxy)-N-(2-(trifluoromethyl)pyridin-4-yl)pyrimidine-4-carboxamide, 6-(1H-imidazol-1-yl)-4-(2-methoxyethoxy)-N-(2-(trifluoromethyl)pyridin-4-yl)picolinamide, 4-cyclopropoxy-6-(1H-imidazol-1-yl)-N-(2-(trifluoromethyl)pyridin-4-yl)picolinamide, 6-(1H-imidazol-1-yl)-N-(pyridin-3-yl)pyrido[3,2-d]pyrimidin-4-amine, 6-(1H-imidazol-1-yl)-N-(pyridin-4-yl)pyrimido[5,4-d]pyrimidin-4-amine, 6-cyclopropyl-2-(1H-imidazol-1-yl)-N-(2-(trifluoromethyl)pyridin-4-yl)pyrimidine-4-carboxamide, 6-(1H-imidazol-1-yl)-4-((3-methyloxetan-3-yl)oxy)-N-(2-(trifluoromethyl)pyridin-4-yl)picolinamide, 2-(3-methyl-4H-3I4-imidazol-4-yl)-6-((3-methyloxetan-3-yl)oxy)-N-(2-(trifluoromethyl)pyridin-4-yl)pyrimidine-4-carboxamide, 2-(1-methyl-1H-imidazol-2-yl)-6-((3-methyloxetan-3-yl)oxy)-N-(2-(trifluoromethyl)pyridin-4-yl)pyrimidine-4-carboxamide, 2-(1-methyl-1H-imidazol-5-yl)-6-((tetrahydro-2H-pyran-4-yl)methoxy)-N-(2-(trifluoromethyl)pyridin-4-yl)pyrimidine-4-carboxamide, 2-(1-methyl-1H-imidazol-2-yl)-6-((tetrahydro-2H-pyran-4-yl)methoxy)-N-(2-(trifluoromethyl)pyridin-4-yl)pyrimidine-4-carboxamide, 6-(2-methoxyethoxy)-2-(1-methyl-1H-imidazol-5-yl)-N-(2-(trifluoromethyl)pyridin-4-yl)pyrimidine-4-carboxamide, 6-(2-methoxyethoxy)-2-(1-methyl-1H-imidazol-2-yl)-N-(2-(trifluoromethyl)pyridin-4-yl)pyrimidine-4-carboxamide, 6-(2-hydroxy-2-methylpropoxy)-2-(1H-imidazol-1-yl)-N-(2-(trifluoromethyl)pyridin-4-yl)pyrimidine-4-carboxamide, and a pharmaceutically acceptable salt, ester, or prodrug thereof.

In another aspect, the disclosure provides a pharmaceutical composition comprising a therapeutically effective amount of a compound of Formula I or I*, including any compound recited supra, and a pharmaceutically acceptable carrier. In some embodiments, the pharmaceutical formulation comprises therapeutically effective amount of at least one additional medicinal or pharmaceutical agent. In one embodiment, this additional agent is a therapeutically effect amount of an anti-aging agent. In another embodiment, this additional agent is a therapeutically effect amount of an anti-rheumatoid arthritis agent.

In yet another aspect, the disclosure provides a method of treating a disease or medical disorder in a subject suffering therefrom and which benefits from modulation of NAD+ level or related metabolites thereof level, comprising administering to the subject a pharmaceutical formulation in an amount effective to modulate the level of NAD+ or related metabolites thereof, the formulation comprising a therapeutically effective amount of a compound of Formula I or I*, including any compound recited supra, and a pharmaceutically acceptable carrier, and optionally comprising another agent which modulate the level of NAD+ or related metabolites thereof.

In some embodiments, the disease or disorder is or is related to nonalcoholic stetohepatits, aging, aging chronical condition, senescence, immunometabolism, sepsis, inflammation, infection, arthritis, rheumatoid arthritis, psoriatic arthritis, osteoarthritis, lupus, lupus erythematosus, Crohn disease, ulcerative colitis, plaque psoriasis, ankylosing spondylitis, juvenile idiopathic arthritis, hidradenitis suppurativa, fibrosis, hepatic fibrosis, renal fibrosis, pulmonary fibrosis, cardiac fibrosis, cancer, multiple myeloma, cardiovascular disorder, neurological disorder, infertility, loss of ovarian follicles, decreased oocyte quality and quantity, ovarian senescence, transient receptor potential melastatin 2 (TRPM2) regulation, calcium flux regulation, ischemia-reperfusion-injury, bipolar disorder, Alzheimer, neuropathic pain, Parkinson, coronary arteries, obesity, type-2 diabetes, hepatotoxicity, pulmonary disorder, metabolic disorder, acute lung injury (ALI), acute respiratory distress syndrome (ARDS), hyperphosphatemia, alcohol intolerance, ataxia-telangiectasia, irritable bowel syndrome, colitis, gout, end stage renal disease, hearing loss, liver disorders, postmenopausal osteoporosis, Hartnup disease, tuberculosis, leishmaniasis, muscular dystrophy, organ reperfusion injury, pellagra, diseases of the skin, damage caused by exposure to radiation, periodontal disease, Leber's hereditary amaurosis, sleep disorder, exercise intolerance, chronic disease associated with cell death, and neurodegeneration, peripheral neuropathy associated with chemotherapy, and the like. In particular embodiments, the disease or disorder is or is related to nonalcoholic steatohepatitis or the like. In other embodiments, the disease or disorder is or is related to an age-related disease or disorder or the like. In still other embodiments, the disease or disorder is or is related to a fibrotic disease of the digestive system, lung, heart, kidney, liver, or lung or the like. In certain embodiments, the disease or disorder is or is related to Multiple Myeloma or the like, and the method further comprises administering an immuno-oncology drug to the subject in need thereof.

In another aspect, the disclosure provides the use of a pharmaceutical formulation comprising a compound of Formula 1, including any compound recited above, to treat a disease or disorder in a subject that benefits from modulation of the level of NAD+ or related metabolites thereof. In some embodiments, the pharmaceutical formulation comprising a compound of Formula 1, including any compound recited above, is used to treat a disease or disorder in a subject that benefits from the subject benefiting from inhibition of CD38. In certain embodiments, the disease or disorder is or is related to agin or the like.

In particular embodiments, the pharmaceutical formulation is used to treat a disease or disorder selected from small lung cell carcinoma, renal clear cell carcinoma, chronic lymphocytic leukemiahas, multiple myeloma, hypertension, hypoxic pulmonary vasoconstriction, cardiac hypertrophy, congestive heart failure, stroke, Alzheimer's disease, bipolar disorder, schizophrenia, Huntington's disease, amyotrophic lateral sclerosis, Parkinson's disease, multiple sclerosis, optic neuropathy, epilepsy, idiopathic pulmonary fibrosis, viral-induced fibrosis of the lung, infection-induced fibrosis of the lung, cystic fibrosis, asthma, chronic obstructive pulmonary disease (COPD), metabolic syndrome, obesity, sarcopenic obesity, dyslipidemia, diabetes (such as type I diabetes), diabetic neuropathy, insulin resistance, pancreatitis, acute lung injury (ALI) acute respiratory distress syndrome (ARDS), hyperphosphatemia, alcohol intolerance, lupus, rheumatoid arthritis, ataxia-telangiectasia, irritable bowel syndrome, colitis, gout, end stage renal disease, hearing loss, steatosis, non-alcoholic steatohepatitis (NASH), postmenopausal osteoporosis, Hartnup disease, tuberculosis, leishmaniasis, muscular dystrophy, organ reperfusion injury, pellagra, skin hyperpigmentation, UV skin damage, psoriasis, X-ray-induced DNA damage, periodontal disease, Leber's hereditary amaurosis, sleep disorders, exercise intolerance, and neurodegeneration and peripheral neuropathies associated with chemotherapy.

In other particular embodiments, the pharmaceutical formulation is used to treat a disease or disorder selected from aging, age-related chronic disease, inflammation, cancer, cardiovascular disorder, neurological disorder, pulmonary disorder, fibrotic diseases, SARS, COVID-19, metabolic disorder, acute lung injury (ALI), acute respiratory distress syndrome (ARDS), hyperphosphatemia, alcohol intolerance, lupus, arthritis, ataxia-telangiectasia, irritable bowel syndrome, colitis, gout, end stage renal disease, hearing loss, liver disorders, postmenopausal osteoporosis, Hartnup disease, tuberculosis, leishmaniasis, muscular dystrophy, organ reperfusion injury, pellagra, diseases of the skin, damage caused by exposure to radiation, periodontal disease, Leber's hereditary amaurosis, sleep disorder, exercise intolerance, chronic disease associated with cell death.

In a particular embodiment, the use is treatment is of Multiple Myeloma, and the treatment further comprises treatment of the subject with an immuno-oncology drug. In another specific embodiment, the use is treatment of nonalcoholic steatohepatitis (NASH), and in certain embodiment, the treatment of NASH is with the use of 2-(1H-imidazol-1-yl)-6-methoxy-N-(2-(trifluoromethyl)pyridin-4-yl)pyrimidine-4-carboxamide.

These aspects and embodiments, as well as others, are disclosed in further detail herein

BRIEF DESCRIPTION OF THE DRAWINGS

The accompanying drawings illustrate embodiments of the present disclosure, and together with the general description given above and the detailed description given below, serve to explain the principles of the present disclosure.

DETAILED DESCRIPTION

Figure 1A:
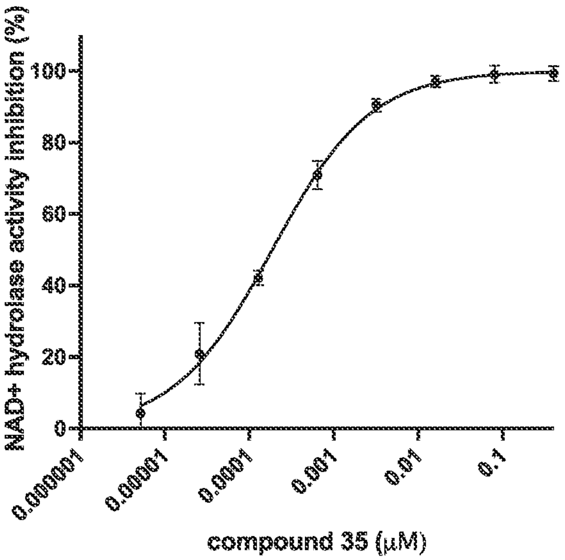
FIG. 1A depicts the in vitro functional potency for Compound 35 in human CD38+ cells as measured by NAD hydrolase activity assay in primary human activated CD4+ T cells. The concentration response plot represents the average+ standard deviation for the % inhibition values at each concentration tested where n=3 biological replicates over one experiment.

The disclosures of patents, patent applications, and publications referred to herein are hereby incorporated by reference in their entireties into this application in order to more fully describe the state of the art as known to those skilled therein as of the date of the invention described and claimed herein. The instant disclosure will govern in the instance that there is any inconsistency between the patents, patent applications, and publications and this disclosure.

Unless defined otherwise, all technical and scientific terms used herein have the same meaning as commonly understood by one of ordinary skill in the art to which this disclosure belongs. The initial definition provided for a group or term herein applies to that group or term throughout the present specification individually or as part of another group, unless otherwise indicated.

As used herein, the singular forms "a", "an," and "the" include both singular and plural referents unless the context clearly dictates otherwise. Thus, for example, reference to "a compound" includes a plurality of such compound.

As used herein, the term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

As used herein, the term "about" or "approximately" refers to a measurable value such as a parameter, an amount, a temporal duration, and the like, are meant to encompass variations of and from the specified value, such as variations of +/−10% or less, +/−5% or less, +/−1% or less, +/−0.5% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Whenever a numerical range is used in this application, for example when 1 to 6 is used in the definition of "alkyl" means that the alkyl group may contain 1 carbon atom, 2 carbon atoms, 3 carbon atoms, 4 carbon atoms, 5 carbon atoms, and 6 carbon atoms.

As used herein, the term "alkyl" encompasses saturated aliphatic hydrocarbons including straight chains and branched chains and 1, 3, 4, 5, and 6 carbon atoms. For example, as used herein, the term "$(C_1\text{-}C_6)$alkyl," as well as the alkyl moieties of other groups referred to herein (e.g., $(C_1\text{-}C_6)$alkoxy), refers to linear or branched radicals of 1, 2, 3, 4, 5, and 6 carbon atoms (e.g., methyl, ethyl, n-propyl, isopropyl, n-butyl, iso-butyl, secondary-butyl, tertiary-butyl), optionally substituted by 1, 2, 3, 4, or 5 suitable substituents. As used herein, "alkyl" also encompasses aliphatic hydrocarbons having at least one carbon-carbon double bond, including straight chains and branched chains having at least one carbon-carbon double bond and 2, 3, 4, 5, and 6 carbon atoms. For example, as used herein, the term "$(C_2\text{-}C_6)$alkyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 5 suitable substituents. When the compounds of Formula I-I* contain an alkenyl group, the alkenyl group may exist as the pure E (entgegen) form, the pure Z (zusammen) form, or any mixture thereof.

As used herein, the term "cycloalkyl" encompasses saturated or unsaturated (non-aromatic) monocyclic or bicyclic hydrocarbon rings (e.g., cyclopropyl, cyclobutyl, cyclopentyl, cyclohexyl, cycloheptyl, cyclooctyl, cyclononyl); optionally substituted by 1, 2, 3, 4, and 5 suitable substituents, such as, but not limited to, H, halo, —CN, $(C_1\text{-}C_3)$alkyl, $—NH_2$, $(C_1\text{-}C_3)$alkyl-(NH)—, $((C_1\text{-}C_3)alkyl)_2N—$, —$CF_3$, —$OCH_3$ and —$OCF_3$. The cycloalkyl group may have 3 to 12 carbon atoms in the ring(s), such as 3 to 10 carbon atoms, 3 to 8 carbon atoms, 3 to 6 carbon atoms, or 3, 4, 6, 7, 8, 9, 10, 11, or 12 carbon atoms. For example, a monocyclic cycloalkyl group may have 3 to 6 carbon atoms, 3 carbon atoms, 4 carbon atoms, 5 carbon atoms, or 6 carbon atoms in the ring, e.g., cyclopropyl, cyclobutyl, cyclopentyl, cyclohexyl, cycloheptyl, cyclooctyl, cyclononyl. In another embodiment the cycloalkyl may optionally contain one, two or more non-cumulative non-aromatic double or triple bonds.

As used herein, the term "heterocycloalkyl" includes a monocyclic, bridged, polycyclic or fused polycyclic saturated or unsaturated non-aromatic 3- to 13-membered ring including 1 or more heteroatoms selected from O, S and N, such as a 3 to 10 membered ring, or a 3 to 6 membered ring, a 3-, 4-, 5-, 6-, 7-, 8-, 9-, 10-, 11-, 12-, or 13-membered ring. Examples of such heterocycloalkyl rings include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Further nonlimiting examples of heterocycloalkyl rings are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, 1,2-tetrahydrothiazin-2-yl, 1,3-tetrahydrothiazin-3-yl, 1,2-tetrahydrodiazin-2-yl, 1,3-tetrahydrodiazin-1-yl, 1,4-oxazin-2-yl, 1,2,5-oxathiazin-4-yl, and the like. The heterocycloalkyl ring is optionally substituted by 1 to 5 suitable substituents, or 1 to 3, or 1, 2, 3, 4, or 5 substituents such as, but not limited to, H, halo, —CN, $(C_1-C_3)$alkyl, —$NH_2$, $(C_1-C_3)$alkyl-(NH)—, $((C_1-C_3)alkyl)_2N$—, —$CF_3$, —$OCH_3$, and —$OCF_3$.

As used herein, the term "aryl" is defined to include all-carbon monocyclic or fused-ring polycyclic (i.e., rings which share adjacent pairs of carbon atoms) groups having a completely conjugated pi-electron system. The aryl group has 6 to 12, 6 to 10, or 6, 8, 9, 10, or 12 carbon atoms in the ring(s). One nonlimiting, exemplary aryl group is a 6-carbon atom phenyl ring. As used herein, the term aryl means aromatic radicals containing from 6 to 10 or 6 to 12 carbon atoms such as, but not limited to, phenyl, naphthyl, tetrahydronaphthyl, anthracenyl, indanyl and the like. The aryl group is optionally substituted by 1 to 5 suitable substituents, more preferably 1 to 3 substituents such as, but not limited to, H, halo, —CN, $(C_1-C_3)$alkyl, —$NH_2$, $(C_1-C_3)$alkyl-(NH)—, $((C_1-C_3)alkyl)_2N$—, —$CF_3$, —$OCH_3$ and —$OCF_3$.

As used herein, the term "heteroaryl" is defined to include monocyclic or fused-ring polycyclic aromatic heterocyclic groups with one or more heteroatoms selected from O, S and N in the ring. The heteroaryl group has 5- to 12-ring atoms including one to 5 heteroatoms selected from O, S, and N, such as 5- to 10-ring atoms, 5- to 8-ring atoms, or 6-, 7-, 8-, 9-, 10-, 11-, or 12-ring atoms. For example, as used herein, the term heteroaryl encompasses aromatic radicals containing at least one ring heteroatom selected from O, S and N and from 1 to 11 carbon atoms, such as from 2 to 9 carbon atoms, from 3 to 8 carbon atoms, or from 3, 4, 5, 6, 7, 8, 9, 10, or 11 carbon atoms, such as, but not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like. The heteroaryl group is optionally substituted by 1 to 5 suitable substituents 1 to 3 substituents such as, but not limited to, H, halo, —CN, $(C_1-C_3)$alkyl, —$NH_2$, $(C_1-C_3)$alkyl-(NH)—, $((C_1-C_3)alkyl)_2$ N—, —$CF_3$, —$OCH_3$ and —$OCF_3$.

An "alkoxy" group refers to an alkyl-O— and alkyl is as defined herein.

An "alkylaminoalkyl" group refers to an -alkyl-NR-alkyl group.

An "amino" group refers to an —$NH_2$ or an —NRR' group.

An "aminoalkyl" group refers to an -alky-NRR' group.

An "aminocarbonyl" refers to a —C(O)NRR'.

An "arylalkyl" group refers to -alkylaryl, where alkyl and aryl are defined herein.

An "aryloxy" group refers to both an —O-aryl and an —O-heteroaryl group, as defined herein.

A "carbonyl" group refers to a —(C═O)R.

A "C-carboxyl" group refers to a —(C═O)OR or RO(C═O) group.

A "carboxylic acid" group refers to a C-carboxyl group in which R is hydrogen.

A "cyano" group refers to a —CN group.

A "dialkylamino" group refers to an —$N(alkyl)_2$ or $NR_2$ group.

A "halo" or "halogen" group refers to fluorine, chlorine, bromine or iodine.

A "hydroxy" group refers to an —OH group.

An "N-amido" group refers to a —R'(C═O)NR group.

A "perfluoroalkyl group" refers to an alkyl group wherein one or more of the hydrogen atoms have been replaced with fluorine atoms.

As used herein, the terms "a compound of Formula I" or "compounds of Formula I", including compounds of Formula IA-IH, or pharmaceutically acceptable salts, esters, or prodrugs thereof" encompass all forms of the compound of Formula I, including compounds of Formulae IA-IH, as well as including all hydrates, solvates, isomers, crystalline and non-crystalline forms, isomorphs, polymorphs, metabolites, and prodrugs thereof.

As used herein, the term "prodrug" means a derivative of a known direct acting drug, which derivative has enhanced delivery characteristics and therapeutic value as compared to the drug, and is transformed into the active drug by an enzymatic or chemical process.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

The present disclosure relates to novel heterocyclic amides of Formula I and I*, to pharmaceutical formulations comprising these heterocyclic amides, and to uses and syntheses thereof.

The compounds of Formula I have the following structure:

(I)

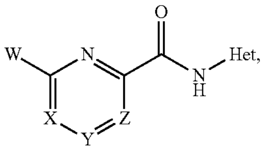

or a pharmaceutically acceptable salt, ester, or prodrug thereof, and the compounds of Formula I* have the following structure:

(I*)

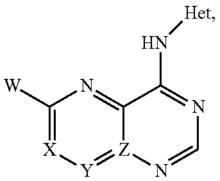

or a pharmaceutically acceptable salt, ester, or prodrug thereof, wherein:

—X—Y—Z— is —$CR^1$—$CR^2$═$CR^3$—, ═N—$CR^2$═$CR^3$—, ═$CR^1$—N═$CR^3$— or ═$CR^1$—$CR^2$═N— if the compound is of Formula I;

—X—Y—Z— is —$CR^1$—$CR^2$═C—, ═N—$CR^2$═C—, or ═$CR^1$—N—C— if the compound is of Formula I*;

$R^1$ is selected from the group consisting of H, halo, —CN, $(C_1$-$C_6)$alkyl, $(C_1$-$C_6)$alkoxy, and perfluoro$(C_1$-$C_6)$alkoxy-, wherein $(C_1$-$C_6)$alkyl is optionally substituted with 1-3 substituents independently selected from the group consisting of H, halo, —CN, $(C_1$-$C_3)$alkyl, —$NH_2$, $(C_1$-$C_3)$alkyl-(NH)—, $((C_1$-$C_3)$alkyl$)_2$N—, —$CF_3$, —$OCH_3$ and —$OCF_3$;

$R^2$ is H, halo, —CN, $(C_1$-$C_6)$alkyl, $(C_1$-$C_6)$alkoxy, perfluoro$(C_1$-$C_6)$alkyl, perfluoro$(C_1$-$C_6)$alkoxy-, cycloalkyl, cycloalkyl-O—, heterocycloalkyl, heterocycloalkyl-O—, aryl, aryl-O—, $R^5$—$(C(R^4)_2)_n$—O— or $(R^6)_2$N—, wherein $(C_1$-$C_6)$alkyl, cycloalkyl, heterocycloalkyl, and aryl are each optionally substituted with 1-3 substituents independently selected from the group consisting of H, halo, —CN, $(C_1$-$C_3)$alkyl, —$NH_2$, $(C_1$-$C_3)$alkyl-(NH)—, $((C_1$-$C_3)$alkyl$)_2$N—, —$CF_3$, —$OCH_3$ and —$OCF_3$;

$R^3$ is H, halo, $(C_1$-$C_3)$alkyl, —$CF_3$, $(C_1$-$C_3)$alkoxy, —$OCF_3$, or $(R^7)_2$N—, wherein $R^7$ is H or $(C_1$-$C_3)$alkyl;

n is an integer from one to three;

each $R^4$ is independently H or $(C_1$-$C_3)$alkyl, wherein $(C_1$-$C_3)$alkyl is optionally substituted with 1-3 substituents independently selected from the group consisting of H, halo, —CN, $(C_1$-$C_3)$alkyl, —$NH_2$, $(C_1$-$C_3)$alkyl-(NH)—, $((C_1$-$C_3)$alkyl$)_2$N—, —$CF_3$, —$OCH_3$ and —$OCF_3$;

$R^5$ is selected from the group consisting of $(C_1$-$C_3)$alkyl, perfluoro$(C_1$-$C_3)$alkyl, HO—$(C_2$-$C_4)$alkyl, cycloalkyl, heterocycloalkyl, and aryl, wherein $(C_1$-$C_3)$alkyl, cycloalkyl, heterocycloalkyl, and aryl are each optionally substituted with 1-3 substituents independently selected from the group consisting of H, halo, —CN, $(C_1$-$C_3)$alkyl, —$NH_2$, $(C_1$-$C_3)$alkyl-(NH)—, $((C_1$-$C_3)$alkyl$)_2$N—, —$CF_3$, —$OCH_3$ and —$OCF_3$;

$R^6$ is independently H or $(C_1$-$C_3)$alkyl, wherein $(C_1$-$C_3)$alkyl is optionally substituted with 1-3 substituents independently selected from the group consisting of H, halo, —CN, $(C_1$-$C_3)$alkyl, —$NH_2$, $(C_1$-$C_3)$alkyl-(NH)—, $((C_1$-$C_3)$alkyl$)_2$N—, —$CF_3$, —$OCH_3$ and —$OCF_3$;

W is (a)

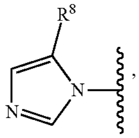

, (b)

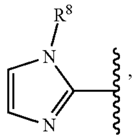

, (c)

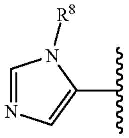

;

(d)

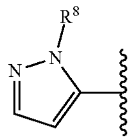

, (e)

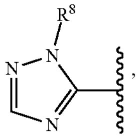

, or (f)

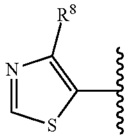

, $R^8$ is H, —$CH_3$ or —$CF_3$;

Het is a heterocycle of the formula i

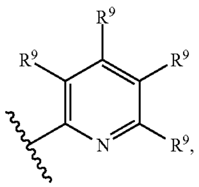

-continued ii

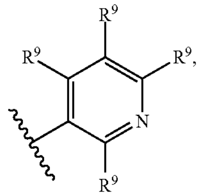

iii

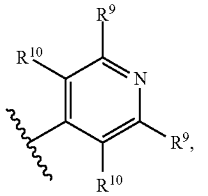

iv

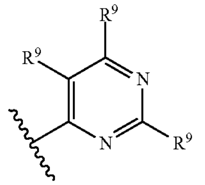

v

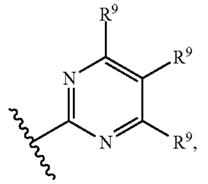

vi

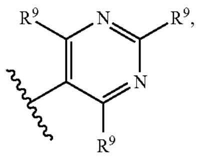

vii

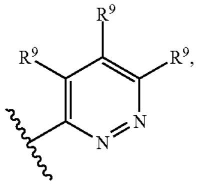

viii

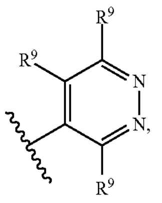

or ix

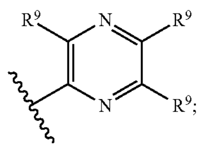

each $R^9$ is independently selected from H, halo, $(C_1-C_6)$alkyl, —$CF_3$, $(C_1-C_6)$alkoxy, —$OCF_3$, —CN, $(R^{11})_2N$—, $R^{12}(O)(C{=}O)$—, $R^{12}O((C_1-C_3)alkyl)-(NR^{11})$—, $R^{13}$—(C═O)—$(NR^{11})$— and $(R^{11})_2N$—(C═O)—;

each $R^{10}$ is independently selected from H, $(C_1-C_3)$alkyl, —$CF_3$, —$OCH_3$, —$OCF_3$, —CN, $(R^{11})_2N$—, $R^{12}(O)(C{=}O)$—, $R^{12}O$—$((C_1-C_3)alkyl)-(NR^{11})$—, $R^{13}$—(C═O)—$(NR^{11})$—, and $(R^{11})_2N$—(C═O); and each $R^{11}$ is independently H or $(C_1-C_3)$alkyl;

$R^{12}$ is H or $(C_1-C_3)$alkyl; and $R^{13}$ is $(C_1-C_3)$alkyl.

The compounds of Formula I-I* may exist in the form of pharmaceutically acceptable salts such as, e.g., acid addition salts and base addition salts of the compounds of Formula I. The phrase "pharmaceutically acceptable salt(s)", as used herein, unless otherwise indicated, includes salts of acidic or basic groups which may be present in the compounds of Formula I.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Stahl and Wermut (2011) *Pharmaceutical Salts: Properties, Selection, and Use*, (2nd Revised Edition) pp. 1-388 (Wiley-VCH), the entire contents of which (and specifically the passages relating to suitable salts) is fully incorporated herein by reference.

The compounds according to the disclosure may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Such materials may not give distinctive X-ray diffraction patterns, and while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds according to the disclosure may also exist in unsolvated and solvated forms. The term 'solvate' is used herein to describe a molecular complex comprising the compound according to the disclosure and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates (see, *Polymorphism in Pharmaceutical Solids*, (1995) Morris (ed. H. G. Brittain, Marcel Dekker), the entire contents of which (and specifically the passages relating to isolated site, channel, or metal-ion coordinated hydrates) is fully incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the disclosure are multi-component complexes (other than salts and solvates) wherein the compound of Formula I or I* and at least one other component is present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallisation from solvents, or by physically grinding the components together (see, Almarsson et. al. (2004) *Chem. Commun.* 1889-1896), the entire contents of which (and specifically the passages relating to preparation of co-crystals by melt crystallization, recrystallisation from solvents, or grinding) is fully incorporated herein by reference. For a general review of multi-component complexes, see Haleblia (1975) *J. Pharm. Sci.* 64 (8):1269-1288 the entire contents of which is fully incorporated herein by reference.

The compounds according to the disclosure may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as, but not limited to, water or another solvent, is described as 'lyotropic'. Compounds that have the potential to form lyotropic mesophases are described as 'amphiphilic' and consist of molecules which possess an ionic (such as, but not limited to, $—COO^{-}Na^{+}$, $—COO^{-}K^{+}$, or $—SO_3^{-}Na^{+}$) or non-ionic (such as, but not limited to, $—N^{-}N^{+}(CH_3)_3$) polar head group. For more information, see Hartshorne and Stuart (1970) *Crystals and the Polarizing Microscope* (1970) 4th Edition (Edward Arnold), the entire contents of which (and specifically the passages relating to compounds in a mesomorphic state) is fully incorporated herein by reference.

Herein all references to compounds of Formula I-I* include references to salts, solvates, multi-component complexes and liquid crystals thereof and to solvates, multi-component complexes and liquid crystals of salts thereof.

The compounds according to the disclosure include compounds of Formula I-I* as hereinbefore defined, including all polymorphs and crystal habits thereof, prodrugs and isomers thereof (including optical, geometric and tautomeric isomers) as hereinafter defined and isotopically-labelled compounds of Formula I.

The disclosure also relates to prodrugs of the compounds of Formula I. Thus, certain derivatives of compounds of Formula I-I* which may have little or no pharmacological activity, themselves may, when administered into or onto the body, be converted into compounds of Formula I-I* can have the desired activity, for example, by hydrolytic cleavage. Such derivatives are referred to as "prodrugs" (see, e.g. Higuchi et al. (1987) "Pro-drugs as Novel Delivery Systems, Vol. 14, ACS Symposium Series; *Bioreversible Carriers in Drug Design*, Pergamon Press Ee. E. B. Roche, American Pharmaceutical Association), the entire contents of which documents (and specifically the passages relating to prodrugs) are fully incorporated herein by reference.

Prodrugs in accordance with the disclosure be produced, for example, by replacing appropriate functionalities present in the compounds of Formula I-I* with certain moieties known to those skilled in the art as 'pro-moieties' (see, Bundgaard (1985) *Design of Prodrugs* (Elsevier, 1985), the entire contents of which (and specifically the passages relating to pro-moieties) is fully incorporated herein by reference.

Some non-limiting examples of prodrugs in accordance with the disclosure include:

(i) where the compound of Formula I or I* contains a carboxylic acid functionality which is functionalized into a suitably metabolically labile group (esters, carbamates, etc.);

(ii) where the compound of Formula I or I* contains an alcohol functionality which is functionalized into a suitably metabolically labile group (ethers, esters, carbamates, acetals, ketals, etc.); and (iii) where the compound of Formula I or I* contains a primary or secondary amino functionality, or an amide which are functionalized into a suitably metabolically labile group, e.g., a hydrolysable group (amides, carbamates, ureas, phosphonates, sulfonates, etc.).

Further examples of replacement groups in accordance with the foregoing examples and examples of other prodrug types may be found in the aforementioned references.

The compounds of Formula I-I* may have asymmetric carbon atoms and may exist as two or more stereoisomers. The carbon-carbon bonds of the compounds of Formula I-I* may be depicted herein using a solid line ( ),( ), a solid wedge ( ),( ), or a dotted wedge ( ). ( ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I-I* may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I-I* may exist as enantiomers and diastereomers or as racemates and mixtures thereof. The use of a solid line to depict bonds to one or more asymmetric carbon atoms in a compound of Formula I or I* and the use of a solid or dotted wedge to depict bonds to other asymmetric carbon atoms in the same compound is meant to indicate that a mixture of diastereomers is present.

Stereoisomers of Formula I-I* include cis and trans isomers, optical isomers such as R and S enantiomers, diastereomers, geometric isomers, rotational isomers, conformational isomers, and tautomers of the compounds of Formula I, including compounds exhibiting more than one type of isomerism; and mixtures thereof (such as racemates and diastereomeric pairs). Also included are acid addition or base addition salts wherein the counterion is optically active, for example, d-lactate or I-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the Formula I-I* may exhibit the phenomena of tautomerism and structural isomerism. For example, the compounds of Formula I-I* may exist in several tautomeric forms, including the enol and imine form, and the keto and enamine form and geometric isomers and mixtures thereof. All such tautomeric forms are included within the scope of compounds of Formula I. Tautomers exist as mixtures of a tautomeric set in solution. In solid form, usually one tautomer predominates. Even though one tautomer may be described, the present disclosure includes all tautomers of the compounds of Formula I.

The present disclosure includes all pharmaceutically acceptable isotopically-labelled compounds of Formula I-I* wherein one or more atoms are replaced by atoms having the same atomic number, but an atomic mass or mass number different from the atomic mass or mass number which predominates in nature.

Examples of isotopes suitable for inclusion in the compounds according to the disclosure include, but are not limited to, isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula I, for example, those incorporating a radioactive isotope, are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with heavier isotopes such as, but not limited to, deuterium, i.e., $^{2}H$, afford certain therapeutic advantages resulting from greater metabolic stability, for example, increased in vivo half-life or reduced dosage requirements.

Substitution with positron emitting isotopes, such as $^{11}C$ $^{18}F$, $^{15}O$ and $^{13}N$, are useful in Positron Emission Topography (PET) studies for examining substrate receptor occupancy. Substitution with isotopes such as $^{123}I$, $^{124}I$, $^{125}I$, or $^{99m}Tc$ are useful in Single Photon Computed Tomography (SPECT).

Isotopically-labeled compounds of Formula I-I* may generally be prepared by conventional techniques known to those skilled in the art or by processes analogous to those described in the accompanying Examples and Preparations using an appropriate isotopically-labeled reagent in place of the non-labeled reagent previously employed.

Moreover, certain compounds of Formula I-I* may, themselves, act as prodrugs of other compounds of Formula I.

Also included within the scope of the disclosure are metabolites of compounds of Formula I, that is, compounds formed in vivo upon administration of the compounds of Formula I Compounds of the Formula I, and IA-IH, may be prepared according to the following reaction schemes and accompanying discussion. Unless otherwise indicated, $R^1$ through $R^{13}$, W, X, Y, Z, Het, and n, and structural Formula I-I* are as defined above in the reaction schemes and discussion that follow. In general, the compounds of this disclosure may be made by processes which include processes analogous to those known in the chemical arts, in light of the description contained herein. Certain processes for the manufacture of the compounds of this disclosure are provided as further features of the disclosure and are illustrated by the following reaction schemes. Other processes may be described in the experimental section.

In the preparation of the Formula I-I* compounds it is noted that some of the preparation methods useful for the preparation of the compounds described herein may require protection of remote functionality (e.g., primary amine, secondary amine, carboxyl in Formula I-I* precursors). The need for such protection varies depending on the nature of the remote functionality and the conditions of the preparation methods. The need for such protection is readily determined by one skilled in the art. The use of such protection/deprotection methods is also within the skill in the art see Greene (1991) *Protective Groups in Organic Synthesis* (John Wiley & Sons, New York), the entire contents of which is fully incorporated herein by reference.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as, but not limited to, N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the Formula I-I* compounds.

Scheme 1

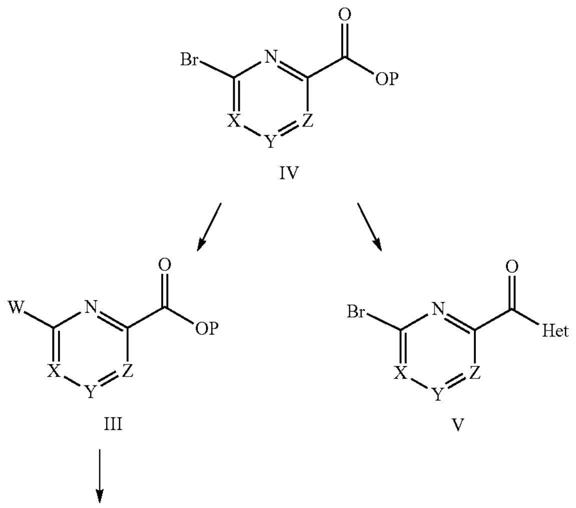

-continued

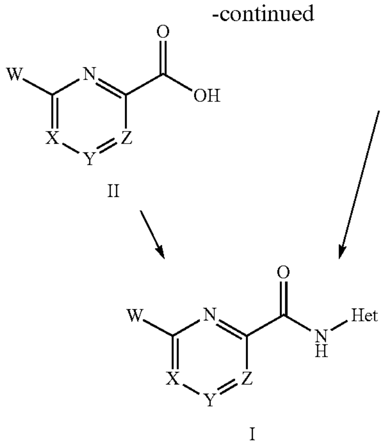

Scheme 1 refers to the preparation of compounds of Formula I from bromo or chloro heteroaryl acids or esters of Formula IV (bromo is depicted but may be replaced with chloro). Referring to Scheme 1, compounds of Formula IV are commercially available or may be made by methods well known to those skilled in the art. To a stirred solution of an activated carboxylate, such as, but not limited to, wherein P is an ethyl ester, in a polar solvent such as, but not limited to, DMSO was added copper iodide (0.2 equivalents), L-proline (0.4 equivalents), potassium carbonate (2 equivalents) and W—H, an imidazole, pyrazole, triazole or thiazole (1.5 equivalents). The reaction mixture may be heated to between about 80° C. to about 110° C., or about 100° C. for about 4 hr to about 24 hr, or for about 16 hr. The reaction mixture may then be cooled to RT, diluted with ice-cold water and extracted with a solvent such as, but not limited to, ethyl acetate which may be dried and evaporated under reduced pressure to afford the compound of Formula III.

The compound of Formula III may be saponified to yield a compound of Formula II by treatment with an excess of lithium hydroxide mono hydrate in a solvent mixture such as, but not limited to, THF, methanol and water. The reaction mixture may be allowed to stir at RT for about 8 hr to about 24 hr or for about 16 hr. The aqueous layer may be acidified using 1 N HCl to adjust the pH to around 2 followed by complete evaporation under reduced pressure to obtain the compound of Formula II.

The compound of Formula II may be converted to the title compound of Formula I by dissolution in DMF followed by the addition of excess N,N-diisopropylethylamine, i.e. Hünig's base or DIPEA, and excess HATU, i.e. 1-[Bis(dimethylamino)methylene]-1H-1,2,3-triazolo[4,5-b]pyridinium 3-oxid hexafluorophosphate, followed by the addition of the desired amino-Het. The reaction mixture may be stirred at RT for about 8 hr to about 24 hr, or for about 16 hr. The reaction may be quenched by the addition of water followed by extraction with an organic solvent such as, but not limited to, ethyl acetate to yield the title compound of Formula I.

Alternatively, a compound of Formula I may be prepared from a compound of Formula V by a so-called Stille reaction with a tributylstannyl-W, wherein W is an imidazolyl, pyrazolyl, triazolyl or thiazolyl. A solution of the bromo or chloro intermediate of Formula V is dissolved in a polar solvent such as, but not limited to, DMF followed by addition of tetrakis(triphenylphosphine)palladium(0) (catalytic). The reaction mixture may be purged with Nitrogen gas for 5 minutes then sealed and heated to between about 80° C. to about 110° C. or about 100° C., for about 4 to about 24 hours or for about 16 hours. After complete reaction, the mixture may be cooled to RT and quenched with water followed by extraction with a solvent such as, but not limited to, ethyl acetate which after drying and evaporation yields the compound of Formula I.

The compound of Formula V may be prepared from a compound of Formula IV by reaction with Het-$NH_2$ in a solvent such as, but not limited to, toluene and trimethylaluminum solution in toluene. The reaction mixture may be stirred in a CEM® microwave at about 100° C. for about 1 hour. The completed reaction mixture may then be cooled to RT, quenched with water then extracted with ethyl acetate to yield the compound of Formula V.

Compounds of Formula I-I* that have chiral centers may exist as stereoisomers, such as racemates, enantiomers, or diastereomers. Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic and one or both of the diastereoisomers converted to the corresponding pure enantiomer(s) by means well known to one skilled in the art. Chiral compounds of Formula I-I* (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2% to 20%, and from %0 to 5% of an alkylamine, or 0.1% diethylamine. Concentration of the eluate affords the enriched mixture. Stereoisomeric conglomerates may be moiety, an acid or base such as, but not limited to, tartaric acid or 1-phenylethylamine. The resulting diastereomeric mixture may be separated by chromatography and/or fractional crystallization separated by conventional techniques known to those skilled in the art (see, e.g., Elie (1994) *Stereochemistry of Organic Compounds* (Wiley, New York), the entire disclosure of which (and specifically the passages relating to the separation of stereoisomeric conglomerates) is incorporated herein by reference.

Where a compound of Formula I or I* contains an alkenyl or alkenylene group, geometric cis/trans (or Z/E) isomers are possible. Cis/trans isomers may be separated by conventional techniques well known to those skilled in the art, for example, chromatography and fractional crystallization. Salts of the present disclosure can be prepared according to methods known to those of skill in the art.

The compounds of Formula I or I* that are basic in nature can form a wide variety of salts with various inorganic and organic acids. Although such salts must be pharmaceutically acceptable for administration to animals, it is useful to initially isolate the compound of the present disclosure from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this disclosure can be prepared by treating the base compound with a substantially equivalent amount of the selected mineral or organic acid in an aqueous solvent medium or in a suitable organic solvent, such as, but not limited to, methanol or ethanol. Upon evaporation of the solvent, the desired solid salt is obtained. The desired acid salt may also be precipitated from a solution of the free base in an organic solvent by adding an appropriate mineral or organic acid to the solution.

Those compounds of Formula I-I* that are acidic in nature can form base salts with various pharmacologically acceptable cations. Examples of such salts include, but are not limited to, the alkali metal or alkaline-earth metal salts and particularly, the sodium and potassium salts. These salts are all prepared by conventional techniques. The chemical bases which are used as reagents to prepare the pharmaceutically acceptable base salts of this disclosure are those which form non-toxic base salts with the acidic compounds of Formula I. These salts may be prepared by any suitable method, for example, treatment of the free acid with an inorganic or organic base, such as, but not limited to, an amine (primary, secondary or tertiary), an alkali metal hydroxide or alkaline earth metal hydroxide, or the like. These salts may also be prepared by treating the corresponding acidic compounds with an aqueous solution containing the desired pharmacologically acceptable cations, and then evaporating the resulting solution to dryness, for example, under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents can be employed in order to ensure completeness of reaction and maximum yields of the desired final product.

If the compound of Formula 1 is a base, the desired pharmaceutically acceptable salt may be prepared by any suitable method available in the art, for example, treatment of the free base with an inorganic acid, such as, but not limited to, hydrochloric acid, hydrobromic acid, sulfuric acid, nitric acid, phosphoric acid and the like, or with an organic acid, such as, but not limited to, acetic acid, maleic acid, succinic acid, mandelic acid, fumaric acid, malonic acid, pyruvic acid, oxalic acid, glycolic acid, salicylic acid, a pyranosidyl acid, such as, but not limited to, glucuronic acid or galacturonic acid, an alpha-hydroxy acid, such as, but not limited to, citric acid or tartaric acid, an amino acid, such as, but not limited to, aspartic acid or glutamic acid, an aromatic acid, such as, but not limited to, benzoic acid or cinnamic acid, a sulfonic acid, such as, but not limited to, p-toluenesulfonic acid or ethanesulfonic acid, or the like.

Pharmaceutically acceptable salts of compounds of Formula I-I* may be prepared e.g., by:

(i) reacting the compound of Formula I or I* with the desired acid or base;

(ii) removing an acid- or base-labile protecting group from a suitable precursor of the compound of Formula I or I* or by ring-opening a suitable cyclic precursor, for example, a lactone or lactam, using the desired acid or base; or (iii) converting one salt of the compound of Formula I or I* to another by reaction with an appropriate acid or base or by means of a suitable ion exchange column.

These reactions are typically carried out in solution. The resulting salt may precipitate out and be collected by filtration or may be recovered by evaporation of the solvent. The degree of ionization in the resulting salt may vary from completely ionized to almost non-ionized.

Certain compounds of Formula 1 according to the disclosure may exist in more than one crystal form ("polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization.

Polymorphs may also be obtained by heating or melting the compound according to the disclosure followed by gradual or fast cooling. The presence of polymorphs may be determined by solid probe NMR spectroscopy, IR spectroscopy, differential scanning calorimetry, powder X-ray diffraction or such other techniques. Polymorphs may be prepared according to techniques well-known to those skilled in the art.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula I or I* contains an acidic or basic moiety, a base or acid such as, but not limited to, 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds according to the disclosure (and chiral precursors thereof) may be obtained in enantiomerically-enriched form using chromatography, typically HPLC, on an asymmetric resin with a mobile phase consisting of a hydrocarbon, typically heptane or hexane, containing from about 0 to about 50% by volume of isopropanol, from about 2% to about 20%, and from about 0 to about 5% by volume of an alkylamine, or about 0.1% diethylamine. Concentration of the eluate affords the enriched mixture.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art (see, for example, Elie et al., (1994) *Stereochemistry of Organic Compounds* (Wiley)), the entire contents of which, as mentioned previously (and specifically the passages relating to the separation of racemic mixtures) is fully incorporated herein by reference. It will be understood that the compounds of Formula I-I* are not limited to the particular enantiomer shown, but also include all stereoisomers and mixtures thereof.

The disclosure also includes isotopically-labeled compounds of Formula I, wherein one or more atoms is replaced by an atom having the same atomic number, but an atomic mass or mass number different from the atomic mass or mass number usually found in nature. Isotopically-labeled compounds of Formula I-I* may generally be prepared by conventional techniques known to those skilled in the art or by processes analogous to those described herein, using an appropriate isotopically-labeled reagent in place of the non-labeled reagent otherwise employed.

The compounds of Formula I-I* are assessed for their biopharmaceutical properties, such as, but not limited to, solubility and solution stability (across pH), permeability, etc., in order to select the appropriate dosage form and route of administration for treatment of the proposed indication.

The compounds of Formula I-I* are useful for modulating or inhibiting NAD+ hydrolase activity of CD38 protein. Accordingly, these compounds are useful for the prevention and/or treatment of disease states associated with NAD+ depletion and NAD+ related metabolites disregulations such as, but not limited to, aging, obesity, diabetes, cancer, heart disease, asthma, and inflammation.

The disclosure is also directed to pharmaceutical compositions comprising a compound of Formula I or I*, or a pharmaceutically acceptable salt, ester, or prodrug thereof, and a pharmaceutically acceptable carrier.

Compounds of Formula 1 according to the disclosure intended for pharmaceutical use may be comprised in pharmaceutical formulations. They may be incorporated into these formulations in the form of crystalline or amorphous products. The compounds may be, for example, as solid plugs, powders, or films obtained by methods such as, but not limited to, precipitation, crystallization, freeze drying, spray drying, or evaporative drying. Microwave or radio frequency drying may be used for this purpose.

These compounds may be administered alone, in combination, and/or in coformulation with one or more other compounds according to the disclosure, or in combination and/or coformulation with one or more other drugs (or as any combination or coformulation thereof). Generally, they are administered as a combination, formulation, or coformulation in association with one or more pharmaceutically acceptable excipients. For example and without any limitation, the compounds disclosed herein can be coformulated with one or more supplements and/or inhibitors, such as NAD supplement and JAK inhibitor.

The term 'excipient' is used herein to describe any ingredient other than the compound(s) according to the disclosure. The choice of excipient depends to a large extent depend on factors such as, but not limited to, the particular mode of administration, the effect of the excipient on solubility and stability, and the nature of the dosage form.

For example, in such pharmaceutical formulations, compounds according to the disclosure may be combined with soluble macromolecular entities, such as, but not limited to, cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, may be useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. For example, commonly used for these purposes are alpha-, beta- and gamma-cyclodextrins, examples of which may be found in International Patent Applications Nos. WO 91/11172, WO 94/02518 and WO 98/55148 (specifically page 3, line 25 to page 6, line 8 inclusive). The entire contents of WO 91/11172, WO 94/02518 and WO 98/55148 (and specifically the cyclodextrins of page 3, line 25 to page 6, line 8 inclusive) are fully incorporated herein by reference.

Pharmaceutical compositions suitable for the delivery of compounds of the present disclosure and methods for their preparation will be readily apparent to those skilled in the art. Such compositions and methods for their preparation may be found, for example, in *Remington's Pharmaceutical Sciences,* 19th Edition (Mack Publishing Company, 1995), the entire contents of which (and specifically the passages relating to pharmaceutical compositions and their methods of preparation) is fully incorporated herein by reference.

The pharmaceutical formulation according to the disclosure may be administered orally. Oral administration may involve swallowing, so that the compound in the formulation enters the gastrointestinal tract, and/or buccal, lingual, or sublingual administration by which the compound enters the blood stream directly from the mouth.

Formulations suitable for oral administration include solid, semi-solid and liquid systems such as, but not limited to, tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds according to the disclosure may also be used in fast-dissolving, fast-disintegrating dosage forms such as, but not limited to, those described in Liang et al. (2001) *Expert Opinion in Therapeutic Patents,* 11 (6): 981-986, the entire contents of which (and specifically the passages relating to fast-dissolving, fast-disintegrating dosage forms) is fully incorporated herein by reference.

For tablet dosage forms, depending on dose, the compound of Formula I or I* may make up from about 1 weight % to about 80 weight % of the dosage form, or from about 5 weight % to about 60 weight % of the dosage form. In addition to the compound of Formula I, tablets generally contain a disintegrant. Nonlimiting examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant comprises from about 1 weight % to about 25 weight %, or from about 5 weight % to about 20 weight % of the dosage form.

Binders are generally used to impart cohesive qualities to a tablet formulation. Suitable binders include, but not are not limited to, microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as, but not limited to, lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as, but not limited to, sodium lauryl sulfate and polysorbate 80, and glidants such as, but not limited to, silicon dioxide and talc. When present, surface active agents may comprise from about 0.2 weight % to about 5 weight % of the tablet, and glidants may comprise from about 0.2 weight % to about 1 weight % of the tablet.

Tablets also generally contain lubricants such as, but not limited to, magnesium stearate, calcium stearate, zinc stearate, sodium stearyl fumarate, and mixtures of magnesium stearate with sodium lauryl sulphate. Lubricants generally comprise from about 0.25 weight % to about 10 weight %, or from about 0.5 weight % to about 3 weight % of the tablet.

Other useful ingredients include, but are not limited to, anti-oxidants, colorants, flavoring agents, preservatives, taste-masking agents, flavorings and flavor enhancers, salivary stimulating agents, cooling agents, co-solvents (including oils), emollients, bulking agents, anti-foaming agents, and surfactants.

Exemplary tablets contain up to about 80% of a compound of Formula I, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may be encapsulated.

The formulation of tablets is discussed in Lieberman et al. (1980) *Pharmaceutical Dosage Forms: Tablets*, Vol. 1, (Marcel Dekker, New York,), the entire contents of which (and specifically the passages relating to the formulation of tablets) is fully incorporated herein by reference.

Consumable oral films for human or veterinary use are typically pliable water-soluble or water-swellable thin film dosage forms which may be rapidly dissolving or mucoadhesive and typically comprise a compound of Formula I, a film-forming polymer, a binder, a solvent, a humectant, a plasticizer, a stabilizer or emulsifier, a viscosity-modifying agent and a solvent. Some components of the formulation may perform more than one function.

The compound of Formula I or I* may be water-soluble or insoluble. A water-soluble compound comprises from about 1 weight % to about 80 weight %, or from about 20 weight % to about 50 weight %, of the solutes. Less soluble compounds may comprise a greater proportion of the composition, typically up to about 88 weight % of the solutes. Alternatively, the compound of Formula I or I* may be in the form of multiparticulate beads.

The film-forming polymer may be selected from natural polysaccharides, proteins, or synthetic hydrocolloids and is typically present in the range 0.01 to 99 weight %, more typically in the range of about 30 weight % to about 80 weight %.

Films in accordance with the disclosure may be prepared by evaporative drying of thin aqueous films coated onto a peelable backing support or paper. This may be done in a drying oven or tunnel, for example, by a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes according to the disclosure are described in U.S. Pat. No. 6,106,864, the entire contents of which (and specifically the modified release formulations from column 2, line 34 to column 4, line 26, in which references to “darifenacin” should be read as referring to the compound of formula I of the disclosure) is fully incorporated herein by reference Details of other suitable release technologies such as high energy dispersions and osmotic and coated particles are to be found in Verma et al. (2001) *Pharm. Technol. On-line,* 25(2):1-14, the entire contents of which (and specifically the passages relating to suitable release technologies including high energy dispersions and osmotic and coated particles) is fully incorporated herein by reference. The use of chewing gum to achieve controlled release is described in International Patent Publication WO 00/35298, the entire contents of which is fully incorporated herein by reference.

The pharmaceutical formulations including a compound of Formula I or I* according to the disclosure may also be administered directly into the blood stream, into muscle, or into an internal organ. Exemplary suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as, but not limited to, salts, carbohydrates and buffering agents (e.g., to a pH of from about 3 to about 9), but, for some applications, they may be formulated as a sterile non-aqueous solution or as a dried form to be used in conjunction with a suitable vehicle such as, but not limited to, sterile, pyrogen-free water.

The preparation of parenteral formulations under sterile conditions, for example, by lyophilisation, may readily be accomplished using standard pharmaceutical techniques well known to those skilled in the art.

The solubility of compounds of Formula I-I* used in the preparation of parenteral pharmaceutical formulations may be increased by the use of appropriate formulation techniques, such as, but not limited to, the incorporation of solubility-enhancing agents. Formulations for parenteral administration may be formulated to be immediate and/or modified release. Modified release formulations include delayed-, sustained-, pulsed-, controlled-, targeted and programmed release. Thus, compounds according to the disclosure may be formulated as a suspension or as a solid, semi-solid, or thixotropic liquid for administration as an implanted depot providing modified release of the active compound. Nonlimiting examples of such formulations include drug-coated stents and semi-solids and suspensions comprising drug-loaded poly(dl-lactic-coglycolic) acid (PGLA) microspheres.

The pharmaceutical formulations according to the disclosure may also be administered topically, (intra)dermally, or transdermally to the skin or mucosa. Typical formulations for this purpose include, but are not limited to, gels, hydrogels, lotions, solutions, creams, ointments, dusting powders, dressings, foams, films, skin patches, wafers, implants, sponges, fibers, bandages and microemulsions. Liposomes may also be used. Typical carriers include, but are not limited to, alcohol, water, mineral oil, liquid petrolatum, white petrolatum, glycerin, polyethylene glycol and propylene glycol. Penetration enhancers may be incorporated (see, Finnin et al. (1999) *J. Pharm. Sci.* 88 (10):955-958), the entire contents of which (and specifically the passages relating to penetration enhancers) is fully incorporated herein by reference.

Other nonlimiting means of topical administration include delivery by electroporation, iontophoresis, phonophoresis, sonophoresis and microneedle or needle-free (e.g., Powderject™, Bioject™, etc.) injection.

Formulations for topical administration may be formulated to be immediate and/or modified release. Exemplary modified release formulations include delayed-, sustained-, pulsed-, controlled-, targeted and programmed release.

The pharmaceutical formulations including a compound of Formula I-I* according to the disclosure may also be administered intranasally or by inhalation, e.g., in the form of a dry powder (either alone, as a mixture, for example, in a dry blend with lactose, or as a mixed component particle, for example, mixed with phospholipids, such as, but not limited to, phosphatidylcholine) from a dry powder inhaler, as an aerosol spray from a pressurized container, pump, spray, atomizer (or an atomizer using electrohydrodynamics to produce a fine mist), or nebulizer, with or without the use of a suitable propellant, such as, but not limited to, 1,1,1,2-tetrafluoroethane or 1,1,1,2,3,3,3-heptafluoropropane, or as nasal drops. For intranasal use, the powder may comprise a bioadhesive agent such as, but not limited to, chitosan or cyclodextrin.

The pressurized container, pump, spray, atomizer, or nebulizer contains a solution or suspension of the compound according to the disclosure comprising, for example, ethanol, aqueous ethanol, or a suitable alternative agent for dispersing, solubilizing, or extending release of the active, a propellant(s) as solvent and an optional surfactant such as, but not limited to, sorbitan trioleate, oleic acid, or an oligolactic acid.

Prior to use in a dry powder or suspension formulation, the pharmaceutical formulation is micronized to a size suitable for delivery by inhalation (e.g., less than about 5 microns). This may be achieved by any appropriate comminuting method, such as, but not limited to, spiral jet milling, fluid bed jet milling, supercritical fluid processing to form nanoparticles, high pressure homogenization, or spray drying.

Capsules (made, for example, from gelatin or hydroxypropylmethylcellulose), blisters and cartridges for use in an inhaler or insufflator may be formulated to contain a powder mix of the compound according to the disclosure, a suitable powder base such as, but not limited to, lactose or starch and a performance modifier such as, but not limited to, l-leucine, mannitol, or magnesium stearate. The lactose may be anhydrous or in the form of the monohydrate. Other exemplary excipients include dextran, glucose, maltose, sorbitol, xylitol, fructose, sucrose and trehalose.

An exemplary pharmaceutical formulation for use in an atomizer using electrohydrodynamics to produce a fine mist may contain from about 1 μg to about 20 mg of the compound according to the disclosure per actuation, and the actuation volume may vary from about 1 μl to about 100 μl. An exemplary formulation comprises a compound of Formula I, propylene glycol, sterile water, ethanol and sodium chloride. Alternative exemplary solvents which may be used instead of propylene glycol include glycerol and polyethylene glycol.

Suitable flavors, such as, but not limited to, menthol and levomenthol, or sweeteners, such as, but not limited to, saccharin or saccharin sodium, may be added to those formulations according to the disclosure intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit may be determined by means of a valve which delivers a metered amount. Units in accordance with the disclosure are provided, e.g., in a metered dose or "puff" containing from about 0.01 μg to about 100 mg of the compound of Formula I. The overall daily dose is in the range of about 1 μg to about 200 mg, which may be administered in a single dose or, as divided doses throughout the day and possibly during multiple days.

The pharmaceutical formulations according to the disclosure may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed, sustained, pulsed, controlled, targeted, and programmed release.

The pharmaceutical formulations according to the disclosure may also be administered directly to the eye or ear, for example, in the form of drops of a micronized suspension or solution in isotonic, pH-adjusted, sterile saline. Other formulations suitable for ocular and aural administration include ointments, gels, biodegradable (e.g., absorbable gel sponges, collagen) and non-biodegradable (e.g. silicone) implants, wafers, lenses and particulate or vesicular systems, such as, but not limited to, niosomes or liposomes. A polymer such as, but not limited to, crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as, but not limited to, benzalkonium chloride. Such formulations may also be delivered by iontophoresis. Formulations for ocular/aural administration may be formulated to be immediate and/or modified release. Modified release formulations include delayed-, sustained-, pulsed-, controlled-, targeted, or programmed release.

Since the present disclosure has an aspect that relates to the treatment of the disease/conditions described herein with a combination of active ingredients which may be administered separately, the disclosure also relates to combining separate pharmaceutical compositions in kit form. Such a kit comprises two separate pharmaceutical compositions: a compound of Formula I or I*, or a salt thereof and a second compound as described above. The kit comprises means for containing the separate compositions such as, but not limited to, a container, a divided bottle or a divided foil packet. The kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

A non-limiting example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet may be such that the tablets or capsules can be removed from the blister pack by manually applying pressure on the recesses whereby an opening is formed in the sheet at the place of the recess. The tablet or capsule can then be removed via said opening.

A memory aid may be provided on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday" etc. "Second Week, Monday, Tuesday" etc. Other variations of memory aids will be readily apparent. A "daily dose" can be a single tablet or capsule or several pills or capsules to be taken on a given day. Also, a daily dose of Formula I or I* compound can consist of one tablet or capsule while a daily dose of the second compound can consist of several tablets or capsules and vice versa. The memory aid can reflect this.

In another specific embodiment according to the disclosure, a dispenser designed to dispense the daily doses one at a time in the order of their intended use is provided. The dispenser may be equipped with a memory-aid, so as to further facilitate compliance with the regimen. A nonlimiting example of such a memory-aid is a mechanical counter which indicates the number of daily doses that has been dispensed. Another nonlimiting example of such a memory-aid is a battery-powered micro-chip memory coupled with a liquid crystal readout, or audible reminder signal which, for example, reads out the date that the last daily dose has been taken and/or reminds one when the next dose is to be taken.

The disclosure includes a method for treating, retarding, or preventing a disease in a subject, e.g., a mammal such as, but not limited to, a human, comprising administering to a subject in need thereof a therapeutically effective amount of a compound of Formula I or I*, or a pharmaceutically acceptable salt, ester, or prodrug thereof.

The compounds of Formula I or I* are also useful for modulating or inhibiting NAD hydrolase activity of CD38 protein. Accordingly, the disclosure further includes the use of compounds of Formula I-I* for the prevention, retardation, and/or treatment of disease states associated with NAD+ depletion or NAD+ metabolites dysregulation such as aging (e.g., age-related chronic diseases), cancer, cardiovascular disorders, neurological disorders, pulmonary disorders, fibrotic diseases, metabolic disorders, inflammation, liver disorders, and diseases of the skin, as well as its identification as a cell-surface marker in hematologic cancers such as multiple myeloma (see, Chin et al. (2018) *Trends Pharmacol. Sci.* 39(4):424-436). The methods comprise administering to a subject in need thereof a therapeutically effective amount of a compound of Formula I or I*, or a pharmaceutically acceptable salt, ester, or prodrug thereof.

Additionally, the disclosure includes the use of compounds of Formula I-I* for the prevention and/or treatment of cancer, such as small lung cell carcinoma, renal clear cell carcinoma, chronic lymphocytic leukemiahas and multiple myeloma.

The role of CD38 dysfunction in cancers has been demonstrated such as in small lung cell carcinoma (see, e.g., Blanco et al. (2010) Can. Res. 70(10):3896-3904) and in renal clear cell carcinoma (see, Sartini et al. (2006) J. Urol. 176(5):2248-2254). The role of CD38 in Chronic lymphocytic leukemiahas been described (see, Deaglio et al. (2010) Can. Biol. 20(6):416-423). The role of CD38 in PD-1/PD-L1 resistant cancers has been described (see, Verma et al., (2019) Nature Immunology 20: 1231-1243; Chen et al., (2018) Cancer Discov. 8(9):1156-1175).

The disclosure includes the use of compounds of Formula I-I* for the prevention and/or treatment of cardiovascular disorders, such as hypertension, hypoxic pulmonary vasoconstriction, cardiac hypertrophy, congestive heart failure and stroke.

The role of CD38 inhibition in cardiovascular disorders has been documented, such as for hypertension (see, e.g., Thai et al. (2009) *Am. J. Renal Physiol.* 297(1):F169-76. Hypoxic pulmonary vasoconstriction, has been described in Wilson et al. (2001) *J. Biol. Chem.* 276(14): 11180-8). Cardiac hypertrophy/CHF has been described in Pillai. et al., (2010) *J. Biolog. Chem.* 285(5): 3133-3144. The role in stroke is described Choe et al. PLoS One (2011), 6(5): e19046.

The disclosure includes the use of compounds of Formula I-I* for the prevention and/or treatment of neurological disorders, such as Alzheimer's disease, bipolar disorder/schizophrenia, Huntington's disease, amyotrophic lateral sclerosis, Parkinson's disease, multiple sclerosis, optic neuropathy and epilepsy. Thus, the agents described herein may be used as neuroprotective agents. The compounds of Formula I-I* may also be administered in the tissue or organ likely to encounter cell death.

Neurological disorders have also been demonstrated to be mediated by CD38 dysfunction such as with Alzheimer's disease in Gong Bing, et al. (2013) *Neurobiol. Aging* 34(6): 1581-8. Neurocognitive disorders and CD38 are described in, e.g., Banerjee et al. (2008) *J. Neuroim. Pharmacol.* 3(3):154-64. Bipolar disorder/schizophrenia CD38 disfunction is described in, e.g., Christoforou (2007) *Mol. Psych.* 12(11); 1011-1025. The role in Huntington's disease has been described, Weydt (2009) *Mol. Neurodeg.* 4:3. Dysfunction in Amyotrophic lateral sclerosis has been described in Lawton et al. (2012) *Amyotrophic Lateral Sclerosis* 13(1): 110-118, and in Parkinson's disease (see, e.g., Aoyama et al. (2001) *Neurosci. Lett.* 298(1):78-80. Multiple sclerosis has been described in Penberthy et al. (2009) *Curr. Pharm. Design* 15(1):64-99. Optic neuropathy has been described in Kitaoka et al., (2009) *J. Neuropathol. Exp. Neurol.* 68(8): 915-927. Epilepsy has been described as a CD38 disorder, for example, Kinton Lucy et al. (2002) *Ann. Neurol.* 51(6); 740-9.

The disclosure includes the use of compounds of Formula I-I* for the prevention and/or treatment of pulmonary disorders, such as idiopathic pulmonary fibrosis, cystic fibrosis, CIVD-19, SARS, asthma, and chronic obstructive pulmonary disease (COPD). The disclosure includes the use of compounds of Formula I-I* for the prevention and/or treatment of fibrotic diseases, such as idiopathic pulmonary fibrosis and cystic fibrosis.

Pulmonary disorders have a CD38 dysfunction such as described for idiopathic pulmonary fibrosis, O'Neill et al. (1994) *Expt. Lung Res.* 20(1):41-56. The role in cystic fibrosis has been described in Wetmoreet et al. (2010) *J. Biolog. Chem.* 285(40):30516-30522. Asthma is described in Kang et al. (2006) *Curr. Res. Med. Rev.* 2(2):143-156. COPD is described in Hageman et al. (2003) *Free Radical Biol. Med.* 35(2):140-148.

The disclosure includes the use of compounds of Formula I-I* for the prevention and/or treatment of metabolic disorders, such as metabolic syndrome, obesity, sarcopenic obesity, dyslipidemia, diabetes (such as type I diabetes), diabetic neuropathy, insulin resistance, infection-induced and viral-induced lung fibrosis, and pancreatitis.

Use of compounds of Formula I-I* for the prevention and/or treatment of obesity may include wherein the subject has or is likely to develop obesity (e.g. mammals having an elevated risk of developing diet-induced obesity). A mammal may be identified as having or being likely to develop obesity using standard clinical techniques. For example, analysis of a human's family history or eating habits may be used to determine whether the human is likely to develop an obesity condition. As described herein, a mammal identified as having or being susceptible to developing an obesity condition may be treated by administering a compound of Formula I.

CD38 dysfunction in metabolic disorders have been described such as in Metabolic Syndrome, Escande Carlos et al. (2013) *Diabetes* 62(4):1084-93. Obesity/sarcopenic obesity have been described in Maria et al. (2007) *FASEB J.* 21(13):3629-39. Dyslipidemia is described in Surakka Ida et al. (2011) *PLoS Gen.* 7(10):e1002333. Dysfunction in Diabetes has been described in Arya et al. (2004) *Am. J. Hum. Gen.* 74(2):272-282 and dysfunction in diabetic neuropathy has been described in Geeta et al. (2010) *Neuropharmacol.* 58(3):585-92. CD38 in Insulin resistance is described in Yoshino et al. (2011) *Cell Metab.* 14(4):528-536. CD38 in Type I diabetes is described in Elliott. et al. (1993) *Annals NY Acad. Sci.* 696: 333-41. Pancreatitis has been described in Chan et al. (2011) *Antiox. Redox Sig.* 15(10):2743-2755.

The disclosure includes the use of compounds of Formula I-I* for the prevention and/or treatment of acute lung injury (ALI) and acute respiratory distress syndrome (ARDS). CD38 dysfunction in acute lung injury/ARDS, has been described, e.g. Su et al. (2007) *Eur. Res. J.* 30(2):199-204.

The disclosure includes the use of compounds of Formula I-I* for the prevention and/or treatment of hyperphosphatemia. For hyperphosphatemia, see Takahashi et al. (2004) *Kidney Int.* 65(3):1099-1104.

The disclosure includes the use of compounds of Formula I-I* for the prevention and/or treatment of alcohol intolerance. For alcohol intolerance, see, e.g., Larson et al. (2005) *J. Biol. Chem.* 280(34):30550-30556.

The disclosure includes the use of compounds of Formula I-I* for the prevention and/or treatment of lupus. For lupus, see, e.g., Gonzalez-Escribano et al. (2004) *Hum. Immunol* (2004) 65(6):660-4; Pavon et al. (2013) *Cytokine* 62(2):232-243.

The disclosure includes the use of compounds of Formula I-I* for the prevention and/or treatment of arthritis, such as rheumatoid arthritis. The role of CD38 in rheumatoid arthritis is described in Jorge Postigo et al. (2012) *PLoS One* 7(3):e33534.

The disclosure includes the use of compounds of Formula I-I* for the prevention and/or treatment of ataxia-telangiectasia. The role of CD38 in ataxia-telangiectasia is described in Stern et al. (2012) *J. Biol. Chem.* 277(1):602-608.

The disclosure includes the use of compounds of Formula I-I* for the prevention and/or treatment of irritable bowel syndrome and colitis. Irritable Bowel Syndrome and colitis involves CD38 dysfunction, for example, Durnin et al. (2012) *J. Physiol.* (Oxford, UK) 590(8):1921-1941.

The disclosure includes the use of compounds of Formula I-I* for the prevention and/or treatment of gout. See, Nik Cummings et al., European Journal of Human Genetics (2010), 18(11), 1243-7.

The disclosure includes the use of compounds of Formula I for the prevention and/or treatment of end stage renal disease. The role of CD38 in end stage renal disease is described in Freedman et al. (2005) *Nephrol. Dialysis, Transpl.* 20(4):712-718.

The disclosure includes the use of compounds of Formula I-I* for the prevention and/or treatment of hearing loss. Hearing loss is described in Someya et al. (2010) *Cell* 43(5):802-812.

The disclosure includes the use of compounds of Formula I-I* for the prevention and/or treatment of liver disorders, such as steatosis and non-alcoholic steatohepatitis (NASH). Liver disorders such as steatosis and NASH are mediated by CD38, for example Choi et al. (2013) *Aging Cell* 2(6):1062-72.

The disclosure includes the use of compounds of Formula I-I* for the prevention and/or treatment of postmenopausal osteoporosis. Postmenopausal osteoporosis disease progression is described in Drummond et al. (2006) *J. Bone Mineral Met.* 24(1):28-35.

The disclosure includes the use of compounds of Formula I-I* for the prevention and/or treatment of fertility disorders or disease. Restoration of oocyte quality and enhancement of ovulation rate and fertility is described in Bertoldo et al., (2020) *Cell Rep* 30(6): 1670-1681.

The disclosure includes the use of compounds of Formula I-I* for the prevention and/or treatment of Hartnup disease. Hartnup disease and CD38 are described in Jepson et al. (1960) *Met. Basis Inherited Dis.* 1338-64. Hansen's disease is described in Dhople et al. (1985) *Microbio. Letts.* 28(109): 17-20.

The disclosure includes the use of compounds of Formula I-I* for the prevention and/or treatment of tuberculosis. The role of CD38 in tuberculosis is described in Vilcheze et al. (2010) *Mol. Microbiol.* 76(2):365-377.

The disclosure includes the use of compounds of Formula I-I* for the prevention and/or treatment of leishmaniasis. The role of CD38 in Leishmaniasis is described in Michels et al. (2011) *Mol. Microbiol.* 82(1):4-8.

The disclosure includes the use of compounds of Formula I-I* for the prevention and/or treatment of muscular dystrophy. Muscular dystrophy and CD38 is described in Goody et al. (2012) *PLoS Biology* 10(10):e1001409.

The disclosure includes the use of compounds of Formula I-I* for the prevention and/or treatment of organ reperfusion injury. Organ reperfusion injury mediated through CD38 is described in Yan Ge et al. (2010) *Biochem. Biophys. Res. Comm.* 399(2):167-172.

The disclosure includes the use of compounds of Formula I-I* for the prevention and/or treatment of pellagra. Pellagra is also a CD38 mediated disease, see, for example, Williams eta. (2007) *Med. Hypoth.* 69(3):618-628.

The disclosure includes the use of compounds of Formula I-I* for the prevention and/or treatment of diseases of the skin, such as skin hyperpigmentation, UV skin damage and psoriasis.

Diseases of the skin are linked to NAD and CD38 dysfunction. Skin hyperpigmentation, for example, has been reported (Van Woert (1967) *Life Sci.* 6(24):2605-12). UV skin damage has been reported (see Benavente et al. (2009) *Curr. Pharm. Design* 15(1); 29-38. Likewise, NAD dysfunction is involved in psoriasis (see, Wozniacka et al. (2007) *Skin Pharmacol. Physiol.* 20(1):37-42).

The disclosure includes the use of compounds of Formula I-I* for the prevention and/or treatment of damage caused by exposure to radiation, such as X-ray-induced DNA damage, e.g. by promoting NAD+ modulated DNA repair and/or cell survival. The disclosure includes a method of promoting DNA repair in cells. Cells exposed to conditions that may trigger DNA damage, e.g., radiation, may be protected by contacting them before, during and/or after exposure to the DNA damaging agent, with a compound of Formula I or I*.

Protection from exposure to radiation has been described, for example, in Caibin et al. (2012) *Internat. J. Physiol. Pathophysiol. Pharmacol.* 4(1):1-9.

The disclosure includes the use of compounds of Formula I-I* for the prevention and/or treatment of periodontal disease. The role of CD38 in periodontal disease has also been reported in, e.g., Fujita et al. (2005) *J. Periodontol.* 76(11):1960-5.

The disclosure includes the use of compounds of Formula I-I* for the prevention and/or treatment of Leber's hereditary amaurosis. Leber's hereditary amaurosis has also been reported see, for example, in Koenekoop et al. (2012) *Nat. Gen.* 44(9):1035-1039.

The disclosure includes the use of compounds of Formula I-I* for the prevention and/or treatment of sleep disorders. NAD+ involvement in sleep disorders has also been reported (see, Robinson et al. (1977) *Biol. Psych.* 12(1):139-43).

The disclosure includes the use of compounds of Formula I-I* for the prevention and/or treatment of exercise intolerance. Exercise intolerance has also been reported (see, e.g., Glick (1966) *Am. J. Physiol.* 210(6):1215-21.

The compounds of Formula I-I* extend the life span of cells and protects them from stress. Accordingly, the disclosure includes the use of compounds of Formula I-I* for the prevention and/or treatment of diseases, e.g., chronic diseases, associated with cell death, such as, but not limited to, e.g., diseases associated with neural cell death or muscular cell death. In addition, the methods may be used to prevent or alleviate neurodegeneration and peripheral neuropathies associated with chemotherapy, such as, but not limited to, cancer chemotherapy (e.g., taxol or cisplatin treatment).

The compounds of Formula I-I* described herein may be administered to subjects in which caloric restriction or the effects thereof is beneficial. Subjects may be subjects suffering from an aging disease, e.g., stroke, heart disease, arthritis, high blood pressure. They may also be administered for treating a metabolic disease, such as, but not limited to, insulin-resistance or other precursor symptom of type II diabetes, type II diabetes or complications thereof. Methods may increase insulin sensitivity or decrease insulin levels in a subject. A method may comprise administering to a subject, such as a subject in need thereof, a pharmaceutically effective amount of an agent that increases the activity or protein level of a protein involved in the NAD+ salvage pathway, i.e., in the synthesis of NAD+ and the degradation of nicotinamide. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as impaired glucose tolerance, high blood glucose sugar level and hypertension.

Compounds of Formula I-I* may also be used for stimulating fat mobilization, e.g., for treating obesity and any condition resulting therefrom or for reducing weight gain.

The disclosure provides a method for treating any of the conditions recited above in a mammal, comprises administering a therapeutically effective amount of a compound of Formula I or a pharmaceutically acceptable salt, ester, or prodrug thereof to the mammal. The mammal may be i a human in need of such treatment or prevention.

The term "therapeutically effective amount" as used herein refers to that amount of the compound being administered which will relieve to some extent one or more of the symptoms of the disorder being treated. In reference to the treatment of Nonalcoholic steatohepatitis (NASH), a therapeutically effective amount refers to that amount which has the effect of reducing or ameliorating the fat and scar tissue present in the liver as well as improving any of the biomarker measures indicative of inflammation.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes, but not limited to, adjuvant and neo-adjuvant treatment of a subject.

Administration of the compounds of Formula I-I* may be affected by any method that enables delivery of the compounds to the site of action. These methods include oral routes, intraduodenal routes, parenteral injection (including intravenous, transdermal, subcutaneous, intramuscular, intravascular or infusion), intra-articular administration, intravitreal administration, topical, ocular, vaginal rectal administration, and the like.

Dosage regimens may be adjusted to provide the optimum desired response. For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the pharmaceutical carrier.

Thus, the skilled artisan would appreciate, based upon the disclosure provided herein, that the dose and dosing regimen is adjusted in accordance with methods well-known in the therapeutic arts. That is, the maximum tolerable dose may be readily established, and the effective amount providing a detectable therapeutic benefit to a patient may also be determined, as may the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present disclosure.

Dosage values may vary with the type and severity of the condition to be alleviated, and may include single or multiple doses. For any subject, specific dosage regimens may be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present disclosure encompasses intra-patient dose-escalation as determined by the skilled artisan. Determining appropriate dosages and regimens for administration of the active agent are well-known in the relevant art and would be understood to be encompassed by the skilled artisan once provided the teachings disclosed herein.

The amount of the compound of Formula I or I* administered is dependent on the subject being treated, the severity of the disorder or condition, the rate of administration, the disposition of the compound and the discretion of the prescribing physician. An effective dosage is in the range of about 0.001 mg/kg body weight/day, to about 100 mg/kg body weight/day, or about 1 mg/kg body weight/day to about 35 mg/kg body weight/day in single or divided doses. For a 70 kg human, this amounts to about 0.05 g/day to about 7 g/day or about 0.1 g/day to about 2.5 g/day. In some instances, dosage levels below the lower limit of the afore-said range may be more than adequate depending on, e.g., the severity of the disorder treated and the age and weight of the subject being treated, while in other cases still larger doses may be employed without causing any harmful side effect, provided that such larger doses are first divided into several small doses for administration throughout the day.

As used herein, the term "combination therapy" refers to the administration of a compound of Formula I or I* together with an at least one additional pharmaceutical or medicinal agent, either sequentially or simultaneously.

The present disclosure includes the use of a combination of a compound of Formula I or I* and one or more additional pharmaceutically active agent(s). If a combination of active agents is administered, then they may be administered sequentially or simultaneously, in separate dosage forms or combined in a single dosage form. Accordingly, the present disclosure also includes pharmaceutical compositions comprising an amount of: (a) a first agent comprising a compound of Formula I or I*, or a pharmaceutically acceptable salt, ester, or prodrug thereof of the compound; (b) a second pharmaceutically active agent; and (c) a pharmaceutically acceptable carrier, vehicle or diluent.

Various pharmaceutically-active agents may be selected for use in conjunction with the compounds of Formula I-I*, depending on the disease, disorder, or condition to be treated. Pharmaceutically active agents that may be used in combination with the compositions of the present disclosure include, without limitation, the following combination therapies.

For treating non-alcoholic steatohepatitis (NASH) and/or non-alcoholic fatty liver disease (NAFLD), combination therapy includes combinations with agents including, but not limited to, an acetyl-CoA carboxylase (ACC) inhibitor, a ketohexokinase (KHK) inhibitor, a GLP-1 receptor agonist, an FXR agonist, a CB1 antagonist, an ASK1 inhibitor, an inhibitor of CCR2 and/or CCR5, a PNPLA3 inhibitor, a hydroxysteroid 17-β dehydrogenase (HSD17B13) inhibitor, a DGAT1 inhibitor, an FGF21 analog, an FGF19 analog, an SGLT2 inhibitor, a PPAR agonist, an AMPK activator, an SCD1 inhibitor or an MPO inhibitor; Orlistat, TZDs and other insulin-sensitizing agents, FGF21 analogs, Metformin, Omega-3-acid ethyl esters (e.g. Lovaza), Fibrates, HMG CoA-reductase Inhibitors, Ezetimibe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 inhibitors (including dapagliflozin, canagliflozin, empagliflozin, tofogliflozin, ertugliflozin), Phentermine, Topiramate, GLP-1 receptor agonists, GIP receptor agonists, dual GLP-1 receptor/glucagon receptor agonists, dual GLP-1 receptor/GIP receptor agonists (Tirzepatide), Angiotensin-receptor blockers an acetyl-CoA carboxylase (ACC) inhibitor, a BCKDK inhibitor, a ketohexokinase (KHK) inhibitor, ASK1 inhibitors, branched-chain alpha keto acid dehydrogenase kinase inhibitors (BCBK inhibitors), inhibitors of CCR2 and/or CCR5, PNPLA3 inhibitors, DGAT1 inhibitors, an FGF21 analog, FGF19 analogs, PPAR agonists, FXR agonists, AMPK activators, SCD1 inhibitors or MPO inhibitors.

For treatment of other disorders, combination therapy also includes combinations with, for example, anti-obesity agents including 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as, but not limited to, sibutramine), sympathomimetic agents, 3 adrenergic agonists, dopamine agonists (such as, but not limited to, bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as, but not limited to, tetrahydrolipstatin, i.e., orlistat), anorectic agents (such as, but not limited to, a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as, but not limited to, Axokine®. available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as, but not limited to, dirlotapide), opioid antagonist, orexin antagonist, the combination of naltrexone with buproprion and the like.

This disclosure also includes combination therapy for the treatment of cancers, such as, but not limited to, Multiple Myeloma. Such treatments include, but are not limited to, combinations of a compound of Formula I or I* with one or more immuno-oncology drugs including, but not limited to, Ipilimumab (Yervoy), Nivolumab (Opdivo), Pembrolizumab (Keytruda), Atezolizumab (Tecentriq), Avelumab (Bavencio), Durvalumab (Imfinzi), and PD-1/PD-L1 agonist antibodies.

Combination therapy also includes combination with neurodegenerative disorder therapeutics including, e.g., acetylcholinesterase inhibitors, such as, but not limited to, donepezil hydrochloride, physostigmine salicylate, physostigmine sulfate, metrifonate, neostigmine, ganstigmine, pyridostigmine, ambenonium, demarcarium, rivastigmine, ladostigil, galantamine hydrobromide, tacrine, tolserine, velnacrine maleate, memoquin, huperzine A, phenserine, and edrophonium; amyloid-β or fragments thereof, such as, but not limited to, $A\beta_{1-15}$ conjugated to pan HLA DR-binding epitope; antibodies to amyloid-β, such as, but not limited to, bapineuzumab; amyloid-lowering or -inhibiting agents (including those that reduce amyloid production, accumulation and fibrillization) such as, but not limited to, colostrinin, bisnorcymserine, pioglitazone, clioquinol, flurbiprofen, tarenflurbil, nitroflurbiprofen, fenoprofen, ibuprofen, meclofenamic acid, meclofenamate sodium, indomethacin, diclofenac, sulindac, diflunisal, naproxen, gingko biloba extract, tramiprosate, eprodisate, and neprilysin; and dopamine receptor agonists, such as, but not limited to, apomorphine, bromocriptine, cabergoline, dihydrexidine, dihydroergocryptine, fenoldopam, lisuride, pergolide, piribedil, pramipexole, quinpirole, ropinirole, rotigotine, and sarizotan; levodopa (or its methyl or ethyl ester), alone or in combination with a DOPA decarboxylase inhibitor (e.g., carbidopa, benserazide, α-methyldopa, monofluromethyldopa, difluoromethyldopa, brocresine, or m-hydroxybenzylhydrazine; monoamine oxidase (MAO) inhibitors, such as, but not limited to, selegiline, dimethylselegilene, brofaromine, phenelzine, tranylcypromine, moclobemide, befloxatone, safinamide, isocarboxazid, nialamide, rasagiline, iproniazide, iproclozide, toloxatone, bifemelane, desoxypeganine, harmine, harmaline, linezolid, and pargyline; and muscarinic receptor (particularly M1 subtype) agonists, such as, but not limited to, bethanechol chloride, itameline, pilocarpine, arecoline, furtrethonium iodide, oxotremorine, sabcomeline and carbachol.

Combination therapy also includes combinations with cardiovascular agents including, but not limited to, beta-adrenergic receptor blocking agents (beta blockers), such as, but not limited to, carteolol, esmolol, labetalol, oxprenolol, pindolol, propanolol, sotalol, timolol, acebutolol, nadolol, metoprolol tartrate, metoprolol succinate, atenolol and butoxamine; calcium channel blockers such as, but not limited to, nilvadipine, diperdipine, amlodipine, felodipine, nicardipine, nifedipine, nimodipine, nisoldipine, nitrendipine, lacidipine, lercanidipine, lifarizine, diltiazem, verapamil, and enecadin.

Combination therapy also includes combinations with anti-rheumatoid arthritis drugs including both symptomatic therapies, including but not limited to NSAIDs and acetaminophen/paracetamol, and oral and parenterally administered disease-modifying antirheumatic drugs (DMARDs), including but not limited to, steroids, methotrexate, anti-IL-6, Il-1 and anti-TNFa antibodies, and JAK inhibitors.

In addition, combination therapy includes combinations with catechol O-methyltransferase (COMT) inhibitors, such as, but not limited to, tolcapone (TASMAR), entacapone (COMTAN), and tropolone.

Combination therapy also includes combinations with immunomodulators such as, but not limited to, glatiramer acetate, dimethyl fumarate, fingolimod, roquinimex, laquinimod, rituximab, alemtuzumab, daclizumab, and natalizumab.

In addition, combination therapy includes combinations with interferons, including, but not limited to, interferon beta-1a and interferon beta-1 b.

Combination therapy also includes combinations with neuroprotective drugs such as, but not limited to, 2,3,4,9-tetrahydro-1H-carbazol-3-one oxime, desmoteplase, anatibant, astaxanthin, neuropeptide NAP, neurostrol, perampenel, ispronicline, bis(4-β-D-glucopyranosyloxybenzyl)-2-β-D-glucopyranosyl-2-isobutyltartrate (also known as dactylorhin B or DHB), formobactin, xaliproden, lactacystin, dimeboline hydrochloride, disufenton, arundic acid, citicoline, edaravone, granulocyte-colony stimulating factor, ancrod, 17-β-hydroxyepiandrosterone, oligotropin, pyridoxal 5'-phosphate, microplasmin, piclozotan, tacrolimus, L-seryl-L-methionyl-L-alanyl-L-lysyl-L-glutamyl-glycyl-L-valine, stilbazulenyl nitrone and zonampanel.

Combination therapy also includes combinations with trophic factors, such as, but not limited to, nerve growth factor (NGF), basic fibroblast growth factor (bFGF), neurotrophin-3, cardiotrophin-1, brain-derived neurotrophic factor (BDNF), neublastin, meteorin, and glial-derived neurotrophic factor (GDNF), and agents that stimulate production of trophic factors, such as, but not limited to, propentofylline and idebenone.

This disclosure also relates to combination therapy for the treatment of aging with a nutraceutical product, i.e., a substance which has physiological benefit or provides protection against chronic disease, including vitamins, e.g., Prenatal Vitamins, Vitamin D3, or Vitamin B12, Garcinia Cambogia, Raspberry Ketones, Green Tea Supplements, *Echinacea*, Probiotics, Omega 3 Fatty Acids, Alpha-lipoic Acid, and NAD+ and NAD+ precursors, e.g., NMN, NR, and NA.

As used herein, the term "another active agent" refers to any therapeutic agent, other than the compound of Formula I, or salt thereof, that is useful for the treatment of a subject suffering from a disease or disorder. Active agents include for example, without limitation, anti-rheumatis arthritis drugs such as NSAIDs, acetaminophen/paracetamol, disease-modifying antirheumatic drugs (DMARDs), steroids, methotrexate, anti-IL-6, Il-1 and anti-TNFa antibodies, JAK inhibitors, and the like.

The disclosure may be according to the follow clauses

Clause 1. A compound of the Formula or a pharmaceutically acceptable salt, ester, or prodrug thereof (I)

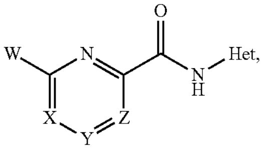

or a compound of Formula I* or a pharmaceutically acceptable salt, ester, or prodrug thereof (I*)

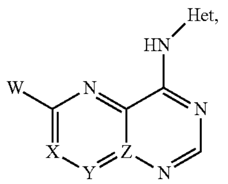

wherein:

—X—Y—Z— is $=CR^1—CR^2=CR^3—$, $=N—CR^2=CR^3—$, $=CR^1—N=CR^3—$ or $=CR^1—CR^2=N—$ if the compound is of Formula I;

—X—Y—Z— is $=CR^1—CR^2=C—$, $=N—CR^2=C—$, or $=CR^1—N=C—$ if the compound is of Formula I*;

$R^1$ is selected from the group consisting of H, halo, —CN, $(C_1-C_6)$alkyl, $(C_1-C_6)$alkoxy, and perfluoro$(C_1-C_6)$alkoxy-; wherein $(C_1-C_6)$alkyl is optionally substituted with 1-3 substituents independently selected from the group consisting of H, halo, —CN, $(C_1-C_3)$alkyl, $—NH_2$, $(C_1-C_3)$alkyl-(NH)—, $((C_1-C_3)alkyl)_2N—$, $—CF_3$, $—OCH_3$ and $—OCF_3$;

$R^2$ is H, halo, —CN, $(C_1-C_6)$alkyl, $(C_1-C_6)$alkoxy, perfluoro$(C_1-C_6)$alkyl, perfluoro$(C_1-C_6)$alkoxy-, cycloalkyl, cycloalkyl-O—, heterocycloalkyl, heterocycloalkyl-O—, aryl, aryl-O—, $R^5—(C(R^4)_2)_n—O—$ or $(R^6)_2N—$; wherein $(C_1-C_6)$alkyl, cycloalkyl, heterocycloalkyl, and aryl are each optionally substituted with 1-3 substituents independently selected from the group consisting of H, halo, —CN, $(C_1-C_3)$alkyl, $—NH_2$, $(C_1-C_3)$alkyl-(NH)—, $((C_1-C_3)alkyl)_2N—$, $—CF_3$, $—OCH_3$ and $—OCF_3$;

n is an integer from one to three;

each $R^4$ is independently H or $(C_1-C_3)$alkyl; wherein $(C_1-C_3)$alkyl is optionally substituted with 1-3 substituents independently selected from the group consisting of H, halo, —CN, $(C_1-C_3)$alkyl, $—NH_2$, $(C_1-C_3)$alkyl-(NH)—, $((C_1-C_3)alkyl)_2N—$, $—CF_3$, $—OCH_3$ and $—OCF_3$;

$R^5$ is selected from the group consisting of $(C_1-C_3)$alkyl, perfluoro$(C_1-C_3)$alkyl, HO—$(C_2-C_4)$alkyl-, cycloalkyl, heterocycloalkyl, and aryl; wherein $(C_1-C_3)$alkyl, cycloalkyl, heterocycloalkyl, and aryl are each optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)$alkyl$)_2$N—, —$CF_3$, —$OCH_3$ and —$OCF_3$;

$R^6$ is independently H or $(C_1\text{-}C_3)$alkyl; wherein $(C_1\text{-}C_3)$alkyl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)$alkyl$)_2$N—, —$CF_3$, —$OCH_3$ and —$OCF_3$;

$R^3$ is H, halo, $(C_1\text{-}C_3)$alkyl, —$CF_3$, $(C_1\text{-}C_3)$alkoxy, —$OCF_3$ or $(R^7)_2$N—; wherein $R^7$ is H or $(C_1\text{-}C_3)$alkyl;

W is (a)

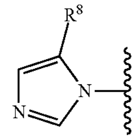
, (b)

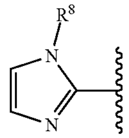
, (c)

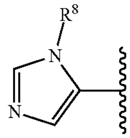
;

(d)

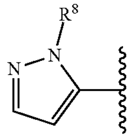
, (e)

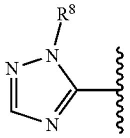
, or (f)

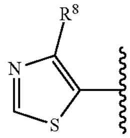
, $R^8$ is H, —$CH_3$ or —$CF_3$;

Het is a heterocycle of the formula i

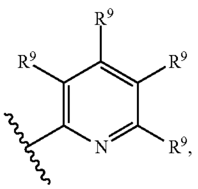

-continued ii

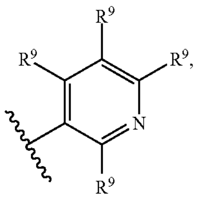

iii

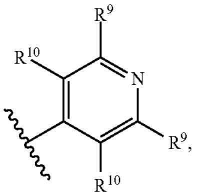

iv

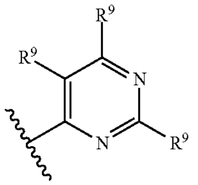

v

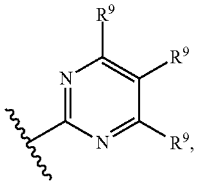

vi

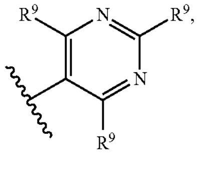

vii

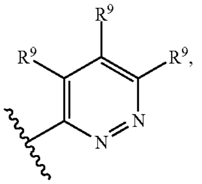

viii

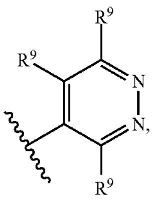
or ix

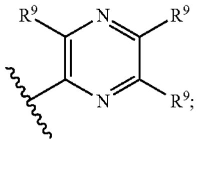

each $R^9$ is independently selected from H, halo, $(C_1\text{-}C_6)$alkyl, —$CF_3$, $(C_1\text{-}C_6)$alkoxy, —$OCF_3$, —CN, $(R^{11})_2$N—, $R^{12}$(O)(C═O)—, $R^{12}$O(($C_1$-$C_3$)alkyl)-($NR^{11}$)—, $R^{13}$—(C═O)—($NR^{11}$)— and $(R^{11})_2$N—(C═O)—;

each $R^{10}$ is independently selected from H, $(C_1\text{-}C_3)$alkyl, —$CF_3$, —$OCH_3$, —$OCF_3$, —CN, $(R^{11})_2$N—, $R^{12}$(O)(C═O)—, $R^{12}$O—(($C_1$-$C_3$)alkyl)-($NR^{11}$)—, $R^{13}$—(C═O)—($NR^{11}$)—, and $(R^{11})_2$N—(C═O); and each $R^{11}$ is independently H or $(C_1\text{-}C_3)$alkyl;

$R^{12}$ is H or $(C_1\text{-}C_3)$alkyl; and $R^{13}$ is $(C_1\text{-}C_3)$alkyl.

Clause 2. A compound according to Clause 1, wherein Het is a ring of the Formula i i

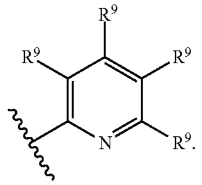

Clause 3. A compound according to Clause 1, wherein Het is a ring of the Formula ii ii

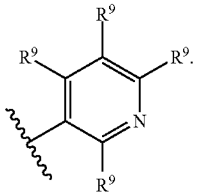

Clause 4. A compound according to Clause 1, wherein Het is a ring of the Formula iii iii

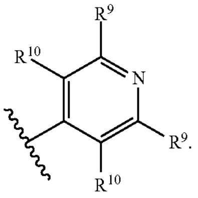

Clause 5. A compound according to Clause 1, wherein Het is a ring of the Formula iv iv

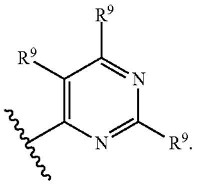

Clause 6. A compound according to Clause 1, wherein Het is a ring of the Formula v v

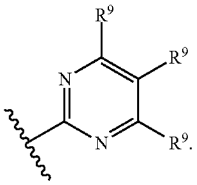

Clause 7. A compound according to Clause 1, Het is a ring of the Formula vi vi

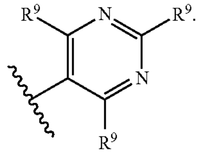

Clause 8. A compound according to Clause 1, wherein Het is a ring of the Formula vii vii

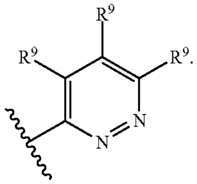

Clause 9. A compound according to Clause 1, wherein Het is a ring of the Formula viii viii

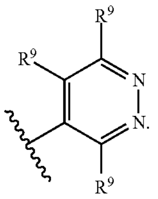

Clause 10. A compound according to Clause 1, wherein Het is a ring of the Formula ix ix

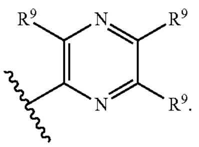

Clause 11. A compound according to any of Clauses 1-10, wherein W is a group of the compound of Formula (a)

(a)

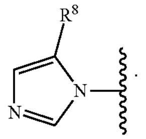

Clause 12. A compound according to any of Clauses 1-10, wherein in W is a group of the compound of Formula (b)

(b)

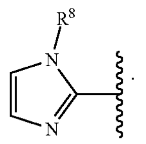

Clause 13. A compound according to any of Clauses 1-10, wherein W is a group of the compound of Formula (c)

(c)

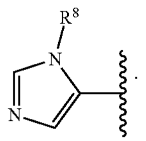

Clause 14. A compound according to any of Clauses 1-10, wherein W is a group of the compound of Formula (d)

(d)

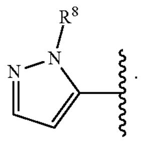

Clause 15. A compound according to any of Clauses 1-10, wherein W is a group of the compound of Formula (e)

(e)

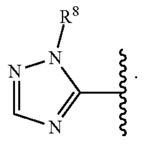

Clause 16. A compound according to any of Clauses 1-10, wherein W is a group of the compound of Formula (f)

(f)

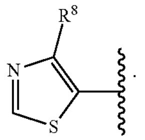

Clause 17. A compound according to any of Clauses 1-16, wherein $R^1$ is selected from the group consisting of H, halo, —CN, $(C_1\text{-}C_3)$alkyl, $(C_1\text{-}C_3)$alkoxy, and perfluoro$(C_1\text{-}C_3)$alkoxy-.

Clause 18. A compound according to any of Clauses 1-17, wherein $R^1$ is selected from the group consisting of H, F, —$CH_3$, and —$OCH_3$.

Clause 19. A compound according to any of Clauses 1-18, wherein $R^1$ is H.

Clause 20. A compound according to any of Clauses 1-19 wherein $R^2$ is selected from the group consisting of H, $(C_1\text{-}C_6)$alkyl, $(C_1\text{-}C_6)$alkoxy-, perfluoro$(C_1\text{-}C_6)$alkyl, perfluoro$(C_1\text{-}C_6)$alkoxy-, cycloalkyl, cycloalkyl-O—, heterocycloalkyl, aryl, $R^5$—$(C(R^4)_2)_n$—O— or $(R^6)_2N$—; wherein $(C_1\text{-}C_6)$alkyl, cycloalkyl, cycloalkyl-O—, heterocycloalkyl and aryl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$;

each $R^4$ is independently H or $(C_1\text{-}C_3)$alkyl optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$;

$R^5$ is selected from $(C_1\text{-}C_3)$alkyl, cycloalkyl, heterocycloalkyl, and aryl; wherein $(C_1\text{-}C_6)$alkyl, cycloalkyl, heterocycloalkyl and aryl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$; and $R^6$ is independently H or $(C_1\text{-}C_3)$alkyl optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$.

Clause 21. A compound according to any of Clauses 1-20, wherein $R^2$ is selected from H, $(C_1\text{-}C_3)$alkyl, $(C_1\text{-}C_3)$alkoxy-, perfluoro$(C_1\text{-}C_3)$alkyl, perfluoro$(C_1\text{-}C_3)$alkoxy-, 3- to 10-membered cycloalkyl, 3- to 10-membered cycloalkyl-O—, 5- to 10-membered heterocycloalkyl, 6- to 10-membered aryl, $R^5$—$(C(R^4)_2)_n$—O— or $(R^6)_2N$—; wherein $(C_1\text{-}C_3)$alkyl, 3- to 10-membered cycloalkyl, 3- to 10-membered cycloalkyl-O—, 5- to 10-membered heterocycloalkyl, 6- to 10-membered aryl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$;

each $R^4$ is independently H or $(C_1\text{-}C_3)$alkyl optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$;

$R^5$ is selected from $(C_1\text{-}C_3)$alkyl, 3- to 10-membered cycloalkyl, 3- to 10-membered heterocycloalkyl, and 6- to 10-membered aryl; wherein $(C_1\text{-}C_3)$alkyl, 3- to 10-membered cycloalkyl, 3- to 10-membered heterocycloalkyl, and 6- to 10-membered aryl is optionally substituted with 1-3 substituents independently selected from the group consisting of H, halo, —CN, $(C_1\text{-}C_3)$alkyl, $—NH_2$, $(C_1\text{-}C_3)$alkyl-(NH)—, $((C_1\text{-}C_3)$ alkyl$)_2N$—, $—CF_3$, $—OCH_3$ and $—OCF_3$; and $R^6$ is independently H or $(C_1\text{-}C_3)$alkyl optionally substituted with 1-3 substituents independently selected from the group consisting of H, halo, —CN, $(C_1\text{-}C_3)$alkyl, $—NH_2$, $(C_1\text{-}C_3)$alkyl-(NH)—, $((C_1\text{-}C_3)$alkyl$)_2N$—, $—CF_3$, $—OCH_3$ and $—OCF_3$.

Clause 22. A compound according to any of Clauses 1-21, wherein $R^2$ is selected from the group consisting of methoxy-, cyclopropoxy- or $R^5—(C(R^4)_2)—O—$; wherein each $R^4$ is H; wherein $R^5$ is selected from $C_1$-alkyl and tetrahydropyran; and wherein said $C_1$-alkyl is substituted with $—OCH_3$.

Clause 23. A compound according to any of Clauses 1-22 wherein $R^3$ is selected from the group consisting of H, halo, $(C_1\text{-}C_3)$alkyl, $—CF_3$, $—OCH_3$, $—OCF_3$ or $(R^7)_2N$—; wherein $R^7$ is H or $(C_1\text{-}C_3)$alkyl.

Clause 24. A compound according to any of Clauses 1-23, wherein $R^3$ is H, F, $—CH_3$, $—OCH_3$, or $H_2N$—.

Clause 25. A compound according to any Clauses 1-24, wherein $R^3$ is H.

Clause 26. A compound according to any Clauses 1-25, wherein $R^9$ is selected from the group consisting of H, halo, $(C_1\text{-}C_3)$alkyl, $—CF_3$, $—OCH_3$, $—OCF_3$, —CN, $R^{12}O((C_1\text{-}C_3)$alkyl)-$(NR^{11})$—, $—CO_2R^{12}$ and $(R^{11})_2N—(C{=}O)—$; -each $R^{11}$ is independently selected from H, $(C_1\text{-}C_3)$alkyl; and $R^{12}$ is H or $(C_1\text{-}C_3)$alkyl.

Clause 27. A compound according to any Clauses 1-26, wherein at least one $R^9$ is selected from the group consisting of F, $(C_1\text{-}C_3)$alkyl, $—CF_3$, $—OCH_3$, $—OCF_3$, —CN.

Clause 28. A compound according to any of Clauses 1-27, wherein at least one $R^9$ is $—CF_3$.

Clause 29. A compound according to any of Clauses 1, 4 or 11 to 28, wherein at least one $R^{10}$ is H.

Clause 30. A compound according to Clauses 29, wherein $R^{10}$ is H.

Clause 31. A compound according to any of Clauses 1-30, wherein Het is a ring of the formula iii

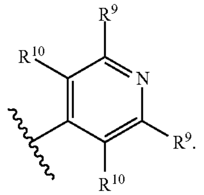

wherein one $R^9$ is H and the other $R^9$ is $—CF_3$, and wherein $R^{10}$ is H.

Clause 32. A compound according to any of Clauses 1-31, wherein $R^8$ is H.

Clause 33. A compound according to any of Clauses 1-32, wherein —X—Y—Z— is ${=}CR^1—CR^2{=}CR^3—$ or $=N—CR^2{=}CR^3—$.

Clause 34. A compound according to any of Clauses 1-33, wherein —X—Y—Z— is $=CR^1—CR^2{=}CR^3—$.

Clause 35. A compound according to any of Clauses 1, 4 or 11, wherein the compound of Formula I is a compound of Formula IA, or a pharmaceutically acceptable salt, ester, or prodrug thereof (IA)

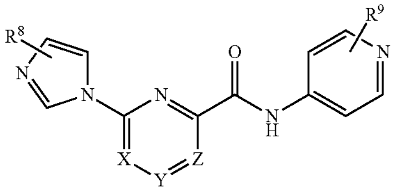

and the compound of Formula I* is a compound of Formula I* A, or a pharmaceutically acceptable salt, ester, or prodrug thereof (I*A)

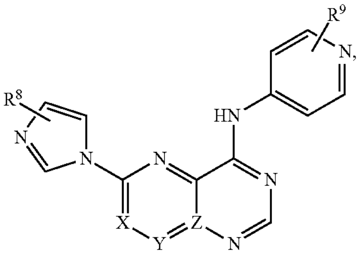

—X—Y—Z— of the Formula IA is $=CR^1—CR^2{=}CR^3—$ or $=N—CR^2{=}CR^3—$;

—X—Y—Z— of the Formula I* A is $CR^1—CR^2{=}C$ or $=N—CR^2{=}C$;

$R^1$ is selected from the group consisting of H, halo, —CN, $(C_1\text{-}C_3)$alkyl, $—OCH_3$, and $—OCF_3$;

$R^2$ is H, $(C_1\text{-}C_6)$alkyl, $(C_1\text{-}C_6)$alkoxy-, perfluoro$(C_1\text{-}C_6)$ alkyl, perfluoro$(C_1\text{-}C_6)$alkoxy-, cycloalkyl, cycloalkyl-O, heterocycloalkyl, aryl, $R^5—(C(R^4)_2)_n—O—$ or $(R^6)_2$ N—; wherein $(C_1\text{-}C_6)$alkyl, cycloalkyl, cycloalkyl-O, heterocycloalkyl and aryl are optionally substituted with 1-3 substituents independently selected from the group consisting of H, halo, —CN, $(C_1\text{-}C_3)$alkyl, $—NH_2$, $(C_1\text{-}C_3)$alkyl-(NH)—, $((C_1\text{-}C_3)$alkyl$)_2N$—, $—CF_3$, $—OCH_3$ and $—OCF_3$;

n is an integer from one to three, each $R^4$ is independently H or $(C_1\text{-}C_3)$alkyl;

$R^5$ is selected from $(C_1\text{-}C_3)$alkyl, cycloalkyl, heterocycloalkyl, and aryl; wherein $(C_1\text{-}C_3)$alkyl, cycloalkyl, heterocycloalkyl and aryl are optionally substituted with 1-3 substituents independently selected from the group consisting of H, halo, —CN, $(C_1\text{-}C_3)$alkyl, $—NH_2$, $(C_1\text{-}C_3)$alkyl-(NH)—, $((C_1\text{-}C_3)$alkyl$)_2N$—, $—CF_3$, $—OCH_3$ and $—OCF_3$;

$R^6$ is independently H or $(C_1\text{-}C_3)$alkyl; wherein $(C_1\text{-}C_3)$ alkyl is optionally substituted with 1-3 substituents independently selected from the group consisting of H, halo, —CN, $(C_1\text{-}C_3)$alkyl, $—NH_2$, $(C_1\text{-}C_3)$alkyl-(NH)—, $((C_1\text{-}C_3)$alkyl$)_2N$—, $—CF_3$, $—OCH_3$ and $—OCF_3$;

$R^3$ is H, halo, $(C_1\text{-}C_3)$alkyl, $—CF_3$, $—OCH_3$, $—OCF_3$ or $(R^7)_2N$—;

$R^7$ is H or $(C_1\text{-}C_3)$alkyl;

$R^8$ is H, $—CH_3$ or $—CF_3$;

$R^9$ is selected from H, halo, $(C_1\text{-}C_3)$alkyl, $—CF_3$, $—OCH_3$, $—OCF_3$, —CN, $R^{12}O((C_1\text{-}C_3)$alkyl)-$(NR^{11})$—, $—CO_2R^{12}$ and $(R^1)_2N—(C{=}O)—$;

each $R^{11}$ is independently selected from H, $(C_1\text{-}C_3)$alkyl; and $R^{12}$ is H or $(C_1\text{-}C_3)$alkyl.

Clause 36. A compound according to any of Clauses 1, 3 or 11, wherein the compound of Formula I is a compound of Formula IB, or a pharmaceutically acceptable salt, ester, or prodrug thereof (IB)

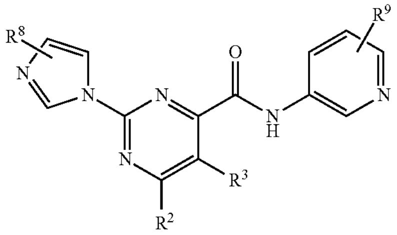

and the compound of Formula I* is a compound of Formula I* B, or a pharmaceutically acceptable salt, ester, or prodrug thereof (I*B)

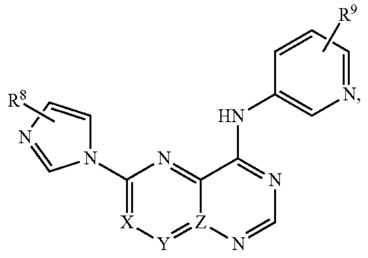

wherein:

—X—Y—Z— of the Formula I* B is CH—$CR^2$═C or ═N—$CR^2$═C;

$R^2$ is H, $(C_1\text{-}C_3)$alkyl, $(C_1\text{-}C_3)$alkoxy-, perfluoro$(C_1\text{-}C_3)$alkyl, perfluoro$(C_1\text{-}C_3)$alkoxy-, cycloalkyl, heterocycloalkyl, aryl, $R^5$—$(C(R^4)_2)_n$—O—, or $(R^6)_2N$—; wherein $(C_1\text{-}C_3)$alkyl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$;

n is an integer from one to three;

each $R^4$ is independently H or $(C_1\text{-}C_3)$alkyl;

wherein $(C_1\text{-}C_3)$alkyl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$;

$R^5$ is selected from $(C_1\text{-}C_3)$alkyl, cycloalkyl, heterocycloalkyl, and aryl; wherein $(C_1\text{-}C_3)$alkyl, cycloalkyl, heterocycloalkyl and aryl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$;

$R^6$ is independently H or $(C_1\text{-}C_3)$alkyl; wherein $(C_1\text{-}C_3)$alkyl is optionally substituted with 1-3 substituents independently selected from the group consisting of H, halo, —CN, $(C_1\text{-}C_3)$alkyl, —$NH_2$, $(C_1\text{-}C_3)$alkyl-(NH)—, $((C_1\text{-}C_3)alkyl)_2N$—, —$CF_3$, —$OCH_3$ and —$OCF_3$;

$R^3$ is H, halo, $(C_1\text{-}C_3)$alkyl, —$CF_3$, —$OCH_3$, —$OCF_3$ or $(R^7)_2N$—; wherein $R^7$ is H or $(C_1\text{-}C_3)$alkyl;

$R^8$ is H, —$CH_3$ or —$CF_3$;

$R^9$ is selected from H, halo, $(C_1\text{-}C_3)$alkyl, —$CF_3$, —$OCH_3$, —$OCF_3$, —CN, —$(NR^{10})$—$((C_1\text{-}C_3)alkyl)$-$OR^{11}$, —$CO_2R^{11}$ and —(C═O)—$N(R^{10})_2$; and $R^{10}$ is H or $(C_1\text{-}C_3)$alkyl; and $R^{11}$ is $(C_1\text{-}C_3)$alkyl.

Clause 37. A compound according to Clause 1, wherein the compound is selected from:

6-(1H-imidazol-1-yl)-4-((tetrahydro-2H-pyran-4-yl)methoxy)-N-(2-(trifluoromethyl)pyridin-4-yl)picolinamide;

6-(1H-imidazol-1-yl)-4-methoxy-N-(2-(trifluoromethyl)pyridin-4-yl)picolinamide;

2-(1H-imidazol-1-yl)-6-(2-methoxyethoxy)-N-(2-(trifluoromethyl)pyridin-4-yl)pyrimidine-4-carboxamide;

6-(1H-imidazol-1-yl)-4-(2-methoxyethoxy)-N-(2-(trifluoromethyl)pyridin-4-yl)picolinamide; or 4-cyclopropoxy-6-(1H-imidazol-1-yl)-N-(2-(trifluoromethyl)pyridin-4-yl)picolinamide;

or a pharmaceutically acceptable salt, ester, or prodrug thereof.

Clause 38. A pharmaceutical composition comprising a compound, salt, ester, or prodrug of any of Clauses 1-37, and a pharmaceutically acceptable carrier.

Clause 39. A method of treating a disease or condition in a subject, that benefits from modulation of NAD+ level or related metabolites thereof level, comprising administering to the subject an amount of a compound according to any of Clauses 1 to 37 or a composition according to Clause 38 effective to modulate NAD+ level or related metabolites thereof level.

Clause 40. The method of Clause 39, wherein said disease or condition is nonalcoholic steatohepatitis.

Clause 41. A compound or composition according to any of Clauses 1 to 38 for use in the treatment of a disease or medical condition in a subject.

Clause 42. A compound or composition for use according to Clause 41, wherein the disease or condition benefits from modulation in NAD+ level or related metabolites thereof level.

Clause 43. A compound or composition for use according to Clause 41 or 42, wherein the disease or condition benefits from inhibition of CD38.

Clause 44. A compound or composition for use according to any of Clauses 41 to 43, wherein the disease or condition is selected from ageing (e.g., age-related chronic disease), inflammation, cancer, such as PD-1/PD-L1 resistant cancers, cardiovascular disorder, neurological disorder, pulmonary disorder, fibrotic diseases, metabolic disorder, acute lung injury (ALI), acute respiratory distress syndrome (ARDS), hyperphosphatemia, alcohol intolerance, lupus, arthritis, ataxia-telangiectasia, irritable bowel syndrome, colitis, gout, end stage renal disease, hearing loss, liver disorders, post-menopausal osteoporosis, Hartnup disease, tuberculosis, leishmaniasis, muscular dystrophy, organ reperfusion injury, pellagra, diseases of the skin, damage caused by exposure to radiation, periodontal disease, Leber's hereditary amaurosis, sleep disorder, exercise intolerance, chronic disease associated with cell death, and neurodegeneration and peripheral neuropathy associated with chemotherapy.

Clause 45. A compound or composition for use according to any of Clauses 41 to 44, wherein the disease or condition is an age-related disease or condition.

Clause 46. A compound or composition for use according to any of Clauses 41 to 45, wherein the disease or condition is selected from small lung cell carcinoma, renal clear cell carcinoma, chronic lymphocytic leukemiahas, multiple myeloma, hypertension, hypoxic pulmonary vasoconstriction, cardiac hypertrophy, congestive heart failure, stroke, Alzheimer's disease, bipolar disorder, schizophrenia, Huntington's disease, amyotrophic lateral sclerosis, Parkinson's disease, multiple sclerosis, optic neuropathy, epilepsy, idiopathic pulmonary fibrosis, cystic fibrosis, asthma, chronic obstructive pulmonary disease (COPD), metabolic syndrome, obesity, sarcopenic obesity, dyslipidemia, diabetes (such as type I diabetes), diabetic neuropathy, insulin resistance, pancreatitis, acute lung injury (ALI) acute respiratory distress syndrome (ARDS), hyperphosphatemia, alcohol intolerance, lupus, rheumatoid arthritis, ataxia-telangiectasia, irritable bowel syndrome, colitis, gout, end stage renal disease, hearing loss, steatosis, non-alcoholic steatohepatitis (NASH), postmenopausal osteoporosis, Hartnup disease, tuberculosis, leishmaniasis, muscular dystrophy, organ reperfusion injury, pellagra, skin hyperpigmentation, UV skin damage, psoriasis, X-ray-induced DNA damage, periodontal disease, Leber's hereditary amaurosis, sleep disorders, exercise intolerance, and neurodegeneration and peripheral neuropathies associated with chemotherapy.

Clause 47. A compound or composition for use according to any of Clauses 41 to 46, wherein the treatment is of multiple myeloma and is a combination treatment with an immuno-oncology drug.

Clause 48. A compound or composition for use according to any of Clauses 41 to 46, wherein the disease or condition is nonalcoholic steatohepatitis (NASH).

Clause 49. A compound or composition for use according to Clause 48, wherein the compound is 2-(1H-imidazol-1-yl)-6-methoxy-N-(2-(trifluoromethyl)pyridin-4-yl)pyrimidine-4-carboxamide.

Clause 50. A compound according to any one of claims 1 to 37 for use in a method of treating a disease or disorder in a subject that benefits from modulation the level of NAD+ or related metabolite thereof, comprising administering to the subject a therapeutically effective amount of the compound.

Clause 51. The compound for use of claim 50, wherein the disease or disorder is or is related to nonalcoholic steatohepatitis, aging, senescence, immunometabolism, inflammation, infection, sepsis, arthritis, rheumatoid arthritis, psoriatic arthritis, osteoarthritis, lupus erythematosus, Crohn disease, ulcerative colitis, plaque psoriasis, ankylosing spondylitis, juvenile idiopathic arthritis, hidradenitis suppurativa, fibrosis, hepatic fibrosis, renal fibrosis, pulmonary fibrosis, cardiac fibrosis, cancer, multiple myeloma, neurodegeneration, infertility, loss of ovarian follicles, decreased oocyte quality and quantity, ovarian senescence, transient receptor potential melastatin 2 (TRPM2) regulation, calcium flux regulation, ischemia-reperfusion-injury, bipolar disoreder, Alzheimer, neuropathic pain, Parkinson, coronary arteries, obesity, type-2 diabetes, hepatotoxicity, digestive system, lung, heart, kidney, or the like.

Clause 52. The compound for use of claim 50, wherein the disease or disorder is related to aging.

Clause 53. The compound for use of claim 52, wherein the age-related disease or disorder is or is related to a chronic age-related disease or disorder.

Clause 54. The compound for use of claim 52, wherein the disease or disorder is or is related to Senescence, Immuno-Metabolism, fibrotic, neurodegenerative, Multiple Myeloma, or Sepsis.

Clause 55. The compound for use of claim 54, wherein the disease or disorder is or is related to a fibrotic disease or disorder of the lung, heart, or kidney.

Clause 56. The compound for use of claim 55, wherein the fibrotic disease is infection-induced fibrosis of the lung or virus-induced infection of the lung.

Clause 57. The compound for use of claim 54, wherein the disease or disorder is or is related to Multiple Myeloma, and the method further comprising administering an immuno-oncology drug to the subject.

Clause 58. The compound for use of claim 50, wherein the modulation is an increase in the level of NAD+ or related metabolite thereof, Clause 59. The compound for use of claim 50, wherein the modulation is a decrease in the level of NAD+ or related metabolite thereof.

Clause 60. The compound for use of claim 50, wherein the NAD+ or related metabolite thereof is selected from the group consisting of NAD+, NMN, ADPR, cADPR, NAM, NAAD, NAADP, NR, MNAM.

Reference will now be made to specific examples illustrating the disclosure. It is to be understood that the examples are provided to illustrate exemplary embodiments and that no limitation to the scope of the disclosure is intended thereby.

EXAMPLES

While several experimental Examples are contemplated, these Examples are intended non-limiting.

In the following nonlimiting Examples, "BOC", "Boc" or "boc" means N-tert-butoxycarbonyl, "DCM" ($CH_2Cl_2$) means methylene chloride, "DIPEA" or "DIEA" means diisopropyl ethyl amine, "DMA" means N,N-dimethylacetamide, "DMF" means N—N-dimethyl formamide, "DMSO" means dimethylsulfoxide, "DPPP" means 1,3-bis (diphenylphosphino) propane, "HOAc" means acetic acid, "IPA" means isopropyl alcohol. "MTBE" means methyl t-butyl ether, "NMP" means 1-methyl 2-pyrrolidinone, "TEA" means triethyl amine, "TFA" means trifluoroacetic acid, "DCM" means dichloromethane, "EtOAc" means ethyl acetate, "$MgSO_4$" means magnesium sulphate, "$NaSO_4$" means sodium sulphate, "MeOH" means methanol, "EtOH" means ethanol, "$H_2O$" means water, "HCl" means hydrochloric acid, "POCIs" means phosphorus oxychloride, "DMSO" means dimethyl sulfoxide, "$K_2CO_3$" means potassium carbonate, "N" means Normal, "M" means molar, "mL" means milliliter, "mmol" means millimoles, "μmol" means micromoles, "eq." means equivalent, "° C." means degrees Celsius, "Pa" means pascals.

Example 1

Synthesis of Methyl 5-[6-(1H-imidazol-1-yl)pyridine-2-amido]pyridine-2-carboxylate (Compound 1)

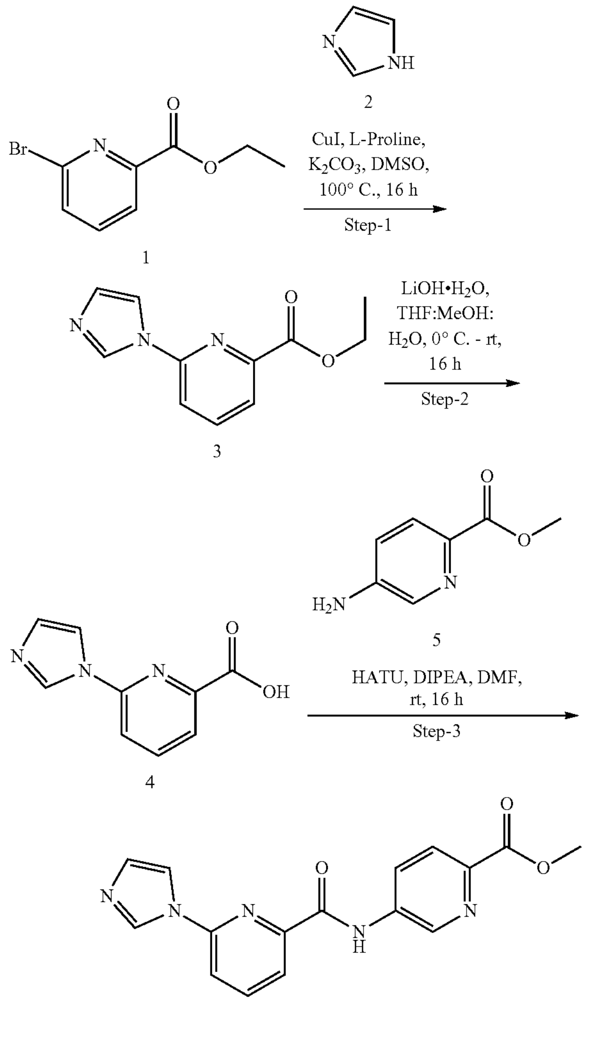

Step-1: ethyl 6-(1H-imidazol-1-yl)picolinate

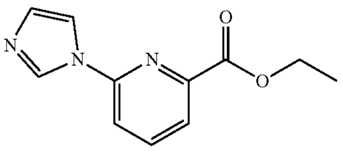 [SMILES: CCOC(=O)c1cccc(-n2ccnc2)n1]

To a stirred solution of ethyl 6-bromopyridine-2-carboxylate (1 g, 4.35 mmol) in DMSO (10 mL) was added copper iodide (0.276 g, 0.869 mmol), L-proline (0.20 g, 1.74 mmol), potassium carbonate (1.20 g, 8.69 mmol) and imidazole (0.444 g, 6.52 mmol). The reaction mixture was heated to 100° C. for 16 h. The reaction mixture was cooled to room temperature (RT), and ice-cold water was added and extracted with ethyl acetate. The organic layer was dried over sodium sulfate and evaporated under reduced pressure to afford ethyl 6-(1H-imidazol-1-yl) picolinate (1 g crude) as a brown solid. LCMS (ES) m/z=218.1 $[M+H]^+$.

Step-2: 6-(1H-imidazol-1-yl)picolinic acid

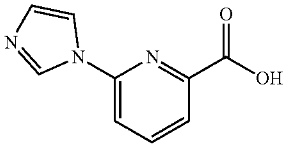 [SMILES: O=C(O)c1cccc(-n2ccnc2)n1]

To a stirred solution of ethyl 6-(1H-imidazol-1-yl)pyridine-2-carboxylate (1 g, 4.60 mmol) in THF (10 mL), MeOH (10 mL) and water (10 mL) was added lithium hydroxide mono hydrate (0.29 g, 6.91 mmol). The reaction mixture was allowed to stir at RT for 16 h. Progress of the reaction was monitored by TLC. The solvents were completely evaporated under reduced pressure and extracted with ethyl acetate. The aqueous layer was acidified using 1 N HCl to adjust the pH to about 2. The aqueous layer was completely evaporated under reduced pressure to obtain crude material which was triturated with acetonitrile and diethyl ether to afford 6-(1H-imidazol-1-yl)pyridine-2-carboxylic acid (1.2 g, crude) as a brown solid. LCMS (ES) m/z=190.2 $[M+H]^+$.

Step-3: methyl 5-(6-(1H-imidazol-1-yl)picolinamido)picolinate

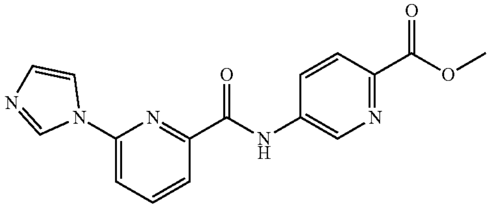 [SMILES: COC(=O)c1ccc(NC(=O)c2cccc(-n3ccnc3)n2)cn1]

To a solution of 6-(1H-imidazol-1-yl)pyridine-2-carboxylic acid (1 g, 5.29 mmol) in DMF (5 mL) was added DIPEA (3.42 mL, 18.5 mmol), HATU (3.01 g, 9.73 mmol) and methyl 5-aminopyridine-2-carboxylate (0.96 g, 6.34 mmol). The reaction mixture was stirred at RT for 16 h. Water (10 mL) was added to the reaction mixture and extracted with ethyl acetate (30 mL). The organic layer was dried over sodium sulfate and evaporated under reduced pressure to obtain crude which was purified by Combiflash column chromatography using MeOH-DCM gradient. The compound eluted out in 4% MeOH: DCM. The pure fractions were collected and evaporated to afford pure methyl 5-[6-(1H-imidazol-1-yl)pyridine-2-amido]pyridine-2-carboxylate (0.5 g, 29% yield) as an off-white solid.

Provided in Table 1 below are characterization data for selected compounds of Formula I prepared by the method shown in Example 1 above.

TABLE 1

(Compounds 1-28)

| Compound | Structure | LCMS (M + H) | HPLC purity (%) | 1H NMR |
|---|---|---|---|---|
| 1 | 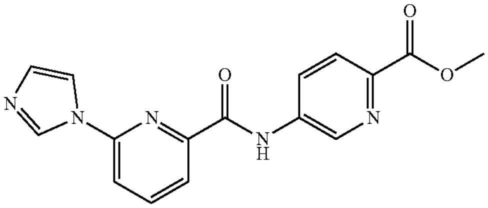 [SMILES: COC(=O)c1ccc(NC(=O)c2cccc(-n3ccnc3)n2)cn1] | 324.3 | 99.28 | $^1$H NMR (400 MHz, DMSO-$d_6$) δ 10.86 (s, 1H), 9.17-9.16 (m, 1H), 9.00 (s, 1H), 8.52-8.49 (m, 1H), 8.32 (s, 1H), 8.25 (t, J = 8 Hz, 1H), 8.08-8.13 (m, 3H), 7.17 (s, 1H), 3.86 (s, 3H). |
| 2 | 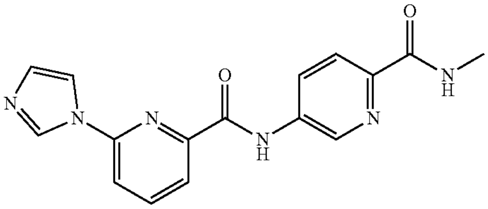 [SMILES: CNC(=O)c1ccc(NC(=O)c2cccc(-n3ccnc3)n2)cn1] | 323.3 | 99.69 | $^1$H NMR (400 MHz, DMSO-$d_6$) δ 10.80 (s, 1H), 9.16 (s, 1H), 9.11 (s, 1H), 8.71-8.70 (m, 1H), 8.47-8.45 (m, 1H), 8.33 (s, 1H), 8.26 (t, J = 8.0 Hz, 1H), 8.11-8.06 (m, 3H), 7.18 (s, 1H), 2.82-2.81 (d, J = 4.4 Hz, 3H). |
| 3 | 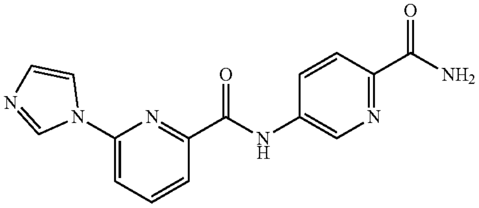 [SMILES: NC(=O)c1ccc(NC(=O)c2cccc(-n3ccnc3)n2)cn1] | 309.3 | 99.17 | $^1$H NMR (400 MHz, DMSO-$d_6$) δ 1HNMR (400 MHz, DMSO-d6): δ 10.80 (s, 1H), 9.11 (s, 1H), 8.99 (s, 1H), 8.46-8.43 (m, 1H), 8.31 (s, 1H), 8.26 (t, J = 8 Hz, 1H), 8.11-8.05 (m, 4H), 7.53 (s, 1H), 7.18 (s, 1H). |
| 4 | 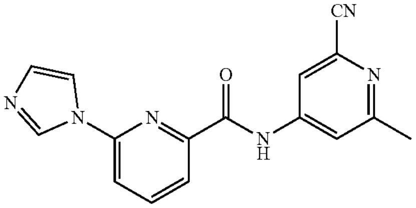 [SMILES: Cc1cc(NC(=O)c2cccc(-n3ccnc3)n2)cc(C#N)n1] | 305.3 | 99.51 | $^1$H NMR (400 MHz, DMSO-$d_6$) δ 10.83 (s, 1H), 8.99 (s, 1H), 8.32 (s, 1H), 8.27 (t, J = 8.0 Hz, 2H), 8.14 (s, 1H), 8.10 (t, J = 6.4 Hz, 2H), 7.18 (s, 1H), 2.53 (s, 3H). |
| 5 | 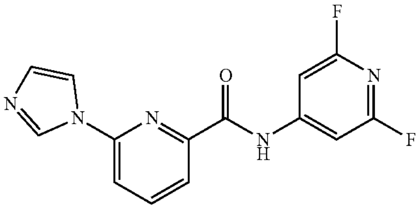 [SMILES: O=C(Nc1cc(F)nc(F)c1)c1cccc(-n2ccnc2)n1] | 302.3 | 99.09 | $^1$H NMR (400 MHz, DMSO-$d_6$) δ 11.06 (s, 1H), 8.98 (s, 1H), 8.30-8.25 (m, 2H), 8.15-8.09 (m, 2H), 7.68 (s, 2H), 7.19 (s, 1H). |
| 6 | 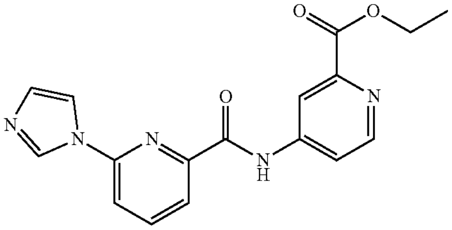 [SMILES: CCOC(=O)c1cc(NC(=O)c2cccc(-n3ccnc3)n2)ccn1] | 338.1 | 99.68 | $^1$H NMR (400 MHz, DMSO-$d_6$) δ 10.87 (s, 1H), 9.00 (s, 1H), 8.66-8.32 (m, 2H), 8.28 (s, 1H), 8.24 (t, J = 8.0 Hz, 1H), 8.20-8.19 (m, 1H), 8.12-8.09 (s, 2H), 7.18 (s, 1H), 4.39-4.33 (q, J = 6.8 Hz, 2H), 1.35-1.32 (t, J = 7.6 Hz, 3H) |

TABLE 1-continued (Compounds 1-28)

| Compound | Structure | LCMS (M + H) | HPLC purity (%) | 1H NMR |
|---|---|---|---|---|
| 7 | 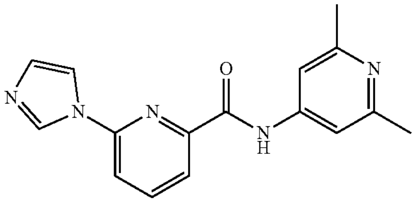 [SMILES: Cc1cc(NC(=O)c2cccc(-n3ccnc3)n2)cc(C)n1] | 294.3 | 98.44 | $^{1}$H NMR (400 MHz, DMSO-$d_6$) δ 10.47 (s, 1H), 8.98 (s, 1H), 8.30 (s, 1H), 8.23 (t, J = 8.0 Hz, 1H), 8.09-8.05 (t, J = 8.0 Hz, 2H), 7.59 (s, 2H), 7.16 (s, 1H), 2.40 (s, 6H). |
| 8 | 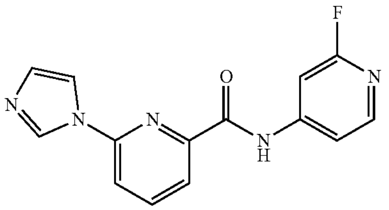 [SMILES: O=C(Nc1ccnc(F)c1)c1cccc(-n2ccnc2)n1] | 282.2 (M −H) | 99.5 | $^{1}$H NMR (400 MHz, DMSO-$d_6$) δ 10.87 (s, 1H), 8.98 (s, 1H), 8.30 (s, 2H), 8.25 (t, J = 8.0 Hz, 1H), 8.19 (d, J = 5.6 Hz, 1H), 8.09 (t, J = 8.0 Hz, 1H), 7.85 (d, J = 5.6 Hz, 1H), 7.72 (s, 1H), 7.18 (s, 1H). |
| 9 | 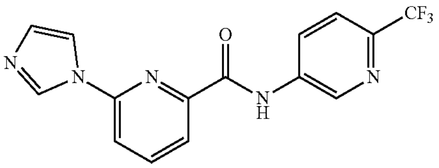 [SMILES: O=C(Nc1ccc(C(F)(F)F)nc1)c1cccc(-n2ccnc2)n1] | 334.4 | 98.3 | $^{1}$H NMR (400 MHz, DMSO-$d_6$) δ 10.88 (s, 1H), 9.22 (s, 1H), 8.99 (s, 1H), 8.57 (d, J = 8.4 Hz, 1H), 8.31 (s, 1H), 8.27-8.23 (m, 1H), 8.11-8.09 (m, 2H), 7.96 (d, J = 8.4 Hz, 1H), 7.18 (s, 1H) |
| 10 | 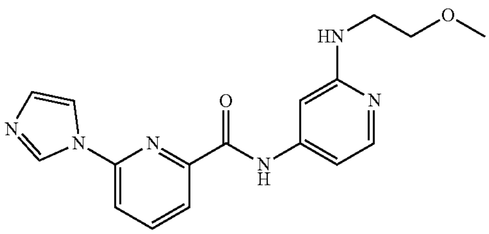 [SMILES: COCCNc1cc(NC(=O)c2cccc(-n3ccnc3)n2)ccn1] | 339.3 | 99.6 | $^{1}$H NMR (400 MHz, DMSO-$d_6$) δ 10.35 (s, 1H), 8.96 (s, 1H), 8.29 (s, 1H), 8.23 (t, J = 8 Hz, 1H), 8.06 (t, J = 8 Hz, 2H), 7.91 (d, J = 5.2 Hz, 1H), 7.16 (s, 2H), 6.96-6.94 (m, 1H), 6.58 (t, J = 5.2 Hz, 1H), 3.48-3.37 (m, 4H), 3.25 (s, 3H). |
| 11 | 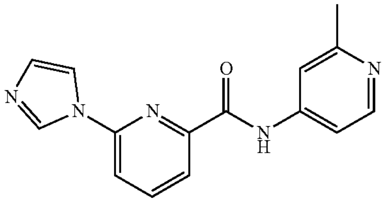 [SMILES: Cc1cc(NC(=O)c2cccc(-n3ccnc3)n2)ccn1] | 280.3 | 99.06 | $^{1}$H NMR (400 MHz, DMSO-$d_6$) δ 10.58 (s, 1H), 8.98 (s, 1H), 8.38 (d, J = 6.0 Hz, 1H), 8.30 (s, 1H), 8.24 (t, J = 8.0 Hz, 1H), 8.08 (t, J = 6.4 Hz, 2H), 7.77-7.74 (m, 2H), 7.17 (s, 1H), 2.46 (s, 3H). |

TABLE 1-continued

| (Compounds 1-28) | | | | |
|---|---|---|---|---|
| Compound | Structure | LCMS (M + H) | HPLC purity (%) | 1H NMR |
| 12 | 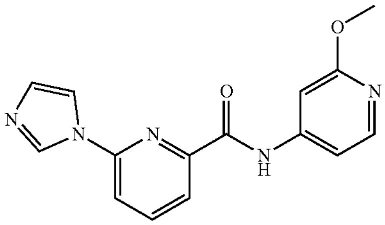 [SMILES: COc1cc(NC(=O)c2cccc(-n3ccnc3)n2)ccn1] | 296.3 | 99.87 | $^1$H NMR (400 MHz, DMSO-$d_6$) δ 10.61 (s, 1H), 8.98 (s, 1H), 8.30 (s, 1H), 8.24 (t, J = 8.0 Hz, 1H), 8.12-8.06 (m, 3H), 7.52 (d, J = 5.6 Hz, 1H), 7.43 (s, 1H), 7.17 (s, 1H), 3.84 (s, 3H). |
| 13 | 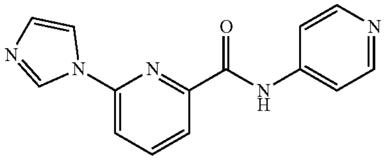 [SMILES: O=C(Nc1ccncc1)c1cccc(-n2ccnc2)n1] | 266.2 | 99.88 | $^1$H NMR (400 MHz, DMSO-$d_6$) δ 10.66 (s, 1H), 8.97 (s, 1H), 8.52 (d, J = 6 Hz, 2H), 8.30 (s, 1H), 8.24 (t, J = 8.0 Hz, 1H), 8.10-8.07 (m, 2H), 7.91 (d, J = 6 Hz, 2H), 7.17 (s, 1H). |
| 14 | 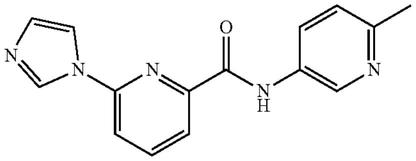 [SMILES: Cc1ccc(NC(=O)c2cccc(-n3ccnc3)n2)cn1] | 280.4 | 99.45 | $^1$H NMR (400 MHz, DMSO-$d_6$) δ 9.59 (s, 1H), 8.72 (d, J = 2.4 Hz, 1H), 8.39 (s, 1H), 8.26 (d, J = 7.6 Hz, 1H), 8.19 (t, J = 8.0 Hz, 1H), 8.10 (d, J = 7.6 Hz, 1H), 7.68 (s, 1H), 7.59 (d, J = 8.4 Hz, 1H), 7.29-7.21 (m, 2H), 2.57 (s, 3H) |
| 15 | 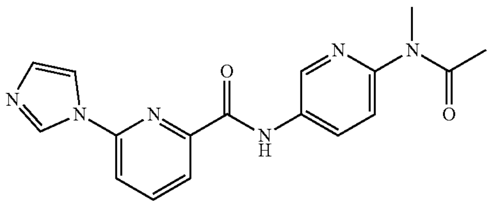 [SMILES: CC(=O)N(C)c1ccc(NC(=O)c2cccc(-n3ccnc3)n2)cn1] | 337.2 | 99.45 | $^1$H NMR (400 MHz, DMSO-$d_6$) δ 10.69 (s, 1H), 9.0 (s, 1H), 8.90-8.89 (m, 1H), 8.32-8.26 (m, 2H), 8.24 (t, J = 8.0 Hz, 1H), 8.09-8.06 (m, 2H), 7.54 (d, J = 8.8 Hz, 1H), 7.17 (s, 1H), 3.25 (s, 3H), 1.99 (s, 3H). |
| 16 | 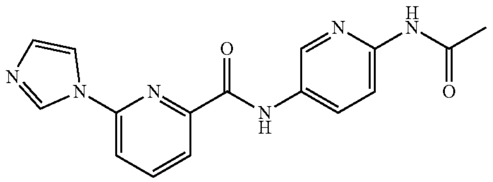 [SMILES: CC(=O)Nc1ccc(NC(=O)c2cccc(-n3ccnc3)n2)cn1] | 323.3 | 99.08 | $^1$H NMR (400 MHz, DMSO-$d_6$) δ 10.58 (s, 1H), 10.52 (s, 1H), 9.04 (s, 1H), 8.74 (s, 1H), 8.34 (s, 1H), 8.23 (t, J = 8.0 Hz, 1H), 8.17 (t, J = 6.4 Hz, 1H), 8.11-8.05 (m, 3H), 7.19 (s, 1H), 2.07 (s, 3H). |

TABLE 1-continued (Compounds 1-28)

| Compound | Structure | LCMS (M + H) | HPLC purity (%) | 1H NMR |
|---|---|---|---|---|
| 17 | 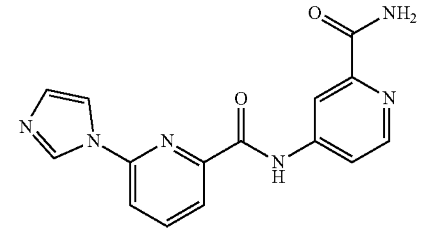 [SMILES: NC(=O)c1cc(NC(=O)c2cccc(-n3ccnc3)n2)ccn1] | 309.3 | 99.07 | $^1$H NMR (400 MHz, DMSO-$d_6$) δ 10.84 (s, 1H), 9.01 (s, 1H), 8.60-8.57 (m, 2H), 8.34 (s, 1H), 8.25 (t, J = 8.0 Hz, 1H), 8.17 (d, J = 5.2 Hz, 1H), 8.12-8.10 (m, 3H), 7.65 (s, 1H), 7.17 (s, 1H) |
| 18 | 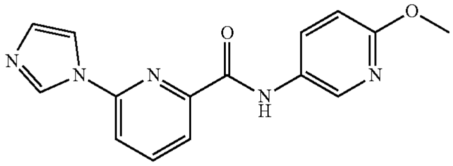 [SMILES: COc1ccc(NC(=O)c2cccc(-n3ccnc3)n2)cn1] | 296 | 99.93 | $^1$H NMR (400 MHz, DMSO-$d_6$) δ 10.53 (s, 1H), 9.00 (s, 1H), 8.57 (d, J = 2.4 Hz, 1H), 8.32 (s, 1H), 8.22 (d, J = 7.6 Hz, 1H), 8.10-8.04 (m, 3H), 7.17 (s, 1H), 6.88 (d, J = 8.8 Hz, 1H), 3.85 (m, 3H). |
| 19 | 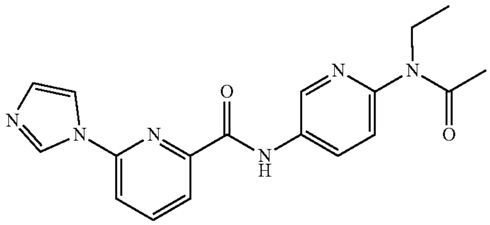 [SMILES: CCN(C(C)=O)c1ccc(NC(=O)c2cccc(-n3ccnc3)n2)cn1] | 351.4 | 99.80 | $^1$H NMR (400 MHz, DMSO-$d_6$) δ 10.71 (s, 1H), 9.0 (s, 1H), 8.93 (s, 1H), 8.34-8.27 (m, 2H), 8.25 (t, J = 8.0 Hz, 1H), 8.11-8.08 (m, 2H), 7.50 (d, J = 8.4 Hz, 1H), 7.18 (s, 1H), 3.78 (q, J = 6.8 Hz, 2H), 1.92 (s, 3H), 1.05 (t, J = 6.8 Hz, 3H) |
| 20 | 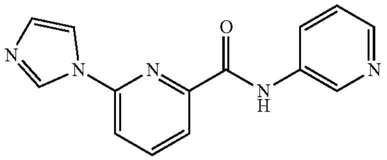 [SMILES: O=C(Nc1cccnc1)c1cccc(-n2ccnc2)n1] | 266.4 | 99.7 | $^1$H NMR (400 MHz, DMSO-$d_6$) δ 10.62 (s, 1H), 9.00 (s, 2H), 8.36-8.31 (m, 2H), 8.29-8.20 (m, 2H), 8.07 (d, J = 6.4 Hz, 2H), 7.48-7.40 (m, 1H), 7.17 (s, 1H); |
| 21 | 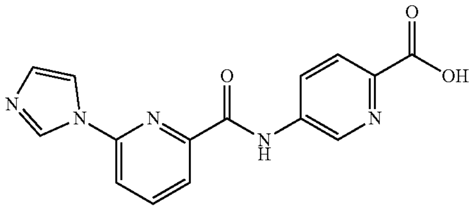 [SMILES: O=C(O)c1ccc(NC(=O)c2cccc(-n3ccnc3)n2)cn1] | 310.3 | 99.3 | $^1$H NMR (400 MHz, DMSO-$d_6$) δ 10.93 (s, 1H), 9.91 (bs, 1H), 9.14 (s, 1H), 8.68 (s, 1H), 8.49-8.48 (m, 1H), 8.47-8.46 (m, 1H), 8.38 (t, J = 8.0 Hz, 2H), 8.12 (d, J = 8.4 Hz, 2H), 7.72 (bs, 1H). |
| 22 | 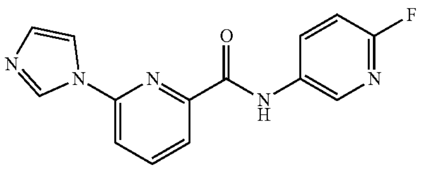 [SMILES: O=C(Nc1ccc(F)nc1)c1cccc(-n2ccnc2)n1] | 284.0 | 99.6 | $^1$H NMR (400 MHz, DMSO-$d_6$) δ 10.70 (s, 1H), 9.0 (s, 1H), 8.66 (s, 1H), 8.39 (t, J = 8.0 Hz, 1H), 8.32 (s, 1H), 8.24 (t, J = 8.0 Hz, 1H), 8.10-8.08 (m, 2H), 7.25 (d, J = 8.8 Hz, 1H), 7.17 (s, 1H). |

TABLE 1-continued (Compounds 1-28)

| Compound | Structure | LCMS (M + H) | HPLC purity (%) | 1H NMR |
|---|---|---|---|---|
| 23 | 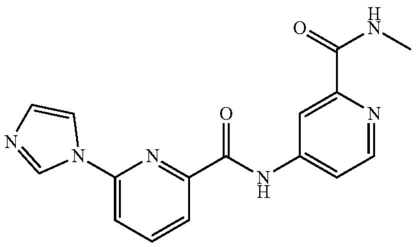 [SMILES: CNC(=O)c1cc(NC(=O)c2cccc(-n3ccnc3)n2)ccn1] | 323.3 | 99.69 | $^1$H NMR (400 MHz, DMSO-$d_6$) δ 10.94 (s, 1H), 9.98 (s, 1H), 8.79 (d, J = 4.8 Hz, 1H), 8.70 (s, 1H), 8.60 (d, J = 6.0 Hz, 1H), 8.54 (s, 1H), 8.39 (t, J = 8.0 Hz, 1H), 8.28-8.22 (m, 3H), 7.74 (s, 1H), 2.82 (d, J = 4.4 Hz, 3H). |
| 24 | 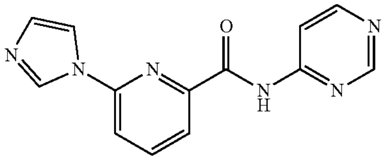 [SMILES: O=C(Nc1ccncn1)c1cccc(-n2ccnc2)n1] | 267.1 | 99.75 | $^1$H NMR (400 MHz, DMSO-$d_6$) δ 11.0 (s, 1H), 9.00 (s, 1H), 8.90 (s, 1H), 8.77 (d, J = 5.6 Hz, 1H), 8.27-8.23 (m, 3H), 8.10-8.08 (m, 2H), 7.15 (s, 1H). |
| 25 | 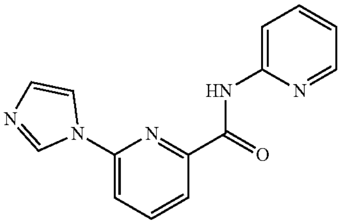 [SMILES: O=C(Nc1ccccn1)c1cccc(-n2ccnc2)n1] | 266.1 | 99.9 | $^1$H NMR (400 MHz, DMSO-$d_6$) δ 10.69 (s, 1H), 8.88 (s, 1H), 8.43-8.41 (m, 2H), 8.30-8.20 (m, 2H), 8.09 (t, J = 8.8 Hz, 2H), 7.91 (t, J = 8.0 Hz, 1H), 7.23 (t, J = 6.0 Hz, 1H), 7.16 (s, 1H). |
| 26 | 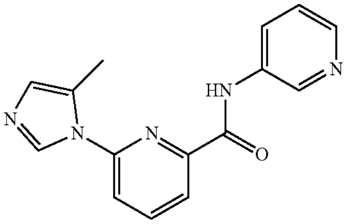 [SMILES: Cc1cncn1-c1cccc(C(=O)Nc2cccnc2)n1] | 280.3 | 99.5 | $^1$H NMR (400 MHz, DMSO-$d_6$) δ 10.57 (s, 1H), 8.99 (s, 1H), 8.37-8.33 (m, 2H), 8.25-8.23 (m, 2H), 8.13 (d, J = 7.6 Hz, 1H), 7.89 (d, J = 8.0 Hz, 1H), 7.42-7.40 (m, 1H), 6.89-6.87 (m, 1H), 2.42 (s, 3H). |
| 27 | 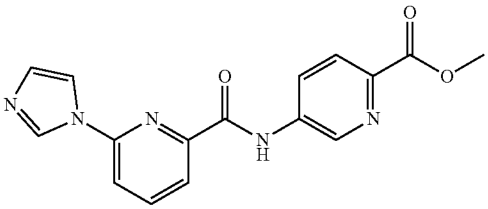 [SMILES: COC(=O)c1ccc(NC(=O)c2cccc(-n3ccnc3)n2)cn1] | 324.3 | 99.28 | $^1$H NMR (400 MHz, DMSO-$d_6$) δ 10.86 (s, 1H), 9.17-9.16 (m, 1H), 9.00 (s, 1H), 8.52-8.49 (m, 1H), 8.32 (s, 1H), 8.25 (t, J = 8 Hz, 1H), 8.13-8.08 (m, 3H), 7.17 (s, 1H), 3.86 (s, 3H). |
| 28 | 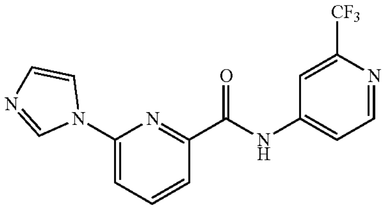 [SMILES: O=C(Nc1ccnc(C(F)(F)F)c1)c1cccc(-n2ccnc2)n1] | 334.1 | 98.74 | $^1$H NMR (400 MHz, DMSO-$d_6$) δ 10.95 (s, 1H), 8.99 (s, 1H), 8.71 (d, J = 5.6 Hz, 1H), 8.44 (s, 1H), 8.31-8.24 (m, 3H), 8.11 (t, J = 7.2 Hz, 2H), 7.18 (s, 1H). |

Example 2

Synthesis of Compound 29

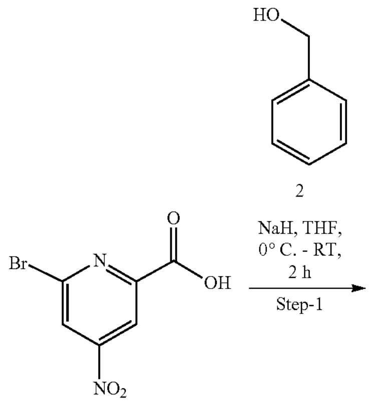

2

1

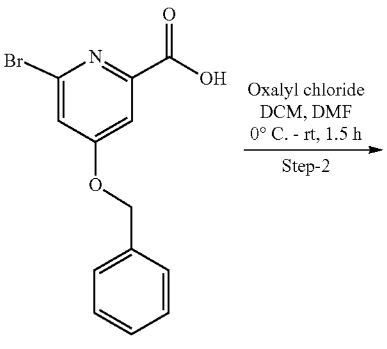

3

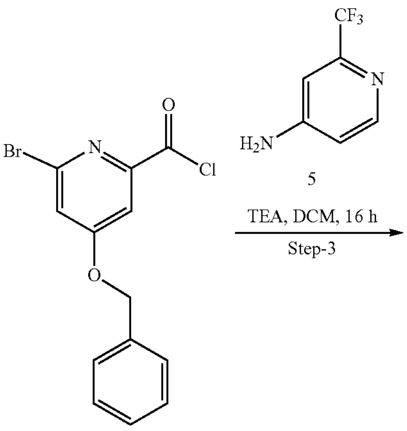

5

4

-continued

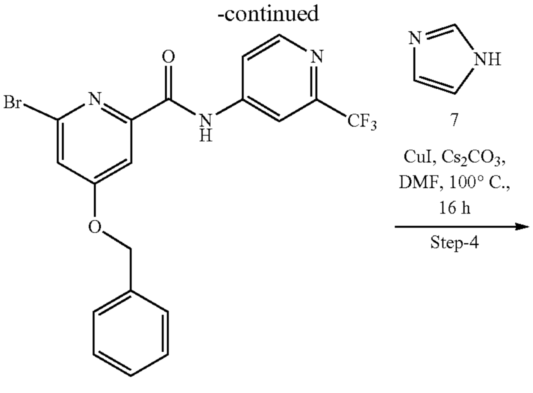

7

6

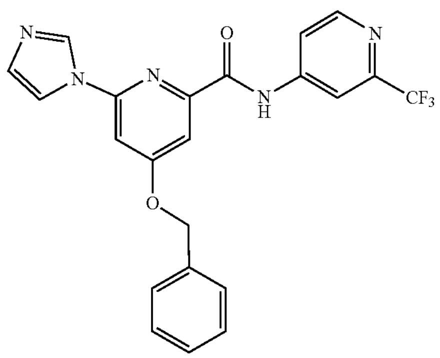

Compound 29

Step-1: 4-(benzyloxy)-6-bromopicolinic acid

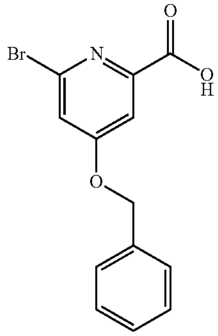

To a stirred suspension of sodium hydride (66.6 mg, 2.77 mmol) in THF was added benzyl alcohol (150 mg, 1.39 mmol) at 0° C. The reaction mixture was stirred at the same temperature for 15 minutes. 6-Bromo-4-nitropyridine-2-carboxylic acid (343 mg, 1.39 mmol) in THF was added to it in a drop-wise manner. The reaction mixture was warmed to RT and stirred for 2 hr. TLC indicated the consumption of starting material. The reaction mixture was acidified with 1 N HCl and extracted into ethyl acetate. The organic layer was dried over sodium sulfate and evaporated to obtain 4-(benzyloxy)-6-bromopyridine-2-carboxylic acid (350 mg, crude) as an oily compound. The crude material was taken for the next step without purification. $^1H$ NMR (400 MHz, DMSO-$d_6$) δ 13.6-13.4 (bs, 1H), 7.59 (s, 1H), 7.53 (s, 1H), 7.45-7.28 (m, 5H), 5.28 (s, 2H). LCMS (ES) m/z=310.2 $[M+H]^+$.

Step-2: 4-(benzyloxy)-6-bromopicolinoyl chloride

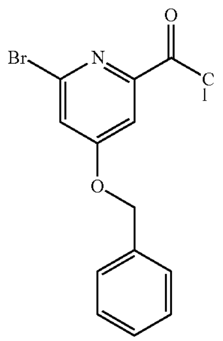 [SMILES: O=C(O)c1cc(OCc2ccccc2)cc(Br)n1]

To a stirred solution of 4-(benzyloxy)-6-bromopyridine-2-carboxylic acid (350 mg, 1.14 mmol) in DCM (10 mL) was added 0.1 mL DMF and oxalyl chloride (292 μL, 3.41 mmol) at 0° C. The reaction mixture was stirred for 1.5 h at RT. The reaction was monitored by TLC. The reaction mixture was completely concentrated to get yellow crude material which was taken into the next step without purification.

Step 3: -(benzyloxy)-6-bromo-N-(2-(trifluoromethyl)pyridin-4-yl)picolinamide

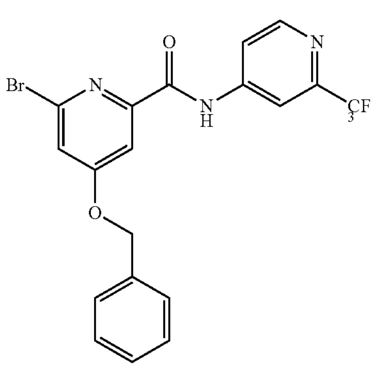 [SMILES: O=C(Nc1ccnc(C(F)(F)F)c1)c1cc(OCc2ccccc2)cc(Br)n1]

To a stirred solution of crude 4-(benzyloxy)-6-bromopyridine-2-carbonyl chloride (350 mg, 1.07 mmol) in DCM was added triethylamine (3.01 μL, 2.14 mmol) at 0° C. 2-(trifluoromethyl)pyridin-4-amine (174 mg, 1.07 mmol) in DCM was added to this solution in a dropwise manner. The reaction mixture was gradually allowed to warm to RT and stirred for 16 hr at which time the reaction mixture was treated with water and extracted in DCM. The organic layer was dried over sodium sulfate and evaporated to obtain crude material that was purified Combiflash column chromatography using ethyl acetate-hexane gradient. The required product eluted at about 30% ethyl acetate-hexane. Pure fractions were collected and evaporated to obtain pure 4-(benzyloxy)-6-bromo-N-[3-(trifluoromethyl)phenyl]pyridine-2-carboxamide (170 mg, 35.2%) as an off-white solid. $^1$H NMR (400 MHz, $CDCl_3$) δ 9.98 (s, 1H), 8.68-8.67 (m, 1H), 8.10 (s, 1H), 7.89-7.84 (m, 3H), 7.42 (s, 5H), 5.21 (s, 2H). LCMS (ES) m/z=452.0 $[M+H]^+$.

Step-4:4-(benzyloxy)-6-(1H-imidazol-1-yl)-N-(2-(trifluoromethyl) pyridin-4-yl) picolinamide

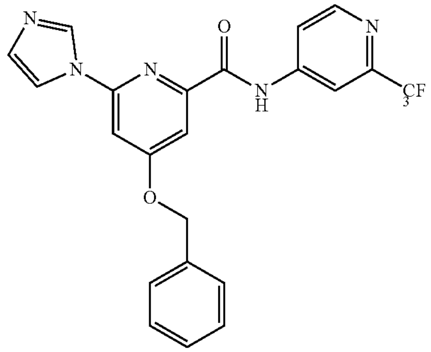 [SMILES: O=C(Nc1ccnc(C(F)(F)F)c1)c1cc(OCc2ccccc2)cc(-n2ccnc2)n1]

To a stirred solution of 4-(benzyloxy)-6-bromo-N-[2-(trifluoromethyl)pyridin-4-yl]pyridine-2-carboxamide (170 mg, 0.38 mmol) in DMF (2 mL) was added 1H-imidazole (38.4 mg, 0.57 mmol), copper iodide (15 mg, 0.075 mmol) and cesium carbonate (245 mg, 0.75 mmol). The reaction mixture was heated to 100° C. for 16 hr. The reaction mixture was cooled to RT and the crude was washed with water and extracted into ethyl acetate. The organic layer was dried over sodium sulfate and evaporated to obtain crude which was purified by Combiflash column chromatography using MeOH-DCM gradient. The target compound eluted out at around 5% MeOH-DCM. The pure fractions were collected and evaporated to obtain 4-(benzyloxy)-6-(1H-imidazol-1-yl)-N-[2-(trifluoromethyl)pyridin-4-yl]pyridine-2-carboxamide (55.0 mg, 33%) as an off-white solid.

Table 2 below shows characterization data for additional compounds of Formula I prepared as described above.

TABLE 2
(Compounds 29- 34)
| Compound | Structure | LCMS (M + H) | HPLC purity (%) | 1H NMR |
|---|---|---|---|---|
| 29 | 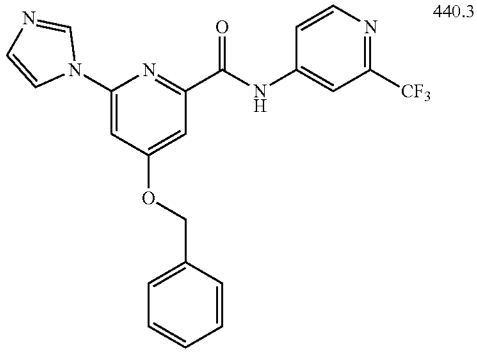 | 440.3 | 99.09 | $^{1}H$ NMR (400 MHz, DMSO-$d_6$) δ 10.91 (s, 1H), 8.99 (s, 1H), 8.72 - 8.70 (m, 1H), 8.44 (s, 1H), 8.31 - 8.24 (m, 2H), 7.76 (s, 1H), 7.69 (s, 1H), 7.52 - 7.50 (m, 2H), 7.44 - 7.37 (m, 3H), 7.16 (s, 1H), 5.40 (s, 2H). |
| 30 | 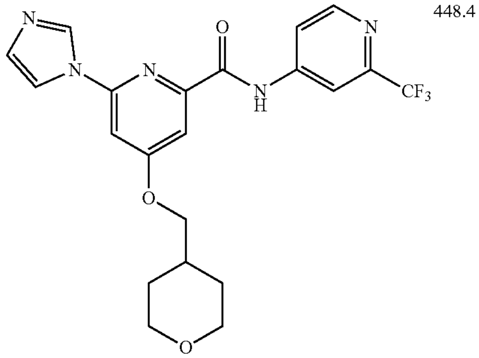 | 448.4 | 99.81 | $^{1}H$ NMR (400 MHz, DMSO-$d_6$) δ 10.90 (s, 1H), 8.98 (s, 1H), 8.71 (d, J = 5.6 Hz, 1H), 8.43 (s, 1H), 8.32 (s, 1H), 8.25 (d, J = 4.8 Hz, 1H), 7.65 (s, 1H), 7.60 (s, 1H), 7.15 (s, 1H), 4.14 (d, J = 6.8 Hz, 2H), 3.89 - 3.87 (m, 2H), 3.36 - 3.34 (m, 2H), 2.11 - 2.07 (m, 1H), 1.69 (m, J = 12.8 Hz, 2H), 1.41 - 1.32 (m, 2H). |
| 31 | 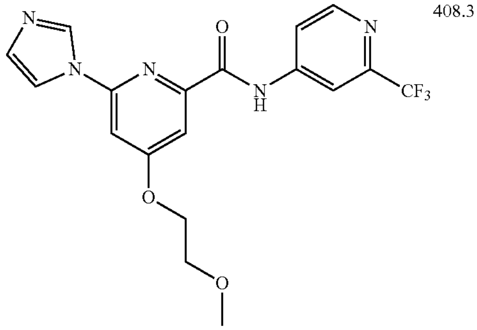 | 408.3 | 99.89 | $^{1}H$ NMR (400 MHz, DMSO-$d_6$) δ 10.90 (s, 1H), 8.98 (s, 1H), 8.71 (d, J = 3.9 Hz, 1H), 8.43 (s, 1H), 8.32 (s, 1H), 8.25 (d, J = 4.0 Hz, 1H), 7.68 (s, 1H), 7.61 (s, 1H), 7.15 (s, 1H), 4.44 - 4.40 (m, 2H), 3.74 - 3.70 (m, 2H), 3.31 (s, 3H). |
| 32 | 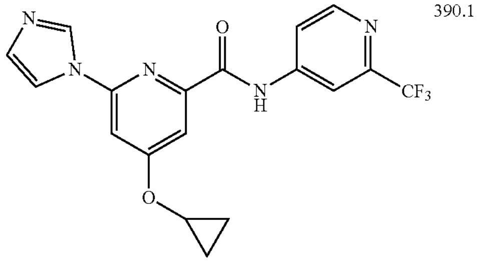 | 390.1 | 99.27 | $^{1}H$ NMR (400 MHz, DMSO-$d_6$) δ 10.92 (s, 1H), 8.98 (s, 1H), 8.71 (d, J = 5.6 Hz, 1H), 8.44 (s, 1H), 8.30 (s, 1H), 8.25 (d, J = 4.4 Hz, 1H), 7.77 (s, 1H), 7.72 (s, 1H), 7.15 (s, 1H), 4.25 - 4.20 (m, 1H), 0.93 - 0.91 (m, 2H), 0.84 - 0.78 (m, 2H). |

TABLE 2-continued
(Compounds 29- 34)
| Compound | Structure | LCMS (M + H) | HPLC purity (%) | 1H NMR |
|---|---|---|---|---|
| 33 | 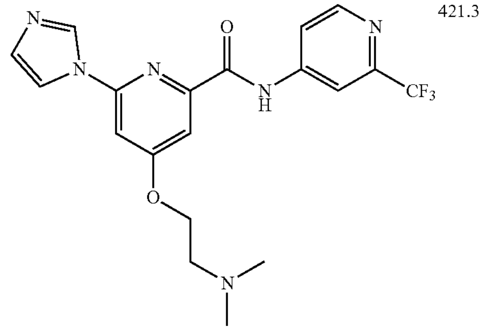 | 421.3 | 98.17 | $^1$H NMR (400 MHz, DMSO-$d_6$) δ 10.89 (s, 1H), 8.97 (s, 1H), 8.71 (s, 1H), 8.43 (s, 1H), 8.31 (s, 1H), 8.24 (s, 1H), 7.65 (s, 1H), 7.59 (s, 1H), 7.14 (s, 1H), 4.35 - 4.30 (m, 2H), 2.74 - 2.70 (m, 2H), 2.24 (s, 6H). |
| 34 | 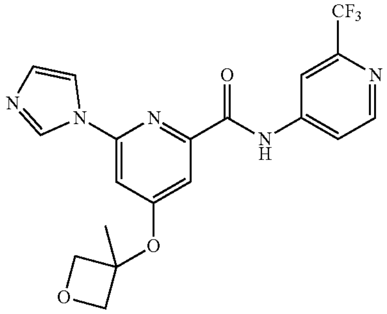 [SMILES: CC1(Oc2cc(C(=O)Nc3ccnc(C(F)(F)F)c3)nc(-n3ccnc3)c2)COC1] | 420.1 | 99.0 | $^1$H NMR (400 MHz, DMSO-$d_6$) δ $^1$H NMR (400 MHz, DMSO-$d_6$) δ 10.92 (s, 1H), 8.98 (s, 1H), 8.71 (d, J = 5.6 Hz, 1H), 8.45 (s, 1H), 8.32 (s, 1H), 8.23 (d, J = 4.8 Hz, 1H), 7.35 (s, 1H), 7.23 (s, 1H), 7.15 (s, 1H), 4.81 (d, J = 6.8 Hz, 2H), 4.73 (d, J = 7.2 Hz, 2H), 1.77 (s, 3H). |
Example 3
Synthesis of Compound 35
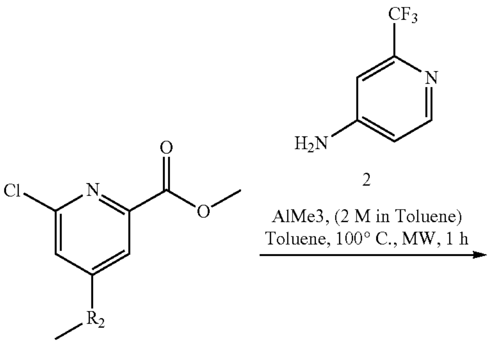
1
-continued
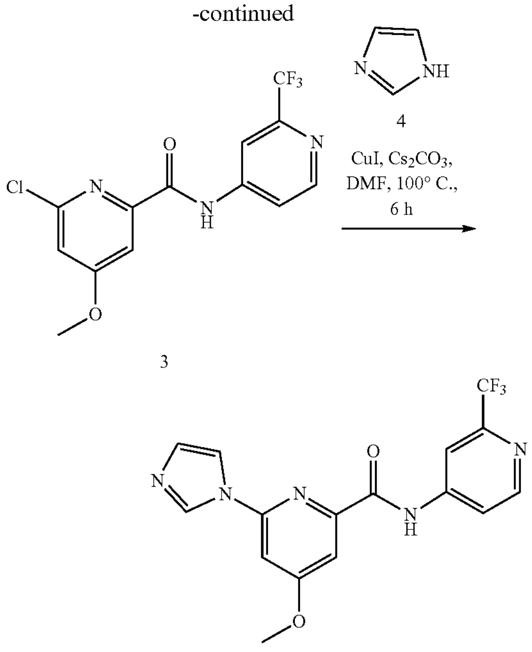
Compound 35

Step-1: 6-chloro-4-methoxy-N-(2-(trifluoromethyl) pyridin-4-yl)picolinamide

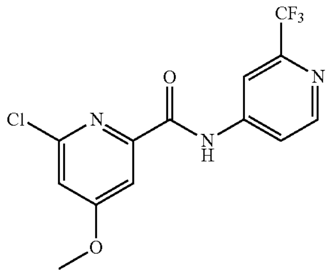 [SMILES: COc1cc(Cl)nc(C(=O)Nc2ccnc(C(F)(F)F)c2)c1]

To a solution of methyl 6-chloro-4-methoxypyridine-2-carboxylate (1.40 g, 6.94 mmol) dissolved in toluene was added 2-(trifluoromethyl)pyridin-4-amine (901 mg, 5.56 mmol) and trimethylaluminum (10.4 mL, 20.8 mmol). The resulting mixture was stirred on CEM® microwave (CEM Corporation, 3100 Smith Farm Road, Matthews, NC 28106) at 100° C. for 1 hr. The reaction mixture was then cooled to ambient temperature and quenched with water and extracted with ethyl acetate. The organic layer was dried over sodium sulfate and evaporated to obtain crude which was purified by Combiflash column chromatography using ethyl acetate-hexane gradient. The required product eluted at around 30% ethyl acetate-hexanes. The pure fractions were collected and evaporated to obtain 6-chloro-4-methoxy-N-[2-(trifluoromethyl)pyridin-4-yl]pyridine-2-carboxamide (1.2 g, 52% yield) as an off-white solid. $^1H$ NMR (400 MHz, DMSO-$d_6$) δ 11.11 (s, 1H), 8.68-8.67 (m, 1H), 8.45 (s, 1H), 8.21-8.20 (m, 1H), 7.63 (s, 1H), 7.43 (s, 1H), 3.96 (s, 3H). LCMS (ES) m/z=332.2 $[M+H]^+$.

Step-2: 6-(1H-imidazol-1-yl)-4-methoxy-N-(2-(trifluoromethyl) pyridin-4-yl)picolinamide

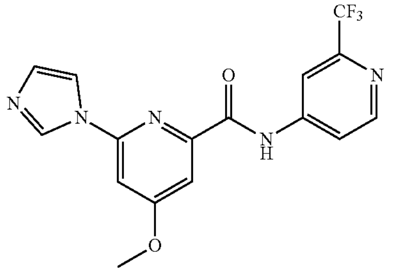 [SMILES: COc1cc(C(=O)Nc2ccnc(C(F)(F)F)c2)nc(-n2ccnc2)c1]

To a solution of 6-chloro-4-methoxy-N-[2-(trifluoromethyl)pyridin-4-yl]pyridine-2-carboxamide (1.20 g, 3.62 mmol) in DMF (10.0 mL) was added copper iodide (230 mg, 0.724 mmol), cesium carbonate (1.41 g, 4.34 mmol) and 1H-imidazole (369 mg, 5.43 mmol). The reaction mixture was heated to 100° C. for 6 h. The reaction mixture was cooled to RT, ice-cold water was added and extracted with ethyl acetate. The organic layer was dried over sodium sulfate and evaporated under reduced pressure to obtain crude material which was purified by Combiflash column chromatography using MeOH-DCM gradient. The required product eluted at about 5% MeOH: DCM. The pure fractions were evaporated to afford 6-(1H-imidazol-1-yl)-4-methoxy-N-[2-(trifluoromethyl)pyridin-4-yl]pyridine-2-carboxamide (0.95 g, 72% yield) as an off-white solid.

Table 3 below shows characterization data for additional compounds of Formula I prepared by the method shown above.

TABLE 3

(Compounds 35-36)

| Compound | Structure | LCMS (M + H) | HPLC purity (%) | 1H NMR |
|---|---|---|---|---|
| 35 | 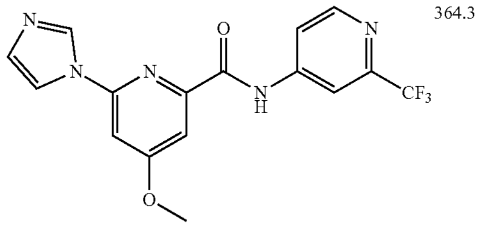 | 364.3 | 99.87 | $^1H$ NMR (400 MHz, DMSO-$d_6$) δ 10.90 (s, 1H), 8.99 (s, 1H), 8.71 (t, J = 5.6 Hz, 1H), 8.44 (s, 1H), 8.33 (s, 1H), 8.25 (t, J = 4.4 Hz, 1H), 7.64 - 7.60 (m, 2H), 7.16 (s, 1H), 4.01 (s, 3H). |
| 36 | 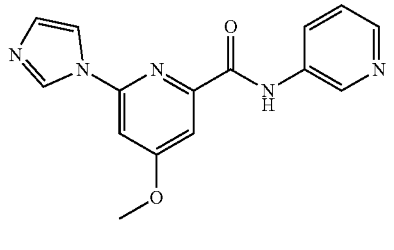 [SMILES: COc1cc(C(=O)Nc2cccnc2)nc(-n2ccnc2)c1] | 296.3 | 99.98 | $^1H$ NMR (400 MHz, DMSO-$d_6$) δ 10.58 (s, 1H), 8.99 (s, 2H), 8.36 - 8.32 (m, 2H), 8.23 (d, J = 8.4 Hz, 1H), 7.59 (d, J= 8.8 Hz, 2H), 7.44 - 7.41 (m, 1H), 7.14 (s, 1H), 4.01 (s, 3H). |

Example 4

Synthesis of Compound 37

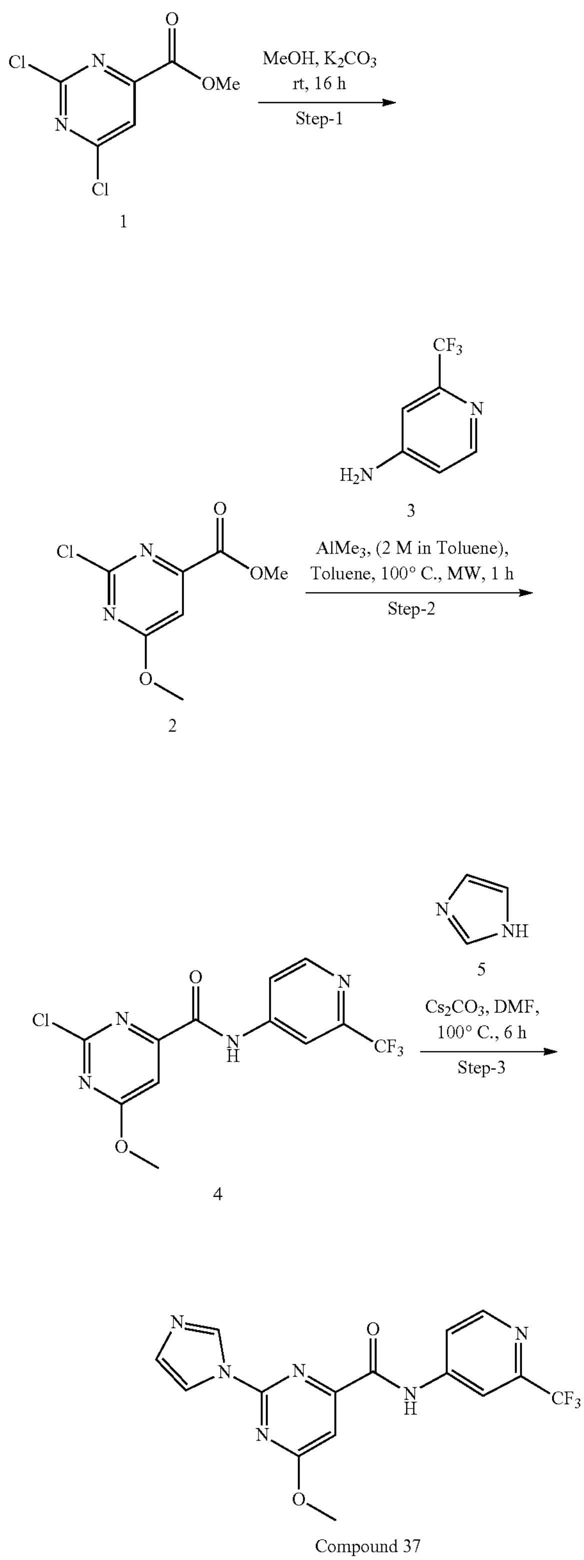

Step-1: methyl 2-chloro-6-methoxypyrimidine-4-carboxylate

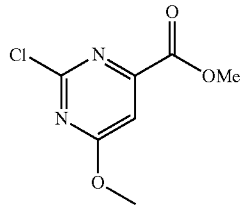

To a solution of methyl 2,6-dichloropyrimidine-4-carboxylate (600 mg, 2.90 mmol) in methanol (12.0 mL) was added potassium carbonate (401 mg, 2.90 mmol) and the reaction mixture was stirred at RT for 16 hr. The solvent was completely evaporated under reduced pressure and water was added to it. The crude was extracted with ethyl acetate. The organic layer was dried over sodium sulfate and evaporated under reduced pressure to obtain crude material which was purified by Combiflash column chromatography using an ethyl acetate-hexane gradient. The target compound eluted at about 25% ethyl acetate-hexane. The pure fractions were collected and evaporated to afford methyl 2-chloro-6-methoxypyrimidine-4-carboxylate (0.5 g, 85% yield) as an off-white solid. $^1$H NMR (400 MHz, DMSO-$d_6$) δ 7.42 (s, 1H), 3.92 (s, 3H), 3.88 (s, 3H). LCMS (ES) m/z=203.0 $[M+H]^+$.

Step-2:2-chloro-6-methoxy-N-(2-(trifluoromethyl) pyridin-4-yl)pyrimidine-4-carboxamide

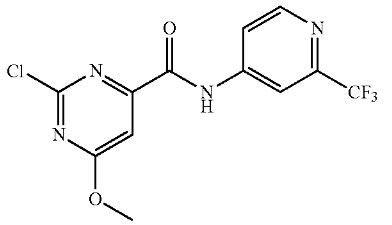 [SMILES: COc1cc(C(=O)Nc2ccnc(C(F)(F)F)c2)nc(Cl)n1]

To a solution of methyl 2-chloro-6-methoxypyrimidine-4-carboxylate (450 mg, 2.22 mmol) in toluene was added 2-(trifluoromethyl)pyridin-4-amine (288 mg, 1.78 mmol). The stirred solution was treated with a 2M solution of trimethyl aluminum in toluene (2.22 mL, 4.44 mmol). The resulting mixture was stirred in CEM microwave at 100° C. for 1 hr. The reaction mixture was cooled to RT, quenched with water and extracted with ethyl acetate. The organic layer was dried over sodium sulfate and evaporated under reduced pressure to obtain crude which was purified by Combiflash column chromatography using ethyl acetate-hexane gradient. The target compound eluted out at about 20% ethyl acetate-hexane. The pure fractions were collected and evaporated to afford 2-chloro-6-methoxy-N-[2-(trifluoromethyl)pyridin-4-yl]pyrimidine-4-carboxamide (0.035 g, 47% yield) as an off-white solid. $^1$H NMR (400 MHz, DMSO-$d_6$) δ 11.28 (s, 1H), 8.70-8.68 (m, 1H), 8.43 (s, 1H), 8.20-8.19 (m, 1H), 7.50 (s, 1H), 4.02 (s, 3H). LCMS (ES) m/z=333.0 $[M+H]^+$.

Step-3:2-(1H-imidazol-1-yl)-6-methoxy-N-(2-(trifluoromethyl)pyridin-4-yl) pyrimidine-4-carboxamide

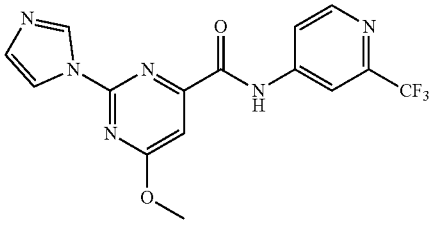

To a stirred solution of 2-chloro-6-methoxy-N-[2-(trifluoromethyl)pyridin-4-yl]pyrimidine-4-carboxamide (300 mg, 0.902 mmol) in DMF (5 mL) was added copper iodide (57.2 mg, 0.180 mmol), cesium carbonate (353 mg, 1.08 mmol), 1H-imidazole (92.1 mg, 1.35 mmol) and heated the reaction mixture to 100° C. for 6 h. The reaction mixture was cooled to RT, added ice cold water and extracted with ethyl acetate. The organic layer was dried over sodium sulfate and evaporated under reduced pressure to obtain crude material which was purified by Combiflash column chromatography using MeOH-DCM gradient. The product eluted at about 5% MeOH-DCM. The pure fractions were collected and evaporated to afford 2-(1H-imidazol-1-yl)-6-methoxy-N-[2-(trifluoromethyl) pyridin-4-yl]pyrimidine-4-carboxamide (0.11 g, 35% yield) as an off-white solid.

Table 4 lists characterization data for compounds of Formula I prepared by the method of Example 4.

TABLE 4

Compounds 37-41)

| Compound | Structure | LCMS (M + H) | HPLC purity (%) | 1H NMR |
|---|---|---|---|---|
| 37 | 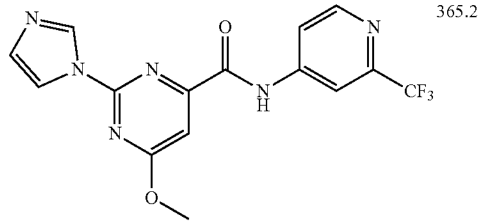 | 365.2 | 99.32 | $^1$H NMR (400 MHz, DMSO-$d_6$) δ 10.99 (s, 1H), 8.99 (s, 1H), 8.74 - 8.73 (m, 1H), 8.42 (s, 1H), 8.27 - 8.23 (m, 2H), 7.39 (s, 1H), 7.18 (s, 1H), 4.11 (s, 3H). |
| 38 | 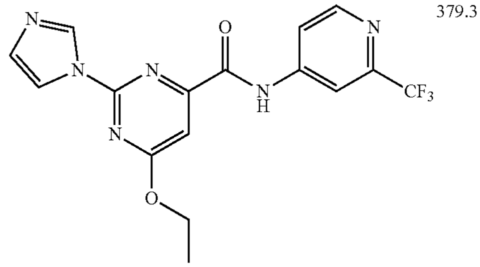 | 379.3 | 99.37 | $^1$H NMR (400 MHz, DMSO-$d_6$) δ 10.98 (s, 1H), 8.97 (s, 1H), 8.74 - 8.73 (m, 1H), 8.42 (s, 1H), 8.27 - 8.25 (m, 2H), 7.35 (s, 1H), 7.17 (s, 1H), 4.58 (q, J = 7.6 Hz, 2H), 1.39 (t, J = 7.2 Hz, 3H). |
| 39 | 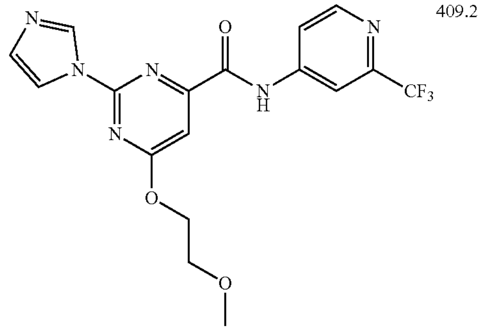 | 409.2 | 98.84 | $^1$H NMR (400 MHz, DMSO-$d_6$) δ 10.99 (s, 1H), 8.98 (s, 1H), 8.74 - 8.73 (m, 1H), 8.42 (s, 1H), 8.27 - 8.13 (m, 2H), 7.39 (s, 1H), 7.18 (s, 1H), 4.68 - 4.66 (m, 2H), 3.74 - 3.70 (m, 2H), 3.30 (s, 3H). |
| 40 | 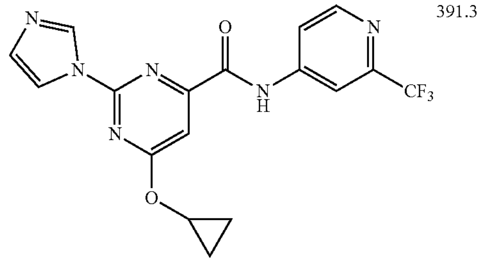 | 391.3 | 98.1 | $^1$H NMR (400 MHz, DMSO-$d_6$) δ 11.02 (s, 1H), 8.97 (s, 1H), 8.75 - 8.74 (m, 1H), 8.43 (s, 1H), 8.25 (s, 2H), 7.47 (s, 1H), 7.18 (s, 1H), 4.56 - 4.50 (m, 1H), 0.92 - 0.84 (m, 4H). |

TABLE 4-continued

Compounds 37-41)

| Compound | Structure | LCMS (M + H) | HPLC purity (%) | 1H NMR |
|---|---|---|---|---|
| 41 | 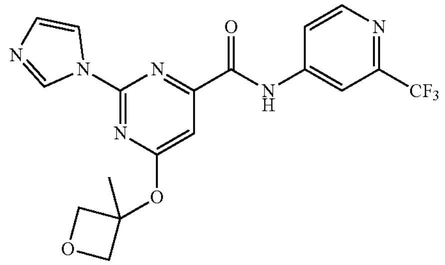 [SMILES: CC1(Oc2cc(C(=O)Nc3ccnc(C(F)(F)F)c3)nc(-n3ccnc3)n2)COC1] | 421.3 | 99.75 | $^1$H NMR (400 MHz, DMSO-$d_6$) δ 11.0 (s, 1H), 8.89 (s, 1H), 8.74 (d, J = 5.2 Hz, 1H), 8.42 (s, 1H), 8.23 (d, J = 4.4 Hz, 1H), 8.16 (s, 1H), 7.40 (s, 1H), 7.18 (s, 1H), 4.86 (d, J = 6.8 Hz, 2H), 4.70 (d, J = 7.2 Hz, 2H), 1.84 (s, 3H). |

Example 5

Synthesis of Compound 42

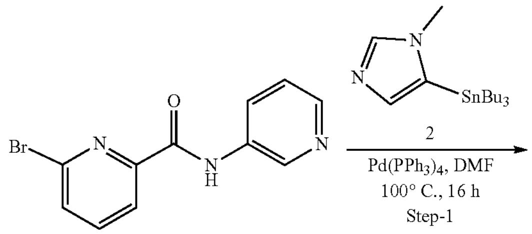

1

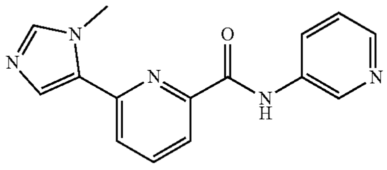

Compound 42

Step-1: 6-(1-methyl-1H-imidazol-5-yl)-N-(pyridin-3-yl)picolinamide

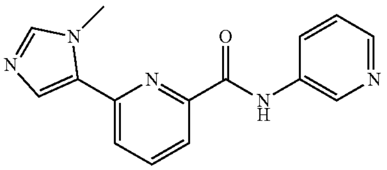 [SMILES: Cn1cncc1-c1cccc(C(=O)Nc2cccnc2)n1]

To a solution of 6-bromo-N-(pyridin-3-yl)picolinamide (0.15 g, 0.539 mmol) in DMF (5 mL) was added 1-methyl-5-(tributylstannyl)-1H-imidazole (0.2 mL, 0.647 mmol) followed by tetrakis(triphenylphosphine)palladium(0) (0.031 g, 0.027 mmol). The reaction mixture was purged with Nitrogen gas for 5 minutes. The reaction vial was sealed and heated to 100° C. for 16 h. The progress of the reaction was monitored by TLC. The reaction mixture was cooled to RT and water was added. The reaction mixture was extracted in ethyl acetate, dried over sodium sulfate and evaporated off to obtain crude which was purified over silica gel flash column chromatography. The compound eluted out in 4% MeOH: DCM. The pure fractions were collected and evaporated to afford 6-(1-methyl-1H-imidazol-5-yl)-N-(pyridin-3-yl)pyridine-2-carboxamide (0.075 g, 50% yield) as an off-white solid.

$^1$H NMR (400 MHz, DMSO-$d_6$) δ 10.48 (s, 1H), 8.99 (s, 1H), 8.33-8.26 (m, 2H), 8.09-8.05 (m, 1H), 7.99-7.97 (m, 2H), 7.83 (s, 1H), 7.66 (s, 1H), 7.42-7.39 (m, 1H), 4.06 (s, 3H).

Provided in Table 5 are characterization data for compounds of Formula I prepared by the method shown in Example 5.

TABLE 5

(Compounds 42 - 48)

| Compound | Structure | LCMS (M + H) | HPLC purity (%) | 1H NMR |
|---|---|---|---|---|
| 42 | 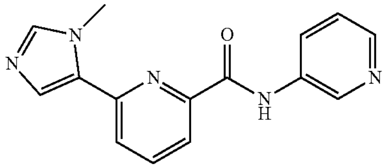 [SMILES: Cn1cncc1-c1cccc(C(=O)Nc2cccnc2)n1] | 280.3 | 99.65 | $^1$H NMR (400 MHz, DMSO-$d_6$) δ 10.48 (s, 1H), 8.99 (s, 1H), 8.33 - 8.26 (m, 2H), 8.09 - 8.05 (m, 1H), 7.99 - 7.97 (m, 2H), 7.83 (s, 1H), 7.66 (s, 1H), 7.42 - 7.39 (m, 1H), 4.06 (s, 3H). |
| 43 | 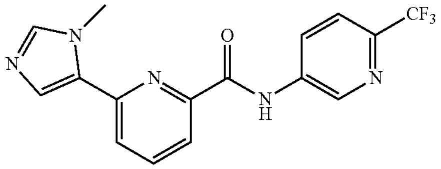 [SMILES: Cn1cncc1-c1cccc(C(=O)Nc2ccc(C(F)(F)F)nc2)n1] | 348.3 | 99.11 | $^1$H NMR (400 MHz, DMSO-$d_6$) δ 10.84 (s, 1H), 9.18 (s, 1H), 8.58 (d, J = 6.8 Hz, 1H), 8.11 - 8.07 (m, 1H), 8.02 - 8.0 (m, 2H), 7.94 (d, J = 8.8 Hz, 1H), 7.85 (m, 1H), 7.66 (m, 1H), 4.05 (s, 3H). |
| 44 | 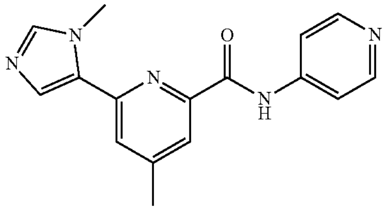 [SMILES: Cc1cc(C(=O)Nc2ccncc2)nc(-c2cncn2C)c1] | 294.3 | 99.58 | $^1$H NMR (400 MHz, DMSO-$d_6$) δ 10.58 (s, 1H), 8.49 - 8.48 (m, 2H), 7.86 - 7.82 (m, 5H), 7.63 (s, 1H), 4.04 (s, 3H), 2.46 (s, 3H). |
| 45 | 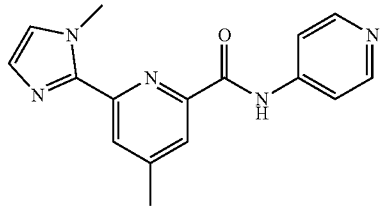 [SMILES: Cc1cc(C(=O)Nc2ccncc2)nc(-c2nccn2C)c1] | 294.3 | 99.66 | $^1$H NMR (400 MHz, DMSO-$d_6$) δ 10.55 (s, 1H), 8.49 - 8.48 (m, 2H), 7.85 - 7.81 (m, 5H), 7.62 (s, 1H), 4.04 (s, 3H), 2.46 (s, 3H). |
| 46 | 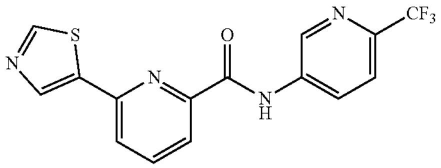 [SMILES: O=C(Nc1ccc(C(F)(F)F)nc1)c1cccc(-c2cncs2)n1] | 351.2 | 99.42 | $^1$H NMR (400 MHz, DMSO-$d_6$) δ 10.86 (s, 1H), 9.25 (s, 1H), 9.20 (s, 1H), 8.87 (s, 1H), 8.58 (d, J = 8.4 Hz, 1H), 8.21 (d, J = 7.2 Hz, 1H), 8.15 (t, J = 7.6 Hz, 1H), 8.07 (d, J = 7.2 Hz, 1H), 7.96 (d, J = 8.4 Hz, 1H). |
| 47 | 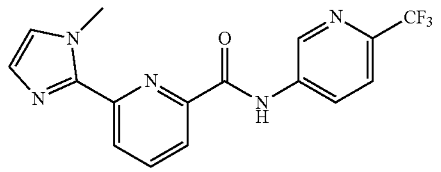 [SMILES: Cn1ccnc1-c1cccc(C(=O)Nc2ccc(C(F)(F)F)nc2)n1] | 348.3 | 98.66 | $^1$H NMR (400 MHz, DMSO-$d_6$) δ 10.82 (s, 1H), 9.18 (s, 1H), 8.58 (d, J = 8.8 Hz, 1H), 8.09 (t, J = 8.0 Hz, 1H), 8.02 - 8.0 (m, 2H), 7.93 (d, J = 8.8 Hz, 1H), 7.84 (s, 1H), 7.66 (s, 1H), 4.05 (s, 3H). |
| 48 | 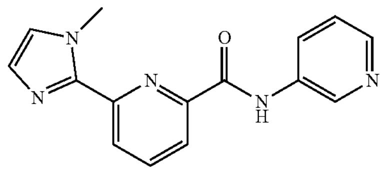 [SMILES: Cn1ccnc1-c1cccc(C(=O)Nc2cccnc2)n1] | 280.3 | 99.78 | $^1$H NMR (400 MHz, DMSO-$d_6$) δ 10.45 (s, 1H), 8.99 - 8.98 (m, 1H), 8.33 - 8.32 (m, 1H), 8.27 (d, J = 7.6 Hz, 1H), 8.08 - 8.04 (m, 1H), 7.98 (d, J = 7.6 Hz, 2H), 7.82 (s, 1H), 7.65 (s, 1H), 7.42 - 7.38 (m, 1H), 4.05 (s, 3H). |

Example 6

Synthesis of Compound 49

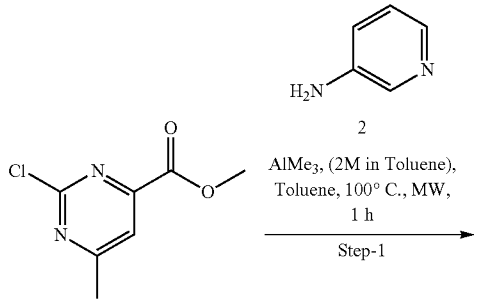

2

1

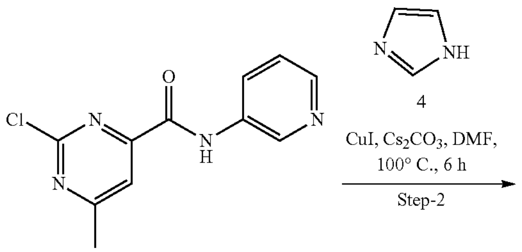

4

3

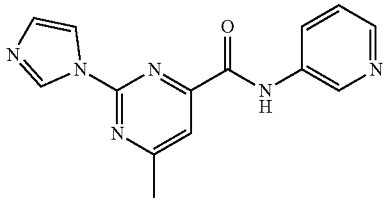

Compound 49

Step-1: 2-chloro-6-methyl-N-(pyridin-3-yl)pyrimidine-4-carboxamide

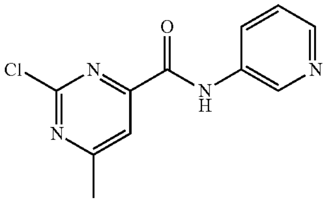 [SMILES: Cc1cc(C(=O)Nc2cccnc2)nc(Cl)n1]

To a solution of methyl 2-chloro-6-methylpyrimidine-4-carboxylate (250 mg, 1.34 mmol) in toluene was added pyridin-3-amine (126 mg, 1.34 mmol) and 2M trimethylaluminum solution in toluene (1.34 mL, 2.68 mmol). The reaction mixture was stirred in a CEM microwave at 100° C. for 1 hr. The reaction mixture was cooled to RT, quenched with water then extracted with ethyl acetate. The organic layer was dried over sodium sulfate and evaporated under reduced pressure to obtain crude material which was purified by Combiflash column chromatography using ethyl acetate-hexane gradient. The target compound eluted at about 50% ethyl acetate-hexane. The pure fractions were collected and evaporated to afford 2-chloro-6-methyl-N-(pyridin-3-yl)pyrimidine-4-carboxamide (0.20 g, 60% yield) as a pale yellow solid. $^1$H NMR (400 MHz, DMSO-$d_6$) δ 10.90 (s, 1H), 9.0 (s, 1H), 8.36-8.35 (m, 1H), 8.25-8.23 (m, 1H), 8.04 (s, 1H), 7.43-7.36 (m, 1H), 2.61 (s, 3H). LCMS(ES) m/z=249.0 $[M+H]^+$.

Step-2:2-(1H-imidazol-1-yl)-6-methyl-N-(pyridin-3-yl)pyrimidine-4-carboxamide

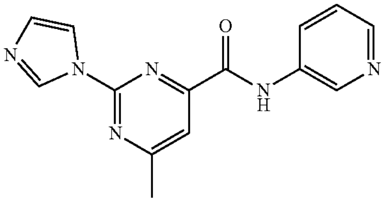

To a stirred solution of 2-chloro-6-methyl-N-(pyridin-3-yl)pyrimidine-4-carboxamide (200 mg, 0.804 mmol) in DMF (5.0 mL) was added copper iodide (51.0 mg, 0.161 mmol), cesium carbonate (314 mg, 0.965 mmol) and 1H-imidazole (82.1 mg, 1.21 mmol). The reaction mixture was heated to 100° C. for 6 h. The reaction mixture was cooled to RT and quenched with ice-cold water, then extracted with ethyl acetate. The organic layer was dried over sodium sulfate and evaporated under reduced pressure to obtain crude material which was purified by Combiflash column chromatography using MeOH-DCM gradient. The target compound eluted at about 5% MeOH-DCM. The pure fractions were evaporated to obtain 6-(1H-imidazol-1-yl)-2-methyl-3-(pyridin-4-yl)-3H,4H-pyrido[3,2-du]pyrimidin-4-one (0.06 g, 27% yield) as an off-white solid.

Provided in Table 6 are characterization data for compounds of Formula I prepared by the method shown in Example 6.

TABLE 6
(Compounds 49 - 51)
| Compound | Structure | LCMS (M + H) | HPLC purity (%) | 1H NMR |
|---|---|---|---|---|
| 49 | 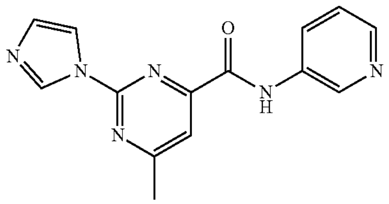 [SMILES: Cc1cc(C(=O)Nc2cccnc2)nc(-n2ccnc2)n1] | 281.3 | 99.93 | $^1$H NMR (400 MHz, DMSO-$d_6$) δ 10.79 (s, 1H), 9.00 (d, J = 11.6 Hz, 2H), 8.40 - 8.39 (m, 1H), 8.25 - 8.24 (m, 2H), 7.95 (s, 1H), 7.48 - 7.45 (m, 1H), 7.18 (s, 1H), 2.67 (s, 3H). |
| 50 | 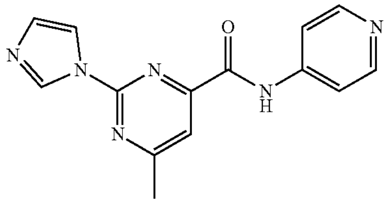 [SMILES: Cc1cc(C(=O)Nc2ccncc2)nc(-n2ccnc2)n1] | 281.3 | 99.78 | $^1$H NMR (400 MHz, DMSO-$d_6$) δ 10.81 (s, 1H), 8.97 (s, 1H), 8.56 - 8.55 (m, 2H), 8.23 (s, 1H), 7.95 - 7.91 (m, 3H), 7.17 (s, 1H), 2.67 (s, 3H). |
| 51 | 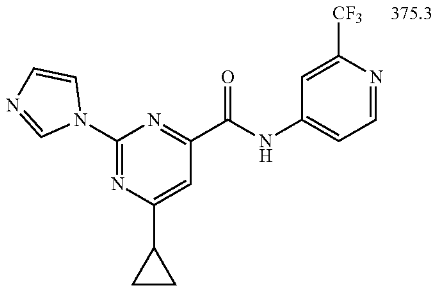 | 375.3 | 98.37 | $^1$H NMR (400 MHz, DMSO-$d_6$) δ 11.04 (s, 1H), 8.94 (s, 1H), 8.75 - 8.73 (m, 1H), 8.42 (s, 1H), 8.26 - 8.21 (m, 2H), 8.02 (s, 1H), 7.16 (s, 1H), 3.30 - 3.1 (m, 1H), 1.25 - 1.22 (m, 4H). |
Example 7
Synthesis of Compound 52
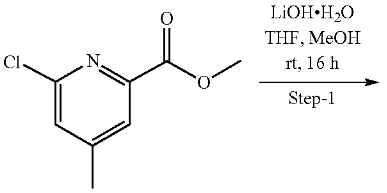
1
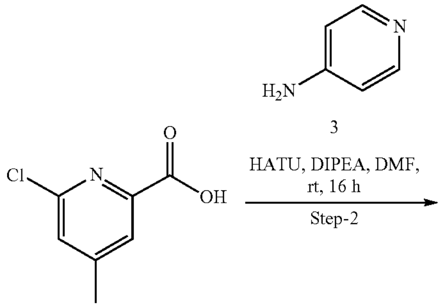
2
-continued
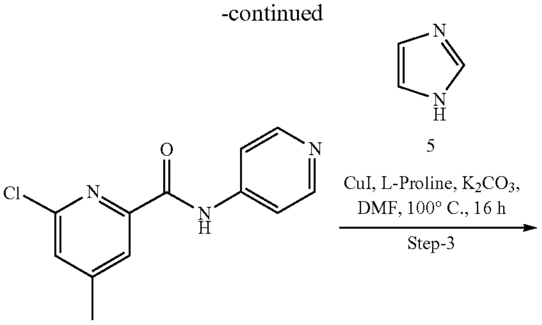
4
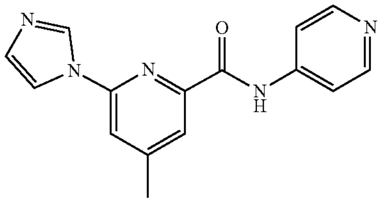
Compound 52

Step-1: 6-chloro-4-methylpicolinic acid

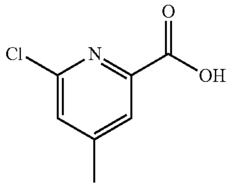

To a stirred solution of methyl 6-chloro-4-methylpyridine-2-carboxylate (2 g, 10.8 mmol) in THF (15 mL), MeOH (15 mL) and water (15 mL) was added lithium hydroxide mono hydrate (0.96 g, 21.6 mmol) and the reaction mixture was allowed to stir at RT for 16 h. Progress of the reaction was monitored by TLC. The solvents were evaporated under reduced pressure to obtain crude material which was treated with water and extracted with ethyl acetate. The aqueous layer was acidified using 1 N HCl to pH about 2 and extracted with ethyl acetate. The organic layer was dried over sodium sulfate, filtered then evaporated under reduced pressure to afford 6-chloro-4-methylpyridine-2-carboxylic acid (1.8 g, 97% yield) as an off-white solid. 1H NMR (400 MHz, DMSO-$d_6$) δ 13.45 (bs, 1H), 7.86 (s, 1H), 7.59 (s, 1H), 2.38 (s, 3H). LCMS (ES) m/z=172.1 $[M+H]^+$.

Step-2: 6-chloro-4-methyl-N-(pyridin-4-yl)picolinamide

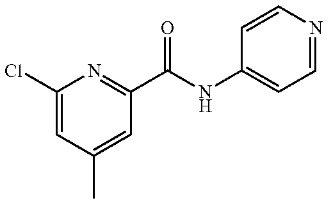 [SMILES: Cc1cc(Cl)nc(C(=O)Nc2ccncc2)c1]

To a stirred solution of 6-chloro-4-methylpyridine-2-carboxylic acid (300 mg, 1.75 mmol) in DMF was added DIPEA (0.968 mL, 5.25 mmol), HATU (0.79 g, 2.10 mmol) and pyridin-4-amine (0.16 g, 1.75 mmol). The reaction mixture was stirred at RT for 16 h. Water was added to the reaction mixture and material was extracted with ethyl acetate. The organic layer was dried over sodium sulfate and evaporated under reduced pressure to obtain crude material which was purified by Combiflash column chromatography using ethyl acetate-hexane gradient. The target compound eluted at about 30% ethyl acetate-hexane. Pure fractions were evaporated to afford 6-chloro-4-methyl-N-(pyridin-4-yl)pyridine-2-carboxamide (0.35 g, 80% yield) as an off-white solid. $^1$H NMR (400 MHz, DMSO-$d_6$) δ 10.64 (s, 1H), 8.48-8.47 (m, 2H), 7.96 (s, 1H), 7.88-7.87 (m, 2H), 7.67 (s, 1H), 2.43 (s, 3H). LCMS (ES) m/z=248.1 $[M+H]^+$.

Step-3: 6-(1H-imidazol-1-yl)-4-methyl-N-(pyridin-4-yl)picolinamide

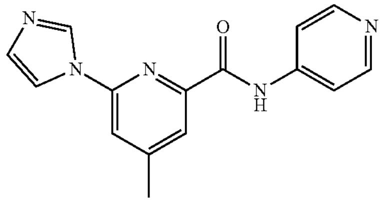 [SMILES: Cc1cc(C(=O)Nc2ccncc2)nc(-n2ccnc2)c1]

To a stirred solution of 6-chloro-4-methyl-N-(pyridin-4-yl)pyridine-2-carboxamide (100 mg, 0.41 mmol) in DMF (1.5 mL) was added copper iodide (25.6 mg, 0.08 mmol), L-proline (18.6 mg, 0.16 mmol), potassium carbonate (112 mg, 0.81 mmol) and 1H-imidazole (41.2 mg, 0.61 mmol). The reaction mixture was heated to 100° C. for 16 h. The reaction mixture was cooled to RT and quenched with water. The crude product was extracted with ethyl acetate, and the organic layer dried over sodium sulfate then evaporated under reduced pressure to obtain crude material which was purified by Combiflash column chromatography using MeOH-DCM gradient. The target compound eluted at about 4% MeOH-DCM. The pure fractions were evaporated to afford 6-(1H-imidazol-1-yl)-4-methyl-N-(pyridin-4-yl)pyridine-2-carboxamide (0.014 g, 12% yield) as an off-white solid.

Provided in Table 7 are characterization data for compounds of Formula I prepared by the method shown in Example 7.

TABLE 7

(Compounds 52-53)

| Compound | Structure | LCMS (M + H) | HPLC purity (%) | 1H NMR |
|---|---|---|---|---|
| 52 | 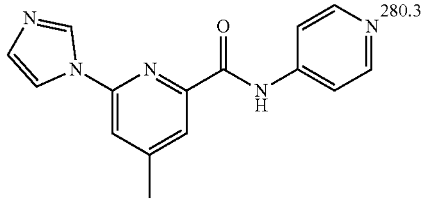 | 280.3 | 99.92 | $^1$H NMR (400 MHz, DMSO-$d_6$) δ 10.64 (s, 1H), 8.96 (s, 1H), 8.52 (d, J = 6.0 Hz, 2H), 8.27 MHz, DMSO-$d_6$) δ 10.64 (s, 1H), 8.96 (s, 1H), 8.52 (d, J = 6.0 Hz, 2H), 8.27 (s, 1H), 7.98 - 7.90 (m, 4H), 7.16 (s, 1H), 2.51 (s, 3H). |

TABLE 7-continued (Compounds 52-53)

| Compound | Structure | LCMS (M + H) | HPLC purity (%) | 1H NMR |
|---|---|---|---|---|
| 53 | 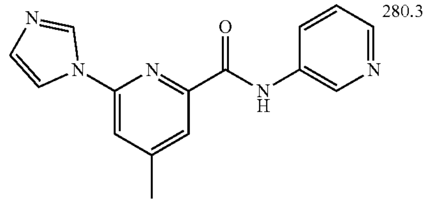 | 280.3 | 98.36 | $^1$H NMR (400 MHz, DMSO-$d_6$) δ 10.58 (s, 1H), 9.01 - 8.96 (m, 2H), 8.35 (d, J = 3.6 Hz, 1H), 8.28 - 8.23 (m, 2H), 7.95 (d, J = 8.4 Hz, 2H), 7.44 - 7.41 (m, 1H), 7.16 (s, 1H), 2.51 (s, 3H). |

Example 8

Synthesis of Compound 54

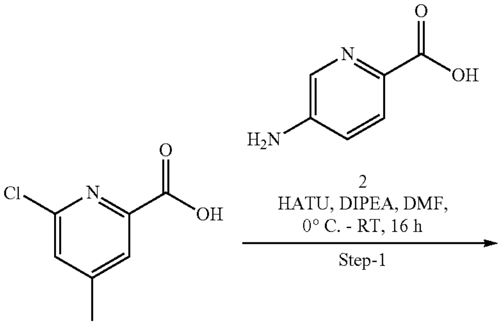

1

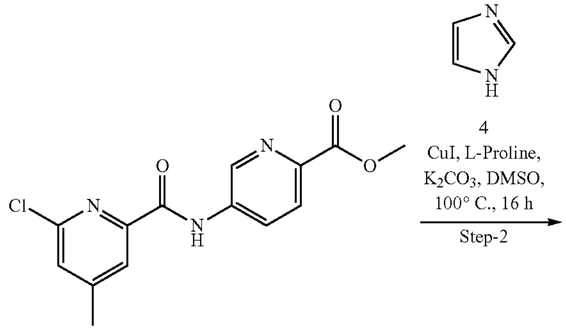

3

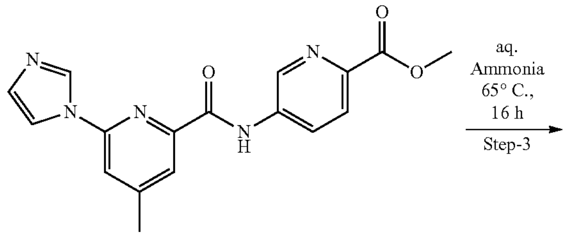

4

-continued

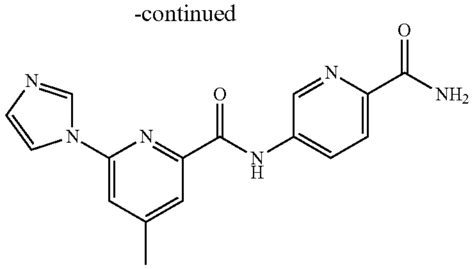

Step1: methyl 5-(6-chloro-4-methylpicolinamido)picolinate

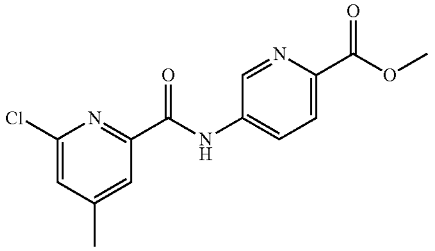 [SMILES: COC(=O)c1ccc(NC(=O)c2cc(C)cc(Cl)n2)cn1]

To a stirred solution of 6-chloro-4-methylpyridine-2-carboxylic acid (0.6 g, 3.5 mmol) in DMF (15 mL) was added methyl 5-aminopyridine-2-carboxylate (0.585 g, 3.85 mmol), HATU (1.6 g, 4.20 mmol), and DIPEA (1.83 mL, 10.5 mmol). The reaction mixture was stirred at RT for 16 hr. The reaction mixture was diluted with ethyl acetate and washed with water. The organic layer was dried over sodium sulfate and evaporated under vacuum to obtain crude material which was purified by Combiflash column chromatography using ethyl acetate-hexane gradient. The target compound eluted at about 60% ethyl acetate-hexanes. The solvent was evaporated to obtain methyl 5-(6-chloro-4-methylpicolinamido)picolinate (600 mg, 56%) as a yellow solid. $^1$H NMR (400 MHz, DMSO-$d_6$) δ 9.94 (s, 1H), 8.92-8.91 (m, 1H), 8.58-8.55 (m, 1H), 8.19 (d, J=8.8 Hz, 1H), 8.05 (s, 1H), 7.38 (s, 1H), 4.01 (s, 3H), 2.39 (s, 3H). LC-MS (ES) m/z=306.1 $[M+H]^+$.

Step 2: methyl 5-(6-(1H-imidazol-1-yl)-4-methylpicolinamido)picolinate

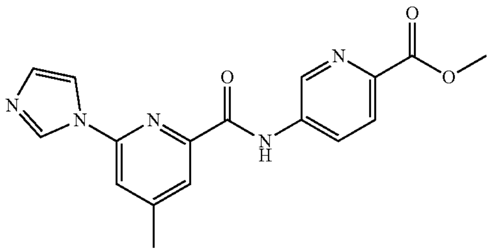 [SMILES: COC(=O)c1ccc(NC(=O)c2cc(C)cc(-n3ccnc3)n2)cn1]

To a stirred solution of methyl 5-(6-chloro-4-methylpyridine-2-amido)pyridine-2-carboxylate (0.6 g, 1.96 mmol) in DMSO (10 mL) was added 1H-imidazole (0.2 g, 2.94 mmol), copper iodide (0.075 g, 0.393 mmol), L-proline (0.0904 g, 0.785 mmol) and potassium carbonate (0.550 g, 3.93 mmol). The reaction mixture was heated to 100° C. for 16 h. The reaction mixture was cooled to RT, diluted with water and extracted with ethyl acetate. The organic layer was dried over sodium sulfate and evaporated under vacuum to obtain crude material which was purified by Combiflash column chromatography using MeOH-DCM gradient. The target compound eluted at about 5% MeOH-DCM. The fractions were evaporated to obtain methyl 5-(6-(1H-imidazol-1-yl)-4-methylpicolinamido)picolinate (0.15 g, 23%) as an off-white solid. $^1$H NMR (400 MHz, DMSO-$d_6$) δ 10.84 (s, 1H), 9.16 (s, 2H), 8.53-8.50 (m, 2H), 8.14-8.12 (m, 2H), 7.99-7.96 (m, 2H), 3.86 (s, 3H), 2.52 (s, 3H). LC-MS (ES) m/z=338.1 $[M+H]^+$.

Step3: N-(6-carbamoylpyridin-3-yl)-6-(1H-imidazol-1-yl)-4-methyl picolinamide

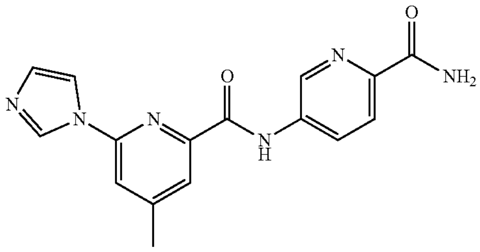 [SMILES: Cc1cc(C(=O)Nc2ccc(C(N)=O)nc2)nc(-n2ccnc2)c1]

A stirred solution of ethyl 4-[6-(1H-imidazol-1-yl)-4-methylpyridine-2-amido]pyridine-2-carboxylate (0.15 g, 0.445 mmol) in 37% aqueous ammonium hydroxide (8 mL) was heated to 65° C. for 16 h. The reaction mixture was cooled to RT and evaporated under vacuum to obtain crude material which was purified by reverse phase HPLC (Column: X-Bridge-C-18 (250 mm×4.6 mm×5 mic); Mobile phase (A): 0.1% Ammonia in water; Mobile phase (B): Acetonitrile; Flow rate: 2.0 mL/min). The pure fractions were evaporated off to obtain N-(6-carbamoylpyridin-3-yl)-6-(1H-imidazol-1-yl)-4-methylpicolinamide (17 mg, 12%) as an off white solid.

Provided in Table 8 are characterization data for compounds of Formula I prepared by the method shown in Example 8.

TABLE 8

(Compounds 54-57)

| Compound | Structure | LCMS (M + H) | HPLC purity (%) | 1H NMR |
|---|---|---|---|---|
| 54 | 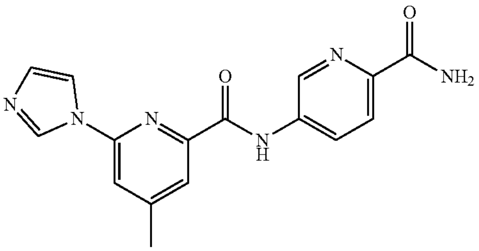 [SMILES: Cc1cc(C(=O)Nc2ccc(C(N)=O)nc2)nc(-n2ccnc2)c1] | 323.1 | 99.48 | $^1$H NMR (400 MHz, DMSO-$d_6$) δ 10.77 (s, 1H), 9.09 (s, 1H), 8.96 (s, 1H), 8.44 (d, J = 6.4 Hz, 1H), 8.28 (s, 1H), 8.08 - 8.04 (m, 2H), 7.96 (d, J = 6.8 Hz, 2H), 7.52 (m, 1H), 7.16 (s, 1H), 2.51 (s, 3H). |
| 55 | 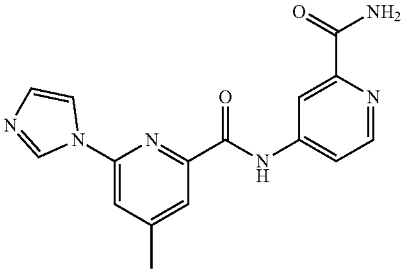 [SMILES: Cc1cc(C(=O)Nc2ccnc(C(N)=O)c2)nc(-n2ccnc2)c1] | 323.3 | 98.05 | $^1$H NMR (400 MHz, DMSO-$d_6$) δ 10.80 (s, 1H), 8.95 (s, 1H), 8.55 (s, 2H), 8.28 (s, 1H), 8.13 - 8.07 (m, 2H), 7.95 (s, 2H), 7.59 (s, 1H), 7.15 (s, 1H), 2.51 (s, 3H) |

TABLE 8-continued (Compounds 54-57)

| Compound | Structure | LCMS (M + H) | HPLC purity (%) | 1H NMR |
|---|---|---|---|---|
| 56 | 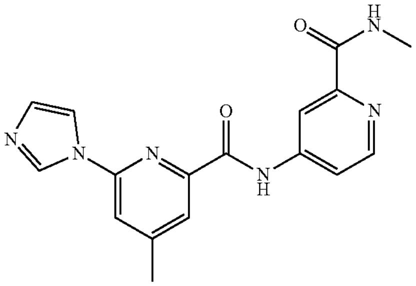 [SMILES: CNC(=O)c1cc(NC(=O)c2cc(C)cc(-n3ccnc3)n2)ccn1] | 337.3 | 98.12 | $^1$H NMR (400 MHz, DMSO-$d_6$) δ 10.82 (s, 1H), 8.99 (s, 1H), 8.77 (d, J = 4.0 Hz, 1H), 8.58 (s, 2H), 8.30 (s, 1H), 8.18 – 8.17 (m, 1H), 7.97 (d, J = 10.4 Hz, 2H), 7.16 (s, 1H), 2.81 (d, J = 4.4 Hz, 3H), 2.51 (s, 3H) |
| 57 | 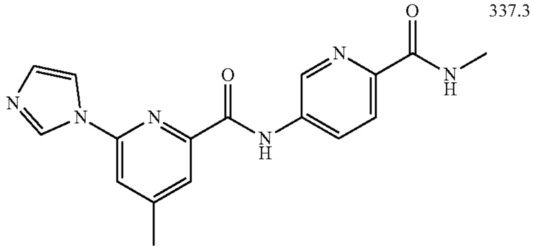 | 337.3 | 98.04 | $^1$H NMR (400 MHz, DMSO-$d_6$) δ 10.77 (s, 1H), 9.09 (s, 1H), 9.0 (s, 1H), 8.69 (s, 1H), 8.46 (d, J = 8.0 Hz, 1H), 8.30 (s, 1H), 8.07 (d, J = 8.4 Hz, 1H), 7.97 (d, J = 9.2 Hz, 2H), 7.19 (s, 1H), 2.81 (d, J = 4.0 Hz, 3H), 2.52 (s, 3H) |

Example 9

Synthesis of Compound 58

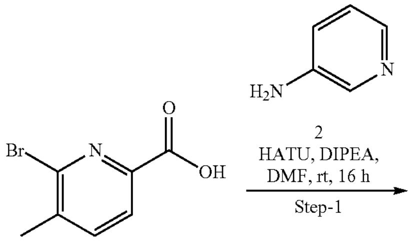

1

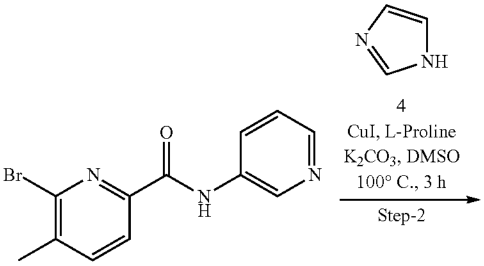

3

-continued

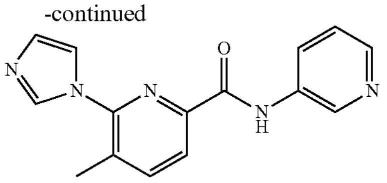

Compound 58

Step-1: 6-bromo-5-methyl-N-(pyridin-3-yl)picolinamide

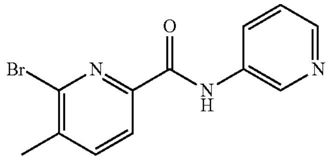 [SMILES: Cc1ccc(C(=O)Nc2cccnc2)nc1Br]

To a stirred solution of 6-bromo-5-methylpyridine-2-carboxylic acid (0.25 g, 1.16 mmol) in DMF (5 mL) was added DIPEA (0.64 mL, 3.47 mmol), HATU (0.528 g, 1.39 mmol) and pyridin-3-amine (0.120 g, 1.27 mmol). The reaction mixture was stirred at RT for 16 h. Water was added to the reaction mixture and the aqueous layer was extracted with ethyl acetate. The organic layer was dried over sodium sulfate and evaporated under reduced pressure to obtain crude material which was purified by Combiflash column chromatography using MeOH-DCM gradient. The target compound eluted at about 4% MeOH-DCM. The pure fractions were evaporated to afford 6-bromo-5-methyl-N-(pyridin-3-yl)pyridine-2-carboxamide (0.23 g, 68% yield) as an off-white solid. $^1$H NMR (400 MHz, DMSO-$d_6$) δ 10.58

(s, 1H), 8.99 (s, 1H), 8.32-8.31 (m, 1H), 8.23 (d, J=7.6 Hz, 1H), 8.06-7.99 (m, 2H), 7.40-7.37 (m, 1H), 2.42 (s, 3H). LCMS (ES) m/z=293.9 $[M+2H]^+$.

Step-2: 6-(1H-imidazol-1-yl)-5-methyl-N-(pyridin-3-yl)picolinamide

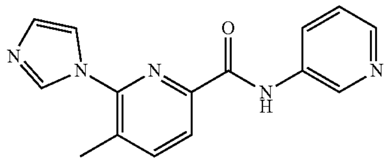 [SMILES: Cc1ccc(C(=O)Nc2cccnc2)nc1-n1ccnc1]

To a stirred solution of 6-bromo-5-methyl-N-(pyridin-3-yl)pyridine-2-carboxamide (0.15 g, 0.513 mmol) in DMSO (3 mL) was added copper iodide (0.032 g, 0.103 mmol), L-proline (0.023 g, 0.205 mmol), potassium carbonate (0.142 g, 1.03 mmol) and imidazole (0.052 g, 0.770 mmol). The stirred reaction mixture was heated to 100° C. for 3 h then cooled to RT and quenched with water. The crude mixture was extracted with ethyl acetate, dried over sodium sulfate and evaporated under reduced pressure to obtain crude material which was purified by Combiflash column chromatography using MeOH-DCM gradient. The target compound eluted at about 4% MeOH-DCM. The pure fractions were evaporated to afford 6-(1H-imidazol-1-yl)-5-methyl-N-(pyridin-3-yl)pyridine-2-carboxamide (0.08 g, 56% yield) as an off-white solid.

Provided in Table 9 are characterization data for compounds of Formula I prepared by the method shown in Example 9.

TABLE 9

(Compound 58)

| Compound | Structure | LCMS (M + H) | HPLC purity (%) | 1H NMR |
|---|---|---|---|---|
| 58 | 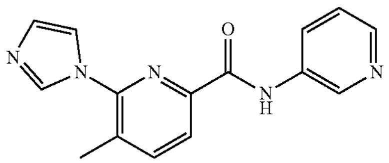 [SMILES: Cc1ccc(C(=O)Nc2cccnc2)nc1-n1ccnc1] | 280.3 | 99.47 | $^1$H NMR (400 MHz, DMSO-$d_6$) δ 10.54 (s, 1H), 8.98 (s, 1H), 8.37 - 8.32 (m, 2H), 8.22 (d, J = 7.6 Hz, 1H), 8.15 - 8.09 (m, 2H), 7.86 (s, 1H), 7.40 - 7.39 (d, J = 4.8 Hz, 1H), 7.14 (s, 1H), 2.44 (s, 3H). |

Example 10

Synthesis of Compound 59

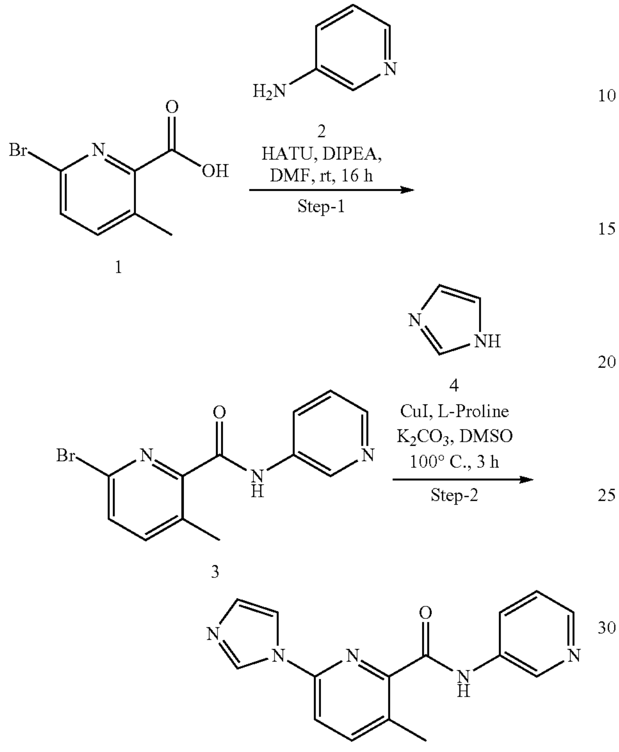

Compound 59

Step-1: 6-bromo-3-methyl-N-(pyridin-3-yl)picolinamide

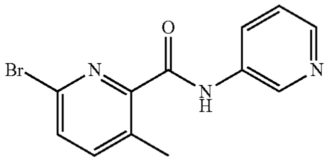 [SMILES: Cc1ccc(Br)nc1C(=O)Nc1cccnc1]

To a solution of 6-bromo-3-methylpyridine-2-carboxylic acid (0.5 g, 2.31 mmol) in DMF (2 mL) was added DIPEA (1.28 mL, 6.94 mmol), HATU (1.06 g, 2.78 mmol) and pyridin-3-amine (0.26 g, 2.78 mmol). The reaction mixture was stirred at RT for 16 h. The crude reaction was quenched with water and extracted with ethyl acetate. The organic layer was dried over sodium sulfate and evaporated to obtain crude material which was purified by Combiflash column chromatography using MeOH-DCM gradient. The target compound eluted at about 2% MeOH-DCM. The pure fractions were evaporated to afford 6-bromo-3-methyl-N-(pyridin-3-yl)pyridine-2-carboxamide (1.3 g, 96% yield) as an off-white solid. LCMS (ES) m/z=294.0 $[M+2H]^+$.

Step-2: 6-(1H-imidazol-1-yl)-3-methyl-N-(pyridin-3-yl)picolinamide

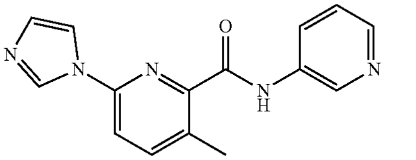 [SMILES: Cc1ccc(-n2ccnc2)nc1C(=O)Nc1cccnc1]

To a stirred solution of 6-bromo-3-methyl-N-(pyridin-3-yl)pyridine-2-carboxamide (0.1 g, 0.342 mmol) in DMSO (2 mL) was added copper iodide (0.021 g, 0.0685 mmol), L-proline (0.015 g, 0.137 mmol), potassium carbonate (0.094 g, 0.685 mmol) and imidazole (0.035 g, 0.513 mmol). The stirred reaction mixture was heated to 100° C. for 3 h. The reaction mixture was cooled to RT, treated with water and extracted with ethyl acetate. The organic layer was dried over sodium sulfate and evaporated under reduced pressure to obtain crude material which was purified by Combiflash column chromatography using MeOH-DCM gradient. The target compound eluted at about 4% MeOH-DCM. The pure fractions were evaporated to afford 6-(1H-imidazol-1-yl)-3-methyl-N-(pyridin-3-yl)pyridine-2-carboxamide (0.080 g, 84% yield) as an off-white solid.

Provided in Table 10 are characterization data for compounds of Formula I prepared by the method shown in Example 10.

TABLE 10

(Compounds 59-63)

| Compound | Structure | LCMS (M + H) | HPLC purity (%) | 1H NMR |
|---|---|---|---|---|
| 59 | 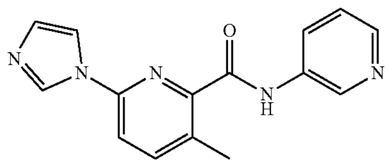 [SMILES: Cc1ccc(-n2ccnc2)nc1C(=O)Nc1cccnc1] | 280.3 | 98.40 | $^1$H NMR (400 MHz, DMSO-$d_6$) δ 10.62 (s, 1H), 8.94 (s, 1H), 8.78 (s, 1H), 8.33 - 8.32 (m, 1H), 8.20 (d, J = 8.4 Hz, 1H), 8.16 (s, 1H), 8.02 (d, J = 8.4Hz, 1H), 7.93 (d, J = 8 Hz, 1H), 7.39 (d, J = 4.4 Hz, 1H), 7.13 (s, 1H), 2.58 (s, 3H). |

TABLE 10-continued
| (Compounds 59-63) | | | | |
|---|---|---|---|---|
| Compound | Structure | LCMS (M + H) | HPLC purity (%) | 1H NMR |
| 60 | 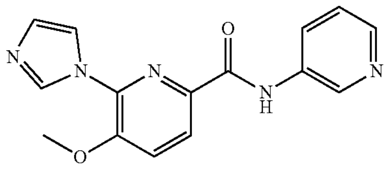 [SMILES: COc1ccc(C(=O)Nc2cccnc2)nc1-n1ccnc1] | 296.3 | 99.00 | $^1$H NMR (400 MHz, DMSO-$d_6$) δ 10.43 (s, 1H), 8.97 (s, 1H), 8.70 (s, 1H), 8.33 - 8.32 (m, 1H), 8.22 - 8.20 (m, 2H), 8.13 (d, J = 8.8 Hz, 1H), 7.91 (d, J = 8.8 Hz, 1H), 7.42 -7.39 (m, 1H), 7.11 (s, 1H), 4.03 (s, 3H). |
| 61 | 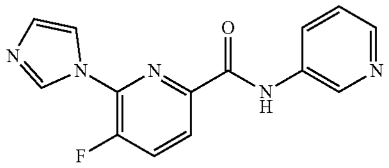 [SMILES: O=C(Nc1cccnc1)c1ccc(F)c(-n2ccnc2)n1] | 284.2 | 99.34 | $^1$H NMR (400 MHz, DMSO-$d_6$) δ 10.6 (bs, 1H), 8.98 (d, J = 1.2 Hz, 1H), 8.74 (s, 1H), 8.36 (d, J = 3.6 Hz, 1H), 8.27 - 8.16 (m, 4H), 7.45 - 7.42 (m, 1H), 7.21 (s, 1H). |
| 62 | 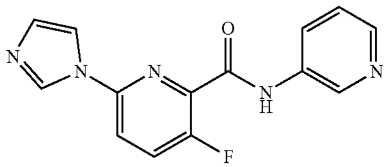 [SMILES: O=C(Nc1cccnc1)c1nc(-n2ccnc2)ccc1F] | 284.3 | 99.88 | $^1$H NMR (400 MHz, DMSO-$d_6$) δ 10.69 (s, 1H), 8.94 - 8.93 (m, 1H), 8.78 (s, 1H), 8.36 - 8.35 (m, 1H), 8.21 - 8.12 (m, 4H), 7.44 - 7.41 (m, 1H), 7.15 (s, 1H). |
| 63 | 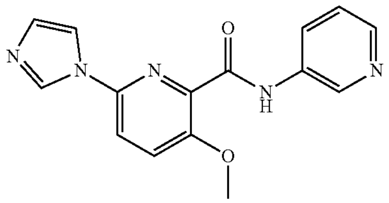 [SMILES: COc1ccc(-n2ccnc2)nc1C(=O)Nc1cccnc1] | 296.3 | 99.0 | $^1$H NMR (400 MHz, DMSO-$d_6$) δ 10.62 (s, 1H), 8.89 (d, J= 1.6 Hz, 1H), 8.53 (s, 1H), 8.31 (d, J = 3.6 Hz, 1H), 8.18 (d, J = 8.4 Hz, 1H), 7.98 -7.89 (m, 3H), 7.41-7.38 (m, 1H), 7.11 (s, 1H), 3.91 (s, 3H). |
Example 11
Synthesis of Compound 64
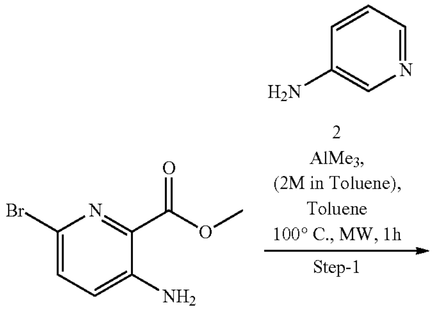
1
-continued
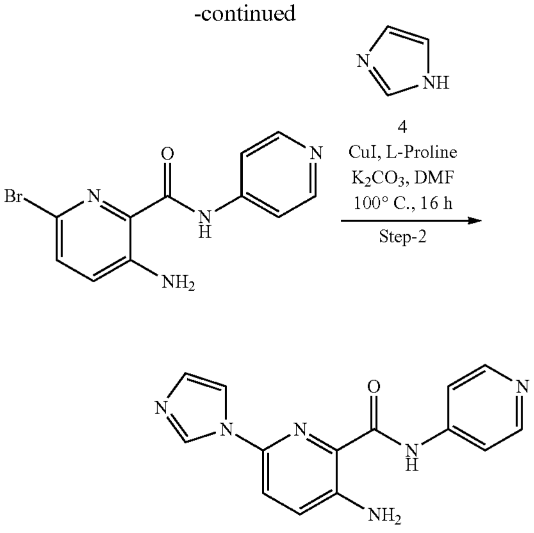
Compound 64

Step-1: 3-amino-6-bromo-N-(pyridin-4-yl) picolinamide

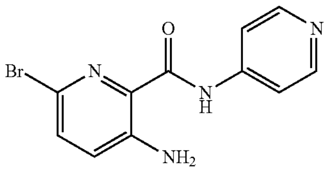 [SMILES: Nc1ccc(Br)nc1C(=O)Nc1ccncc1]

To a stirred solution of methyl 3-amino-6-bromopyridine-2-carboxylate (500 mg, 2.16 mmol) in toluene was added pyridin-4-amine (204 mg, 2.16 mmol) and 2M trimethylaluminum solution in toluene (5.41 mL, 10.8 mmol). The reaction mixture was stirred in a CEM microwave at 100° C. for 1 hr. The reaction mixture was cooled to RT, quenched with water and extracted with ethyl acetate. The organic layer was dried over sodium sulfate and evaporated under reduced pressure to obtain crude material which was purified by Combiflash column chromatography using MeOH-DCM gradient. The target compound eluted at about 3% MeOH-DCM. Pure fractions were evaporated to afford 3-amino-6-bromo-N-(pyridin-4-yl)pyridine-2-carboxamide (0.5 g, 79% yield) as a yellow solid. $^{1}$H NMR (400 MHz, DMSO-$d_6$) δ 10.33 (s, 1H), 8.44 (d, J=5.6 Hz, 2H), 7.81 (d, J=5.6 Hz, 2H), 7.48 (d, J=8.8 Hz, 1H), 7.22 (d, J=8.8 Hz, 1H), 7.08 (s, 2H). LCMS (ES) m/z=295.2 $[M+2H]^+$.

Step-2: 3-amino-6-(1H-imidazol-1-yl)-N-(pyridin-4-yl)picolinamide

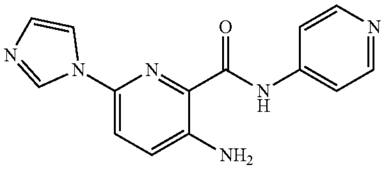 [SMILES: Nc1ccc(-n2ccnc2)nc1C(=O)Nc1ccncc1]

To a stirred solution of 3-amino-6-bromo-N-(pyridin-4-yl)pyridine-2-carboxamide (220 mg, 0.751 mmol) in DMF (3 mL) was added copper iodide (47.6 mg, 0.150 mmol), (2S)-pyrrolidine-2-carboxylic acid (34.6 mg, 0.300 mmol), potassium carbonate (207 mg, 1.50 mmol) and 1H-imidazole (76.6 mg, 1.13 mmol). The reaction mixture was heated to 100° C. for 16 h then cooled to RT and treated with ice-cold water. The crude mixture was extracted with ethyl acetate, the organic layer dried over sodium sulfate and evaporated under reduced pressure to obtain crude material which was purified by Combiflash column chromatography using MeOH-DCM gradient. The target compound eluted at about 4% MeOH-DCM. The pure fractions were evaporated to afford 3-amino-6-(1H-imidazol-1-yl)-N-(pyridin-4-yl) pyridine-2-carboxamide (0.060 g, 28% yield) as a yellow solid. $^{1}$H NMR (400 MHz, DMSO-$d_6$) 10.36 (s, 1H), 8.68 (s, 1H), 8.48-8.46 (m, 2H), 8.08 (s, 1H), 7.86-7.85 (m, 2H), 7.78 (d, J=8.8 Hz, 1H), 7.46 (d, J=8.8 Hz, 1H), 7.08-7.04 (in, 3H). LCMS (ES) m/z=281.3 $[M+H]^+$.

Provided in Table 11 are characterization data for compounds of Formula I prepared by the method shown in Example 11.

TABLE 11

(Compounds 64-68)

| Compound | Structure | LCMS (M + H | HPLC purity (%) | 1H NMR |
|---|---|---|---|---|
| 64 | 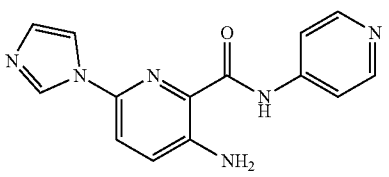 [SMILES: Nc1ccc(-n2ccnc2)nc1C(=O)Nc1ccncc1] | 281.3 | 99.18 | $^{1}$H NMR (400 MHz, DMSO-$d_6$) δ 10.36 (s, 1H), 8.68 (s, 1H), 8.47 (d, J = 6.0 Hz, 2H), 8.08 (s, 1H), 7.86 (d, J = 5.6 Hz, 2H), 7.78 (d, J = 8.8 Hz, 1H), 7.46 (d, J = 8.8 Hz, 1H), 7.08 - 7.03 (m, 3H). |

TABLE 11-continued
| (Compounds 64-68) | | | | |
|---|---|---|---|---|
| Compound | Structure | LCMS (M + H | HPLC purity (%) | 1H NMR |
| 65 | 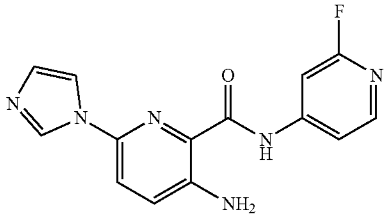 [SMILES: Nc1ccc(-n2ccnc2)nc1C(=O)Nc1ccnc(F)c1] | 299.3 | 98.89 | $^1H$ NMR (400 MHz, DMSO-$d_6$) 10.57 (s, 1H), 8.70 (s, 1H), 8.15 (d, J = 6 Hz, 1H), 8.10 (s, 1H), 7.82 - 7.80 (m, 2H), 7.69 (s, 1H), 7.47 (d, J = 8.8 Hz, 1H), 7.09 (s, 3H). |
| 66 | 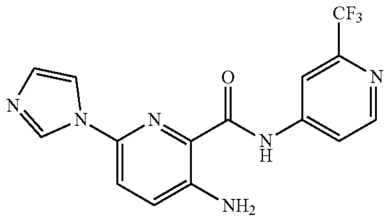 [SMILES: Nc1ccc(-n2ccnc2)nc1C(=O)Nc1ccnc(C(F)(F)F)c1] | 349.2 | 99.15 | $^1H$ NMR (400 MHz, DMSO-$d_6$) δ 10.65 (s, 1H), 8.72 (s, 1H), 8.66 (d, J = 5.2 Hz, 1H), 8.43 (s, 1H), 8.18 (d, J = 4.8 Hz, 1H), 8.11 (s, 1H), 7.81 (d, J = 8.8 Hz, 1H), 7.48 (d, J = 9.2 Hz, 1H), 7.10 (s, 3H). |
| 67 | 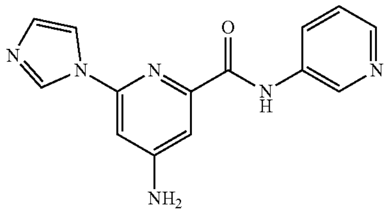 [SMILES: Nc1cc(C(=O)Nc2cccnc2)nc(-n2ccnc2)c1] | 281.3 | 99.6 | $^1H$ NMR (400 MHz, DMSO-$d_6$) δ 10.42 (s, 1H), 8.99 (s, 1H), 8.78 (s, 1H), 8.34 - 8.33 (m, 1H), 8.24 (d, J = 8.4 Hz, 1H), 8.02 (s, 1H), 7.43 - 7.40 (m, 1H), 7.29 (s, 1H), 7.10 (s, 1H), 6.87 (s, 1H), 6.74 (s, 2H). |
| 68 | 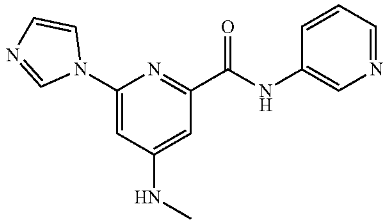 [SMILES: CNc1cc(C(=O)Nc2cccnc2)nc(-n2ccnc2)c1] | 295.3 | 99.0 | $^1H$ NMR (400 MHz, DMSO-$d_6$) δ 10.46 (s, 1H), 9.00 (s, 1H), 8.90 (s, 1H), 8.35 - 8.33 (m, 1H), 8.26 -8.21 (m, 2H), 7.43 - 7.40 (m, 1H), 7.32 - 7.28 (m, 2H), 7.11 (s, 1H), 6.89 (s, 1H), 3.15 (s, 3H). |

Example 12
Synthesis of Compound 70
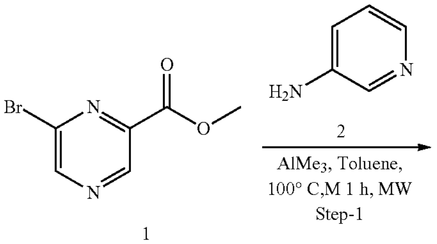
1
-continued
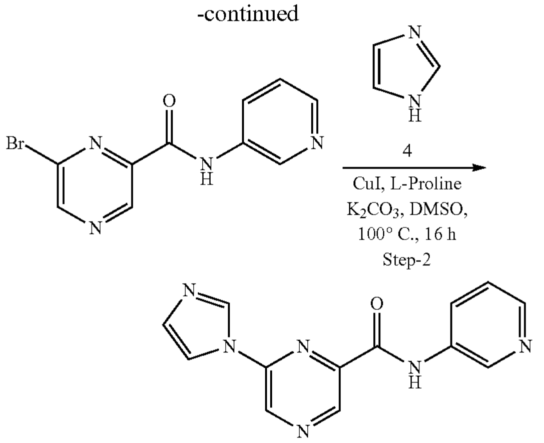
Compound 70
Provided in Table 12 are characterization data for compounds of Formula I prepared by the method shown in Example 12.
TABLE 12
(Compounds 69-70)
| Compound | Structure | LOMS (M + H) | HPLC Purity (%) | $^1$H NMR |
|---|---|---|---|---|
| 69 | 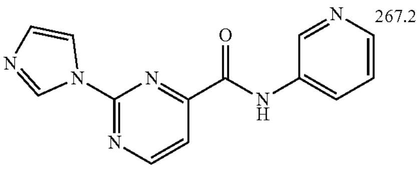 | 267.2 | 99.31 | (400 MHz, DMSO-$d_6$) δ 10.85 (s, 1H), 9.13 (d, J = 4.8 Hz, 1H), 9.01 (s, 2H), 8.39 (d, J = 4.4 Hz, 1H), 8.29 (s, 1H), 8.24 (d, J = 8.8 Hz, 1H), 8.03 (d, J = 4.4 Hz, 1H), 7.48 - 7.45 (m, 1H), 7.20 (s, 1H). |
| 70 | 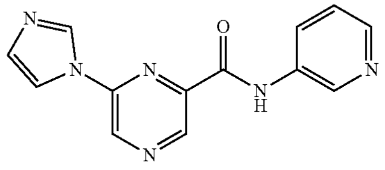 [SMILES: O=C(Nc1cccnc1)c1cncc(-n2ccnc2)n1] | 266.3 | 99.97 | $^1$H NMR (400 MHz, DMSO-$d_6$) δ 10.73 (s, 1H), 9.45 (s, 1H), 9.19 (s, 1H), 9.03 - 8.99 (m, 2H), 8.39 - 8.38 (m, 2H), 8.23 (d, J = 8.4 Hz, 1H), 7.47 - 7.44 (m, 1H), 7.23 (s, 1H). |

Example 13

Synthesis of Compound 71

Synthesis of Intermediate-1A

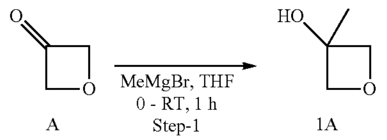

A 1A

To a solution of oxetan-3-one (1.0 g, 13.9 mmol) in Tetrahydrofuran (10 mL) was added bromo(methyl)magnesium (9.25 mL, 2738 mmol) at 0° C. The resulting mixture was stirred for 1 hour at room temperature. The progress of reaction was monitored by TLC. The reaction mixture was quenched with saturated ammonium chloride solution (10 mL), extracted with Dichloromethane (50 mL). to afford 3-methyloxetan-3-ol (0.7 g, 57.25% yield) as a light yellow colour liquid.

Synthesis of Compound 71

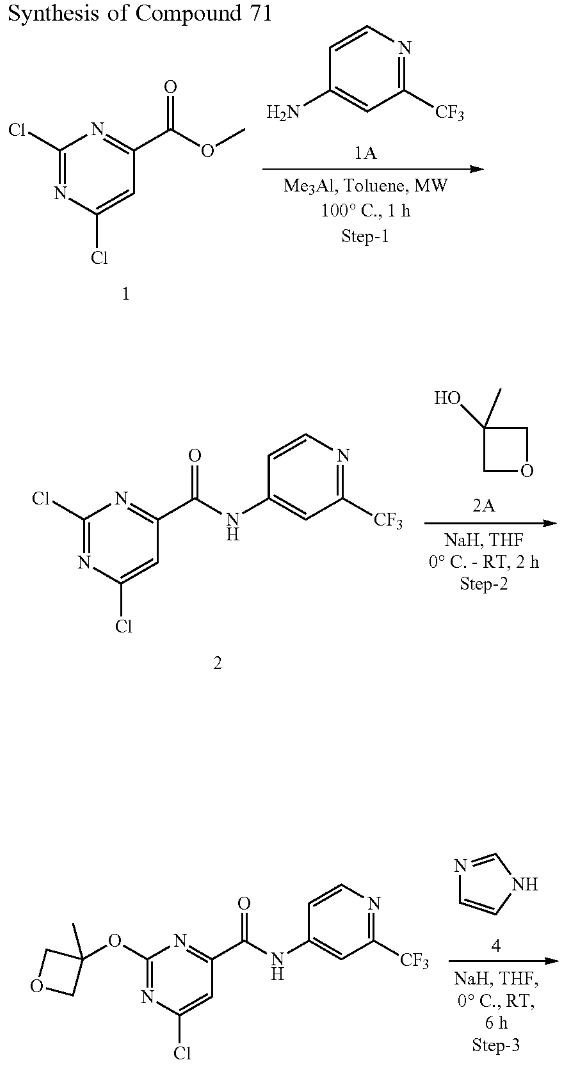

3A

-continued

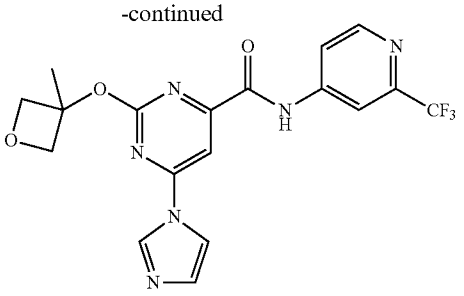

T-189

Step-1: 2,6-dichloro-N-(2-(trifluoromethyl)pyridin-4-yl)pyrimidine-4-carboxamide

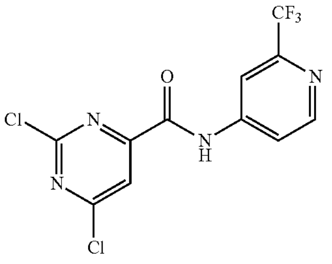 [SMILES: O=C(Nc1ccnc(C(F)(F)F)c1)c1cc(Cl)nc(Cl)n1]

To a solution of methyl 6-chloro-4-methoxypyridine-2-carboxylate (0.4 g, 1.93 mmol) in toluene (5 mL) was added 2-(trifluoromethyl)pyridin-4-amine (313 mg, 1.93 mmol) and Trimethyl aluminum (1.45 mL, 2.90 mmol) at 0° C. The resulting mixture was stirred in CEM microwave at 100 00 for 1 hour. The progress of reaction was monitored by TLC. The reaction mixture was cooled to ambient temperature was quenched with ice water (10 mL), extracted with ethyl acetate (50 mL). The crude residue was purified by gradient column chromatography using 0-30% ethyl acetate in hexane to afford 2,6-dichloro-N-(2-(trifluoromethyl)pyridin-4-yl)pyrimidine-4-carboxamide (0.5 g, 76.7% yield) as a offwhite solid.

Step-2: 6-chloro-2-((3-methyloxetan-3-yl)oxy)-N-(2-(trifluoromethyl)pyridin-4-yl)pyrimidine-4-carboxamide

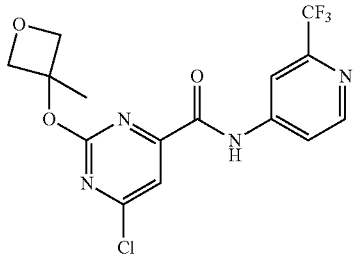 [SMILES: CC1(Oc2nc(Cl)cc(C(=O)Nc3ccnc(C(F)(F)F)c3)n2)COC1]

To a solution of Sodium hydride (60% in mineral oil) (0.136 g, 3.40 mmol) in Tetrahydrofuran (5 mL) was added 3-methyloxetan-3-ol (200 mg, 2.27 mmol) at 0° C., the reaction mixture was stirred for 10 minutes at room temperature and added 2,6-dichloro-N-(2-(trifluoromethyl)pyridin-4-yl)pyrimidine-4-carboxamide dissolved in Tetrahydrofuran (5 ml) (0.612 g, 1.82 mmol) The resulting mixture was stirred in room temperature for 16 hour. The progress of reaction was monitored by TLC. The reaction mixture was quenched with saturated ammonium chloride solution (10 mL), extracted with ethyl acetate (50 mL). The crude residue was purified by gradient column chromatography using 0-30% ethyl acetate in hexane to afford 6-chloro-2-((3-methyloxetan-3-yl)oxy)-N-(2-(trifluoromethyl)pyridin-4-yl)pyrimidine-4-carboxamide (0.15 g, 17% yield) and 2-chloro-6-[(3-methyloxetan-3-yl)oxy]-N-[2-(trifluoromethyl)pyridin-4-yl]pyrimidine-4-carboxamide (0.2 g, 22.6% yield) as a offwhite solid.

Step-3: 6-(1H-imidazol-1-yl)-2-((3-methyloxetan-3-yl)oxy)-N-(2 (trifluoromethyl)pyridin-4-yl) pyrimidine-4-carboxamide

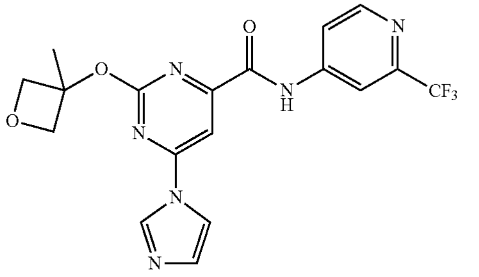 [SMILES: CC1(Oc2nc(C(=O)Nc3ccnc(C(F)(F)F)c3)cc(-n3ccnc3)n2)COC1]

To a solution of Sodium hydride (60% in mineral oil) (0.023 g, 0.386 mmol) in Tetrahydrofuran (5 mL) was added 1H-imidazole (39.4 mg, 0.579 mmol) at 0° C., the reaction mixture was stirred for 10 minutes at room temperature and added 6-chloro-2-((3-methyloxetan-3-yl)oxy)-N-(2-(trifluoromethyl)pyridin-4-yl)pyrimidine-4-carboxamide dissolved in Tetrahydrofuran (5 ml) (0.15 g, 0.386 mmol) at 0° C. The resulting mixture was stirred in room temperature for 2 hour. The progress of reaction was monitored by TLC. The reaction mixture was quenched with saturated ammonium chloride solution (10 mL), extracted with ethyl acetate (50 mL). The crude residue was purified by gradient column chromatography using 0-5% Methano in Dichloromethane to afford 6-(1H-imidazol-1-yl)-2-((3-methyloxetan-3-yl)oxy)-N-(2 (trifluoromethyl)pyridin-4-yl)pyrimidine-4-carboxamide (0.03 g, 18.5% yield) as a off white solid.

Provided in Table 13 are characterization data for the compound of Formula I prepared by the method shown in Example 13.

TABLE 13

(Compound 71)

| Compound | Structure | LCMS (M + H) | HPLC Purity (%) | $^1$H NMR |
|---|---|---|---|---|
| 71 | 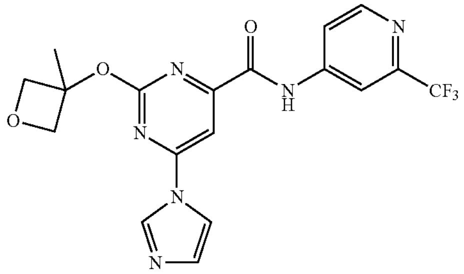 [SMILES: CC1(Oc2nc(C(=O)Nc3ccnc(C(F)(F)F)c3)cc(-n3ccnc3)n2)COC1] | 421.3 | 99.65% | 1HNMR (400 MHz, DMSO-d6): δ 11.32 (s, 1H), 8.74 (d, J = 13.2 Hz, 2H), 8.47 (s, 1H), 8.23-8.11 (m, 3H), 7.21 (s, 1H), 4.86 (d, J = 6.4 Hz, 2H), 4.70 (d, J = 6.8 Hz 2H), 1.84 (s, 3H). |

Example 14

Synthesis of Compound 72

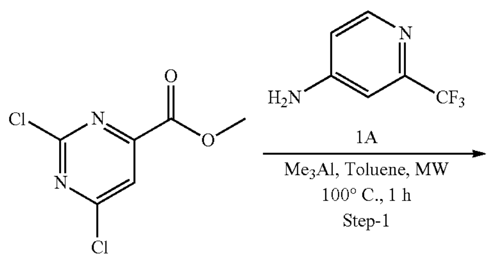

1

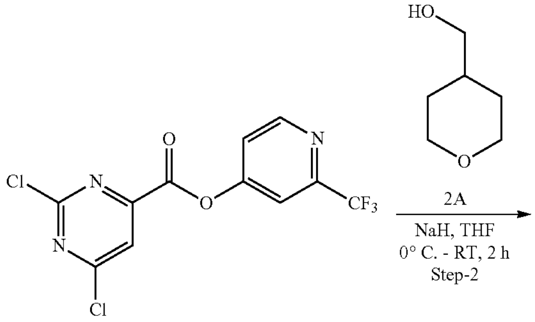

2

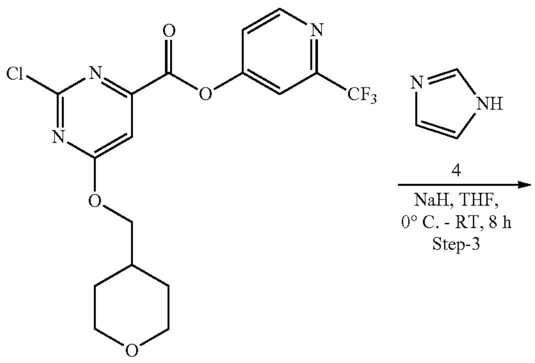

3

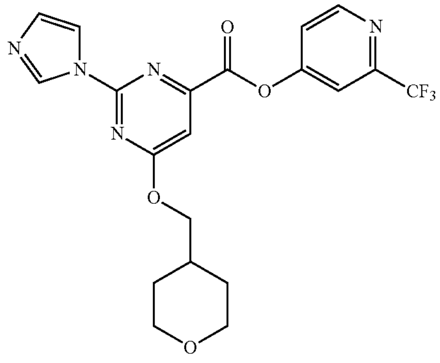

T-195

Step-1: 2,6-dichloro-N-(2-(trifluoromethyl)pyridin-4-yl)pyrimidine-4-carboxamide

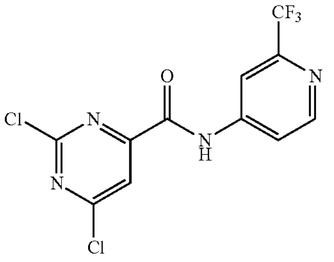 [SMILES: O=C(Nc1ccnc(C(F)(F)F)c1)c1cc(Cl)nc(Cl)n1]

To a solution of methyl 6-chloro-4-methoxypyridine-2-carboxylate (1.0 g, 4.83 mmol) in toluene (5 mL) was added 2-(trifluoromethyl)pyridin-4-amine (783 mg, 4.83 mmol) and Trimethyl aluminum (3.62 mL, 7.25 mmol) at 0° C. The resulting mixture was stirred in CEM microwave at 100° C. for 1 hour. The progress of reaction was monitored by TLC. The reaction mixture was cooled to ambient temperature was quenched with ice water (10 mL), extracted with ethyl acetate (50 mL). The crude residue was purified by gradient column chromatography using 0-30% ethyl acetate in hexane to afford 2,6-dichloro-N-(2-(trifluoromethyl)pyridin-4-yl)pyrimidine-4-carboxamide (1.15 g, 70.62% yield) as an off white solid.

Step-2: 2-chloro-6-((tetrahydro-2H-pyran-4-yl)methoxy)-N-(2-(trifluoromethyl)pyridin-4-yl)pyrimidine-4-carboxamide

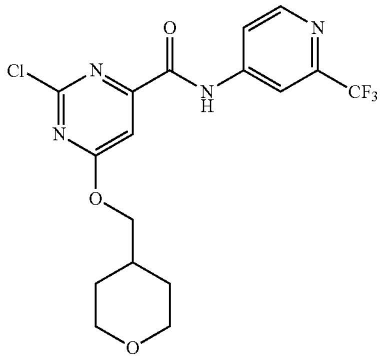 [SMILES: O=C(Nc1ccnc(C(F)(F)F)c1)c1cc(OCC2CCOCC2)nc(Cl)n1]

To a solution of Sodium hydride (60% in mineral oil) (0.059 g, 0.89 mmol) in Tetrahydrofuran (5 mL) was added (tetrahydro-2H-pyran-4-yl)methanol (69 mg, 0.59 mmol) at 0° C., the reaction mixture was stirred for 10 minutes at room temperature and added 2,6-dichloro-N-(2-(trifluoromethyl)pyridin-4-yl)pyrimidine-4-carboxamide dissolved in Tetrahydrofuran (5 ml) (0.2 g, 0.59 mmol) The resulting mixture was stirred in room temperature for 16 hour. The progress of reaction was monitored by TLC. The reaction mixture was quenched with saturated ammonium chloride solution (10 mL), extracted with ethyl acetate (50 mL). The crude residue was purified by gradient column chromatography using 0-30% ethyl acetate in hexane to afford 2-chloro-6-((tetrahydro-2H-pyran-4-yl)methoxy)-N-(2-(trifluoromethyl)pyridin-4-yl)pyrimidine-4-carboxamide (0.13 g, 52.5% yield) and 6-chloro-2-[(oxan-4-yl)methoxy]-N-[2-(trifluoromethyl)pyridin-4-yl]pyrimidine-4-carboxamide (0.13 g, 52.5% yield) as a off white solids.

Step-3: 2-(1H-imidazol-1-yl)-6-((tetrahydro-2H-pyran-4-yl)methoxy)-N-(2-(trifluoromethyl) pyridin-4-yl) pyrimidine-4-carboxamide

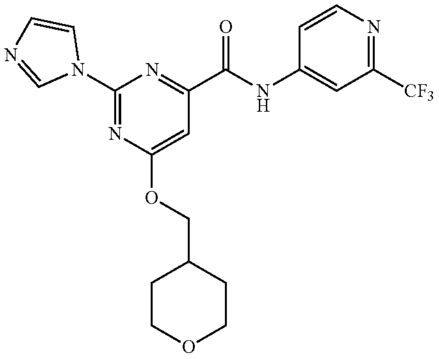 [SMILES: O=C(Nc1ccnc(C(F)(F)F)c1)c1cc(OCC2CCOCC2)nc(-n2ccnc2)n1]

To a solution of 2-chloro-6-((tetrahydro-2H-pyran-4-yl) methoxy)-N-(2-(trifluoromethyl)pyridin-4-yl)pyrimidine-4-carboxamide (0.13 g, 0.312 mmol) in N,N-dimethylformamide (2 mL) was added caesium carbonate (0.15 g, 0.468 mmol), diiodocopper (29.7 mg, 0.094 mmom) and 1H-imidazole (31.9 mg, 0.468 mmol). The resulting mixture was stirred at 100° C. for 5 hour. The progress of reaction was monitored by TLC. The reaction mixture was cooled to room temperature dilute with water (20 mL), extracted with ethyl acetate (20 mL). The crude residue was purified by gradient column chromatography using 0-10% Methano in Dichloromethane to afford 6-(1H-imidazol-1-yl)-2-((3-methyloxetan-3-yl)oxy)-N-(2 (trifluoromethyl)pyridin-4-yl) pyrimidine-4-carboxamide (0.044 g, 31.46% yield) as a off white solid.

Provided in Table 14 are characterization data for the compound of Formula I prepared by the method shown in Example 14.

TABLE 14

(Compound 72)

| Compound | Structure | LCMS (M + H) | HPLC Purity (%) | $^1$H NMR |
|---|---|---|---|---|
| 72 | 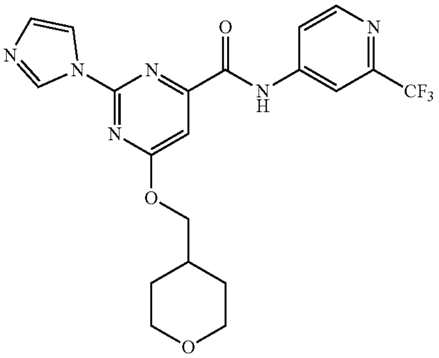 [SMILES: O=C(Nc1ccnc(C(F)(F)F)c1)c1cc(OCC2CCOCC2)nc(-n2ccnc2)n1] | 449.3 | 98.68 | 1HNMR (400 MHz, DMSO-d6): δ 10.99 (s, 1H), 8.99 (s, 1H), 8.75 (d, J = 6.0 Hz, 1H), 8.43 (s, 1H), 8.27 (s, 1H), 8.25 (d, J = 4.8 Hz, 1H), 7.38 (s,1H), 7.18 (s, 1H), 4.43 (d, J = 6.0 Hz, 2H), 4.87 (d, J = 8.8 Hz 2H), 3.40 (d, J = 7.2 Hz 2H), 2.09 (m, 1H), 1.68 (q, J =12.8 Hz 2H), 1.38 (q, J = 11.2 Hz 2H) |

Example 15

Synthesis of Compound 73

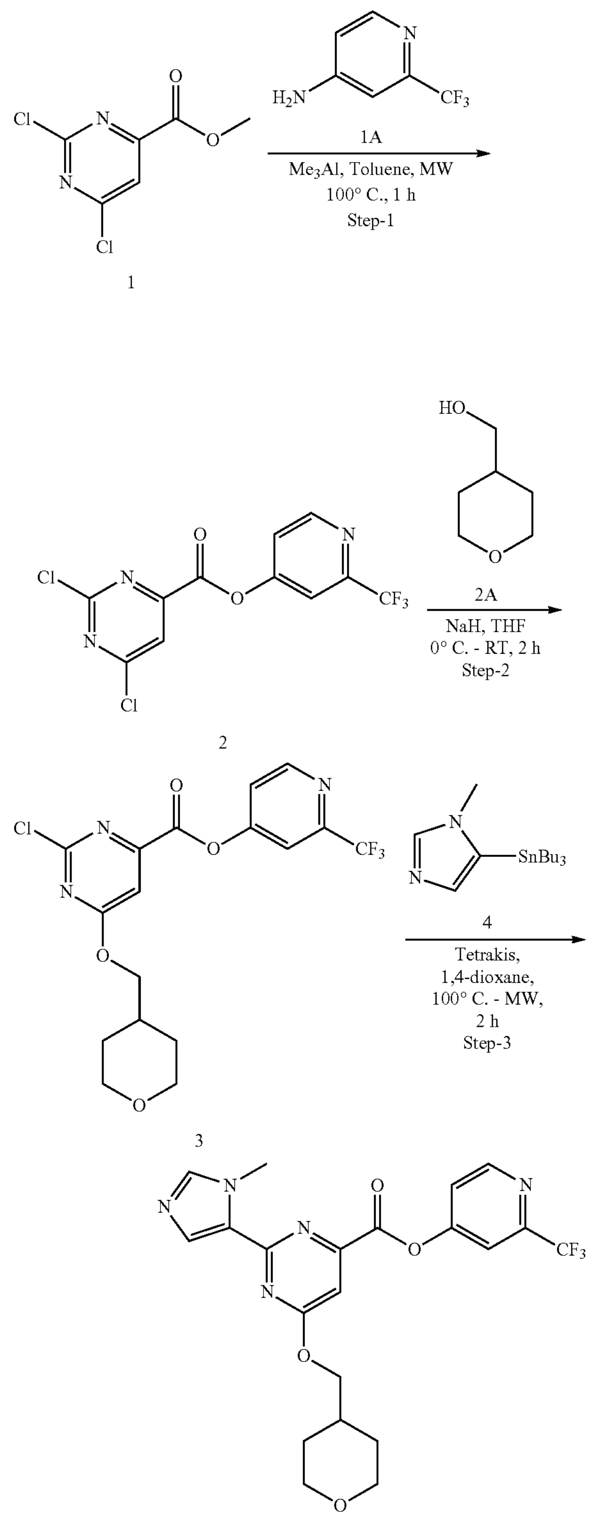

1

2

3

T-196

Step-1: 2,6-dichloro-N-(2-(trifluoromethyl pyridin-4-yl)pyrimidine-4-carboxamide

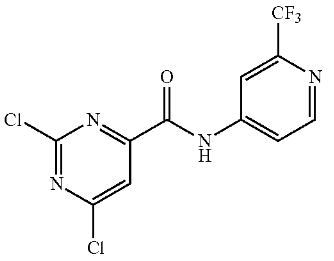 [SMILES: O=C(Nc1ccnc(C(F)(F)F)c1)c1cc(Cl)nc(Cl)n1]

To a solution of methyl 6-chloro-4-methoxypyridine-2-carboxylate (1.0 g, 4.83 mmol) in toluene (5 mL) was added 2-(trifluoromethyl)pyridin-4-amine (783 mg, 4.83 mmol) and Trimethyl aluminum (3.62 mL, 7.25 mmol) at 0° C. The resulting mixture was stirred in CEM microwave at 100° C. for 1 hour. The progress of reaction was monitored by TLC. The reaction mixture was cooled to ambient temperature was quenched with ice water (10 mL), extracted with ethyl acetate (50 mL). The crude residue was purified by gradient column chromatography using 0-30% ethyl acetate in hexane to afford 2,6-dichloro-N-(2-(trifluoromethyl)pyridin-4-yl)pyrimidine-4-carboxamide (1.15 g, 70.62% yield) as an off white solid.

Step-2: 2-chloro-6-((tetrahydro-2H-pyran-4-yl)methoxy)-N-(2-(trifluoromethyl)pyridin-4-yl)pyrimidine-4-carboxamide

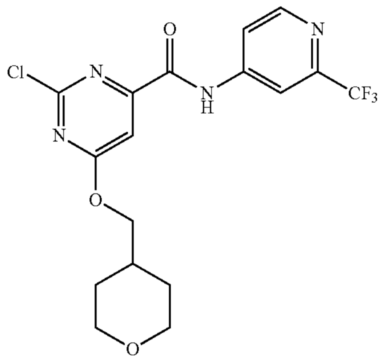 [SMILES: O=C(Nc1ccnc(C(F)(F)F)c1)c1cc(OCC2CCOCC2)nc(Cl)n1]

To a solution of Sodium hydride (60% in mineral oil) (0.237 g, 3.56 mmol) in Tetrahydrofuran (10 mL) was added (tetrahydro-2H-pyran-4-yl)methanol (0.26 mL, 2.37 mmol) at 0° C., the reaction mixture was stirred for 10 minutes and added 2,6-dichloro-N-(2-(trifluoromethyl)pyridin-4-yl)pyrimidine-4-carboxamide dissolved in Tetrahydrofuran (5 ml) (0.8 g, 2.37 mmol) The resulting mixture was stirred in room temperature for 16 hour. The progress of reaction was monitored by TLC. The reaction mixture was quenched with saturated ammonium chloride solution (10 mL), extracted with ethyl acetate (50 mL). The crude residue was purified by gradient column chromatography using 0-30% ethyl acetate in hexane to afford 2-chloro-6-((tetrahydro-2H-pyran-4-yl)methoxy)-N-(2-(trifluoromethyl)pyridin-4-yl) pyrimidine-4-carboxamide (0.25 g, 25.27% yield as a off white solid.

Step-3: 2-(1-methyl-1H-imidazol-5-yl)-6-((tetrahydro-2H-pyran-4-yl)methoxy)-N-(2-(trifluoromethyl)pyridin-4-yl)pyrimidine-4-carboxamide

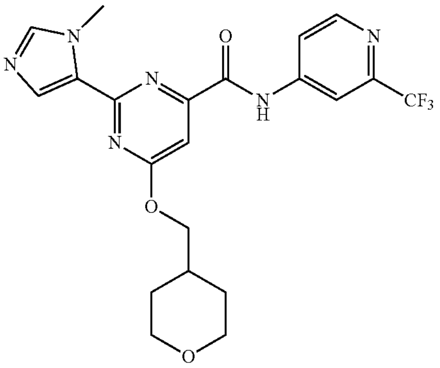 [SMILES: Cn1cncc1-c1nc(OCC2CCOCC2)cc(C(=O)Nc2ccnc(C(F)(F)F)c2)n1]

To a solution of 2-chloro-6-((tetrahydro-2H-pyran-4-yl)methoxy)-N-(2-(trifluoromethyl)pyridin-4-yl)pyrimidine-4-carboxamide (0.1 g, 0.24 mmol) in 1,4-dioxane (3 mL) was added 1-methyl-5-(tributylstannyl)-1H-imidazole (134 mg, 0.36 mmom) and tetrakis(triphenylphosphine)palladium(0) (84 mg, 0.072 mmol). The resulting mixture was stirred at 100° C. for 2 hour in CEM microwave. The progress of reaction was monitored by TLC. The reaction mixture was cooled to room temperature dilute with water (20 mL), extracted with ethyl acetate (20 mL) washed with brain solution. The crude residue was purified by gradient column chromatography using 0-10% Methano in Dichloromethane then purified through prep TLC, to afford 2-(1-methyl-1H-imidazol-5-yl)-6-((tetrahydro-2H-pyran-4-yl)methoxy)-N-(2-(trifluoromethyl)pyridin-4-yl)pyrimidine-4-carboxamide (0.017 g, 15.32% yield) as a off white solid.

Provided in Table 15 are characterization data for the compound of Formula I prepared by the method shown in Example 15.

TABLE 15

(Compound 73)

| Compound | Structure | LCMS (M + H) | HPLC Purity (%) | $^1$H NMR |
|---|---|---|---|---|
| 73 | 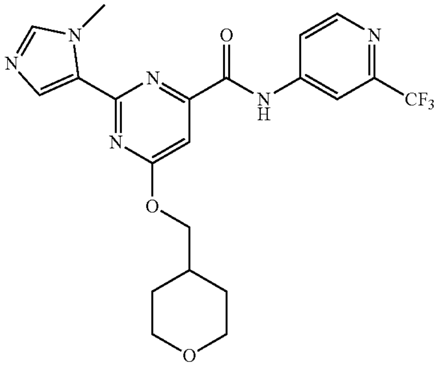 [SMILES: Cn1cncc1-c1nc(OCC2CCOCC2)cc(C(=O)Nc2ccnc(C(F)(F)F)c2)n1] | 463.3 | 97.5 | $^1$H NMR (400 MHz, DMSO-d6): δ 11.02 (s, 1H), 8.90 (s, 1H), 8.74 (d, J = 5.6 Hz, 1H), 8.69 (s, 1H), 8.41 (s, 1H), 8.22 (d, J = 5.2 Hz, 1H), 7.41 (s, 1H), 4.37 (d, J = 6.0 Hz, 2H), 4.22 (s, 3H), 3.87 (d, J = 9.2 Hz 2H), 3.77 (d, J = 15.6 Hz 2H), 2.09 (m, 1H), 1.67 (q, J = 11.6 Hz 2H), 1.36 (q, J = 8.8 Hz 2H) |

Example 1

Synthesis of Compound 74

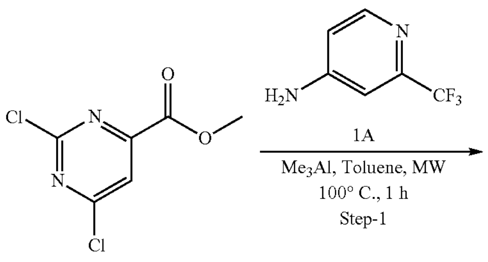

1

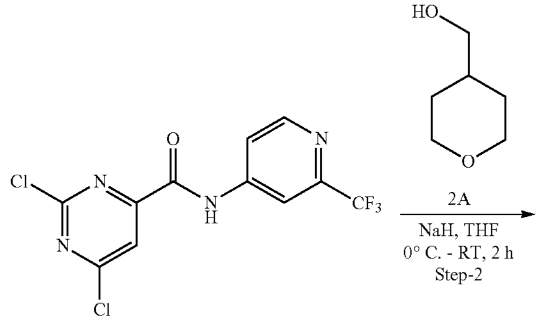

2

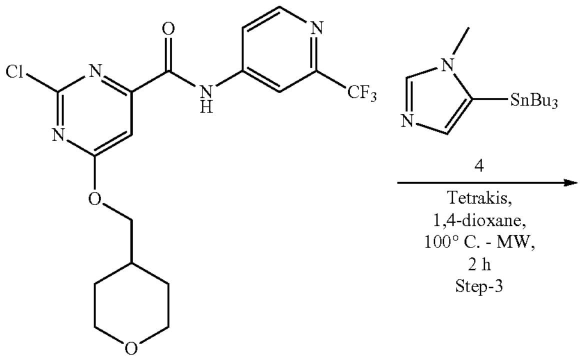

3

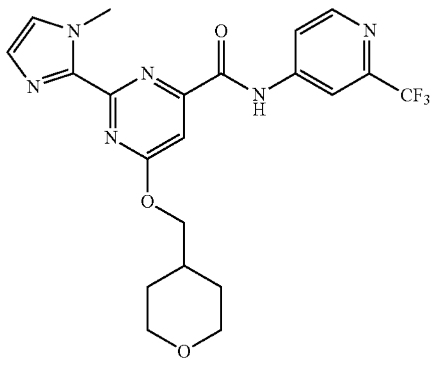

T-197

Step-1: 2,6-dichloro-N-(2-(trifluoromethyl)pyridin-4-yl)pyrimidine-4-carboxamide

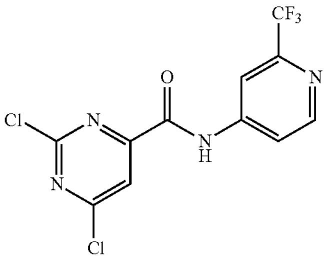 [SMILES: O=C(Nc1ccnc(C(F)(F)F)c1)c1cc(Cl)nc(Cl)n1]

To a solution of methyl 6-chloro-4-methoxypyridine-2-carboxylate (1.0 g, 4.83 mmol) in toluene (5 mL) was added 2-(trifluoromethyl)pyridin-4-amine (783 mg, 4.83 mmol) and Trimethyl aluminum (3.62 mL, 7.25 mmol) at 0° C. The resulting mixture was stirred in CEM microwave at 100° C. for 1 hour. The progress of reaction was monitored by TLC. The reaction mixture was cooled to ambient temperature was quenched with ice water (10 mL), extracted with ethyl acetate (50 mL). The crude residue was purified by gradient column chromatography using 0-30% ethyl acetate in hexane to afford 2,6-dichloro-N-(2-(trifluoromethyl)pyridin-4-yl)pyrimidine-4-carboxamide (1.15 g, 70.62% yield) as an off white solid.

Step-2: 2-chloro-6-((tetrahydro-2H-pyran-4-yl)methoxy)-N-(2-(trifluoromethyl)pyridin-4-yl)pyrimidine-4-carboxamide

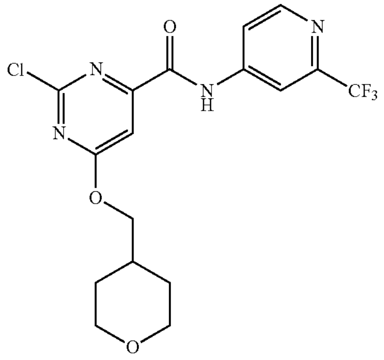 [SMILES: O=C(Nc1ccnc(C(F)(F)F)c1)c1cc(OCC2CCOCC2)nc(Cl)n1]

To a solution of Sodium hydride (60% in mineral oil) (0.237 g, 3.56 mmol) in Tetrahydrofuran (10 mL) was added (tetrahydro-2H-pyran-4-yl)methanol (0.26 mL, 2.37 mmol) at 0° C., the reaction mixture was stirred for 10 minutes and added 2,6-dichloro-N-(2-(trifluoromethyl)pyridin-4-yl)pyrimidine-4-carboxamide dissolved in Tetrahydrofuran (5 ml) (0.8 g, 2.37 mmol) The resulting mixture was stirred in room temperature for 16 hour. The progress of reaction was monitored by TLC. The reaction mixture was quenched with saturated ammonium chloride solution (10 mL), extracted with ethyl acetate (50 mL). The crude residue was purified by gradient column chromatography using 0-30% ethyl acetate in hexane to afford 2-chloro-6-((tetrahydro-2H-pyran-4-yl)methoxy)-N-(2-(trifluoromethyl)pyridin-4-yl) pyrimidine-4-carboxamide (0.25 g, 25.27% yield as a off white solid.

Step-3: 2-(1-methyl-1H-imidazol-2-yl)-6-((tetrahydro-2H-pyran-4-yl)methoxy)-N-(2-(trifluoromethyl)pyridin-4-yl)pyrimidine-4-carboxamide

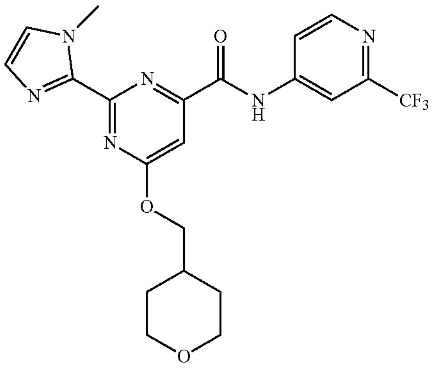 [SMILES: Cn1ccnc1-c1nc(OCC2CCOCC2)cc(C(=O)Nc2ccnc(C(F)(F)F)c2)n1]

To a solution of 2-chloro-6-((tetrahydro-2H-pyran-4-yl)methoxy)-N-(2-(trifluoromethyl)pyridin-4-yl)pyrimidine-4-carboxamide (0.13 g, 0.312 mmol) in 1,4-dioxane (10 mL) was added 1-methyl-2-(tributylstannyl)-1H-imidazole (174 mg, 0.468 mmom) and tetrakis(triphenylphosphine)palladium(0) (108 mg, 0.094 mmol). The resulting mixture was stirred at 100° C. for 2 hour in CEM microwave. The progress of reaction was monitored by TLC. The reaction mixture was cooled to room temperature dilute with water (20 mL), extracted with ethyl acetate (20 mL) washed with brain solution. The crude residue was purified by gradient column chromatography using 0-10% Methano in Dichloromethane then purified through prep TLC, to afford 2-(1-methyl-1H-imidazol-2-yl)-6-((tetrahydro-2H-pyran-4-yl)methoxy)-N-(2-(trifluoromethyl)pyridin-4-yl)pyrimidine-4-carboxamide (0.052 g, 36.05% yield) as a off white solid.

Provided in Table 16 are characterization data for the compound of Formula I prepared by the method shown in Example 16.

TABLE 16

(Compound 74)

| Compound | Structure | LCMS (M + H) | HPLC Purity (%) | $^1$H NMR |
|---|---|---|---|---|
| 74 | 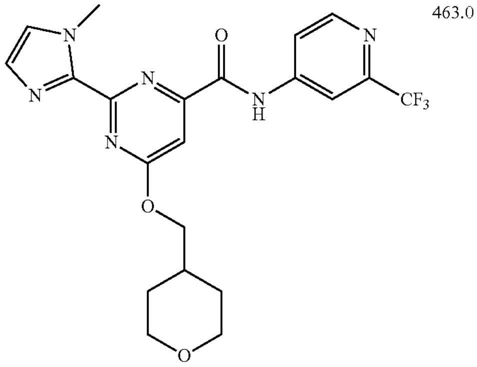 | 463.0 | 98.89 | 1HNMR (400 MHZ, DMSO-d6): δ 11.00 (s, 1H), 8.74 (d, J = 5.2 Hz, 1H), 8.52 (m, 2H), 8.42 (s, 1H), 8.23 (d, J = 4.4 Hz, 1H), 7.36 (s,1H), 4.37 (d, J = 6.0 Hz, 2H), 4.18 (s, 3H), 3.88 (d, J = 9.2 Hz 2H), 2.10 (m, 1H), 1.67 (q, J = 12,4 Hz 2H), 1.38 (q, J = 10 Hz 2H),. |

Example 17

Synthesis of Compound 75

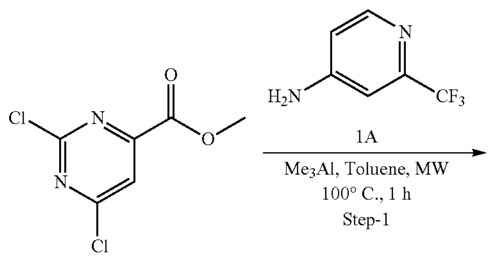

1

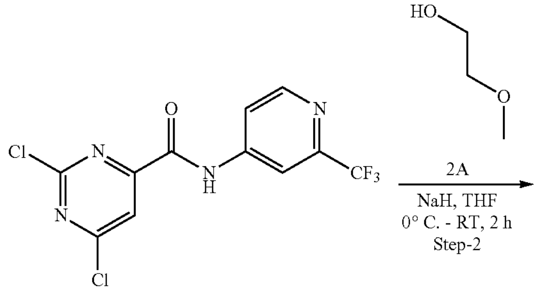

2

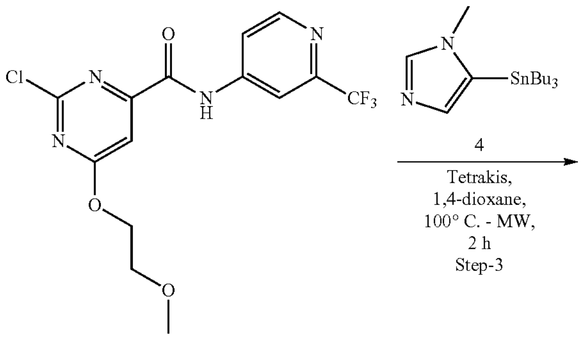

3

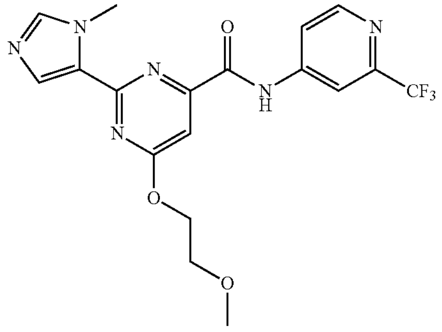

T-199

Step-1: 2,6-dichloro-N-(2-(trifluoromethyl)pyridin-4-yl)pyrimidine-4-carboxamide

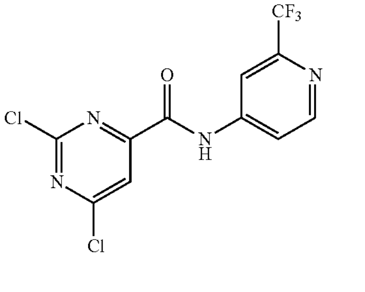 [SMILES: O=C(Nc1ccnc(C(F)(F)F)c1)c1cc(Cl)nc(Cl)n1]

To a solution of methyl 6-chloro-4-methoxypyridine-2-carboxylate (1.0 g, 4.83 mmol) in toluene (5 mL) was added 2-(trifluoromethyl)pyridin-4-amine (783 mg, 4.83 mmol) and Trimethyl aluminum (3.62 mL, 7.25 mmol) at 0° C. The resulting mixture was stirred in CEM microwave at 100° C. for 1 hour. The progress of reaction was monitored by TLC. The reaction mixture was cooled to ambient temperature was quenched with ice water (10 mL), extracted with ethyl acetate (50 mL). The crude residue was purified by gradient column chromatography using 0-30% ethyl acetate in hexane to afford 2,6-dichloro-N-(2-(trifluoromethyl)pyridin-4-yl)pyrimidine-4-carboxamide (1.2 g, 73.7% yield) as an off white solid.

Step-2: 2-chloro-6-(2-methoxyethoxy)-N-[2-(trifluoromethyl)pyridin-4-yl]pyrimidine-4-carboxamide

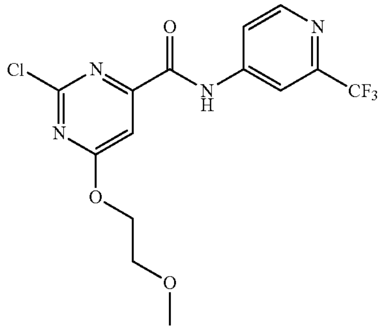 [SMILES: COCCOc1cc(C(=O)Nc2ccnc(C(F)(F)F)c2)nc(Cl)n1]

To a solution of Sodium hydride (60% in mineral oil) (0.208 g, 3.11 mmol) in Tetrahydrofuran (10 mL) was added 2-methoxyethan-1-ol (0.237 g, 3.11 mmol) at 0° C., the reaction mixture was stirred for 10 minutes and added 2,6-dichloro-N-(2-(trifluoromethyl)pyridin-4-yl)pyrimidine-4-carboxamide dissolved in Tetrahydrofuran (5 ml) (1.05 g, 3.11 mmol) The resulting mixture was stirred in room temperature for 1 hour. The progress of reaction was monitored by TLC. The reaction mixture was quenched with saturated ammonium chloride solution (30 mL), extracted with ethyl acetate (50 mL). The crude residue was purified by gradient column chromatography using 0-30% ethyl acetate in hexane to afford 2-chloro-6-(2-methoxyethoxy)-N-[2-(trifluoromethyl)pyridin-4-yl]pyrimidine-4-carboxamide (0.4 g, 34.09% yield) as an off white solid.

Step-3: 6-(2-methoxyethoxy)-2-(1-methyl-1H-imidazol-5-yl)-N-[2-(trifluoromethyl)pyridin-4-yl]pyrimidine-4-carboxamide

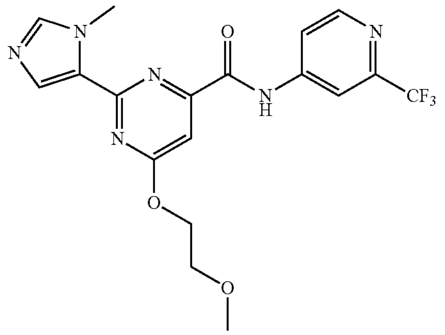 [SMILES: COCCOc1cc(C(=O)Nc2ccnc(C(F)(F)F)c2)nc(-c2cncn2C)n1]

To a solution of 2-chloro-6-(2-methoxyethoxy)-N-[2-(trifluoromethyl)pyridin-4-yl]pyrimidine-4-carboxamide (0.1 g, 0.265 mmol) in 1,4-dioxane (5 mL) was added 1-methyl-5-(tributylstannyl)-1H-imidazole (148 mg, 0.398 mmom) and tetrakis(triphenylphosphine)palladium(0) (92 mg, 0.08 mmol). The resulting mixture was stirred at 100° C. for 2 hour in CEM microwave. The progress of reaction was monitored by TLC. The reaction mixture was cooled to room temperature dilute with water (20 mL), extracted with ethyl acetate (20 mL) washed with brain solution. The crude residue was purified by gradient column chromatography using 0-100% Ethyl acetate in hexane and 0-10% Methanol in Dichloromethane then purified through prep TLC, to afford 6-(2-methoxyethoxy)-2-(1-methyl-1H-imidazol-5-yl)-N-[2-(trifluoromethyl)pyridin-4-yl]pyrimidine-4-carboxamide (0.031 g, 36.05% yield) as a off white solid.

Provided in Table 17 are characterization data for the compound of Formula I prepared by the method shown in Example 17.

TABLE 17

(Compound 75)

| Compound | Structure | LCMS (M + H) | HPLC Purity (%) | 1H NMR |
|---|---|---|---|---|
| 75 | 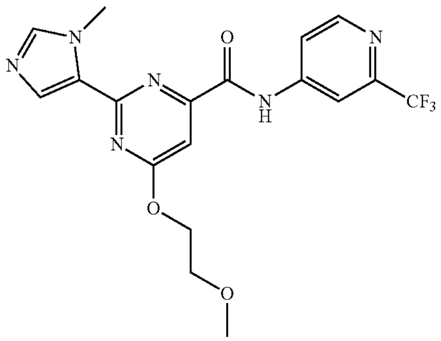 [SMILES: COCCOc1cc(C(=O)Nc2ccnc(C(F)(F)F)c2)nc(-c2cncn2C)n1] | 423.0 | 99.91 | 1HNMR (400 MHz, DMSO-d6): δ 10.97 (s, 1H), 8.72 (d, J = 5.6 Hz, 1H), 8.45 (s, 1H), 8.24 (s, 2H), 7.93 (s, 1H), 7.26 (s,1H), 4.60 (m, 2H), 4.08 (s, 3H), 3.72 (m, 2H), 3.31 (s, 3H). |

Example 18

Synthesis of Compound 76

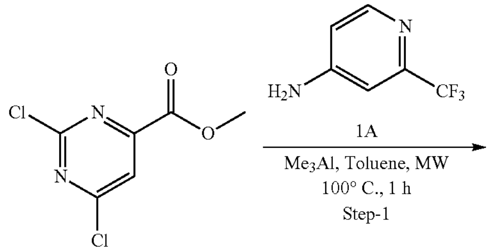

1

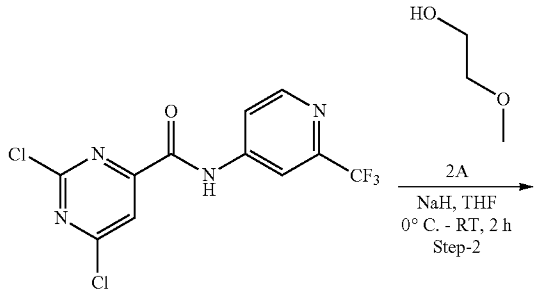

2

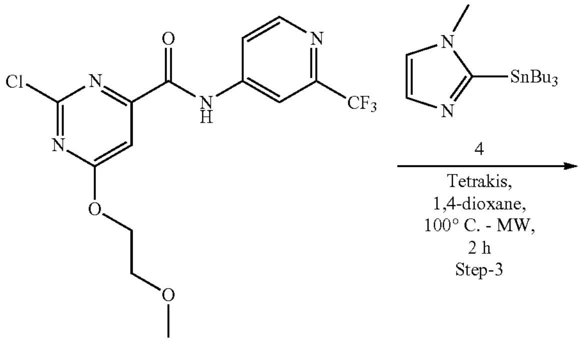

3

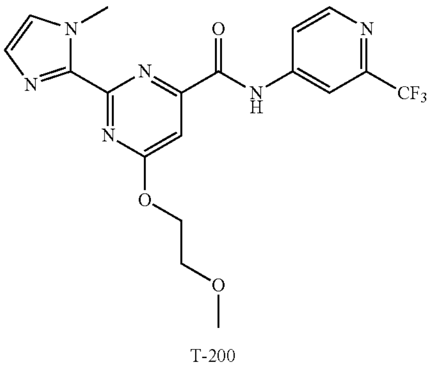

T-200

Step-1: 2,6-dichloro-N-(2-(trifluoromethyl)pyridin-4-yl)pyrimidine-4-carboxamide

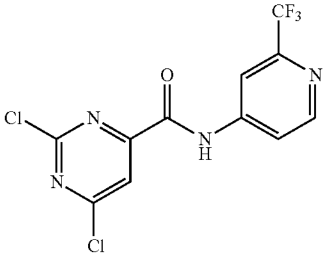 [SMILES: O=C(Nc1ccnc(C(F)(F)F)c1)c1cc(Cl)nc(Cl)n1]

To a solution of methyl 6-chloro-4-methoxypyridine-2-carboxylate (1.0 g, 4.83 mmol) in toluene (5 mL) was added 2-(trifluoromethyl)pyridin-4-amine (783 mg, 4.83 mmol) and Trimethyl aluminum (3.62 mL, 7.25 mmol) at 0° C. The resulting mixture was stirred in CEM microwave at 100° C. for 1 hour. The progress of reaction was monitored by TLC. The reaction mixture was cooled to ambient temperature was quenched with ice water (10 mL), extracted with ethyl acetate (50 mL). The crude residue was purified by gradient column chromatography using 0-30% ethyl acetate in hexane to afford 2,6-dichloro-N-(2-(trifluoromethyl)pyridin-4-yl)pyrimidine-4-carboxamide (1.2 g, 73.7% yield) as an off white solid.

Step-2: 2-chloro-6-(2-methoxyethoxy)-N-[2-(trifluoromethyl)pyridin-4-yl]pyrimidine-4-carboxamide

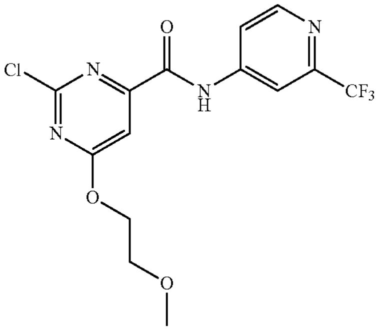 [SMILES: COCCOc1cc(C(=O)Nc2ccnc(C(F)(F)F)c2)nc(Cl)n1]

To a solution of Sodium hydride (60% in mineral oil) (0.208 g, 3.11 mmol) in Tetrahydrofuran (10 mL) was added 2-methoxyethan-1-ol (0.237 g, 3.11 mmol) at 0° C., the reaction mixture was stirred for 10 minutes and added 2,6-dichloro-N-(2-(trifluoromethyl)pyridin-4-yl)pyrimidine-4-carboxamide dissolved in Tetrahydrofuran (5 ml) (1.05 g, 3.11 mmol) The resulting mixture was stirred in room temperature for 1 hour. The progress of reaction was monitored by TLC. The reaction mixture was quenched with saturated ammonium chloride solution (30 mL), extracted with ethyl acetate (50 mL). The crude residue was purified by gradient column chromatography using 0-30% ethyl acetate in hexane to afford 2-chloro-6-(2-methoxyethoxy)-N-[2-(trifluoromethyl)pyridin-4-yl]pyrimidine-4-carboxamide (0.4 g, 34.09% yield) as an off white solid.

Step-3: 6-(2-methoxyethoxy)-2-(1-methyl-1H-imidazol-2-yl)-N-[2-(trifluoromethyl)pyridin-4-yl]pyrimidine-4-carboxamide

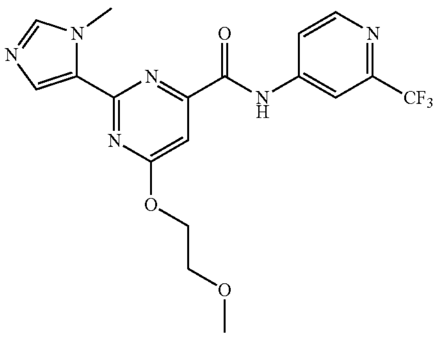 [SMILES: COCCOc1cc(C(=O)Nc2ccnc(C(F)(F)F)c2)nc(-c2cncn2C)n1]

To a solution of 2-chloro-6-(2-methoxyethoxy)-N-[2-(trifluoromethyl)pyridin-4-yl]pyrimidine-4-carboxamide (0.13 g, 0.345 mmol) in 1,4-dioxane (5 mL) was added 1-methyl-2-(tributylstannyl)-1H-imidazole (192 mg, 0.518 mmom) and tetrakis(triphenylphosphine)palladium(0) (120 mg, 0.104 mmol). The resulting mixture was stirred at 100° C. for 2 hour in CEM microwave. The progress of reaction was monitored by TLC. The reaction mixture was cooled to room temperature dilute with water (20 mL), extracted with ethyl acetate (20 mL) washed with brain solution. The crude residue was purified by gradient column chromatography using 0-100% Ethyl acetate in hexane and 0-10% Methanol in Dichloromethane then purified through prep HPLC, to afford 6-(2-methoxyethoxy)-2-(1-methyl-1H-imidazol-2-yl)-N-[2-(trifluoromethyl)pyridin-4-yl]pyrimidine-4-carboxamide (0.042 g, 28.82% yield) as a off white solid.

Provided in Table 18 are characterization data for the compound of Formula I prepared by the method shown in Example 18.

TABLE 18

(Compound 76)

| Compound | Structure | LCMS (M + H) | HPLC Purity (%) | $^1$H NMR |
|---|---|---|---|---|
| 76 | 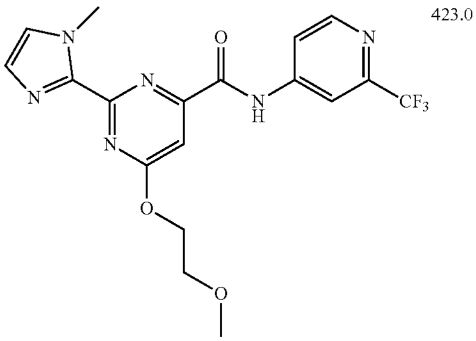 | 423.0 | 99.97 | 1HNMR (400 MHz, DMSO-d6): δ 10.97 (s, 1H), 8.72 (bs, 1H), 8.45 (s, 1H), 8.22 (m, 2H), 7.89 (s, 1H), 7.25 (s, 1H), 4.60 (m, 2H), 4.08 (s, 3H), 3.73 (m, 2H), 3.32 (s, 3M). |

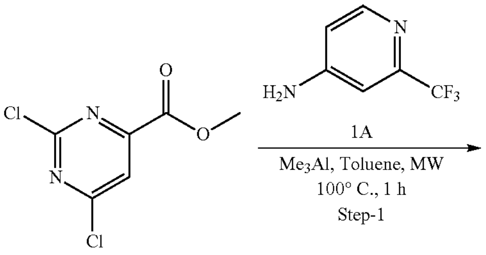

1

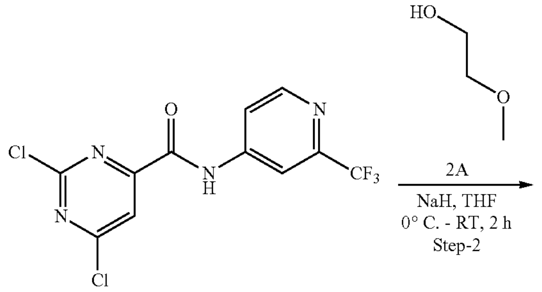

2

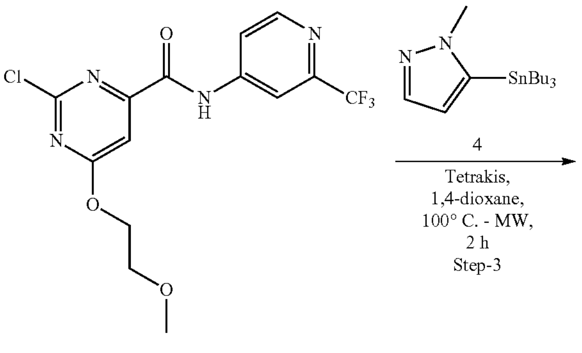

3

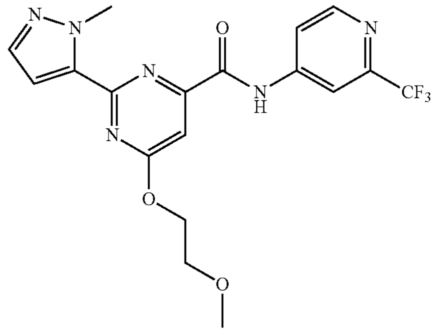

T-201

Step-1: 2,6-dichloro-N-(2-(trifluoromethyl)pyridin-4-yl)pyrimidine-4-carboxamide

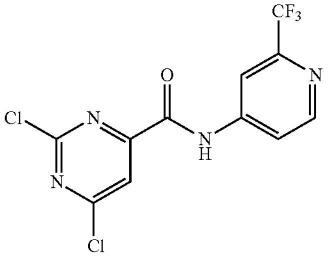 [SMILES: O=C(Nc1ccnc(C(F)(F)F)c1)c1cc(Cl)nc(Cl)n1]

To a solution of methyl 6-chloro-4-methoxypyridine-2-carboxylate (1.0 g, 4.83 mmol) in toluene (5 ml-) was added 2-(trifluoromethyl)pyridin-4-amine (783 mg, 4.83 mmol) and Trimethyl aluminum (3.62 mL, 7.25 mmol) at 0° C. The resulting mixture was stirred in CEM microwave at 100° C. for 1 hour. The progress of reaction was monitored by TLC. The reaction mixture was cooled to ambient temperature was quenched with ice water (10 mL), extracted with ethyl acetate (50 mL). The crude residue was purified by gradient column chromatography using 0-30% ethyl acetate in hexane to afford 2,6-dichloro-N-(2-(trifluoromethyl)pyridin-4-yl)pyrimidine-4-carboxamide (1.2 g, 73.7% yield) as an off white solid.

Step-2: 2-chloro-6-(2-methoxyethoxy)-N-[2-(trifluoromethyl) pyridin-4-yl]pyrimidine-4-carboxamide

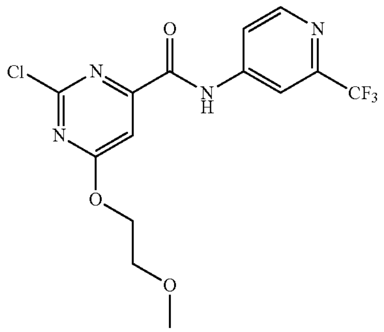 [SMILES: COCCOc1cc(C(=O)Nc2ccnc(C(F)(F)F)c2)nc(Cl)n1]

To a solution of Sodium hydride (60% in mineral oil) (0.208 g, 3.11 mmol) in Tetrahydrofuran (10 mL) was added 2-methoxyethan-1-ol (0.237 g, 3.11 mmol) at 0° C., the reaction mixture was stirred for 10 minutes and added 2,6-dichloro-N-(2-(trifluoromethyl)pyridin-4-yl)pyrimidine-4-carboxamide dissolved in Tetrahydrofuran (5 ml) (1.05 g, 3.11 mmol) The resulting mixture was stirred in room temperature for 1 hour. The progress of reaction was monitored by TLC. The reaction mixture was quenched with saturated ammonium chloride solution (30 mL), extracted with ethyl acetate (50 mL). The crude residue was purified by gradient column chromatography using 0-30% ethyl acetate in hexane to afford 2-chloro-6-(2-methoxyethoxy)-N-[2-(trifluoromethyl)pyridin-4-yl]pyrimidine-4-carboxamide (0.4 g, 34.09% yield) as an off white solid.

Step-3: 6-(2-methoxyethoxy)-2-(1-methyl-1H-imidazol-2-yl)-N-[2-(trifluoromethyl)pyridin-4-yl]pyrimidine-4-carboxamide

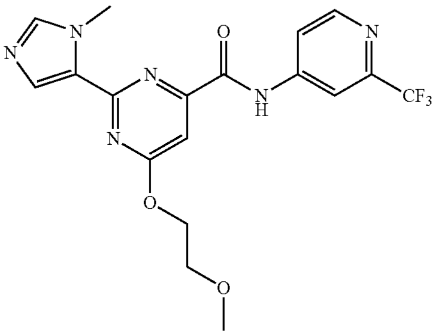 [SMILES: COCCOc1cc(C(=O)Nc2ccnc(C(F)(F)F)c2)nc(-c2cncn2C)n1]

To a solution of 2-chloro-6-(2-methoxyethoxy)-N-[2-(trifluoromethyl)pyridin-4-yl]pyrimidine-4-carboxamide (0.13 g, 0.345 mmol) in 1,4-dioxane (5 ml) was added 1-methyl-2-(tributylstannyl)-1H-imidazole (192 mg, 0.518 mmom) and tetrakis(triphenylphosphine)palladium(0) (120 mg, 0.104 mmol). The resulting mixture was stirred at 10000 for 2 hour in CEM microwave. The progress of reaction was monitored by TLC. The reaction mixture was cooled to room temperature dilute with water (20 mL), extracted with ethyl acetate (20 ml-) washed with brain solution. The crude residue was purified by gradient column chromatography using 0-100% Ethyl acetate in hexane and 0-10% Methanol in Dichloromethane then purified through prep HPLC, to afford 6-(2-methoxyethoxy)-2-(1-methyl-1H-imidazol-2-yl)-N-[2-(trifluoromethyl) pyridin-4-yl]pyrimidine-4-carboxamide (0.048 g, 32.93% yield) as an off white solid.

Provided in Table 19 are characterization data for the compound of Formula I prepared by the method shown in Example 19.

TABLE 19

(Compound 77)

| Compound | Structure | LCMS (M + H) | HPLC Purity (%) | $^1$H NMR |
|---|---|---|---|---|
| 77 | 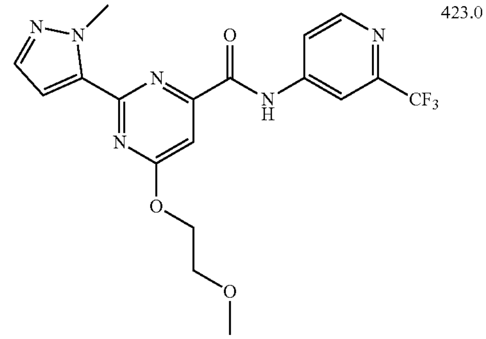 | 423.0 | 99.53 | 1HNMR (400 MHz, DMSO-d6): δ 11.06 (s, 1H), 8.72 (d, J = 5.2 Hz, 1H), 8.44 (s, 1H), 8.22 (J = 5.2 Hz, 1H), 7.58 (s, 1H), 7.44 (s,1H), 7.38 (s, 1H), 4.63 (m, 2H), 4.31 (s, 3H), 3.74 (m, 2H), 3.31 (s, 3H). |

Example 20

Synthesis of Compound 78

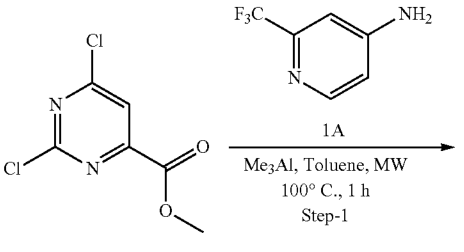

1

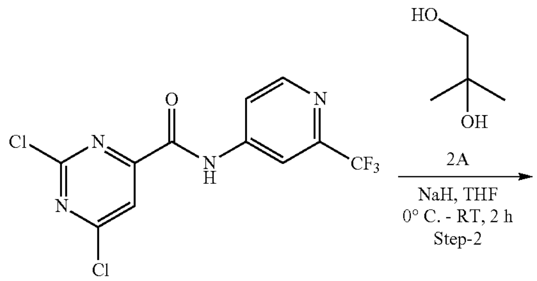

2

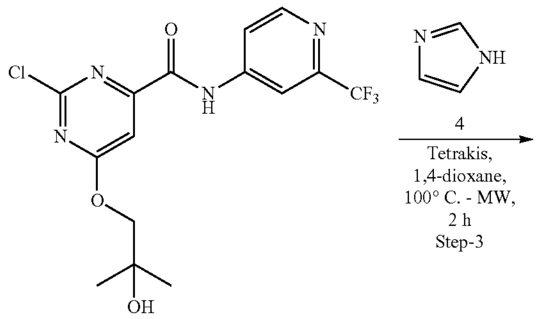

3

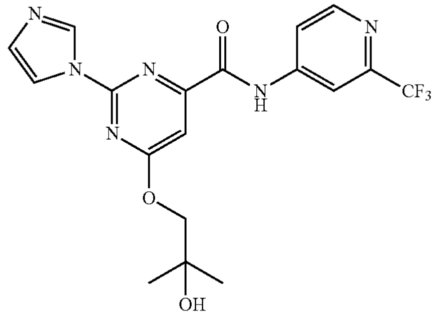

T-202

Step-1: 2,6-dichloro-N-(2-(trifluoromethyl)pyridin-4-yl)pyrimidine-4-carboxamide 89879

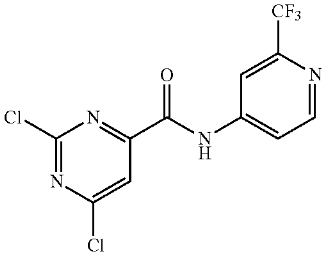 [SMILES: O=C(Nc1ccnc(C(F)(F)F)c1)c1cc(Cl)nc(Cl)n1]

To a solution of methyl 6-chloro-4-methoxypyridine-2-carboxylate (0.5 g, 2.42 mmol) in toluene (5 mL) was added 2-(trifluoromethyl)pyridin-4-amine (392 mg, 2.42 mmol) and Trimethyl aluminum (1.8 mL, 3.62 mmol) at 0° C. The resulting mixture was stirred in CEM microwave at 100° C. for 1 hour. The progress of reaction was monitored by TLC. The reaction mixture was cooled to ambient temperature was quenched with ice water (10 mL), extracted with ethyl acetate (50 mL). The crude residue was purified by gradient column chromatography using 0-30% ethyl acetate in hexane to afford 2,6-dichloro-N-(2-(trifluoromethyl)pyridin-4-yl)pyrimidine-4-carboxamide (0.6 g, 73.7% yield) as an off white solid.

Step-2: 2-chloro-6-(2-hydroxy-2-methylpropoxy)-N-(2-(trifluoromethyl)pyridin-4-yl)pyrimidine-4-carboxamide 90016

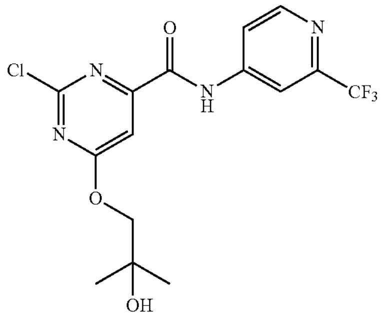 [SMILES: CC(C)(O)COc1cc(C(=O)Nc2ccnc(C(F)(F)F)c2)nc(Cl)n1]

To a solution of Sodium hydride (60% in mineral oil) (0.1 g, 1.48 mmol) in Tetrahydrofuran (10 mL) was added 2-methylpropane-1,2-diol (0.134 g, 1.48 mmol) at 0° C., the reaction mixture was stirred for 10 minutes and added 2,6-dichloro-N-(2-(trifluoromethyl)pyridin-4-yl)pyrimidine-4-carboxamide dissolved in Tetrahydrofuran (5 ml) (0.5 g, 1.48 mmol) The resulting mixture was stirred in room temperature for 1 hour. The progress of reaction was monitored by TLC. The reaction mixture was quenched with saturated ammonium chloride solution (30 mL), extracted with ethyl acetate (20 mL). The crude residue was purified by gradient column chromatography using 0-30% ethyl acetate in hexane to afford 2-chloro-6-(2-hydroxy-2-methylpropoxy)-N-(2-(trifluoromethyl)pyridin-4-yl)pyrimidine-4-carboxamide (0.25 g, 43.13% yield) as Thick solid.

Step-3: 6-(2-hydroxy-2-methylpropoxy)-2-(1H-imidazol-1-yl)-N-(2-(trifluoromethyl)pyridin-4-yl)pyrimidine-4-carboxamide

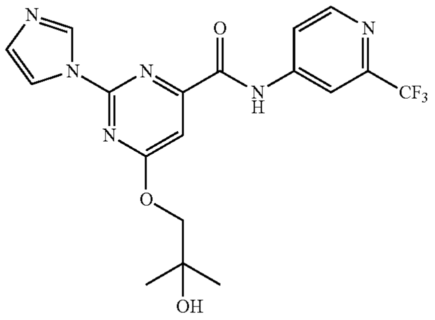 [SMILES: CC(C)(O)COc1cc(C(=O)Nc2ccnc(C(F)(F)F)c2)nc(-n2ccnc2)n1]

To a solution of 2-chloro-6-(2-hydroxy-2-methylpropoxy)-N-(2-(trifluoromethyl)pyridin-4-yl)pyrimidine-4-carboxamide (0.2 g, 0.512 mmol) in N,N-dimethylformamide (5 mL) was added caesium carbonate (0.25 g, 0.768 mmol), diiodocopper (49.0 mg, 0.154 mmom) and 1H-imidazole (52.3 mg, 0.768 mmol). The resulting mixture was stirred at 100° C. for 8 hour. The progress of reaction was monitored by TLC. The reaction mixture was cooled to room temperature dilute with water (20 mL), extracted with ethyl acetate (20 mL). The crude residue was purified by gradient column chromatography using 0-10% Methanol in Dichloromethane then purified through Prep-HPLC to afford 6-(2-hydroxy-2-methylpropoxy)-2-(1H-imidazol-1-yl)-N-(2-(trifluoromethyl)pyridin-4-yl)pyrimidine-4-carboxamide (0.03 g, % yield) as an off white solid.

Prep Conditions:

Column: Inertsil C18, (20 mm×250 mm×5 mic)

Mobile phase(A): 0.1% Ammoni in Water

Mobile phase(B): Acetonitrile

Flow rate: 19 mL/min

Gradient B: 0/8%, 9-14/55%, 15-20/90%, 22-25/10%.

Provided in Table 20 are characterization data for the compound of Formula I prepared by the method shown in Example 20. Table 20 (Compound 78)

TABLE 20

(Compound 78)

| Compound | Structure | LCMS (M + H) | HPLC Purity (%) | $^1$H NMR |
|---|---|---|---|---|
| 78 | 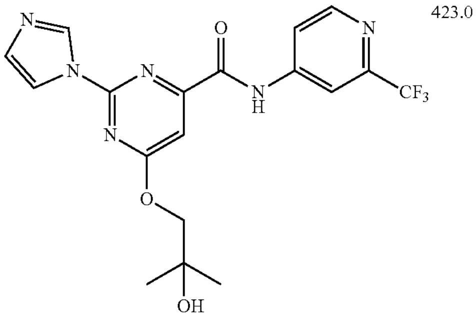 | 423.0 | 98.27 | 1HNMR (400 MHz, DMSO-d6): δ 10.99 (s, 1H), 8.98 (s, 1H), 8.73 (d, J = 5.2 Hz, 1H), 8.41 (s, 1H), 8,26-8.23 (m, 2H), 7.38 (s, 1H), 7.17 (s, 1H), 4.76 (s, 1H), 4.32 (s, 2H), 1.21 (s, 6H), |

Example 21

Synthesis of Compound 79

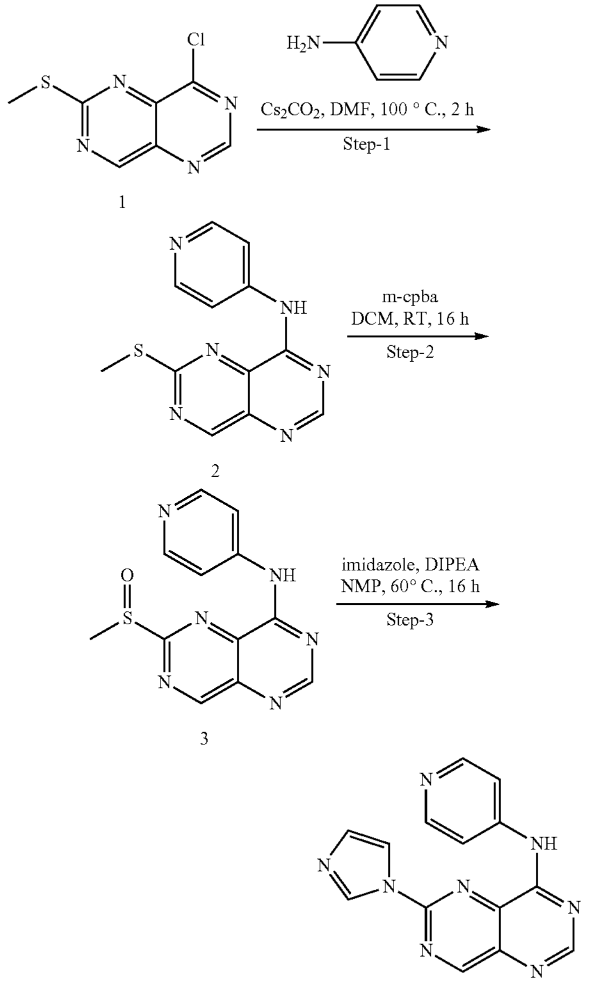

1 2 3 4

Step-1: 6-(methylthio)-N-(pyridin-4-yl)pyrimido[5,4-d]pyrimidin-4-amine

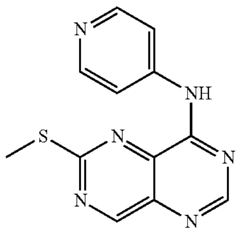 [SMILES: CSc1ncc2ncnc(Nc3ccncc3)c2n1]

To a stirred solution of 8-chloro-2-(methylsulfanyl)-[1,3]diazino[5,4-d]pyrimidine (300 mg, 1.41 mmol) in DMF was added pyridin-4-amine (119 mg, 0.9 eq., 1.27 mmol) and cesium(1+) carbonate (689 mg, 1.5 eq., 2.12 mmol). The reaction mixture was heated to 100° C. for 3 hours. The reaction mixture was cooled to room temperature and completely evaporated off to obtain crude compound which was purified over silica gel flash column chromatography. The compound eluted out in 5% MeOH: DCM. The fractions were evaporated off to obtain crude N-[6-(methylsulfanyl)-[1,3]diazino[5,4-d]pyrimidin-4-yl]pyridin-4-amine (200 mg, 740 μmol) as a yellow solid. LCMS (ES) m/z=271.1 [M+H]+

Step-2: N-{6-methanesulfinyl-[1,3]diazino[5,4-d]pyrimidin-4-yl}pyridin-4-amine

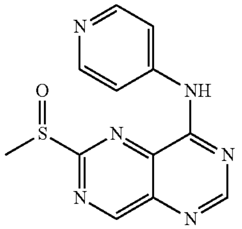 [SMILES: CS(=O)c1ncc2ncnc(Nc3ccncc3)c2n1]

To a stirred solution of N-[6-(methylsulfanyl)-[1,3]diazino[5,4-d]pyrimidin-4-yl]pyridin-4-amine (200 mg, 740 μmol) in DCM was added 3-chlorobenzene-1-carboperoxoic acid (255 mg, 2 eq., 1.48 mmol). The reaction mixture was stirred at room temperature for 16 hours. The reaction mixture was quenched with sat.NaHCO3 solution and extracted in DCM. The organic layer was dried over sodium sulfate and evaporated off to obtain crude N-{6-methanesulfinyl-[1,3]diazino[5,4-d]pyrimidin-4-yl}pyridin-4-amine (180 mg, 629 μmol) as an oily compound.

LCMS (ES) m/z=287.1 [M+H]+

Step-4: 6-(1H-imidazol-1-yl)-N-(pyridin-4-yl)pyrimido[5,4-d]pyrimidin-4-amine

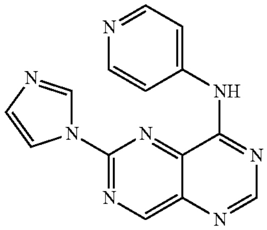 [SMILES: c1cc(Nc2ncnc3cnc(-n4ccnc4)nc23)ccn1]

To a stirred solution of N-{6-methanesulfinyl-[1,3]diazino[5,4-d]pyrimidin-4-yl}pyridin-4-amine (200 mg, 699 μmol) in NMP was added ethylbis(propan-2-yl)amine (579 μL, 5 eq., 3.49 mmol) followed by 6-(1H-imidazol-1-yl)-N-phenyl-[1,3]diazino[5,4-d]pyrimidin-4-amine (10.0 mg, 34.6 μmol). The reaction mixture was heated to 60° C. for 16 hours. The reaction mixture was cooled to room temperature and extracted in ethyl acetate. The organic layer was dried over sodium sulfate and evaporated off to obtain crude which was purified over silica gel flash column chromatography. The compound eluted out as a mixture in 5% MeOH:DCM. The fractions were evaporated off to obtain crude which was re-purified by prep TLC. The silica gel band was taken and passed through 4 g silica gel column. The fractions were evaporated off to obtain the final compound as an off white solid.

Provided in Table 21 are characterization data for the compound of Formula I prepared by the method shown in Example 21.

TABLE 21

(Compound 79)

| Compound | Structure | LCMS (M + H) | HPLC Purity (%) | $^1$H NMR |
|---|---|---|---|---|
| 79 | 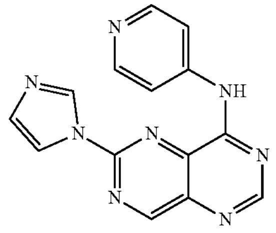 [SMILES: c1cc(Nc2ncnc3cnc(-n4ccnc4)nc23)ccn1] | 291.1 | | 1HNMR (400 DMSO-d6): δ 10.36 (s, 1H), 9.60 (s, 1H), 9.02 (s, 1H), 8.85 (s, 1H), 8.57 (d, J = 5.6 Hz, 2H), 8.38 (s, 1H), 8.11 (d, J = 5.6 Hz, 2H), 7.22 (s, 1H) |

Example 22

Heteroaryl Amide Derivatives

Provided in Table 22 are characterization data for compounds of Formula I.

TABLE 22

(Compounds 80-83)

| Compound | Structure | LCMS (M + H) | HPLC Purity (%) | $^1$H NMR |
|---|---|---|---|---|
| 80 | 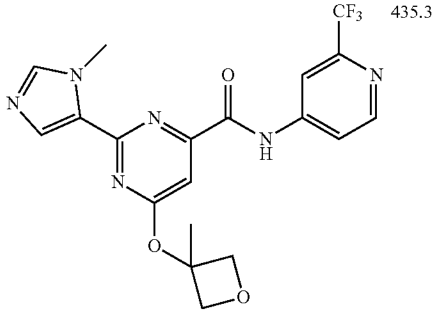 | 435.3 | 99.3 | $^1$H NMR (400 MHz, DMSO-$d_6$) δ 10.92 (s, 1H), 8.71 (d, J = 5.2 Hz, 1H), 8.41 (s, 1H), 8.18 (d, J = 4.4 Hz, 1H), 8.04 (s, 1H), 7.89 (s, 1H), 7.25 (s, 1H), 4.84 (d, J = 7.2 Hz, 2H), 4.66 (d, J = 7.2 Hz, 2H), 4.04 (s, 3H), 1.83 (s, 3H). |
| 81 | 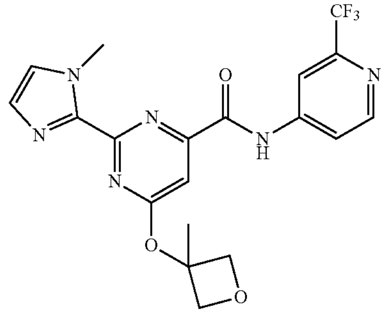 [SMILES: Cn1ccnc1-c1nc(OC2(C)COC2)cc(C(=O)Nc2ccnc(C(F)(F)F)c2)n1] | 435.3 | 97.8 | $^1$H NMR (400 MHz, DMSO-$d_6$) δ 10.82 (s, 1H), 8.71 (d, J = 5.2 Hz, 1H), 8.38 (s, 1H), 8.14 (s, 1H), 8.04 (s, 1H), 7.92 (s, 1H), 7.26 (s, 1H), 4.84 (d, J = 7.2 Hz, 2H), 4.66 (d, J = 7.2 Hz, 2H), 4.04 (s, 3H), 1.85 (s, 3H). |

TABLE 22-continued

| Compound | Structure | LCMS (M + H) | HPLC Purity (%) | $^1$H NMR |
|---|---|---|---|---|
| (Compounds 80-83) | | | | |
| 82 | 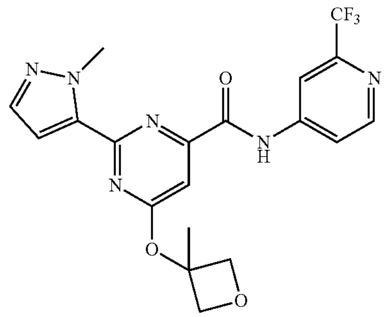 [SMILES: Cn1nccc1-c1nc(OC2(C)COC2)cc(C(=O)Nc2ccnc(C(F)(F)F)c2)n1] | 435.3 | 99.43 | $^1$H NMR (400 MHz, DMSO-$d_6$) δ 11.04 (s, 1H), 8.72 (d, J = 4.8 Hz, 1H),8.43 (s, 1H), 8.20 (s, 1H),7.57 (s, 1H), 7.39 (s, 1H), 7.25 (s, 1H), 4.86 (d, J = 6.4 Hz, 2H), 4.66 (d, J = 7.2 Hz, 2H), 4.26 (s, 3H), 1.84 (s, 3H). |

Example 23

Fluorescence-based NAD+ Hydrolase Activity Assay with Human T Cell Line NH7-dCas9 Cells-Jurkat Clone (Assay 1)

The following protocol was modified from the following references: de Oliveira et al. (2018). *Bio. Protoc.* 8(14). doi:10.21769/BioProtoc.2938; Matalonga et al. (2017) *Cell Rep.* 18(5), 1241-1255; doi:10.1016/j.celrep.2017.01.007; Muller et al. (1983) *Biochem J.* 212(2), 459-464. doi: 10.1042/bj2120459; Schultzet et al. (2018). *Meth. Mol. Bio.* 1813, 77-90. doi:10.1007/978-1-4939-8588-3_6.

For the modified assay, the performance validation criteria of the assay as a High Throughput Screening (HTS): Z-factor within the plate was greater than 0.89 (optimal HTS z-factor >0.5) and the Intra-plate, inter-plate and day to day variability (CV) was less than 20%.

NAD+ hydrolase activity of a human T cell line treated with test compounds was measured using a fluorescence-based assay. NH7-dCas9 cells (Jurkat clone) were provided by the Weissman Lab (UCSF 1700 4th St., Byers Hall, Room 403B, San Francisco, CA 94158-2330). Briefly, cells were centrifuged, resuspended in 44 μl PBS/$10^6$ cells and plated in a 96 well black plate (CORNING) at a density of $1\times10^6$ per well.

Each test compound was received in a powder state and dissolved in DMSO as a 25 mM stock solution. Each test compound was serially diluted in order to generate a dose-response curve. The dilution series of each test compound in DMSO was prepared at 50 times the concentrations to be assayed. Each test compound was diluted to generate a 5-fold dilution series of 8 concentrations from 20 μM to 0.256 nM in order to assay 8 final concentrations ranging from 400 nM to 25.6 pM. One μl of the 50× concentration compound series was added to each well of the plate containing $1\times10^6$ cells in PBS.

Each plate had the following intra plate controls: 3 wells containing cells treated with vehicle only (DMSO), 3 wells of cells treated with the reference compound 78c at a final concentration of 50 nM and 2 wells containing only PBS (used as a background value).

The reaction was started by adding nicotinamide 1,$N^6$-etheno-adenine dinucleotide (Sigma Aldrich) to reach a final concentration of 80 □M. The samples were excited at 321-15 nm, and the emission of fluorescence was measured at 410-20 nm at 37° C. every minute for 1 hr in a Clariostar® microplate reader (BMG LABTECH). NAD+ hydrolase activity was calculated as the slope of the linear portion of the fluorescence-time curve using the MARS data analysis software (BMG LABTECH). The data were uploaded in the Collaborative Drug Design (CDD) Software and for each compound the IC50 was calculated by the software. Each compound was tested in 3 independent experiments on 3 separate days to establish the reproducibility of the results. For each plate, the z-factor was also calculated as a plate quality using the CDD software.

Example 24

Fluorescence-Based NAD+ Cyclase Activity Assay with Human Recombinant CD38 Protein (Assay 2)

This protocol was modified from the de Oliveira et al., 2018 reference, supra.

NAD+ cyclase activity of the human recombinant CD38 protein treated with test compounds was measured using a fluorescence-based assay. Briefly, recombinant human CD38 Protein (R&D System) was resuspended in 44 μl/well of Sucrose-Tris Buffer (Sucrose 0.25 M, Tris pH 7.4 40 mM) and plated in a 96-well black plate (CORNING) at a density of 125 ng/well.

Each test compound was received in a powder state and dissolved in DMSO as a 25 mM stock solution. Each test compound was serially diluted in order to generate a dose-response curve. The dilution series of each test compound in DMSO was prepared at 50 times the concentrations to be assayed. Each test compound was diluted to generate a 5-fold dilution series of 8 concentrations from 100 μM to 32 nM in order to assay 8 final concentrations ranging from 2 μM to 0.64 nM. One μl of the 50× concentration compound series was added to each well of the plate containing 125 ng of protein in Sucrose-Tris buffer.

Each plate had the following intra plate controls: 3 wells containing cells treated with vehicle only (DMSO), 3 wells of cells treated with the reference compounds 78c at a final concentration of 500 nM and 2 wells containing only Sucrose-Tris buffer (used as a background value).

The reaction was started adding nicotinamide guanine dinucleotide (NGD+) (Sigma Aldrich) to reach a final concentration of 150 □M. The samples were excited at 337-15 nm, and the emission of fluorescence was measured at 442-20 nm at 37° C. every minute for 1 hr in a Clariostar microplate reader (BMG LABTECH). NAD+ cyclase activity was calculated as the slope of the linear portion of the fluorescence-time curve using the MARS data analysis software (BMG LABTECH). The data were uploaded in the Collaborative Drug Design (CDD) Software, and for each compound the IC50 was calculated by the software. For each plate, the z-factor was also calculated as a plate quality using the CDD software.

Example 25

Fluorescence-based NAD+ Hydrolase Activity Assay with Human Recombinant CD38 Protein (Assay 3)

This protocol was modified from the following references (Muller et al. (1983); (Schultz et al. (2018); (Matalonga et al. (2017); and de Oliveira et al. (2018), supra.

For the modified assay, the performance validation criteria of the assay as a High Throughput Screening (HTS): Z-factor within the plate was greater than 0.9 (optimal HTS z-factor >0.5) and the Intra-plate, inter-plate and day to day variability (CV) was less than 20%.

NAD+ hydrolase activity of the human recombinant CD38 protein treated with test compounds was measured using a fluorescence-based assay. Briefly, recombinant human CD38 Protein (R&D System) was resuspended in 44 μl/well of Sucrose-Tris Buffer (Sucrose 0.25 M, Tris pH 7.4 40 mM) and plated in a 96-well black plate (CORNING) at a density of 10 ng/well.

Each test compound was received in a powder state and dissolved in DMSO as a 25 mM stock solution. Each test compound was serially diluted in order to generate a dose-response curve. The dilution series of each test compound in DMSO was prepared at 50× the concentrations to be assayed. Each test compound was diluted to generate a 5-fold dilution series of 8 concentrations from 20 μM to 0.256 nM in order to assay 8 final concentrations ranging from ranging from 400 nM to 25.6 pM. One μl of the 50× concentration compound series was added to each well of the plate containing 10 ng protein in Sucrose-Tris buffer.

Each plate had the following intra plate controls: 3 wells containing cells treated with vehicle only (DMSO), 3 wells of cells treated with the reference compounds 78c at a final concentration of 50 nM and 2 wells containing only Sucrose-Tris buffer (used as a background value).

The reaction was started adding nicotinamide 1,$N^6$-etheno-adenine dinucleotide (Sigma Aldrich) to reach a final concentration of 80 □M. The samples were excited at 321-15 nm and the emission of fluorescence was measured at 410-20 nm at 37° C. every minute for 1 hr in a Clariostar® microplate reader (BMG LABTECH). NAD+ hydrolase activity was calculated as the slope of the linear portion of the fluorescence-time curve using the MARS data analysis software (BMG LABTECH). The data were uploaded in the Collaborative Drug Design (CDD) Software and for each compound the IC50 was calculated by the software. Each compound was tested in 3 independent experiments on 3 separate days to establish the reproducibility of the results. For each plate, the z-factor was also calculated as a plate quality using the CDD software.

Example 26

Fluorescence-based NAD+ Cyclase Activity Assay with Mouse Recombinant CD38 Protein (Assay 4)

This protocol was modified from de Oliveira et al. (2018) supra.

NAD+ cyclase activity of the human recombinant CD38 protein treated with test compounds was measured using a fluorescence-based assay. Briefly, recombinant mouse CD38 Protein (R&D System) was resuspended in 44 μl/well of Sucrose-Tris Buffer (Sucrose 0.25 M, Tris pH 7.4 40 mM) and plated in a 96-well black plate (CORNING) at a density of 32 ng/well.

Each test compound was received in a powder state and dissolved in DMSO as a 25 mM stock solution. Each test compound was serially diluted in order to generate a dose-response curve. The dilution series of each test compound in DMSO was prepared at 50 times the concentrations to be assayed. Each test compound was diluted to generate a 5-fold dilution series of 8 concentrations from 100 μM to 32 nM in order to assay 8 final concentrations ranging from 2 μM to 0.64 nM. One μl of the 50× concentration compound series was added to each well of the plate containing 125 ng of protein in Sucrose-Tris buffer.

Each plate had the following intra plate controls: 3 wells containing cells treated with vehicle only (DMSO), 3 wells of cells treated with the reference compounds 78c at a final concentration of 500 nM and 2 wells containing only Sucrose-Tris buffer (used as a background value).

The reaction was started adding nicotinamide guanine dinucleotide (NGD+) (Sigma Aldrich) to reach a final concentration of 150 □M. The samples were excited at 337-15 nm and the emission of fluorescence was measured at 442-20 nm at 37° C. every minute for 1 hr in a Clariostar® microplate reader (BMG LABTECH). NAD+ cyclase activity was calculated as the slope of the linear portion of the fluorescence-time curve using the MARS data analysis software (BMG LABTECH). The data were uploaded in the Collaborative Drug Design (CDD) Software and for each compound the IC50 was calculated by the software. Each compound was tested in 3 independent experiments on 3 separate days to establish the reproducibility of the results. For each plate, the z-factor was also calculated as a plate quality using the CDD software.

Example 27

Fluorescence-Based NAD+ Hydrolase Activity Assay with Mouse Recombinant CD38 Protein (Assay 5)

This protocol was modified from the following references: Muller et al. (1983); Schultz et al. (2018); Matalonga et al. (2017); and de Oliveira et al. (2018), supra.

NAD+ hydrolase activity of the mouse recombinant CD38 protein treated with test compounds was measured using a fluorescence-based assay. Briefly, recombinant mouse CD38 Protein (R&D System) was resuspended in 44 μl/well of Sucrose-Tris Buffer (Sucrose 0.25 M, Tris pH 7.4 40 mM) and plated in a 96 well black plate (CORNING) at a density of 2.5 ng/well.

Each test compound was received in a powder state and dissolved in DMSO as a 25 mM stock solution. Each test compound was serially diluted in order to generate a dose-response curve. The dilution series of each test compound in DMSO was prepared at 50 times the concentrations to be assayed. Each test compound was diluted to generate a 5-fold dilution series of 8 concentrations from 20 μM to 0.256 nM in order to assay 8 final concentrations ranging from 400 nM to 25.6 pM. One μl of the 50× concentration compound series was added to each well of the plate containing 2.5 ng of protein in Sucrose-Tris buffer.

Each plate had the following intra plate controls: 3 wells containing cells treated with vehicle only (DMSO), 3 wells of cells treated with the reference compounds 78c at a final concentration of 50 nM and 2 wells containing only Sucrose-Tris buffer (used as a background value).

The reaction was started adding nicotinamide 1,$N^6$-etheno-adenine dinucleotide (Sigma Aldrich) to reach a final concentration of 80 □M. The samples were excited at 321-15 nm and the emission of fluorescence was measured at 410-20 nm at 37° C. every minute for 1 hr in a Clariostar Microplate® reader (BMG LABTECH). NAD+ hydrolase activity was calculated as the slope of the linear portion of the fluorescence-time curve using the MARS data analysis software (BMG LABTECH). The data were uploaded in the Collaborative Drug Design (CDD) Software and for each compound the IC50 was calculated by the software. Each compound was tested in 3 independent experiments on 3 separate days to establish the reproducibility of the results. For each plate, the z-factor was also calculated as a plate quality using the CDD software.

Example 28

Fluorescence-Based NAD+ Hydrolase Activity Assay with Rat Recombinant CD38 Protein (Assay 6)

This protocol was modified from the following references: Muller et al. (1983); Schultz et al. (2018); Matalonga et al. (2017); and de Oliveira et al. (2018), supra.

NAD+ hydrolase activity of the rat recombinant CD38 protein treated with test compounds was measured using a fluorescence-based assay. Briefly, recombinant rat CD38 Protein (Sino Biological) was resuspended in 44 μl/well of Sucrose-Tris Buffer (Sucrose 0.25 M, Tris pH 7.4 40 mM) and plated in a 96 well black plate (CORNING) at a density of 2.5 ng/well.

Each test compound was received in a powder state and dissolved in DMSO as a 25 mM stock solution. Each test compound was serially diluted in order to generate a dose-response curve. The dilution series of each test compound in DMSO was prepared at 50 times the concentrations to be assayed. Each test compound was diluted to generate a 5-fold dilution series of 8 concentrations from 20 μM to 0.256 nM in order to assay 8 final concentrations ranging from 400 nM to 25.6 pM. One μl of the 50× concentration compound series was added to each well of the plate containing 2.5 ng of protein in Sucrose-Tris buffer.

Each plate had the following intra plate controls: 3 wells containing cells treated with vehicle only (DMSO), 3 wells of cells treated with the reference compounds 78c at a final concentration of 50 nM and 2 wells containing only Sucrose-Tris buffer (used as a background value).

The reaction was started adding nicotinamide 1,$N^6$-etheno-adenine dinucleotide (Sigma Aldrich) to reach a final concentration of 80 □M. The samples were excited at 321-15 nm and the emission of fluorescence was measured at 410-20 nm at 37° C. every minute for 1 hr in a Clariostar Microplate® reader (BMG LABTECH). NAD+ hydrolase activity was calculated as the slope of the linear portion of the fluorescence-time curve using the MARS data analysis software (BMG LABTECH). The data were uploaded in the Collaborative Drug Design (CDD) Software and for each compound the IC50 was calculated by the software. Each compound was tested in 3 independent experiments on 3 separate days to establish the reproducibility of the results. For each plate, the z-factor was also calculated as a plate quality using the CDD software.

The compounds according to the disclosure are potent inhibitors of CD38 and as such possess activity in the treatment of numerous disorders. The compounds according to the disclosure that were tested had the following activity in the aforesaid assays (Assay 1-6). The results are shown in Table 23.

TABLE 23

| Assay 1-5 Activity reported as Arithmetic mean IC50 (μM) | | | | | | |
|---|---|---|---|---|---|---|
| Compound | Assay 1 | Assay 2 | Assay 3 | Assay 4 | Assay 5 | Assay 6 |
| 1 | *** | ** | *** | | *** | |
| 2 | **** | *** | **** | | **** | |
| 3 | **** | *** | *** | | *** | |
| 4 | **** | ** | **** | | | |
| 5 | **** | ** | **** | | | |
| 6 | **** | ** | *** | | | |
| 7 | **** | * | *** | | **** | |
| 8 | **** | ** | *** | | *** | |
| 9 | *** | ** | *** | | *** | |
| 10 | *** | | *** | | | |
| 11 | *** | ** | *** | | *** | |
| 12 | *** | ** | *** | | *** | |
| 13 | *** | ** | *** | | *** | |
| 14 | *** | * | *** | | *** | |
| 15 | *** | * | *** | | *** | |
| 16 | *** | ** | *** | | *** | |
| 17 | *** | | *** | | *** | |
| 18 | *** | * | *** | | *** | |
| 19 | *** | | *** | | *** | |
| 20 | *** | * | *** | | *** | |
| 21 | *** | | *** | | *** | |
| 22 | *** | * | *** | | *** | |
| 23 | *** | | *** | | | |
| 24 | *** | * | *** | | *** | |
| 25 | ** | | ** | | | |
| 26 | ** | | ** | | ** | |
| 27 | *** | ** | *** | | *** | |
| 28 | **** | * | *** | | *** | |
| 29 | **** | ** | *** | | **** | |
| 30 | **** | ** | *** | | **** | |
| 31 | **** | ** | *** | | **** | |
| 32 | **** | ** | **** | | ** | |
| 33 | **** | ** | **** | *** | **** | |
| 34 | | ** | *** | ** | **** | |
| 35 | **** | ** | *** | *** | **** | |
| 36 | *** | ** | *** | | *** | |
| 37 | **** | ** | **** | ** | **** | |
| 38 | **** | ** | **** | ** | **** | |
| 39 | **** | *** | **** | *** | **** | *** |
| 40 | | ** | *** | ** | **** | |
| 41 | | ** | *** | ** | *** | |
| 42 | *** | * | *** | | *** | |
| 43 | **** | ** | *** | | *** | |
| 44 | **** | | *** | | *** | |
| 45 | **** | ** | *** | | **** | |
| 46 | | | *** | | | |
| 47 | **** | ** | *** | | *** | |
| 48 | *** | * | *** | | *** | |
| 49 | **** | *** | **** | | **** | |
| 50 | **** | *** | **** | | **** | |
| 51 | | ** | **** | *** | **** | |
| 52 | **** | *** | *** | | **** | |
| 53 | **** | ** | *** | | **** | |
| 54 | **** | *** | *** | | **** | |
| 55 | **** | ** | **** | | **** | |
| 56 | **** | ** | *** | | **** | |
| 57 | **** | *** | **** | | **** | |
| 58 | ** | | ** | | *** | |
| 59 | *** | ** | *** | | *** | |
| 60 | ** | | ** | | *** | |
| 61 | *** | * | *** | | *** | |
| 62 | *** | * | *** | | *** | |
| 63 | *** | | *** | | *** | |
| 64 | **** | | *** | | **** | |
| 65 | **** | | **** | | **** | |

TABLE 23-continued

| Assay 1-5 Activity reported as Arithmetic mean IC50 (μM) | | | | | | |
|---|---|---|---|---|---|---|
| Compound | Assay 1 | Assay 2 | Assay 3 | Assay 4 | Assay 5 | Assay 6 |
| 66 | **** | | *** | | **** | |
| 67 | **** | ** | *** | | *** | |
| 68 | **** | | **** | | | |
| 69 | **** | | *** | | | |
| 70 | **** | * | **** | | | |

(KEY: ** <I nM; * 1-50 nM; ** 51 nM-1 μM; * 1 μM-10 μM)

Example 29

In Vitro Functional Potency of Compound 35 Against CD38 Hydrolase Activity in Primary Human Cells (Immune Cells and Liver Cells) (Assay 7)

Figure 1B:
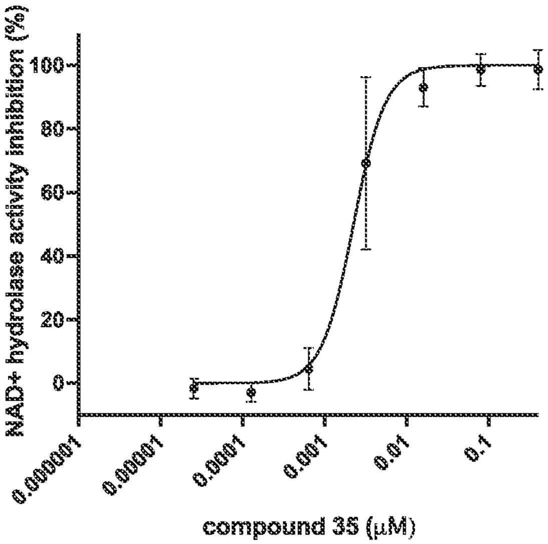
FIG. 1B depicts the in vitro functional potency for Compound 35 in human CD38+ cells as measured by NAD hydrolase activity assay in primary human M1 macrophages. The concentration response plot represents the average (+/−) standard deviation for the % inhibition values at each concentration tested where n=3 biological replicates over one experiment.

The in vitro potency of Compound 35 against the human CD38 enzyme was determined by a fluorescence-based NAD+ hydrolase activity assay using the NAD+ analog nicotinamide 1,$N^6$-etheno-adenine dinucleotide (εNAD+) as substrate. The assay utilized: 1) whole primary human CD4+ T cells (from healthy donors) activated with anti-CD3/CD28 antibodies and expressing human CD38; or II) whole primary human macrophages (from healthy donors) stimulated with LPS to polarize in a pro-inflammatory M1 state expressing human CD38. The cells were incubated in the presence of 8 different concentrations of Compound 35 for 10 minutes and the reaction was started adding the substrate εNAD+. The emission of fluorescence was measured at 410-20 nm at 37° C. every minute for 1 hr. The NAD+ hydrolase activity was calculated as the slope of the linear portion of the fluorescence-time curve and used to calculate the IC50 value. The IC50 value for Compound 35 was 0.1.8 nM (0.065 ng/mL) in primary human CD4+ T cells (see FIG. 1A) and 2.25 nM (0.817 ng/mL) in primary human M1 macrophages (see FIG. 1B).

Figure 2A:
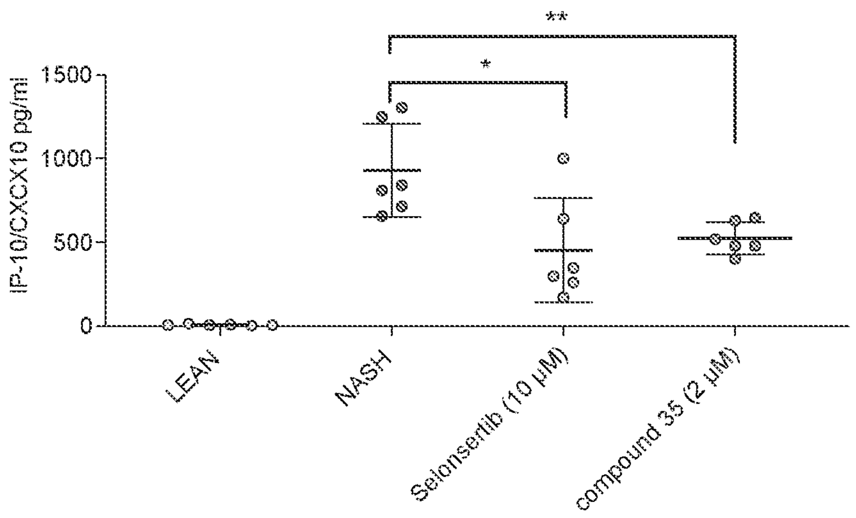
FIG. 2A depicts the in vitro efficacy of Compound 35 in the Human 3D NASH model as measured by release of inflammatory marker IP-10/CXCL10. The response plot represents the average (+/−) standard deviation for the measurement of each cytokine/chemokine released in the supernatant at each condition tested where n=6 biological replicates over one experiment. *, $p \leq 0.05$; , $p \leq 0.01$; *, $p \leq 0.001$; ****, $p < 0.0001$ compared with NASH sample, unpaired t-test.
Figure 2B:
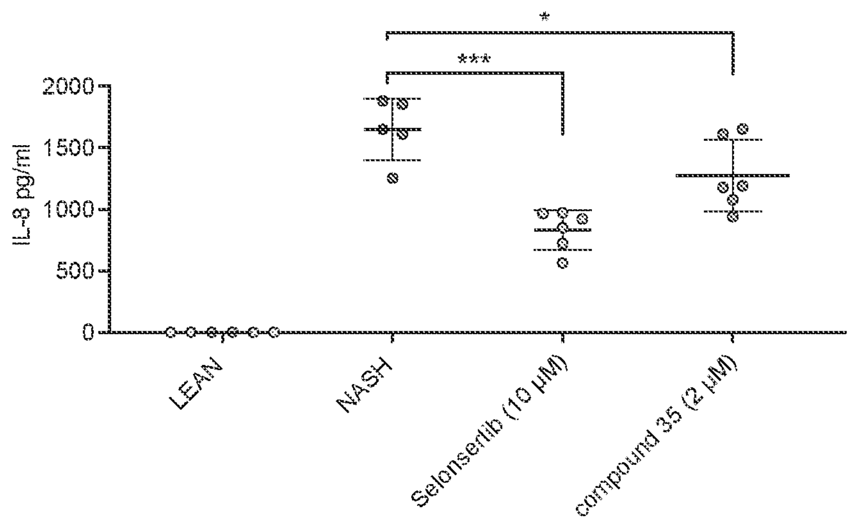
FIG. 2B depicts the in vitro efficacy of Compound 35 in the Human 3D NASH model as measured by release of inflammatory marker IL-10. The response plot represents the average (+/−) standard deviation for the measurement of each cytokine/chemokine released in the supernatant at each condition tested where n=6 biological replicates over one experiment. *, $p \leq 0.05$; , $p \leq 0.01$; *, $p \leq 0.001$; ****, $p < 0.0001$ compared with NASH sample, unpaired t-test.
Figure 2C:
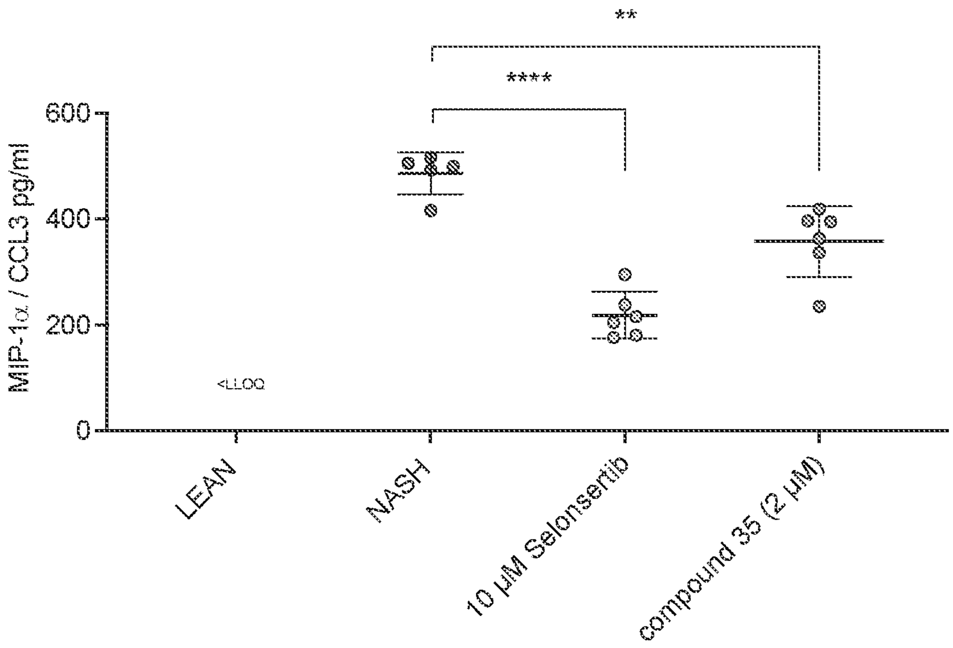
FIG. 2C depicts the in vitro efficacy of Compound 35 in the Human 3D NASH model as measured by release of inflammatory marker MIP-1α/CCL3. The response plot represents the average (+/−) standard deviation for the measurement of each cytokine/chemokine released in the supernatant at each condition tested where n=6 biological replicates over one experiment. *, $p \leq 0.05$; , $p \leq 0.01$; *, $p \leq 0.001$; ****, $p < 0.0001$ compared with NASH sample, unpaired t-test.
Figure 2D:
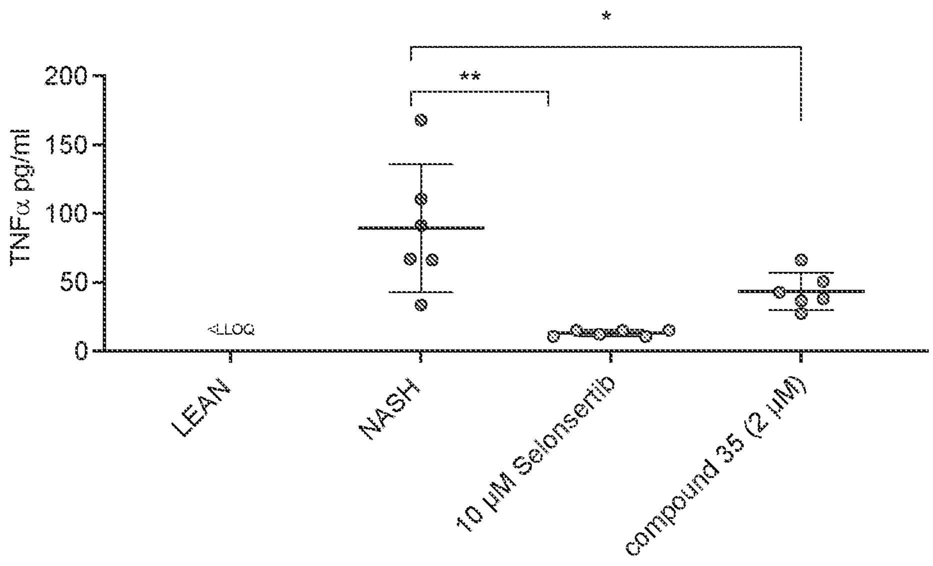
FIG. 2D depicts the in vitro efficacy of Compound 35 in the Human 3D NASH model as measured by release of inflammatory marker TNFα. The response plot represents the average (+/−) standard deviation for the measurement of each cytokine/chemokine released in the supernatant at each condition tested where n=6 biological replicates over one experiment. *, $p \leq 0.05$; , $p \leq 0.01$; *, $p \leq 0.001$; ****, $p < 0.0001$ compared with NASH sample, unpaired t-test.

The efficacy of Compound 35 was also determined in a NASH model (see InSphero Human 3D InSight™ Brunswick, ME) to investigate the effect of the molecule on the pathophysiological phenotype of NASH such as release of inflammatory markers. The microtissue model used is a co-culture of 4 different cell types of human liver cells (hepatocytes, Kupffer cells, endothelial and stellate cells) cultured for 10 days in a NASH induction media containing FFA, LPS and high levels of sugars. In the LEAN group the microtissues were cultured for 10 days in physiological-like medium. The reference compound, Selonsertib, a selective ASK1 inhibitor, was used as a down regulator of inflammatory markers. Cytokine and chemokine release in the supernatant were measured at day 5 using Magnetic Luminex® Assay (R&D Systems). CD38 pharmacological inhibition with Compound 35 results demonstrate effectiveness in downregulating the release of NASH-induced inflammatory markers, such as IP-10/CXCL-10 (FIG. 2A), IL-8 (FIG. 2B), MIP-1α/CCL3 (FIG. 2C) and TNFα (FIG. 2D).

Example 30

In Vivo Efficacy of Compound 35 Against CD38 in Aged Mice

The in vivo efficacy of Compound 35 against the human CD38 enzyme was tested in aged mice after oral administration and determined by mass spec analysis of NAD+ metabolites levels in liver tissue. The two main CD38 substrates, NAD+ and NMN, and the 2 main byproducts of the CD38 enzymatic reaction, NAM and ADPR, were measured.

Briefly, aged mice (male C57BL6/J, 22 months old) were fasted for 4 hr and compound 35 was administered via oral gavage at a concentration of 3 mg/kg and 10 mg/kg. Mice were humanely euthanized for liver tissue harvesting at 1-, 3-, and 6-hr post-dosing. A vehicle control (DMSO:Solutol: SBE-CD, 2:5:93, v/v) was included to assess baseline NAD+ metabolites levels.

The procedure for tissue sample preparation and UPLC-MS/MS methods were adapted from Trammell et al. (2013) *Compu. Struct. Biotechnol. J.* 20:4 (https://www.ncbi.nlm-.nih.gov/pmc/articles/PMC3962138/). Briefly, frozen liver tissue was pulverized and resuspended in the extraction buffer (3:1 ethanol:10 mM aq. HEPES, pH 7.1). The samples were vortexed, sonicated briefly in a bath sonicator, and shaken at 55° C. for 3 min at 1,200 rpm. Samples were then centrifuged at 16,000×g for 10 min at 4° C., and the supernatant was dried by speedvac. The dried pellet was resuspended in 97% 10 mM ammonium acetate/3% acetonitrile, centrifuged at 16,000×g for 10 min at 4° C. and 2 μL was injected for LCMS analysis.

The UPLC-MS/MS analysis to measure NAD+ metabolites was performed using a Vanquish UHPLC system and a Q Exactive Orbitrap mass spectrometer with H-ESI ion source both from Thermo Scientific. UPLC separation was performed on a Hypercarb (2.1×100 mm, 5 μm particle size, Thermo) column following the method described in Trammell et al. (2013). Acquisition was carried out in positive ion, Parallel Reaction Monitoring (PRM) mode and targeted Single Reaction Monitoring (t-SIM). The Thermo Xcalibur QualBrowser system software (version 4.2.47) and Freestyle (version 1.8.51.0) softwares was used for the data processing. For relative fold change, peak areas were normalized with respective internal standards, normalized to weight of the tissue sample used, and calculated as fold change relative at 0 h timepoint/vehicle group.

Figure 3A:
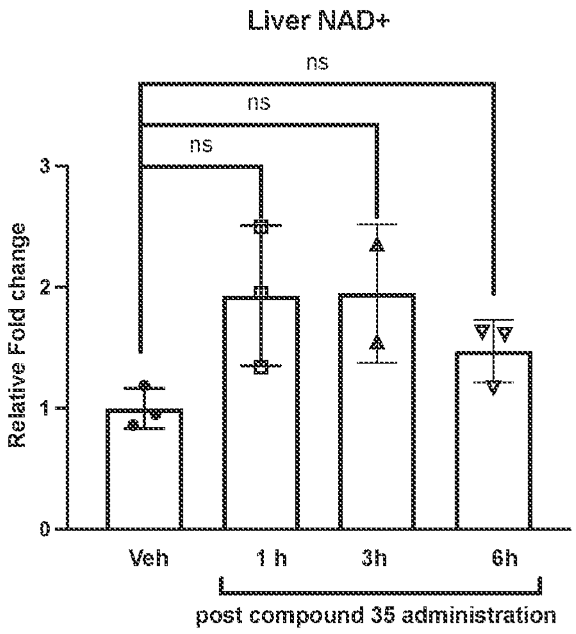
FIGS. 3A-3D depict in vivo efficacy of oral administration of Compound 35 (3 mg/kg) against CD38 in aged mouse model as measured by liver NAD+(FIG. 3A), NMN (FIG. 3B), NAM (FIG. 3C), and ADPR (FIG. 3D) levels. The response plot represents the average (+/−) standard deviation for the measurement of NAD+ metabolites at each condition tested where n=3 over one experiment. *, $p \leq 0.05$; , $p \leq 0.01$; * $p \leq 0.001$; ****, $p < 0.0001$ compared with Vehicle sample, one-way ANOVA.
Figure 3B:
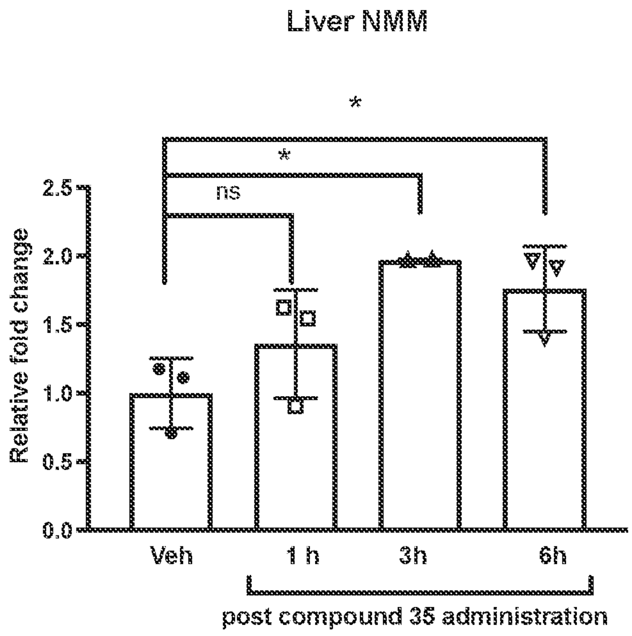
Figure 3C:
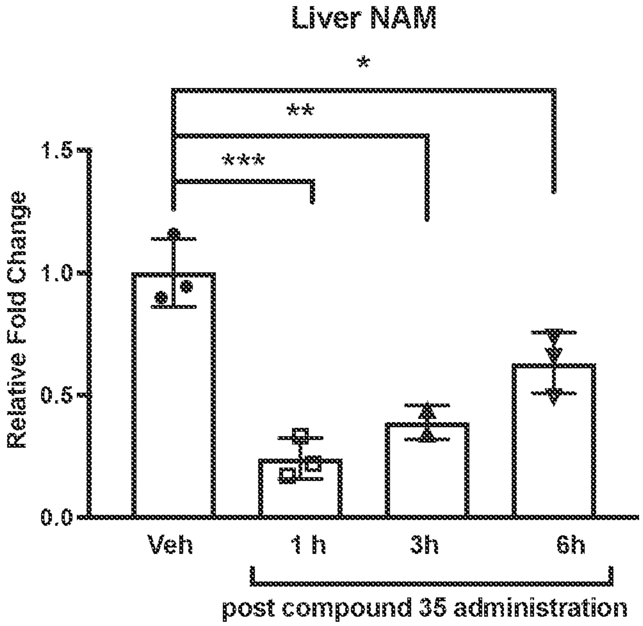
Figure 3D:
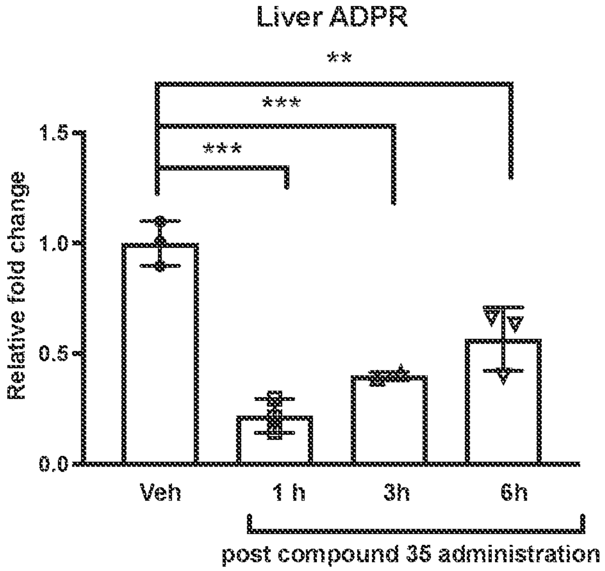
Figure 4A:
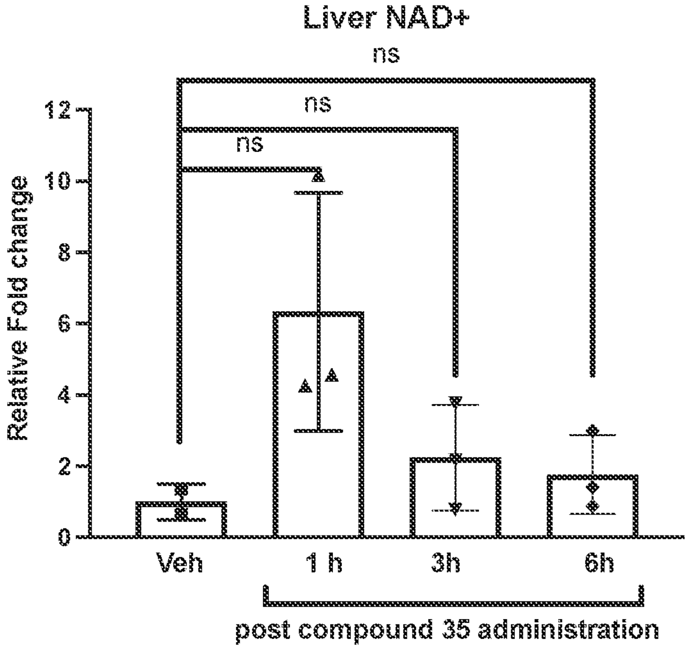
FIGS. 4A-4D depict in vivo efficacy of oral administration of Compound 35 (10 mg/kg) against CD38 in aged mouse model as measured by liver NAD+(FIG. 4A), NMN (FIG. 4B), NAM (FIG. 4C), and ADPR (FIG. 4D) levels. The response plot represents the average (+/−) standard deviation for the measurement of NAD+ metabolites at each condition tested where n=3 over 1 experiment. *, $p \leq 0.05$; , $p \leq 0.01$; *, $p \leq 0.001$; ****, $p < 0.0001$ compared with Vehicle sample, one-way ANOVA.
Figure 4B:
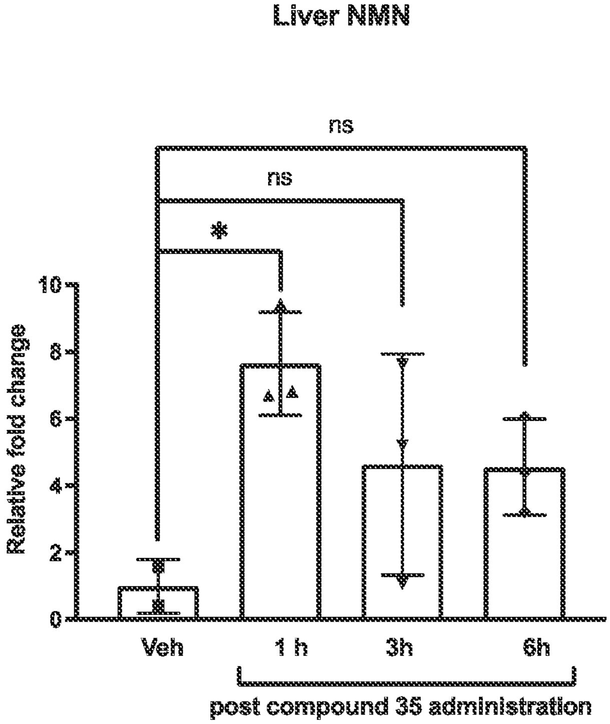
Figure 4C:
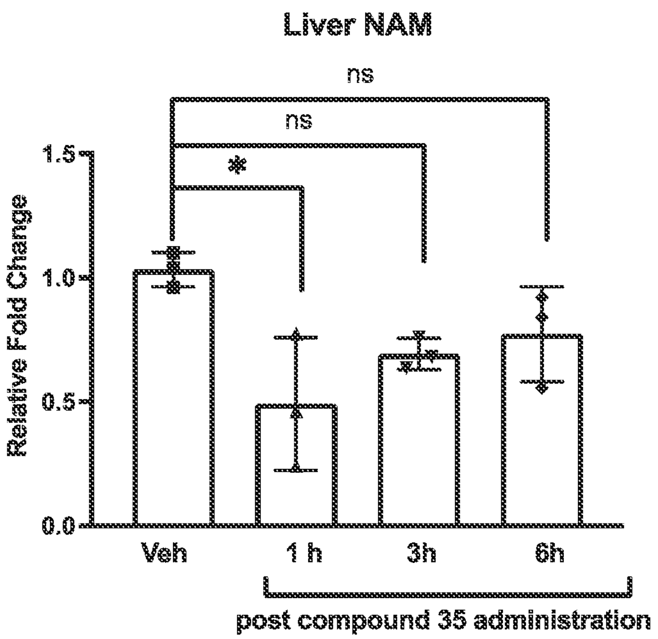
Figure 4D:
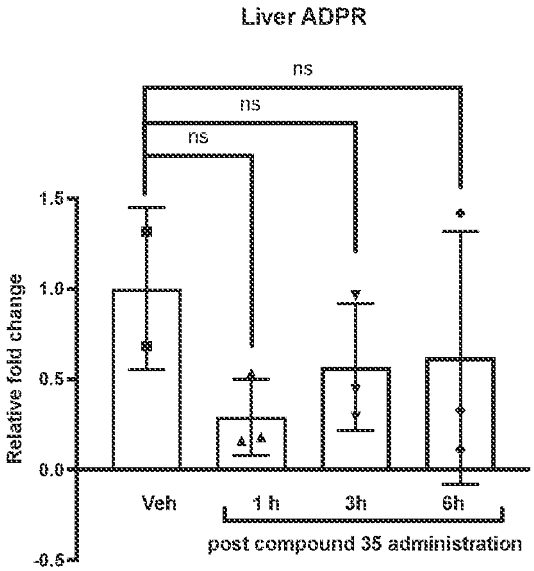

A single 3 mg/kg dose oral administration of Compound 35 was able to increase NAD+ and NMN levels and to decrease NAM and ADPR levels in liver (FIGS. 3A-3B). A single 10 mg/kg dose oral administration of Compound 35 was able to increase NAD+ and NMN levels and to decrease NAM and ADPR levels in liver (FIGS. 4A-4B).

Example 31

In Vitro Efficacy of Compound 32 Against CD38

Figure 5:
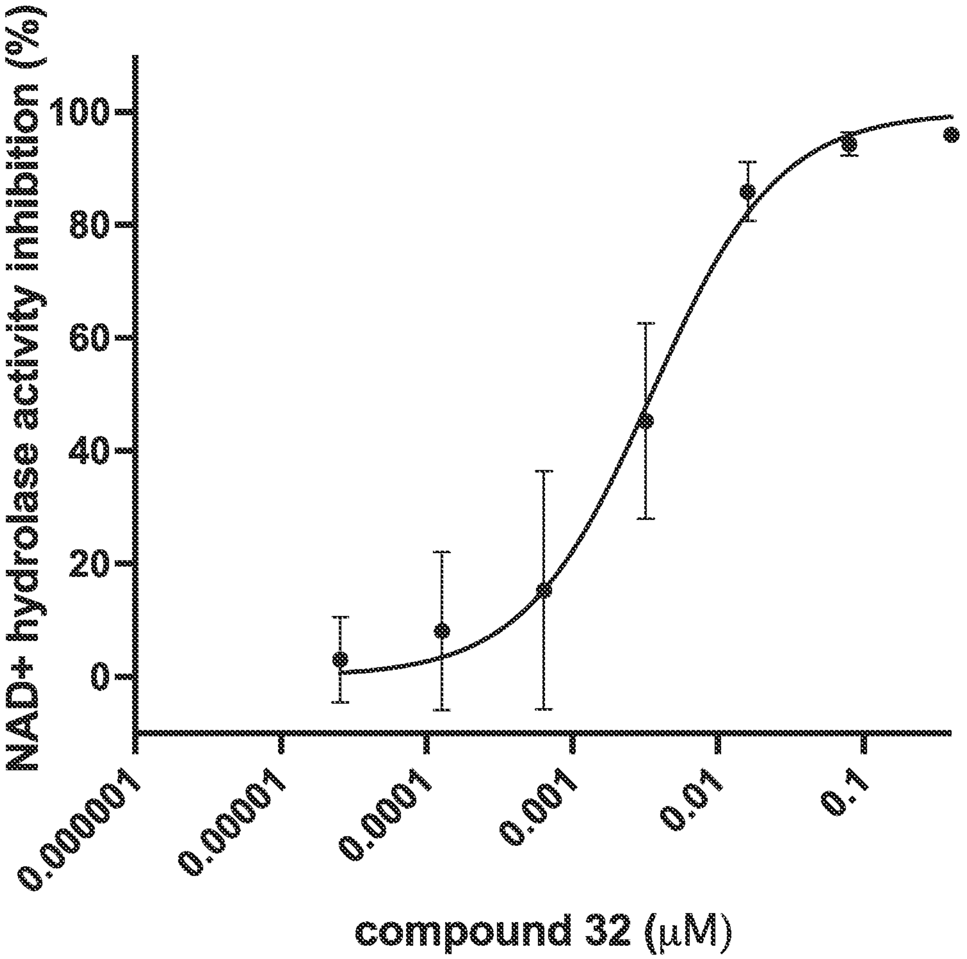
FIG. 5 depicts in vitro efficacy of Compound 32 in human CD38+ cells as measured by NAD hydrolase activity assay in primary human M1 macrophages. The response plot represents the average (+/−) standard deviation for the % inhibition values at each concentration tested where n=3 biological replicates over one experiment.
Figure 6A:
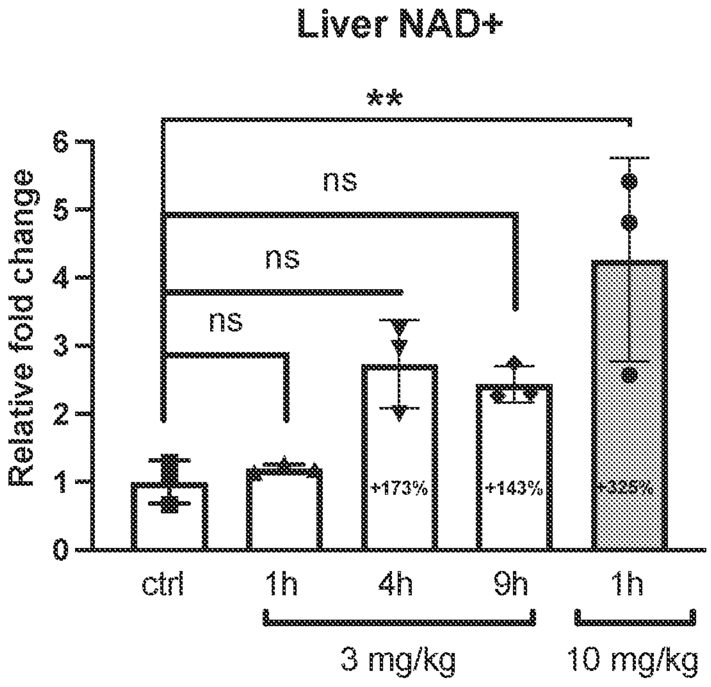
FIGS. 6A-6D depict in vivo efficacy of acute oral administration of Compound 32 (3 and 10 mg/kg) against CD38 in obese mouse model as measured by liver NAD+(FIG. 6A), NMN (FIG. 6B), NAM (FIG. 6C), and ADPR (FIG. 6D) levels. The response plot represents the average (+/−) standard deviation for the measurement of NAD+ metabolites at each condition tested where n=3 over 1 experiment (example 32). *, $p \leq 0.05$; , $p \leq 0.01$; *, $p \leq 0.001$; ****, $p < 0.0001$ compared with Vehicle sample, one-way ANOVA.
Figure 6B:
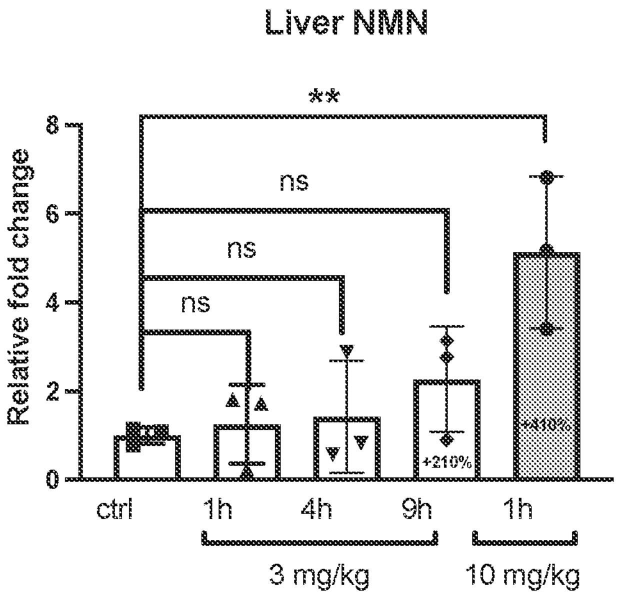
Figure 6C:
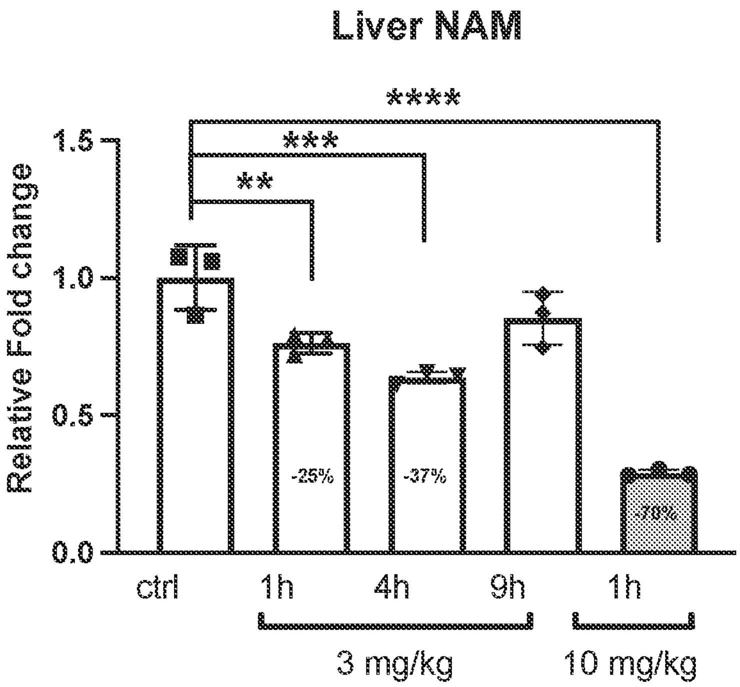
Figure 6D:
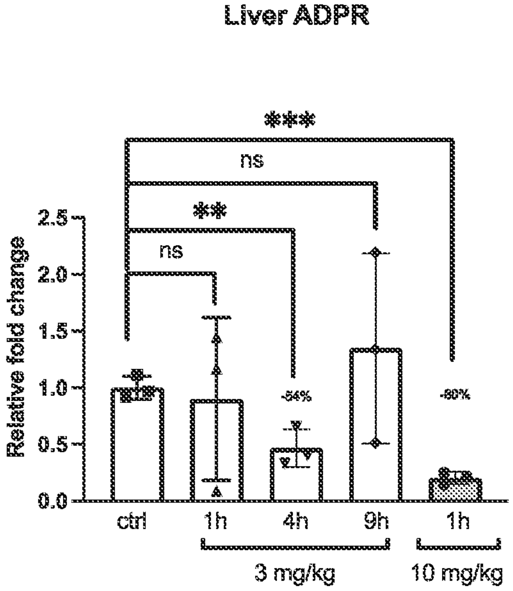
Figure 7A:
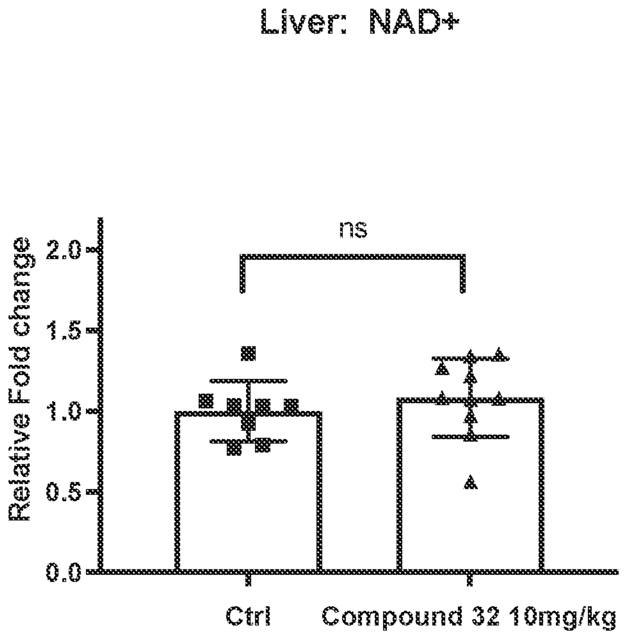
FIGS. 7A-7D depict in vivo efficacy of chronic oral administration of Compound 32 (10 mg/kg) against CD38 in obese mouse model as measured by liver NAD+(FIG. 7A), NMN (FIG. 7B), NAM (FIG. 7C), and ADPR (FIG. 7D) levels. The response plot represents the average (+/−) standard deviation for the measurement of NAD+ metabolites at each condition tested where n=8-10 over 1 experiment (example 33). *, $p \leq 0.05$; , $p \leq 0.01$; *, $p \leq 0.001$; ****, $p < 0.0001$ compared with Vehicle sample, one-way ANOVA.
Figure 7B:
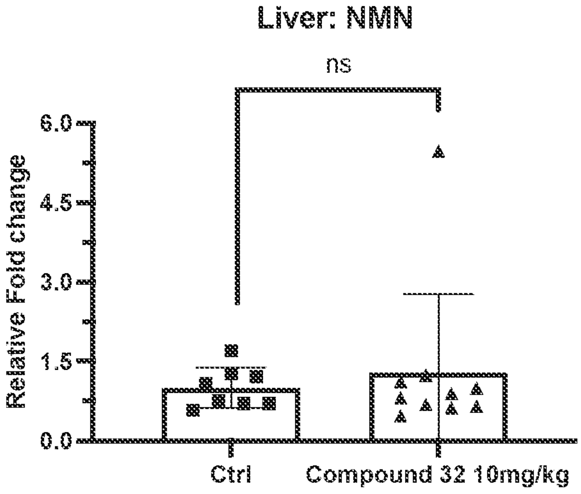
Figure 7C:
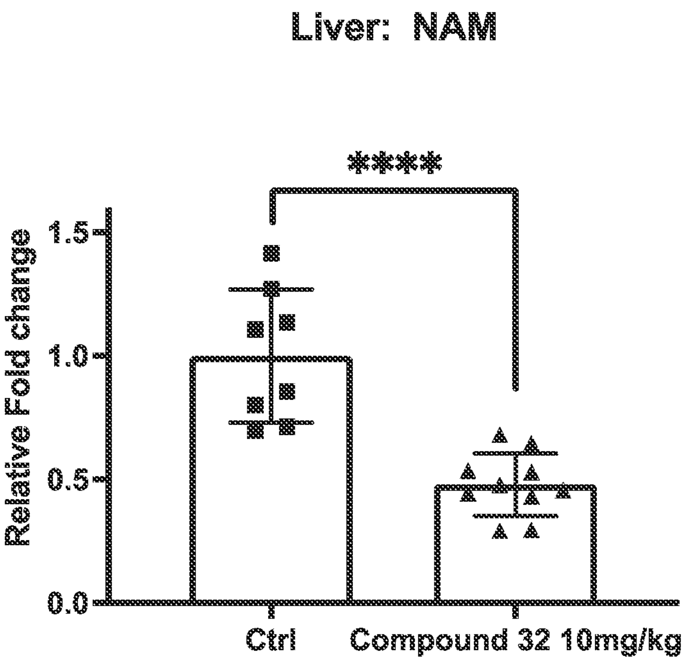
Figure 7D:
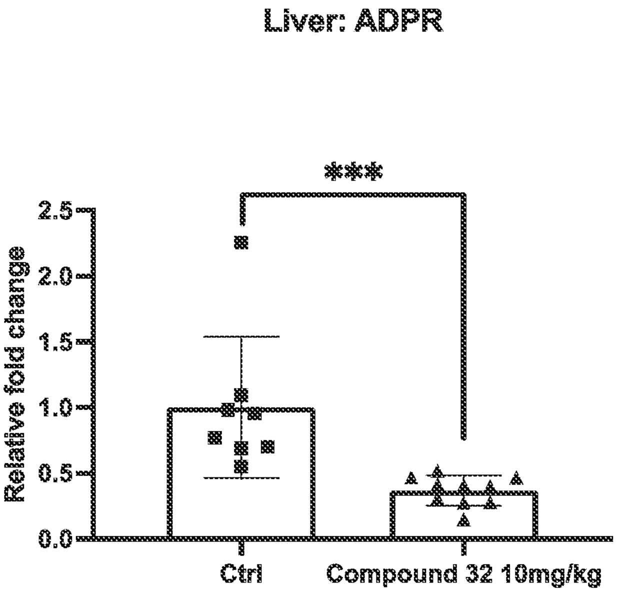
Figure 8A:
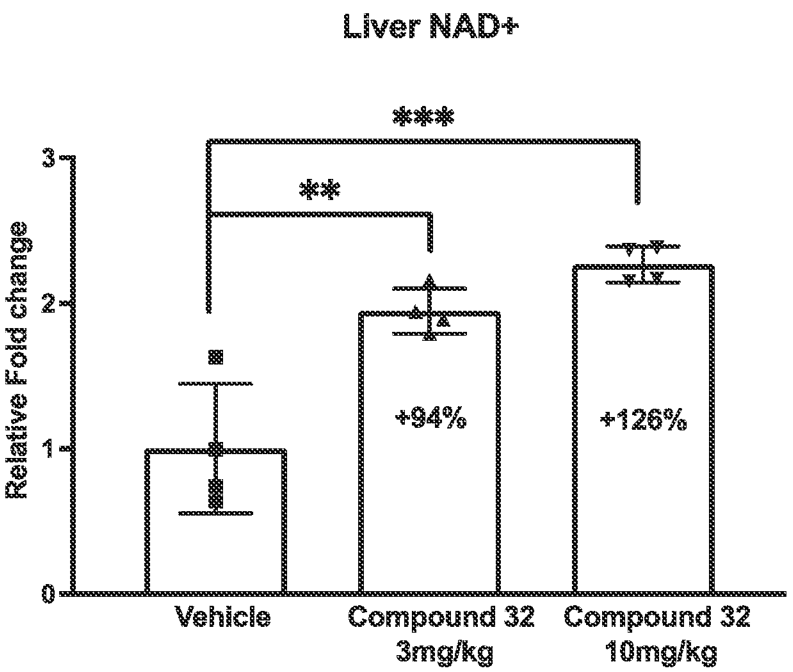
FIGS. 8A-8D depict in vivo efficacy of chronic oral administration of Compound 32 (3 and 10 mg/kg) against CD38 in aged mouse model as measured by liver NAD+ (FIG. 8A), NMN (FIG. 8B), NAM (FIG. 8C), and ADPR (FIG. 8D) levels. The response plot represents the average (+/−) standard deviation for the measurement of NAD+ metabolites at each condition tested where n=4 over 1 experiment (example 34). * $p \leq 0.05$; , $p \leq 0.01$; *, $p \leq 0.001$; ****, $p < 0.0001$ compared with Vehicle sample, one-way ANOVA.
Figure 8B:
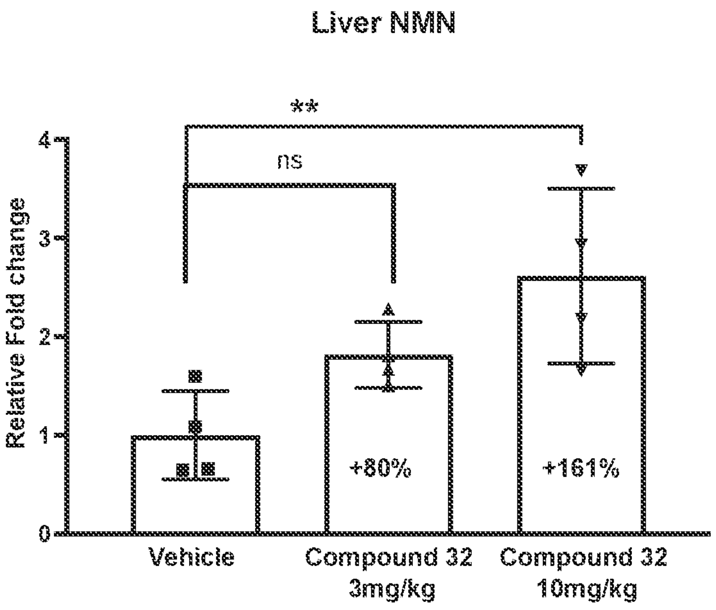
Figure 8C:
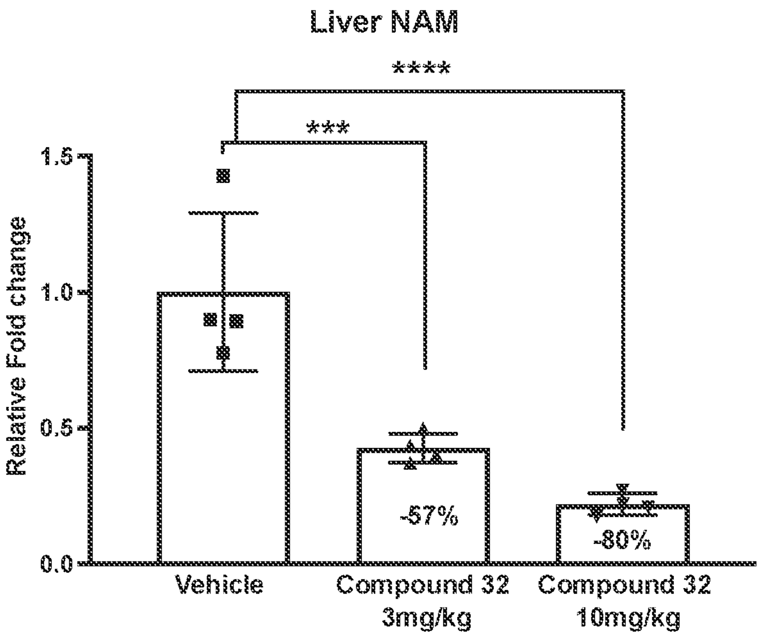
Figure 8D:
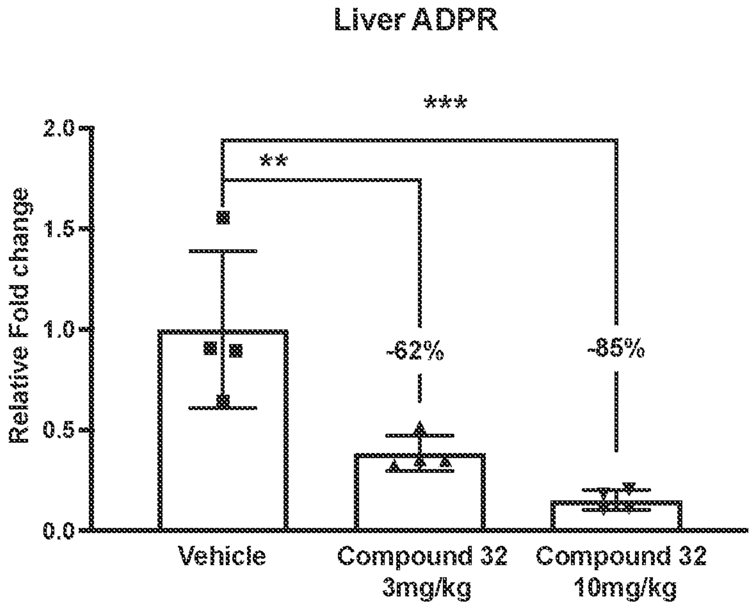

The in vitro potency of Compound 32 against the human CD38 enzyme was determined by a fluorescence-based NAD+ hydrolase activity assay using the NAD+ analog nicotinamide 1,N6-etheno-adenine dinucleotide (εNAD+) as substrate. The assay utilized whole primary human macrophages (from healthy donors) stimulated with LPS to polarize in a pro-inflammatory M1 state expressing human CD38. The cells were incubated in the presence of 8 different concentrations of Compound 32 for 10 minutes and the reaction was started adding the substrate εNAD+. The emission of fluorescence was measured at 410-20 nm at 37° C. every minute for 1 hr. The NAD+ hydrolase activity was calculated as the slope of the linear portion of the fluorescence-time curve and used to calculate the IC50 value. The IC50 value for Compound 32 was 3.5 nM (1.36 ng/mL) in primary human M1 macrophages (see FIG. 5).

Example 32

In Vivo Efficacy of Compound 32 Against CD38 in Obese Mice

The in vivo efficacy of Compound 32 against the human CD38 enzyme was tested in obese mice after oral administration and determined by mass spec (MS) analysis of NAD+ metabolites levels in liver tissue. The two main CD38 substrates, NAD+ and NMN, and the 2 main byproducts of the CD38 enzymatic reaction, NAM and ADPR, were measured.

Obese mice (male DIO C57BL6/J, 7.5 months old) were fasted for 4 hr and compound 32 was administered via oral gavage at a concentration of 3 mg/kg and 10 mg/kg. Mice were humanely euthanized for liver tissue harvesting at 1-, 3-, and 6-hr post-dosing. A vehicle control (DMSO: Solutol HS 15: 80% Captisol (20% in water)(5:15:80 v/v)) was included to assess baseline NAD+ metabolites levels.

The procedure for tissue sample preparation and UPLC-MS/MS methods were adapted from Trammell et al. (2013) Compu. Struct. Biotechnol. J. 20:4 (https://www.ncbi.nlm-.nih.gov/pmc/articles/PMC3962138/). Frozen liver tissue was pulverized and resuspended in the extraction buffer (3:1 ethanol:10 mM aq. HEPES, pH 7.1). The samples were vortexed, sonicated briefly in a bath sonicator, and shaken at 55° C. for 3 min at 1,200 rpm. Samples were then centrifuged at 16,000×g for 10 min at 4° C., and the supernatant was dried by speedvac. The dried pellet was resuspended in 97% 10 mM ammonium acetate/3% acetonitrile, centrifuged at 16,000×g for 10 min at 4° C. and 2 μL was injected for LCMS analysis The UPLC-MS/MS analysis to measure NAD+ metabolites was performed using a Vanquish UHPLC system and a Q Exactive Orbitrap mass spectrometer with H-ESI ion source both from Thermo Scientific. UPLC separation was performed on a Hypercarb (2.1×100 mm, 5 μm particle size, Thermo) column following the method described in Trammell et al. (2013). Acquisition was carried out in positive ion, Parallel Reaction Monitoring (PRM) mode and targeted Single Reaction Monitoring (t-SIM). The Thermo Xcalibur QualBrowser system (version 4.2.47) and Freestyle (version 1.8.51.0) softwares was used for the data processing. For relative fold change, peak areas were normalized with respective internal standards, normalized to weight of the tissue sample used, and calculated as fold change relative at 0 h timepoint/vehicle group.

A single 3 mg/kg dose oral administration of Compound 32 was able to increase NAD+ and NMN levels and to decrease NAM and ADPR levels in liver (FIGS. 6B-6E). A single 10 mg/kg dose oral administration of Compound 32 was able to remarkably increase NAD+ and NMN levels and to decrease NAM and ADPR levels in liver 1 hour post administration (FIGS. 6B-6E).

Example 33

In Vivo Efficacy of Compound 32 Against CD38 in Obese Mice

The in vivo efficacy of Compound 32 against the human CD38 enzyme was tested in obese mice after oral administration and determined by mass spec (MS) analysis of NAD+ metabolites levels in liver tissue. The two main CD38 substrates, NAD+ and NMN, and the 2 main byproducts of the CD38 enzymatic reaction, NAM and ADPR, were measured.

Obese mice (male DIO C57BL6/J, 65 weeks old) treated for 49 days with compound 32 via oral gavage at a concentration of 10 mg/kg BID. On day 49, mice were humanely euthanized for liver tissue harvesting at 4 hr post-dosing. A vehicle control (1% Methylcellulose) was included to assess baseline NAD+ metabolites levels.

The procedure for tissue sample preparation and UPLC-MS/MS methods were adapted from Trammell et al. (2013) Compu. Struct. Biotechnol. J. 20:4 (https://www.ncbi.nlm-.nih.gov/pmc/articles/PMC3962138/). Frozen liver tissue was pulverized and resuspended in the extraction buffer (3:1 ethanol:10 mM aq. HEPES, pH 7.1). The samples were vortexed, sonicated briefly in a bath sonicator, and shaken at 55° C. for 3 min at 1,200 rpm. Samples were then centrifuged at 16,000×g for 10 min at 4° C., and the supernatant was dried by speedvac. The dried pellet was resuspended in 97% 10 mM ammonium acetate/3% acetonitrile, centrifuged at 16,000×g for 10 min at 4° C. and 2 μL was injected for LCMS analysis.

The UPLC-MS/MS analysis to measure NAD+ metabolites was performed using a Vanquish UHPLC system and a Q Exactive Orbitrap mass spectrometer with H-ESI ion source both from Thermo Scientific. UPLC separation was performed on a Hypercarb (2.1×100 mm, 5 μm particle size, Thermo) column following the method described in Trammell et al. (2013). Acquisition was carried out in positive ion, Parallel Reaction Monitoring (PRM) mode and targeted Single Reaction Monitoring (t-SIM). The Thermo Xcalibur QualBrowser system (version 4.2.47) and Freestyle (version 1.8.51.0) softwares was used for the data processing. For relative fold change, peak areas were normalized with respective internal standards, normalized to weight of the tissue sample used, and calculated as fold change relative at 0 h timepoint/vehicle group.

Chronic administration of Compound 32 10 mg/kg BID in obese mice was able to significantly decrease NAM and ADPR levels in liver (FIGS. 7A-7D).

Example 34

In Vivo Efficacy of Compound 32 Against CD38 in Aged Mice

The in vivo efficacy of Compound 32 against the human CD38 enzyme was tested in aged mice after oral administration and determined by mass spec (MS) analysis of NAD+ metabolites levels in liver tissue. The two main CD38 substrates, NAD+ and NMN, and the 2 main byproducts of the CD38 enzymatic reaction, NAM and ADPR, were measured.

Compound 32 was administered to aged mice (male DIO C57BL6/J, 19-22 months old) via oral gavage at a concentration of 3 mg/kg and 10 mg/kg BID for 5 days. At day 5, mice were humanely euthanized for liver tissue harvesting 3 hr post-dosing. A vehicle control (DMSO: Solutol HS 15: 80% Captisol (20% in water)(5:15:80 v/v)) was included to assess baseline NAD+ metabolites levels.

The procedure for tissue sample preparation and UPLC-MS/MS methods were adapted from Trammell et al. (2013) Compu. Struct. Biotechnol. J. 20:4 (https://www.ncbi.nlm.nih.gov/pmc/articles/PMC3962138/). Frozen liver tissue was pulverized and resuspended in the extraction buffer (3:1 ethanol:10 mM aq. HEPES, pH 7.1). The samples were vortexed, sonicated briefly in a bath sonicator, and shaken at 55° C. for 3 min at 1,200 rpm. Samples were then centrifuged at 16,000×g for 10 min at 4° C., and the supernatant was dried by speedvac. The dried pellet was resuspended in 97% 10 mM ammonium acetate/3% acetonitrile, centrifuged at 16,000×g for 10 min at 4° C. and 2 μL was injected for LCMS analysis.

The UPLC-MS/MS analysis to measure NAD+ metabolites was performed using a Vanquish UHPLC system and a Q Exactive Orbitrap mass spectrometer with H-ESI ion source both from Thermo Scientific. UPLC separation was performed on a Hypercarb (2.1×100 mm, 5 μm particle size, Thermo) column following the method described in Trammell et al. (2013). Acquisition was carried out in positive ion, Parallel Reaction Monitoring (PRM) mode and targeted Single Reaction Monitoring (t-SIM). The Thermo Xcalibur QualBrowser system (version 4.2.47) and Freestyle (version 1.8.51.0) softwares was used for the data processing. For relative fold change, peak areas were normalized with respective internal standards, normalized to weight of the tissue sample used, and calculated as fold change relative at 0 h timepoint/vehicle group.

Chronic administration of compound 32 at 3 mg/kg and 10 mg/kg was able to significantly increase NAD+ and NMN levels and to decrease NAM and ADPR levels in liver (FIGS. 8A-8D).

Example 35

In Vitro Efficacy of Compound 39 Against CD38

Figure 9:
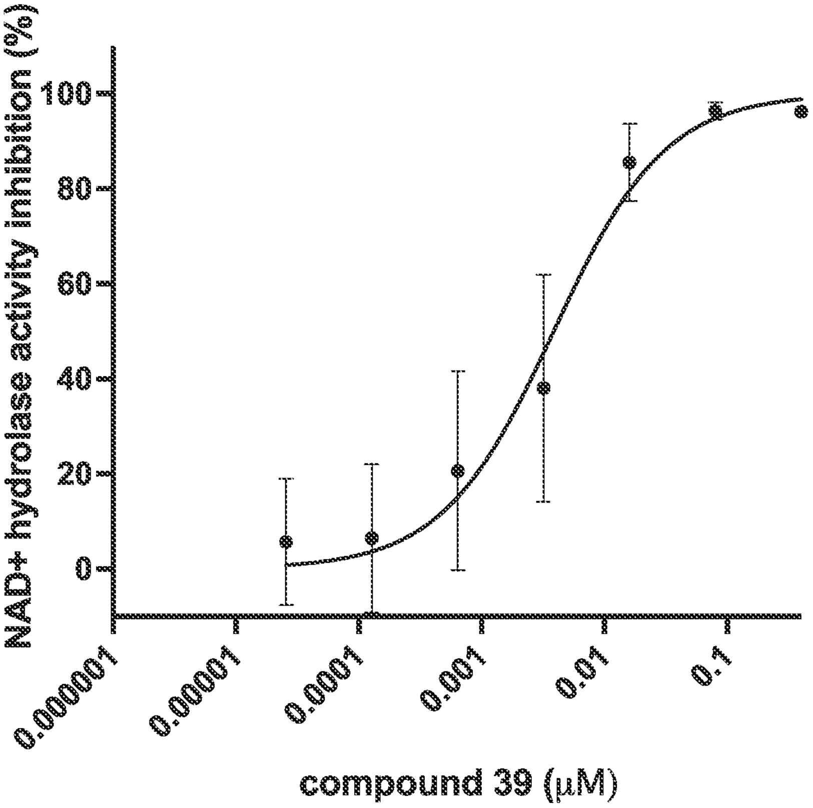
FIG. 9 depicts in vitro efficacy of Compound 39 in human CD38+ cells as measured by NAD hydrolase activity assay in primary human M1 macrophages. The response plot represents the average (+/−) standard deviation for the % inhibition values at each concentration tested where n=3 biological replicates over one experiment.
Figure 10A:
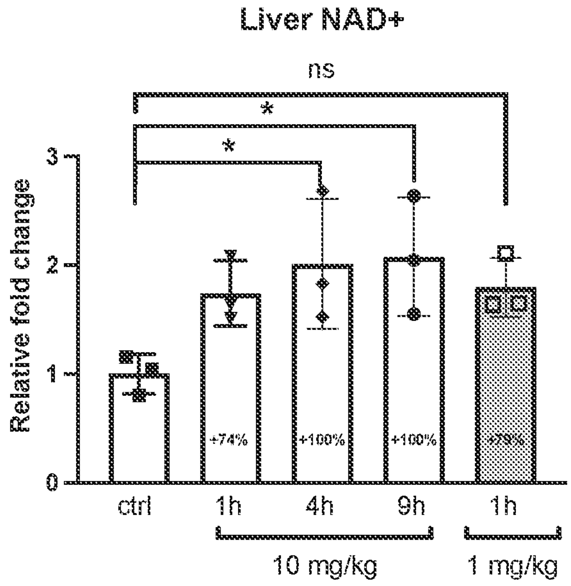
FIGS. 10A-10D depict in vivo efficacy of acute oral administration of Compound 39 (3 and 10 mg/kg) against CD38 in obese mouse model as measured by liver NAD+ (FIG. 10A), NMN (FIG. 10B), NAM (FIG. 10C), and ADPR (FIG. 10D) levels. The response plot represents the average (+/−) standard deviation for the measurement of NAD+ metabolites at each condition tested where n=3 over 1 experiment. *, $p \leq 0.05$; , $p \leq 0.01$; *, $p \leq 0.001$; ****, $p < 0.0001$ compared with Vehicle sample, one-way ANOVA.
Figure 10B:
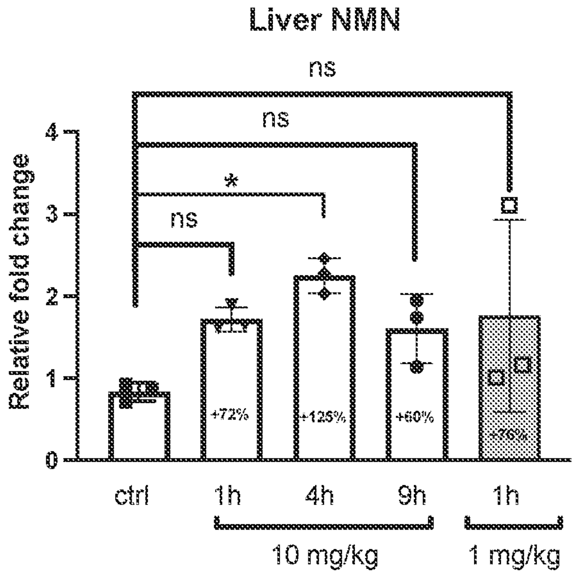
Figure 10C:
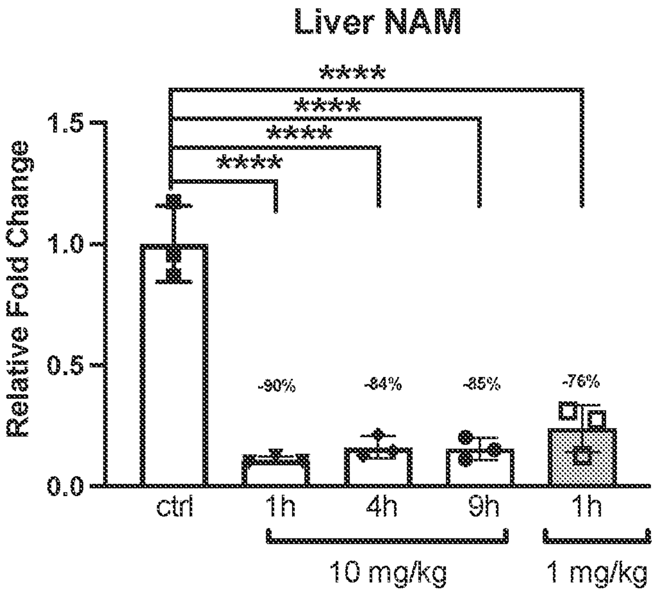
Figure 10D:
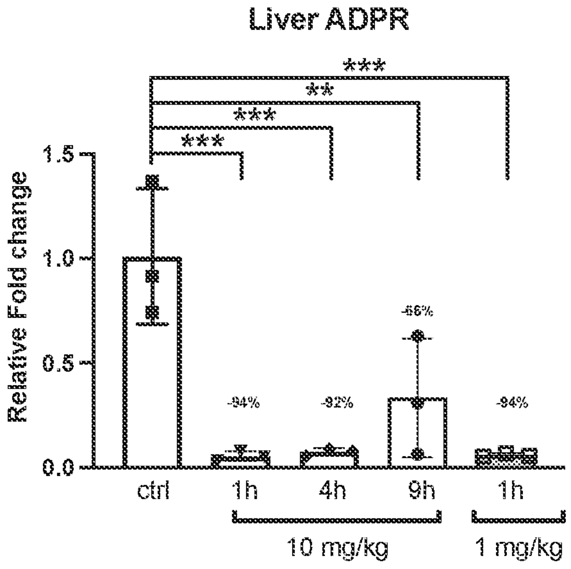
Figure 11A:
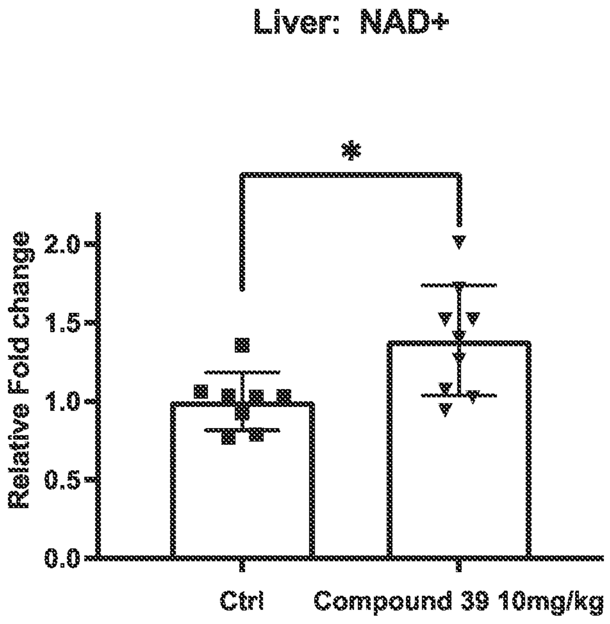
FIGS. 11A-11D depict in vivo efficacy of chronic oral administration of Compound 39 (10 mg/kg) against CD38 in obese mouse model as measured by liver NAD+(FIG. 11A), NMN (FIG. 11B), NAM (FIG. 11C), and ADPR (FIG. 11D) levels. The response plot represents the average (+/−) standard deviation for the measurement of NAD+ metabolites at each condition tested where n=8-10 over 1 experiment. *, $p \leq 0.05$; , $p \leq 0.01$; *, $p \leq 0.001$; ****, $p < 0.0001$ compared with Vehicle sample, one-way ANOVA.
Figure 11B:
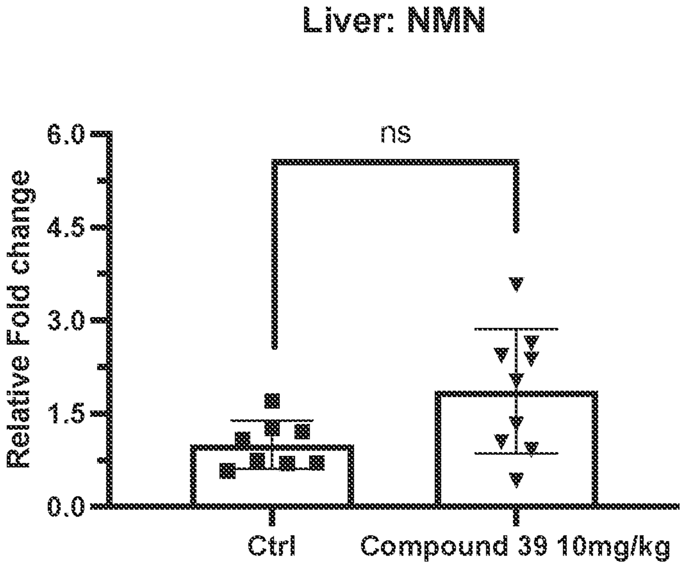
Figure 11C:
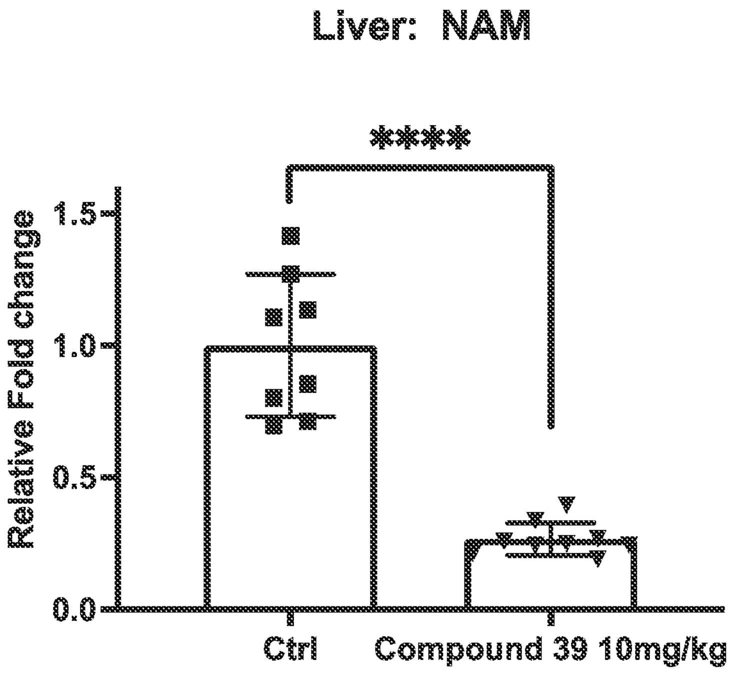
Figure 11D:
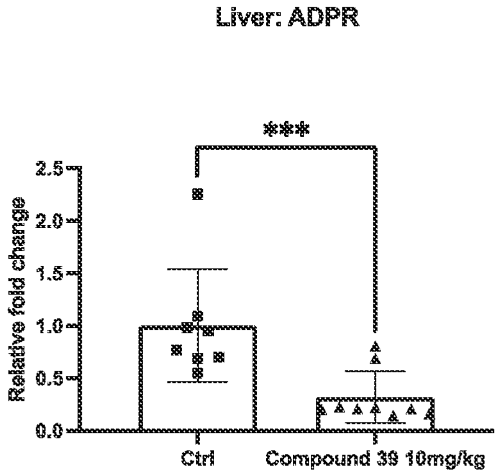
Figure 12A:
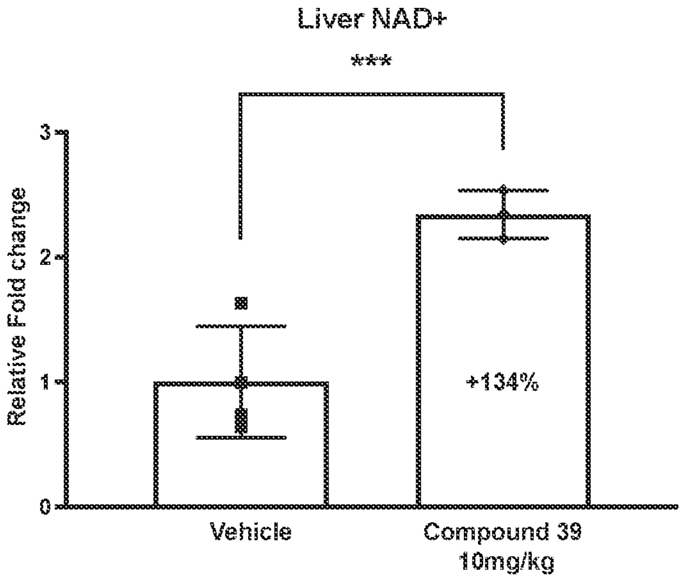
FIGS. 12A-12D depict in vivo efficacy of chronic oral administration of Compound 39 (3 and 10 mg/kg) against CD38 in aged mouse model as measured by liver NAD+ (FIG. 12A), NMN (FIG. 12B), NAM (FIG. 12C), and ADPR (FIG. 12D) levels. The response plot represents the average (+/−) standard deviation for the measurement of NAD+ metabolites at each condition tested where n=3-4 over 1 experiment. *, $p \leq 0.05$; , $p \leq 0.01$; *, $p \leq 0.001$; ****, $p < 0.0001$ compared with Vehicle sample, one-way ANOVA.
Figure 12B:
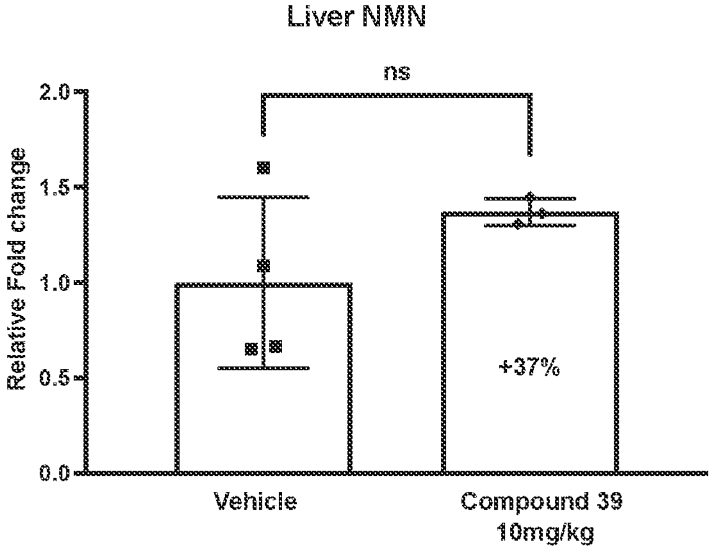
Figure 12C:
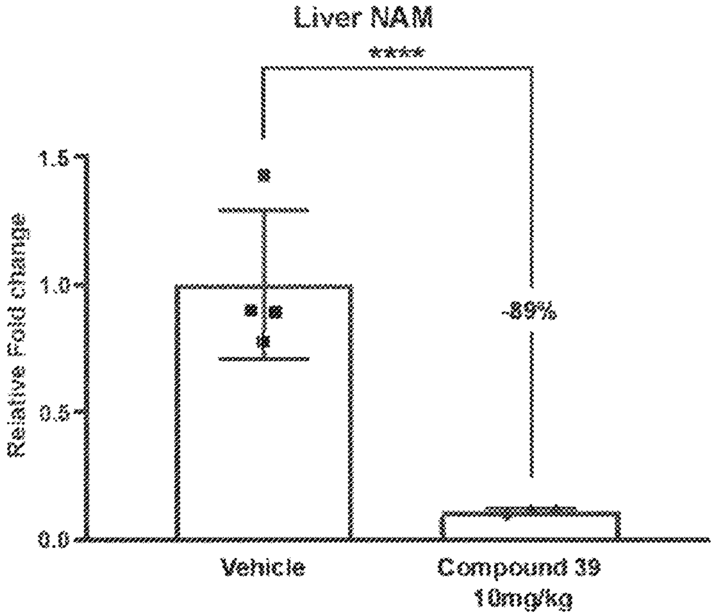
Figure 12D:
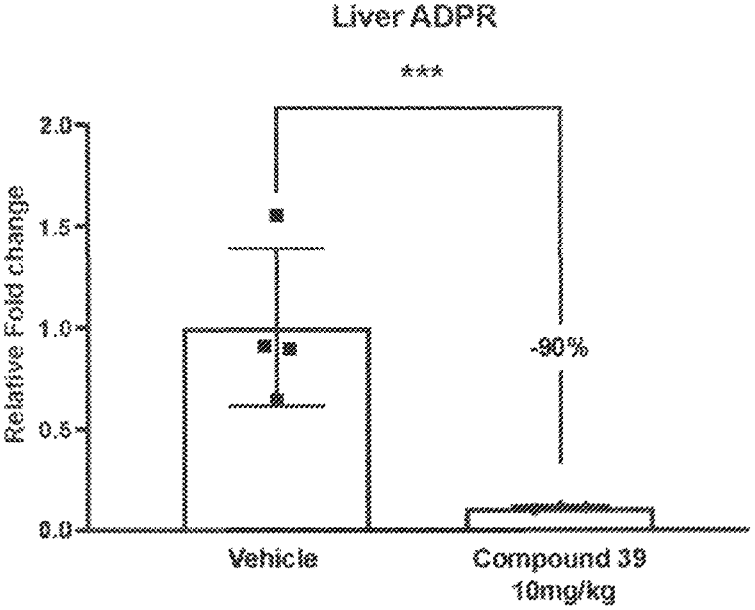

The in vitro potency of Compound 39 against the human CD38 enzyme was determined by a fluorescence-based NAD+ hydrolase activity assay using the NAD+ analog nicotinamide 1,N6-etheno-adenine dinucleotide (εNAD+) as substrate. The assay utilized whole primary human macrophages (from healthy donors) stimulated with LPS to polarize in a pro-inflammatory M1 state expressing human CD38. The cells were incubated in the presence of 8 different concentrations of Compound 39 for 10 minutes and the reaction was started adding the substrate εNAD+. The emission of fluorescence was measured at 410-20 nm at 37° C. every minute for 1 hr. The NAD+ hydrolase activity was calculated as the slope of the linear portion of the fluorescence-time curve and used to calculate the IC50 value. The IC50 value for Compound 39 was 3.9 nM (1.6 ng/mL) in primary human M1 macrophages (FIG. 9).

Example 36

In Vivo Efficacy of Compound 39 Against CD38 in Obese Mice

The in vivo efficacy of Compound 39 against the human CD38 enzyme was tested in obese mice after oral administration and determined by mass spec analysis of NAD+ metabolites levels in liver tissue. The two main CD38 substrates, NAD+ and NMN, and the 2 main byproducts of the CD38 enzymatic reaction, NAM and ADPR, were measured.

Obese mice (male DIO C57BL6/J, 7.5 months old) were fasted for 4 hr and compound 39 was administered via oral gavage at a concentration of 1 mg/kg and 10 mg/kg. Mice were humanely euthanized for liver tissue harvesting at 1-, 3-, and 6-hr post-dosing. A vehicle control (DMSO: Solutol HS 15: 80% Captisol (20% in water)(5:15:80 v/v)) was included to assess baseline NAD+ metabolites levels.

The procedure for tissue sample preparation and UPLC-MS/MS methods were adapted from Trammell et al. (2013) Compu. Struct. Biotechnol. J. 20:4 (https://www.ncbi.nlm-.nih.gov/pmc/articles/PMC3962138/). Frozen liver tissue was pulverized and resuspended in the extraction buffer (3:1 ethanol:10 mM aq. HEPES, pH 7.1). The samples were vortexed, sonicated briefly in a bath sonicator, and shaken at 55° C. for 3 min at 1,200 rpm. Samples were then centrifuged at 16,000×g for 10 min at 4° C., and the supernatant was dried by speedvac. The dried pellet was resuspended in 97% 10 mM ammonium acetate/3% acetonitrile, centrifuged at 16,000×g for 10 min at 4° C. and 2 μL was injected for LCMS analysis.

The UPLC-MS/MS analysis to measure NAD+ metabolites was performed using a Vanquish UHPLC system and a Q Exactive Orbitrap mass spectrometer with H-ESI ion source both from Thermo Scientific. UPLC separation was performed on a Hypercarb (2.1×100 mm, 5 μm particle size, Thermo) column following the method described in Trammell et al. (2013). Acquisition was carried out in positive ion, Parallel Reaction Monitoring (PRM) mode and targeted Single Reaction Monitoring (t-SIM). The Thermo Xcalibur QualBrowser system (version 4.2.47) and Freestyle (version 1.8.51.0) softwares was used for the data processing. For relative fold change, peak areas were normalized with respective internal standards, normalized to weight of the tissue sample used, and calculated as fold change relative at 0 h timepoint/vehicle group.

A single 1 mg/kg and 10 mg/kg dose oral administration of Compound 39 was able to increase NAD+ and NMN levels and to decrease NAM and ADPR levels in liver (FIGS. 10A-10D).

Example 37

In Vivo Efficacy of Compound 39 Against CD38 in Obese Mice

The in vivo efficacy of Compound 39 against the human CD38 enzyme was tested in obese mice after oral administration and determined by mass spec analysis of NAD+ metabolites levels in liver tissue. The two main CD38 substrates, NAD+ and NMN, and the 2 main byproducts of the CD38 enzymatic reaction, NAM and ADPR, were measured.

Obese mice (male DIO C57BL6/J, 65 weeks old) treated for 49 days with compound 39 via oral gavage at a concentration of 10 mg/kg BID. On day 49, mice were humanely euthanized for liver tissue harvesting at 4 hr post-dosing. A vehicle control (1% Methylcellulose) was included to assess baseline NAD+ metabolites levels.

The procedure for tissue sample preparation and UPLC-MS/MS methods were adapted from Trammell et al. (2013) Compu. Struct. Biotechnol. J. 20:4 (https://www.ncbi.nlm-.nih.gov/pmc/articles/PMC3962138/). Frozen liver tissue was pulverized and resuspended in the extraction buffer (3:1 ethanol:10 mM aq. HEPES, pH 7.1). The samples were vortexed, sonicated briefly in a bath sonicator, and shaken at 55° C. for 3 min at 1,200 rpm. Samples were then centrifuged at 16,000×g for 10 min at 4° C., and the supernatant was dried by speedvac. The dried pellet was resuspended in 97% 10 mM ammonium acetate/3% acetonitrile, centrifuged at 16,000×g for 10 min at 4° C. and 2 μL was injected for LCMS analysis.

The UPLC-MS/MS analysis to measure NAD+ metabolites was performed using a Vanquish UHPLC system and a Q Exactive Orbitrap mass spectrometer with H-ESI ion source both from Thermo Scientific. UPLC separation was performed on a Hypercarb (2.1×100 mm, 5 μm particle size, Thermo) column following the method described in Trammell et al. (2013). Acquisition was carried out in positive ion, Parallel Reaction Monitoring (PRM) mode and targeted Single Reaction Monitoring (t-SIM). The Thermo Xcalibur QualBrowser system (version 4.2.47) and Freestyle (version 1.8.51.0) softwares was used for the data processing. For relative fold change, peak areas were normalized with respective internal standards, normalized to weight of the tissue sample used, and calculated as fold change relative at 0 h timepoint/vehicle group.

Chronic administration of Compound 39 10 mg/kg BID in obese mice was able to significantly increase NAD+ and NMN levels and to decrease NAM and ADPR levels in liver (FIGS. 11A-11D).

Example 38

In Vivo Efficacy of Compound 39 Against CD38 in Aged Mice

The in vivo efficacy of Compound 39 against the human CD38 enzyme was tested in aged mice after oral administration and determined by mass spec analysis of NAD+ metabolites levels in liver tissue. The two main CD38 substrates, NAD+ and NMN, and the 2 main byproducts of the CD38 enzymatic reaction, NAM and ADPR, were measured.

Compound 39 was administered to aged mice (male DIO C57BL6/J, 19-22 months old) via oral gavage at a concentration of 10 mg/kg BID for 5 days. At day 5, mice were humanely euthanized for liver tissue harvesting 3 hr post-dosing. A vehicle control (DMSO: Solutol HS 15: 80% Captisol (20% in water)(5:15:80 v/v)) was included to assess baseline NAD+ metabolites levels.

The procedure for tissue sample preparation and UPLC-MS/MS methods were adapted from Trammell et al. (2013) Compu. Struct. Biotechnol. J. 20:4 (https://www.ncbi.nlm.nih.gov/pmc/articles/PMC3962138/). Frozen liver tissue was pulverized and resuspended in the extraction buffer (3:1 ethanol:10 mM aq. HEPES, pH 7.1). The samples were vortexed, sonicated briefly in a bath sonicator, and shaken at 55° C. for 3 min at 1,200 rpm. Samples were then centrifuged at 16,000×g for 10 min at 4° C., and the supernatant was dried by speedvac. The dried pellet was resuspended in 97% 10 mM ammonium acetate/3% acetonitrile, centrifuged at 16,000×g for 10 min at 4° C. and 2 μL was injected for LCMS analysis.

The UPLC-MS/MS analysis to measure NAD+ metabolites was performed using a Vanquish UHPLC system and a Q Exactive Orbitrap mass spectrometer with H-ESI ion source both from Thermo Scientific. UPLC separation was performed on a Hypercarb (2.1×100 mm, 5 μm particle size, Thermo) column following the method described in Trammell et al. (2013). Acquisition was carried out in positive ion, Parallel Reaction Monitoring (PRM) mode and targeted Single Reaction Monitoring (t-SIM). The Thermo Xcalibur QualBrowser system (version 4.2.47) and Freestyle (version 1.8.51.0) softwares was used for the data processing. For relative fold change, peak areas were normalized with respective internal standards, normalized to weight of the tissue sample used, and calculated as fold change relative at 0 h timepoint/vehicle group.

Chronic administration of compound 39 10 mg/kg was able to increase NAD+ levels and to decrease NAM and ADPR levels in liver (FIGS. 12A-12D).

Example 39

In Vivo Efficacy of Compound 39 Against CD38 in Mice After LPS-induced Inflammation The in vivo efficacy of Compound 39 against the human CD38 enzyme after LPS challenge was assessed. The effects of Compound 39 (10 mg/kg and 30 mg/kg) on inflammato cytokines, inflammation markers and NAD+ levels at 4 h and 8 h points after LPS-induced inflammation in 12 weeks old male C57BL/6J mice were evaluated.

In this study: (1) the animals displayed normal behavior (appearance, behavior, posture, respiratory rate and pattern), normal urination and defecation, and no signs of distress throughout the study; (2) no changes in fecal material and/or in urine were observed; and (3) there were normal signs of distress observed by gentle handling during oral gavage procedure. Animals were euthanized by terminal cardiac blood puncture immediately after terminal $CO_2$, 4 h and 8 h after LPS administration. At necropsy, the tissues (Liver, Plasma, Spleen, Kidney, Lungs, Heart, Visceral Adipose Tissue, Muscle-Gastrocnemius) were collected and quick frozen in liquid nitrogen. The blood was collected in a BD Microtainer® K2EDTA Additive Tube, centrifuge at 1000 g for 10 min at 4° C. and plasma was store at −80° C.).

Cytokines Quantification in Plasma

Figure 13A:
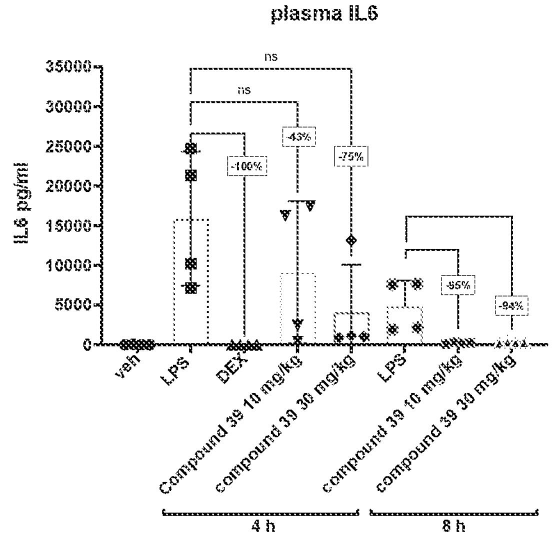
FIGS. 13A-13C depict cytokines quantification in plasma for IL-6 (FIG. 13A), TNF□ (FIG. 13B) and IP-10 (FIG. 13C). The response plot represents the average (+/−) standard deviation for the measurement of cytokines levels at each condition tested where n=4 over 1 experiment *, p≤0.05; , p≤0.01; *, p≤0.001; **** p<0.0001 compared with LPS samples at each time point, one-way ANOVA.
Figure 13B:
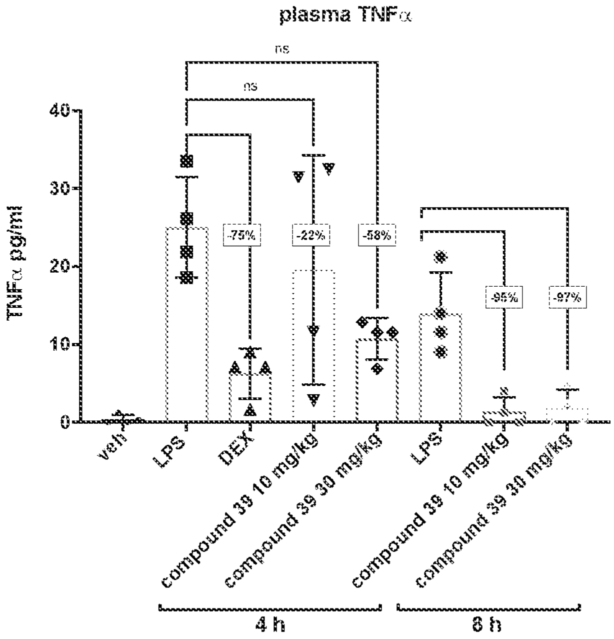
Figure 13C:
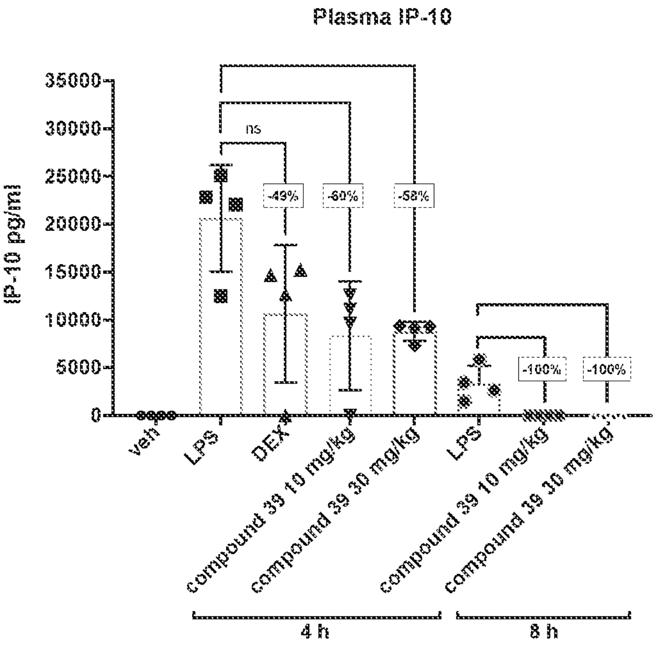

Cytokines were quantified in plasma: (1) statistically significant decrease of plasma IL-6, TNFα and IP-10 8 h post LPS challenge in the two compound 39 treatment arms (10 mg/kg and 30 mg/kg); (2) statistically significant decrease of plasma IP-10 4 hour post LPS challenge in the two compound 39 treatment arms (10 mg/kg and 30 mg/kg) and in the control arm (Dexamethasone 1 mg/kg); (3) 43% and 75% decrease of plasma IL-6 4 hour post LPS challenge with compound 39 10 mg/kg and 30 mg/kg, respectively; (4) 22% and 58% decrease of plasma TNFα 4 hour post LPS challenge with compound 39 10 mg/kg and 30 mg/kg, respectively; and (5) statistically significant decrease of plasma IL-6, TNFα and IP-10 4 hour post LPS challenge in control arm (Dexamethasone 1 mg/kg) (FIGS. 13A-13C).

MS Analysis of NAD+ Metabolism

Figure 14A:
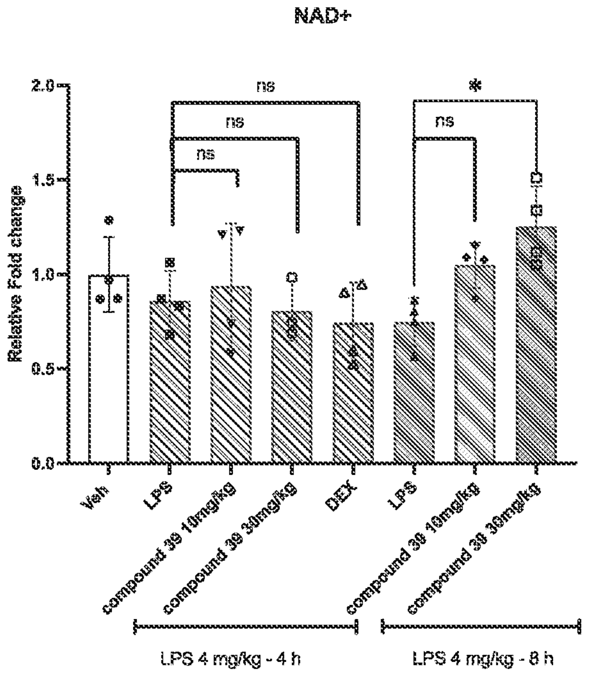
FIGS. 14A-14C depict MS analysis of NAD+(FIG. 14A), NAM (FIG. 14B), and ADPR (FIG. 14C) levels in spleen tissue. The response plot represents the average (+/−) standard deviation for the measurement of NAD+ metabolites levels at each condition tested where n=4 over 1 experiment. *, p≤0.05; , p≤0.01; *, p≤0.001; ****, p<0.0001 compared with Vehicle sample, one-way ANOVA.
Figure 14B:
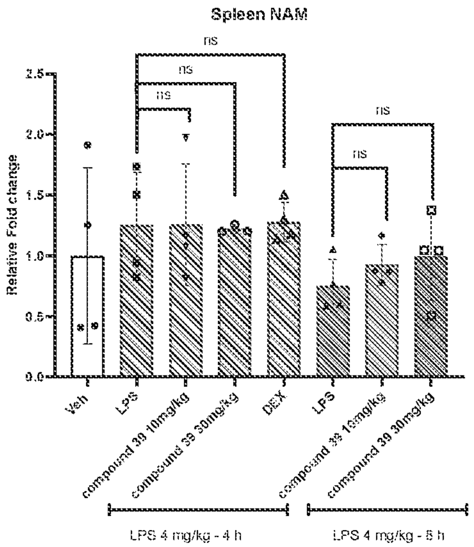
Figure 14C:
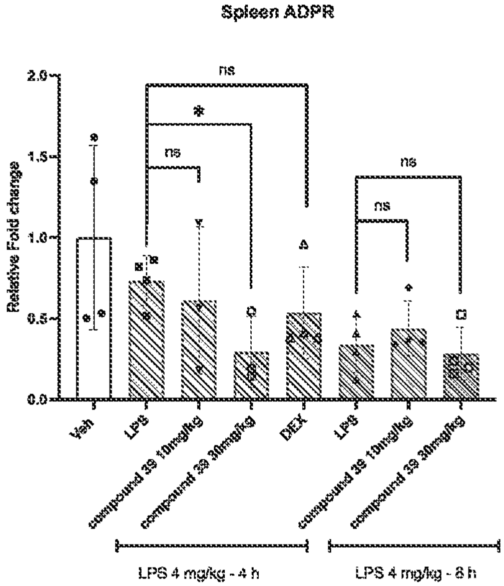

NAD+ metabolism in spleen was assessed using Mass Spectrometry (MS): an increase of NAD+ levels (2.3-fold) in the compound 39 30 mg/kg treatment arm at 8 hours post LPS challenge and a statistically significant decrease in ADPR levels (40% decrease) after 8 h treatment with 30 mg/kg compound 39 were observed (FIGS. 14A-14C).

Figure 15A:
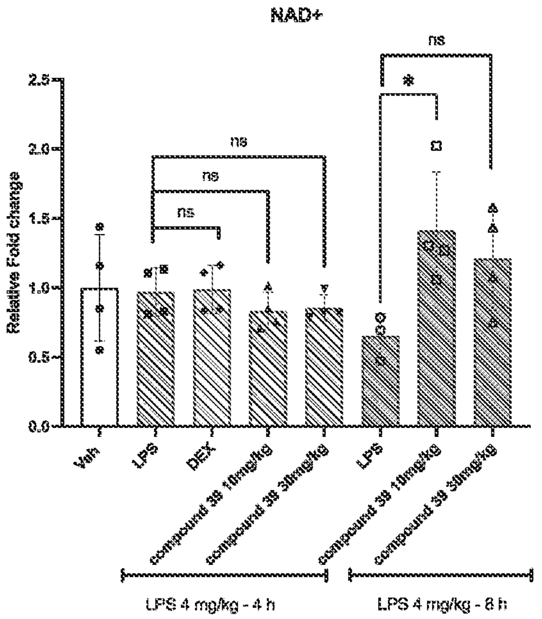
FIGS. 15A-15C depict MS analysis of NAD+(FIG. 15A), NAM (FIG. 15B), and ADPR (FIG. 15C) levels in live tissue. The response plot represents the average (+/−) standard deviation for the measurement of NAD+ metabolites levels at each condition tested where n=4 over 1 experiment.*, p≤0.05; , p≤0.01; *, p≤0.001; ****, p<0.0001 compared with LPS samples at each time point, one-way ANOVA.
Figure 15B:
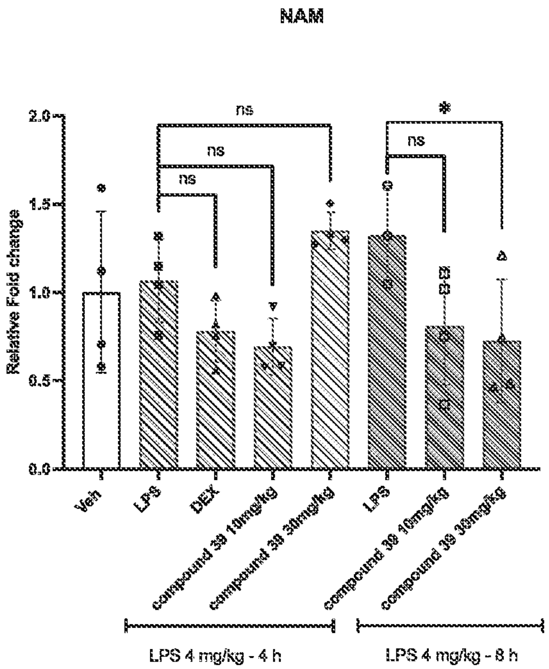
Figure 15C:
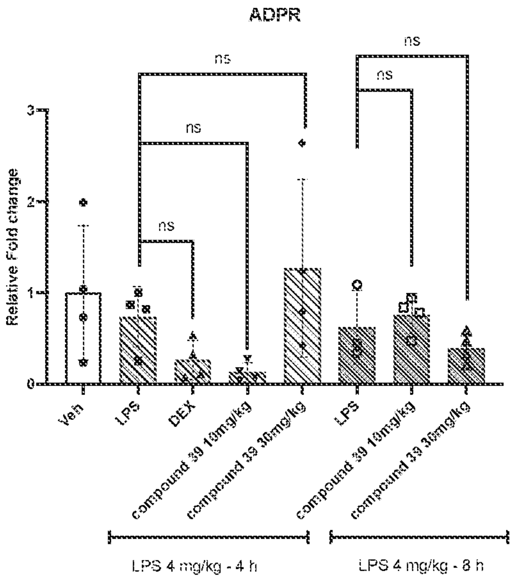

NAD+ metabolism in liver was assessed using Mass Spectrometry (MS): a statistically significant increase of NAD+ levels (2-fold) with compound 39 10 mg/kg treatment arm at 8 hours post LPS challenge, a significant decrease of NAM levels (38% decrease) in the compound 39 30 mg/kg treatment arm at 8 hours post LPS challenge, and a decrease of ADPR levels in the Compound 39 treatment arms at 4 hours post LPS challenge were observed (FIGS. 15A-15C).

Gene Expression Analysis

Figure 16:
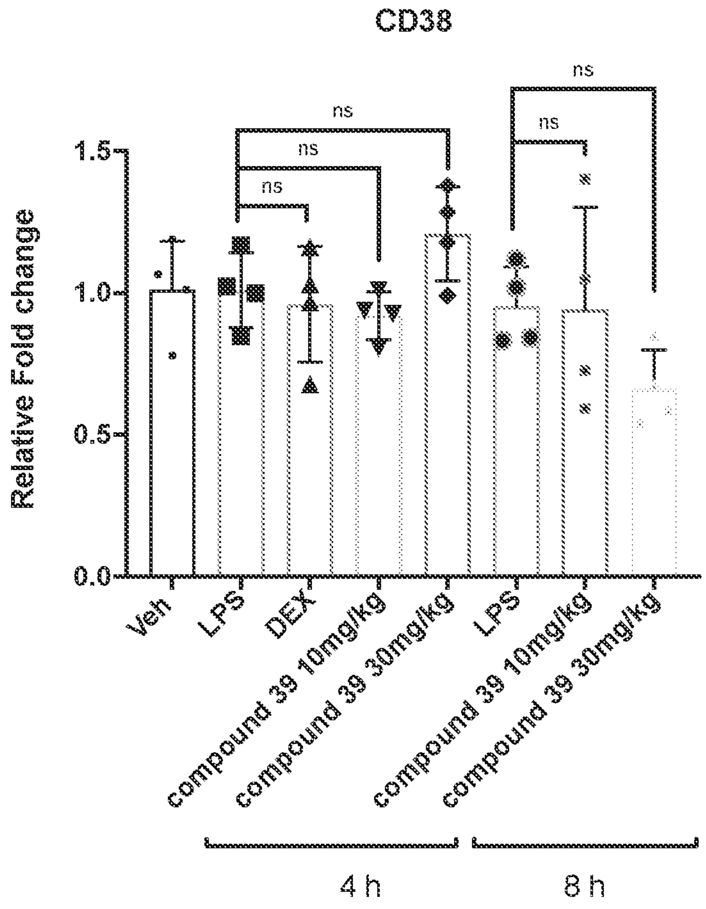
FIG. 16 depicts CD38 expression in spleen tissue. The response plot represents the average (+/−) standard deviation for the measurement of CD38 gene expression at each condition tested where n=4 over 1 experiment. *, p≤0.05; , p≤0.01; *, p≤0.001; ****, p<0.0001 compared with LPS samples at each time point, one-way ANOVA.
Figure 17A:
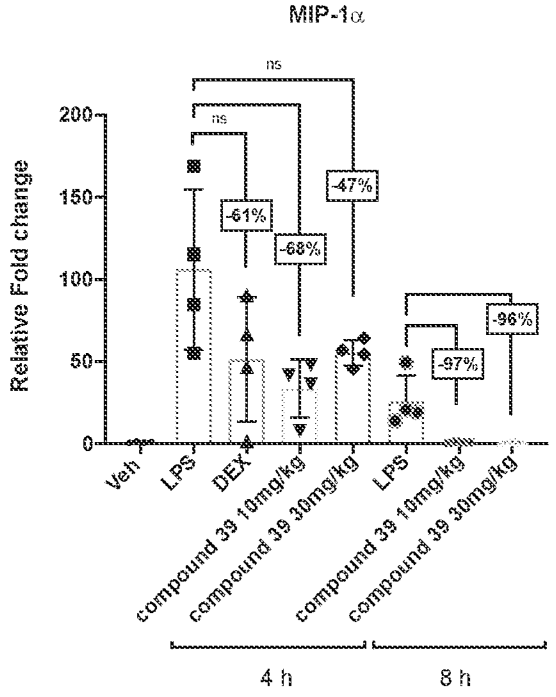
FIGS. 17A-17I depict the expression in spleen of MIP1□□ (FIG. 17A), MIP2 (FIG. 17B), TNF□□ (FIG. 17C), RANTES (FIG. 17D), MCP1 (FIG. 17E), IL-1p (FIG. 17F), IL-6 (FIG. 17G), IP-10 (FIG. 17H), and IFN□□ (FIG. 17I). The response plot represents the average (+/−) standard deviation for the measurement of gene expression at each condition tested where n=4 over 1 experiment. *, p≤0.05; , p≤0.01; *, p≤0.001; ****, p<0.0001 compared with LPS samples at each time point, one-way ANOVA.
Figure 17B:
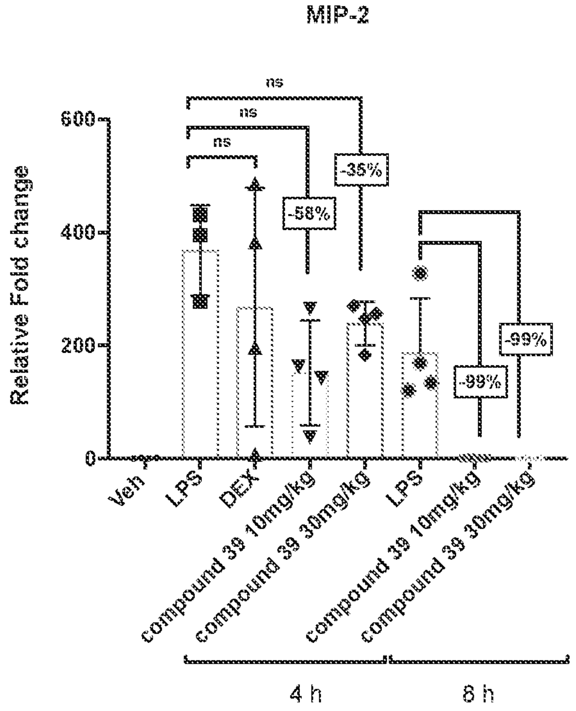
Figure 17C:
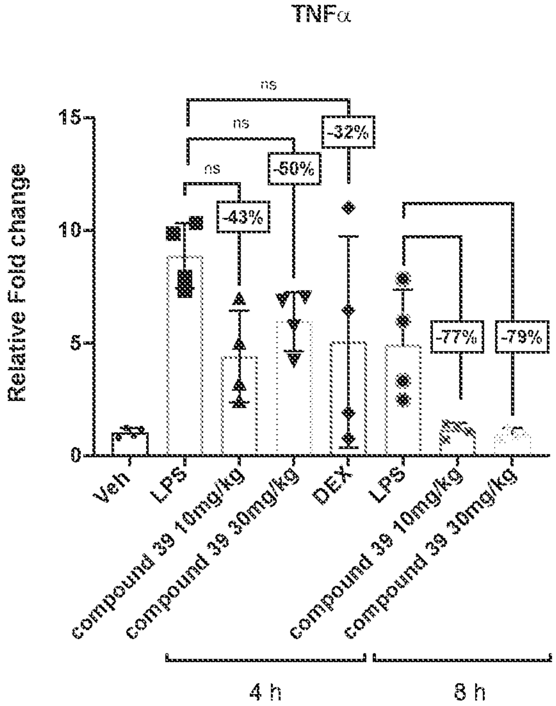
Figure 17D:
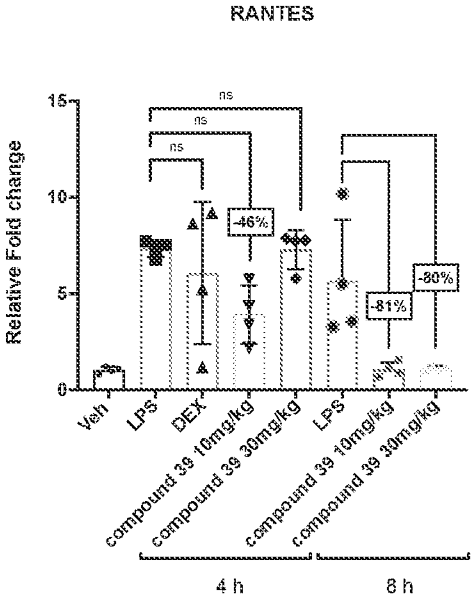
Figure 17E:
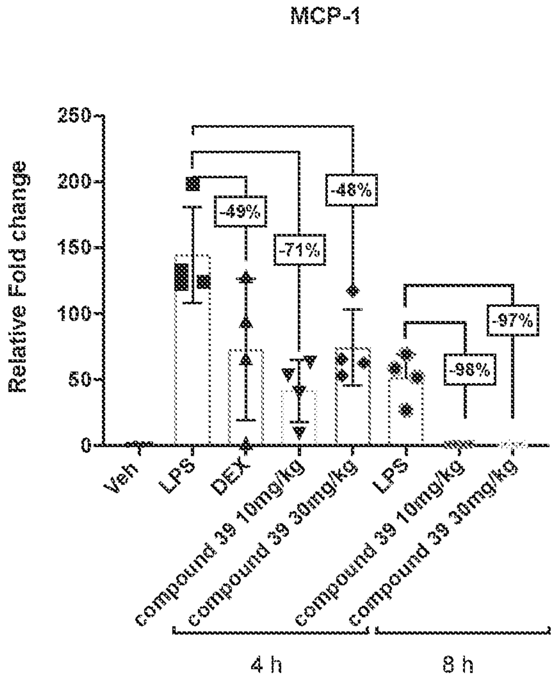
Figure 17F:
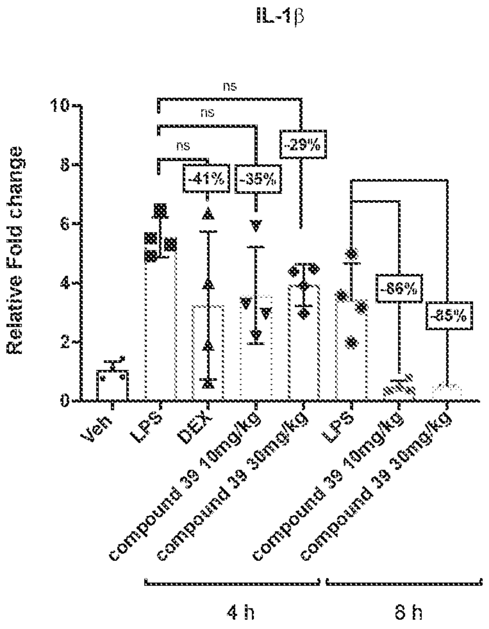
Figure 17G:
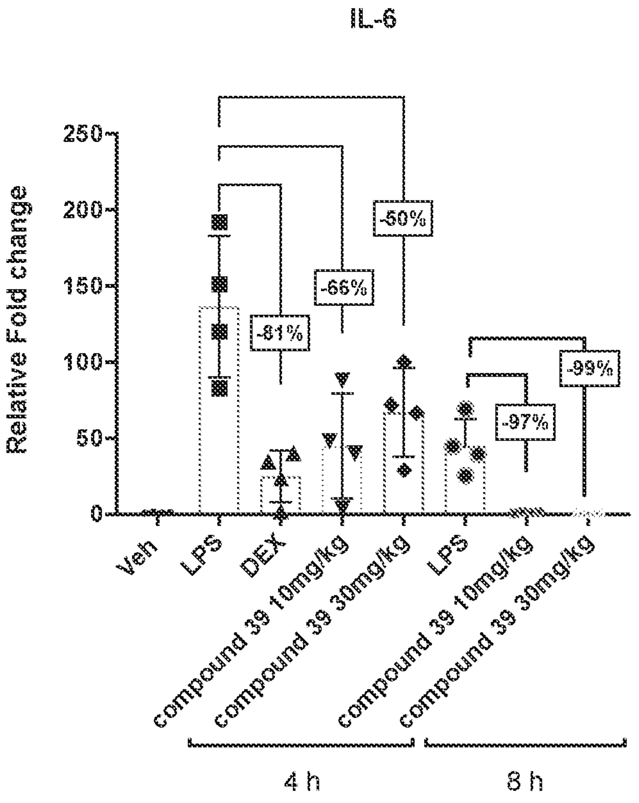
Figure 17H:
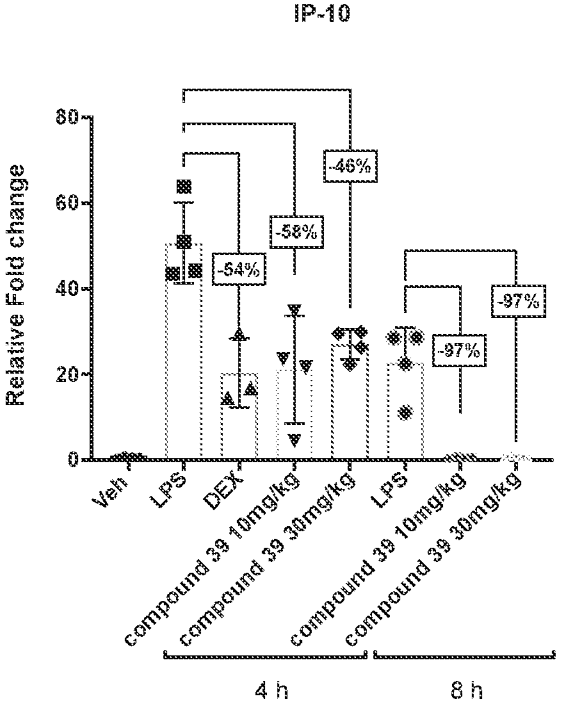
Figure 17I:
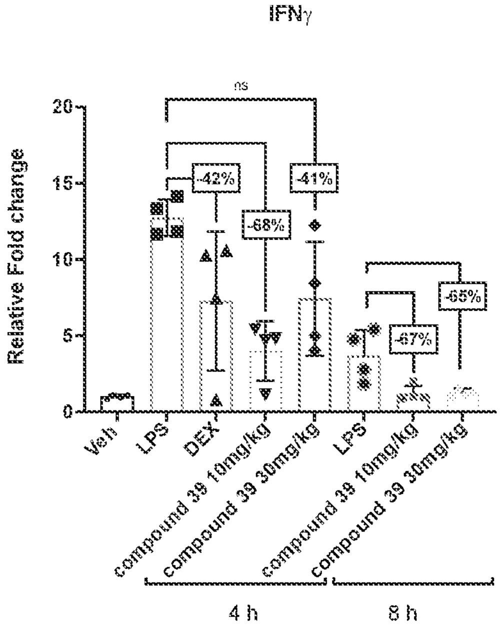

Upon compound 39 treatment, in spleen no significant changes in CD38 expression (FIG. 16) and a statistically significant decrease of MIP1α (FIG. 17A), MIP2 (FIG. 17B), TNFα (FIG. 17C), RANTES (FIG. 17D), MCP1 (FIG. 17E), IL-1β (FIG. 17F), IL-6 (FIG. 17G), IP-10 (FIG. 17H), and IFNγ (FIG. 17I) levels were observed.

Figure 18:
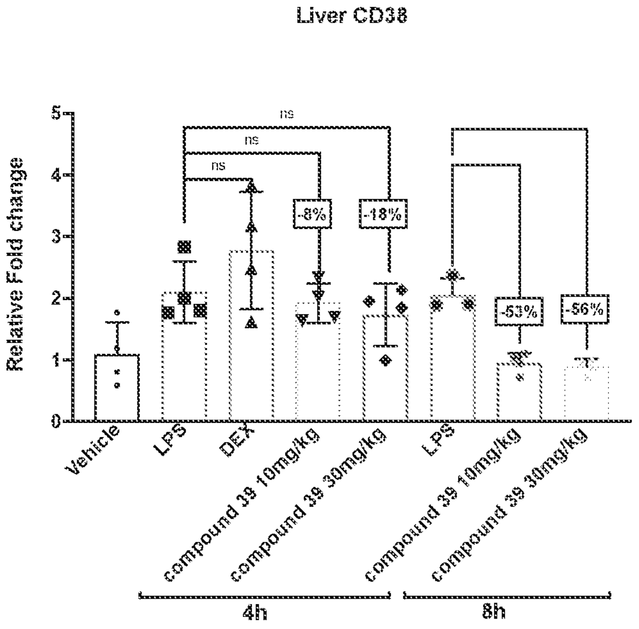
FIG. 18 depicts CD38 expression in liver. The response plot represents the average (+/−) standard deviation for the measurement of CD38 gene expression at each condition tested where n=4 over 1 experiment. *, p≤0.05; , p≤0.01; *, p≤0.001; ****, p<0.0001 compared with LPS samples at each time point, one-way ANOVA.
Figure 19A:
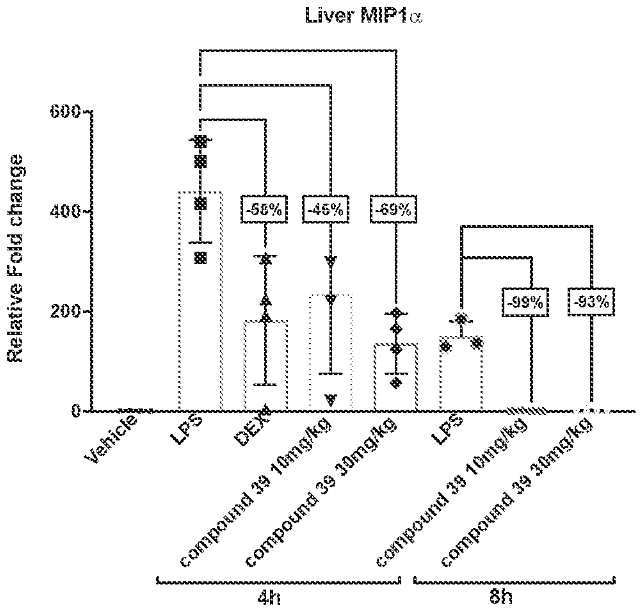
FIGS. 19A-19I depict the expression in liver of MIP1□□ (FIG. 19A), MIP2 (FIG. 19B), TNF□□ (FIG. 19C), RANTES (FIG. 19D), MCP1 (FIG. 19E), IL-1β (FIG. 19F), IL-6 (FIG. 19G), IP-10 (FIG. 19H), and IFN□□ (FIG. 19I).□ The response plot represents the average (+/−) standard deviation for the measurement of gene expression at each condition tested where n=4 over 1 experiment. *, p≤0.05; , p≤0.01; *, p≤0.001; ****, p<0.0001 compared with Vehicle sample, one-way ANOVA.
Figure 19B:
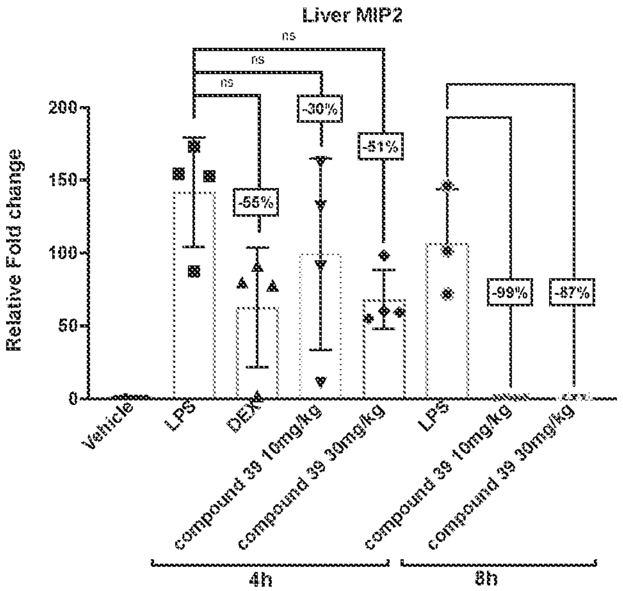
Figure 19C:
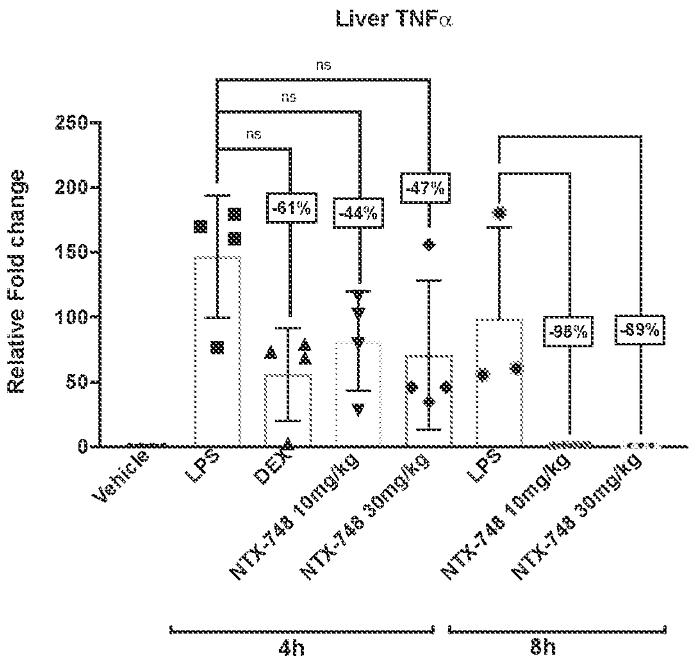
Figure 19D:
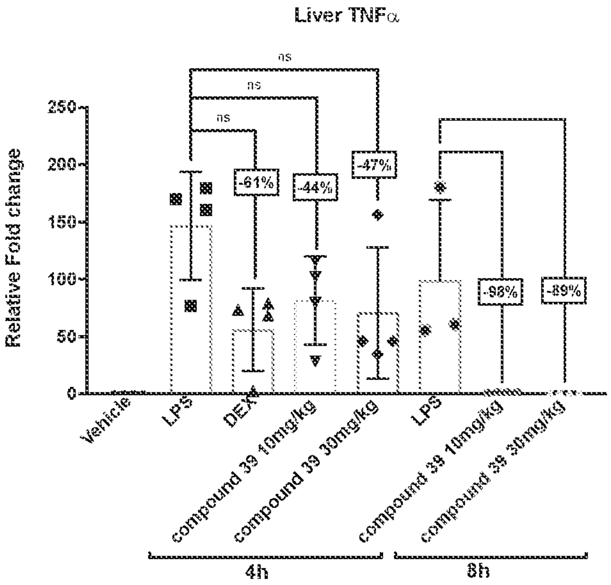
Figure 19E:
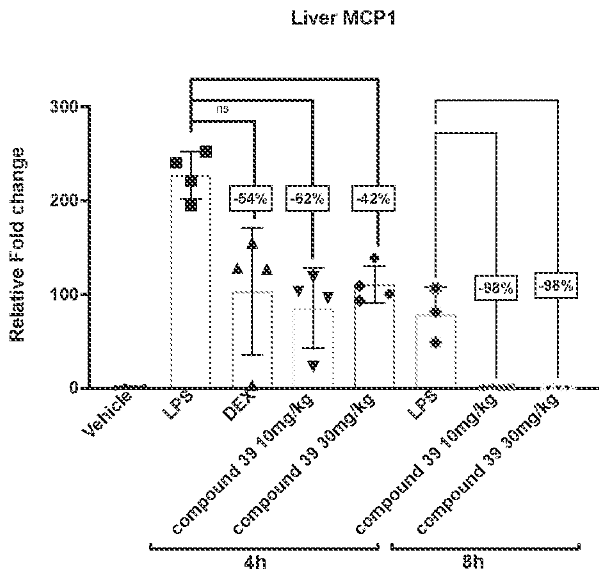
Figure 19F:
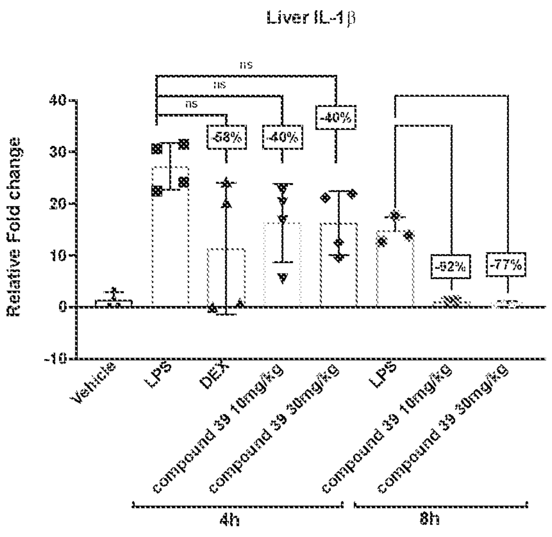
Figure 19G:
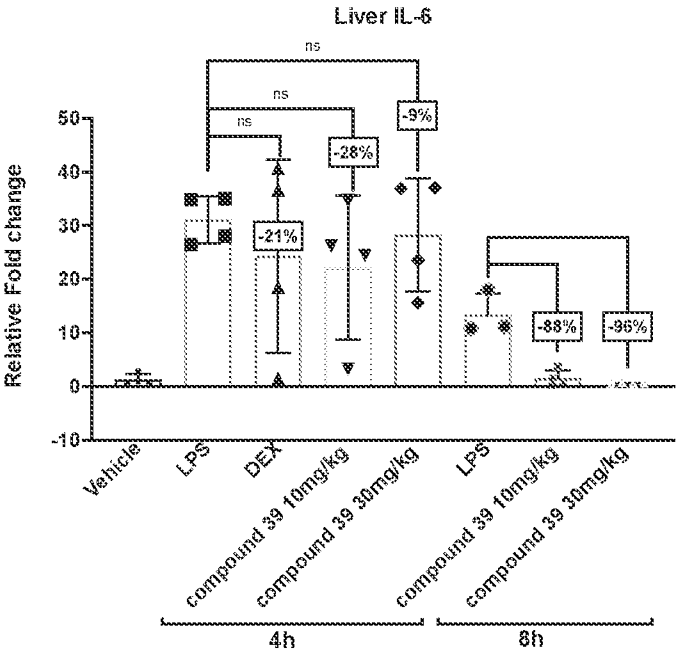
Figure 19H:
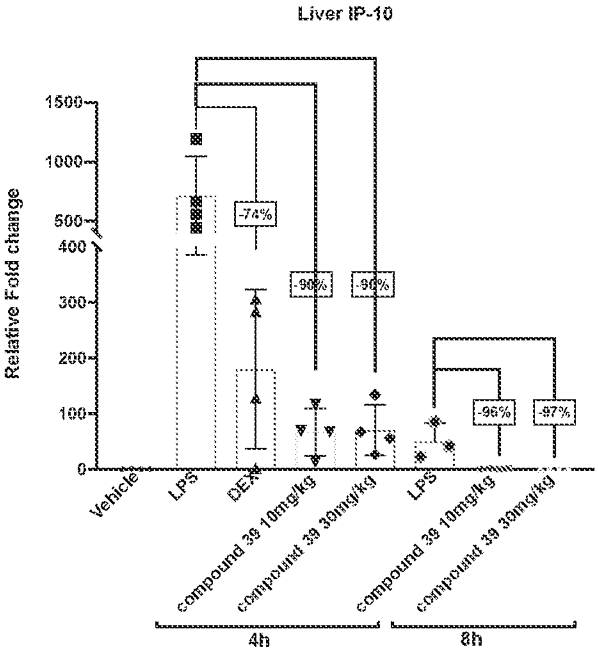
Figure 19I:
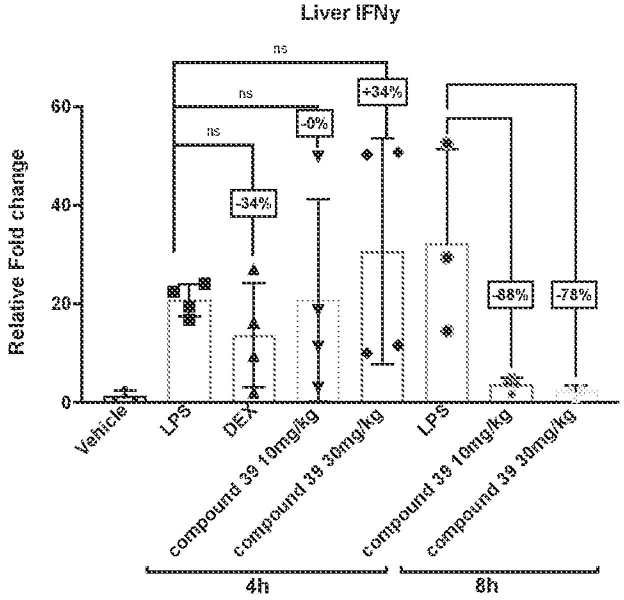

Upon compound 39 treatment, in liver a statistically significant decrease of CD38 expression in the two treatment arms (10 mg/kg and 30 mg/kg) 8 hour post LPS challenge (FIG. 18) and a statistically significant decrease of MIP1α (FIG. 19A), MIP2 (FIG. 19B), TNFα (FIG. 19C), RANTES (FIG. 19D), MCP1 (FIG. 19E), IL-1β (FIG. 19F), IL-6 (FIG. 19G), IP-10 (FIG. 19H), and IFNγ (FIG. 19I) levels were observed.

Example 40

In Vitro Efficacy of Compound 32 Against CD38 in Modulating Calcium Flux in T Cell Line The in vitro efficacy of compound 32 against the human CD38 enzyme in modulating cellular Ca2+ flux was determined by a fluorescence-based assay using Flow Citometry. The assay utilized CD38 expressing NH7-dCas9 cells (Jurkat clone) provided by the Weissman Lab (UCSF1700 4th St., Byers Hall, Room 403B, San Francisco, CA 94158-2330).

The cells were seeded in complete RPMI medium in the presence of absence of 50 nM of Compound 32 at a density of $1\times10^6$ cells/ml and then incubated at 37° C. for 24 h. In preparation for flow cytometry, equal numbers of cells were washed and incubated with the membrane-permeable calcium sensor dye eFluor 514 (eBioscience, catalogue no. 65-0859) in PBS for 15 min at room temperature. Changes in calcium intracellular free concentration were measured over 200 s by flow cytometric analysis on a BD LSRII flow cytometer (BD Biosciences). Ionomycin (1 μg ml-1, Thermo Fisher Scientific) was added after 30-s related fluorescence was measured on a BD FACSCalibur system (BD Biosciences) in an uncompensated setting. Data were analysed using FlowJo v.10.1 software (Tree Star).

Figure 20A:
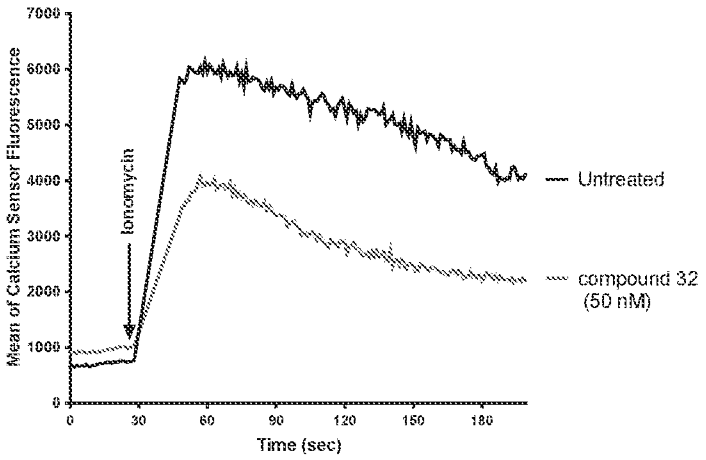
FIG. 20A-20B depicts in vitro efficacy of Compound 32 in human CD38+ T cell line as measured by total calcium flux analysis. Data in FIG. 20B are represented as AUC mean±s.d. of n=3 independent experiments. *, p≤0.05; , p≤0.01; *, p≤0.001; ****, p<0.0001 compared with untreated WT sample, unpaired t-test.
Figure 20B:
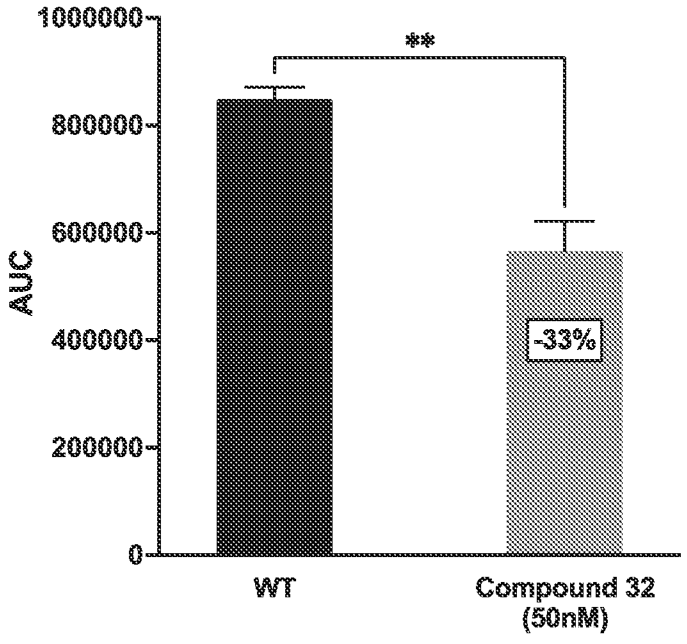

A representative plot of intracellular calcium-flux kinetics in NH7-dCas9 cells in the presence of compound 32 (50 nM) is shown in FIG. 20A. The parameter area under the curve (AUC) relative to the calcium flux was calculated and shown in FIG. 20B. Compound 32 at a final concentration of 50 nM was able to significantly decrease the total Ca2+ cellular flux of about 33% (FIGS. 20A and 20B). Data are represented as mean±s.d. of n=3 independent experiments.

Example 41

In Vitro Efficacy of Compound 39 Against CD38 in Modulating Calcium Flux in T Cell Line The in vitro efficacy of compound 39 against the human CD38 enzyme in modulating cellular Ca2+ flux was determined by a fluorescence-based assay using Flow Citometry. The assay utilized CD38 expressing NH7-dCas9 cells (Jurkat clone) provided by the Weissman Lab (UCSF1700 4th St., Byers Hall, Room 403B, San Francisco, CA 94158-2330).

The cells were seeded in complete RPMI medium in the presence of absence of 50 nM of Compound 39 at a density of $1\times10^6$ cells/ml and then incubated at 37° C. for 24 h. In preparation for flow cytometry, equal numbers of cells were washed and incubated with the membrane-permeable calcium sensor dye eFluor 514 (eBioscience, catalogue no. 65-0859) in PBS for 15 min at room temperature. Changes in calcium intracellular free concentration were measured over 200 s by flow cytometric analysis on a BD LSRII flow cytometer (BD Biosciences). Ionomycin (1 μg ml-1, Thermo Fisher Scientific) was added after 30-s related fluorescence was measured on a BD FACSCalibur system (BD Biosciences) in an uncompensated setting. Data were analysed using FlowJo v.10.1 software (Tree Star).

Figure 21A:
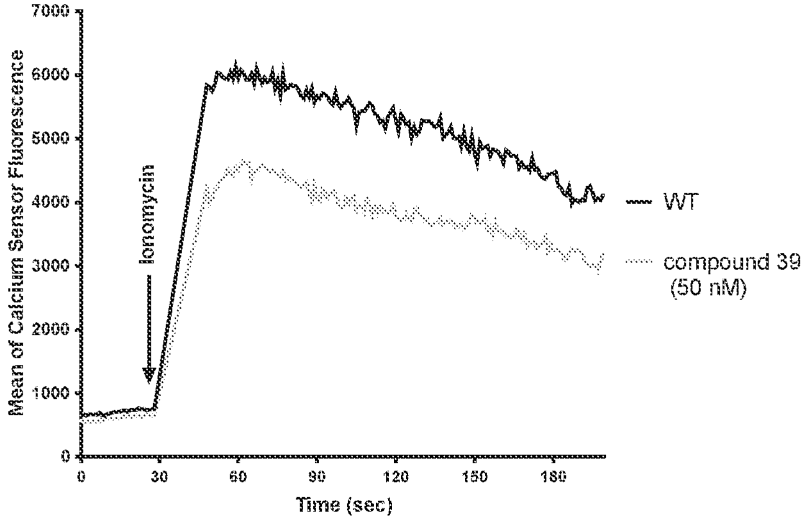
FIG. 21A-21B depicts in vitro efficacy of Compound 39 in human CD38+ T cell line as measured by total calcium flux analysis. Data in FIG. 21B are represented as AUC mean±s.d. of n=3 independent experiments. *, p≤0.05; , p≤0.01; *, p≤0.001; ****, p<0.0001 compared with untreated WT sample, unpaired t-test.
Figure 21B:
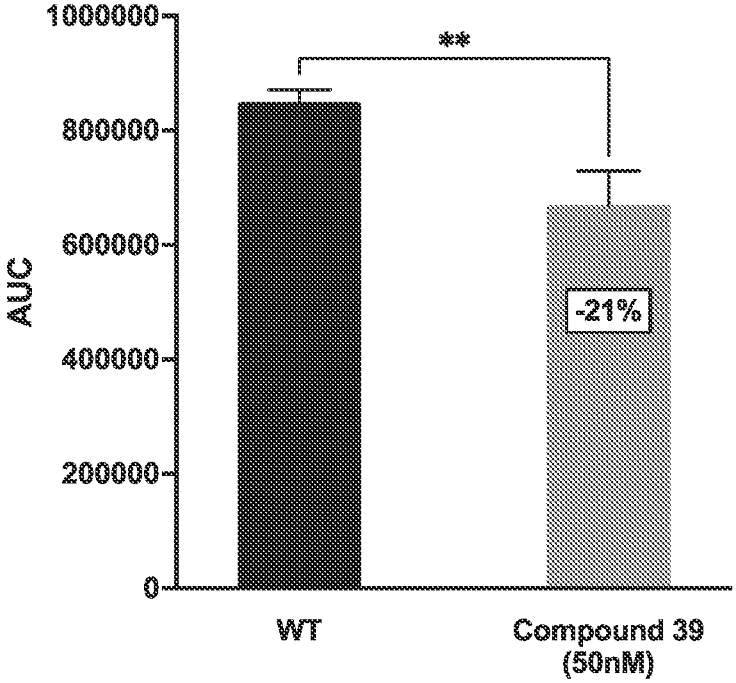

A representative plot of intracellular calcium-flux kinetics in NH7-dCas9 cells in the presence of compound 39 (50 nM) is shown in FIG. 21A. The parameter area under the curve (AUC) relative to the calcium flux was calculated and shown in FIG. 21B. Compound 32 at a final concentration of 50 nM was able to significantly decrease the total Ca2+ cellular flux of about 21% (FIGS. 21A and 21B). Data are represented as mean±s.d. of n=3 independent experiments.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

Those skilled in the art will appreciate further features and advantages of the invention based on the above-described disclosures, aspects and embodiments. Accordingly, the invention is not to be limited by what has been particularly shown and described, except as indicated by the appended claims. All publications and references cited herein are expressly incorporated herein by reference in their entirety.

The invention claimed is:

1. A compound of Formula I or a pharmaceutically acceptable salt, ester, or prodrug thereof (I)

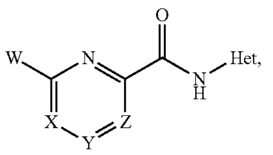

or a compound of Formula I* or a pharmaceutically acceptable salt, ester, or prodrug thereof (I*)

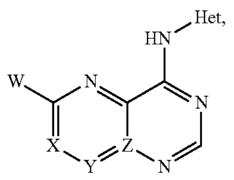

wherein:

—X—Y—Z— is $=CR^1—CR^2=CR^3—$, $=N—CR^2=CR^3—$, $=CR^1—N=CR^3—$ or $=CR^1—CR^2=N$ if the compound is of Formula I;

—X—Y—Z— is $CR^1—CR^2=C$, $N—CR^2=C$, or $CR^1—N=C$ if the compound is of Formula I*;

$R^1$ is selected from the group consisting of H, halo, —CN, $(C_1\text{-}C_6)$alkyl, $(C_1\text{-}C_6)$alkoxy, and perfluoro$(C_1\text{-}C_6)$alkoxy-; wherein $(C_1\text{-}C_6)$alkyl is optionally substituted with 1-3 substituents independently selected from the group consisting of H, halo, —CN, $(C_1\text{-}C_3)$alkyl, $—NH_2$, $(C_1\text{-}C_3)$alkyl-(NH)—, $((C_1\text{-}C_3)alkyl)_2N—$, $—CF_3$, $—OCH_3$, and $—OCF_3$;

$R^2$ is H, halo, —CN, ($C_1$-$C_6$)alkyl, ($C_1$-$C_6$)alkoxy, perfluoro($C_1$-$C_6$)alkyl, perfluoro($C_1$-$C_6$)alkoxy-, cycloalkyl, cycloalkyl-O—, heterocycloalkyl, heterocycloalkyl-O—, aryl, aryl-O—, $R^5$—$(C(R^4)_2)_n$—O—, or $(R^6)_2$ N—; wherein ($C_1$-$C_6$)alkyl, cycloalkyl, heterocycloalkyl, and aryl are each optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$)alkyl)$_2$N—, —$CF_3$, —$OCH_3$, and —$OCF_3$;

$R^3$ is H, halo, ($C_1$-$C_3$)alkyl, —$CF_3$, ($C_1$-$C_3$)alkoxy, —$OCF_3$, or $(R^7)_2$N—; wherein $R^7$ is H or ($C_1$-$C_3$)alkyl;

n is an integer from one to three;

each $R^4$ is independently H or ($C_1$-$C_3$)alkyl; wherein ($C_1$-$C_3$) alkyl is optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$)alkyl)$_2$N—, —$CF_3$, —$OCH_3$, and —$OCF_3$;

$R^5$ is selected from the group consisting of ($C_1$-$C_3$) alkyl, perfluoro ($C_1$-$C_3$)alkyl, HO—($C_2$-$C_4$)alkyl-, cycloalkyl, heterocycloalkyl, and aryl; wherein ($C_1$-$C_3$)alkyl, cycloalkyl, heterocycloalkyl, and aryl are each optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$) alkyl)$_2$N—, —$CF_3$, —$OCH_3$, and —$OCF_3$;

$R^6$ is independently H or ($C_1$-$C_3$)alkyl; wherein ($C_1$-$C_3$) alkyl is optionally substituted with 1-3 substituents independently selected from the group consisting of H, halo, —CN, ($C_1$-$C_3$)alkyl, —$NH_2$, ($C_1$-$C_3$) alkyl-(NH)—, (($C_1$-$C_3$)alkyl)$_2$N—, —$CF_3$, —$OCH_3$, and —$OCF_3$;

W is (a)

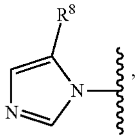

(b)

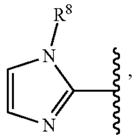

(c)

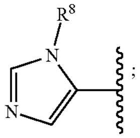

(d)

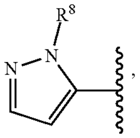

(e)

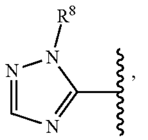

or

-continued (f)

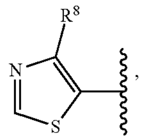

$R^8$ is H, —$CH_3$ or —$CF_3$;

Het is a heterocycle of the formulae i

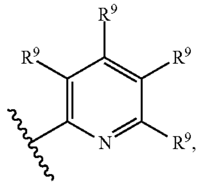

ii

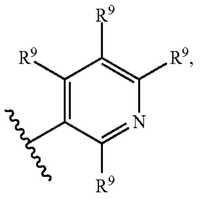

iii

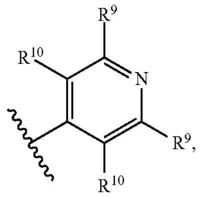

iv

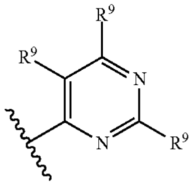

v

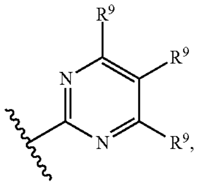

vi

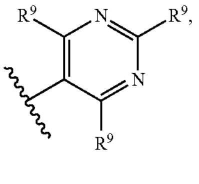

-continued vii

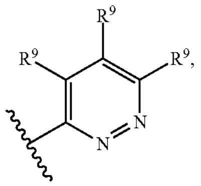

viii

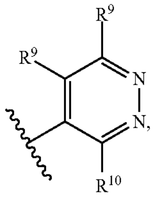

or ix

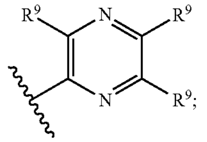

each $R^9$ is independently selected from H, halo, $(C_1-C_6)$ alkyl, $-CF_3$, $(C_1-C_6)$alkoxy, $-OCF_3$, $-CN$, $(R^{11})_2N-$, $R^{12}(O)(C{=}O)-$, $R^{12}O((C_1-C_3)$alkyl)-$(NR^{11})-$, $R^{13}-(C{=}O)-(NR^{11})-$, and $(R^{11})_2N-(C{=}O)-$;

each $R^{10}$ is independently selected from H, $(C_1-C_3)$ alkyl, $-CF_3$, $-OCH_3$, $-OCF_3$, $-CN$, $(R^{11})_2N-$, $R^{12}(O)(C{=}O)-$, $R^{12}O-((C_1-C_3)$alkyl)-$(NR^{11})-$, $R^{13}-(C{=}O)-(NR^{11})-$, and $(R^{11})_2N-(C{=}O)$;

$R^{11}$ is independently H or $(C_1-C_3)$ alkyl;

$R^{12}$ is H or $(C_1-C_3)$alkyl; and $R^{13}$ is $(C_1-C_3)$alkyl.

2. A compound according to claim 1, wherein in the compound of Formula I or I*, $R^8$ is $-CH_3$ or $-CF_3$; and W is

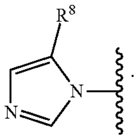

3. A compound according to claim 1, wherein in the compound of Formula I or I*, $R^8$ is $-CH_3$ or $-CF_3$; and W is

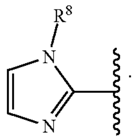

4. A compound according to claim 1, wherein in the compound of Formula I or I*, $R^8$ is $-CH_3$ or $-CF_3$; and W is

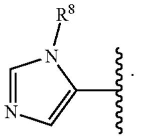

5. A compound according to claim 1, wherein in the compound of Formula I or I*, $R^8$ is $-CH_3$ or $-CF_3$; and W is

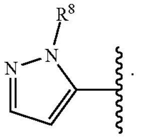

6. A compound according to claim 1, wherein in the compound of Formula I or I *:

$R^8$ is $-CH_3$ or $-CF_3$; and

W is

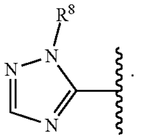

7. A compound according to claim 1, wherein in the compound of Formula I or I *:

$R^8$ is $-CH_3$ or $-CF_3$; and

W is

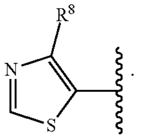

8. A compound according to claim 1, wherein:

$R^2$ is selected from the group consisting of H, $(C_1-C_6)$ alkyl, $(C_1-C_6)$alkoxy-, perfluoro$(C_1-C_6)$alkyl, perfluoro$(C_1-C_6)$alkoxy-, cycloalkyl, cycloalkyl-O—, heterocycloalkyl, aryl, $R^5-(C(R^4)_2)_n-O-$ and $(R^6)_2N-$; wherein $(C_1-C_6)$alkyl, cycloalkyl, heterocycloalkyl and aryl is optionally substituted with 1-3 substituents independently selected from the group consisting of H, halo, $-CN$, $(C_1-C_3)$alkyl, $-NH_2$, $(C_1-C_3)$alkyl-(NH)—, $((C_1-C_3)$alkyl$)_2N-$, $-CF_3$, $-OCH_3$ and $-OCF_3$;

each $R^4$ is independently H or $(C_1-C_3)$ alkyl optionally substituted with 1-3 substituents independently selected from the group consisting of H, halo, $-CN$, $(C_1-C_3)$alkyl, $-NH_2$, $(C_1-C_3)$alkyl-(NH)—, $((C_1-C_3)$alkyl$)_2N-$, $-CF_3$, $-OCH_3$ and $-OCF_3$;

$R^5$ is selected from the group consisting of $(C_1-C_3)$alkyl, cycloalkyl, heterocycloalkyl, and aryl; wherein $(C_1-C_3)$ alky, cycloalkyl, heterocycloalkyl and aryl is optionally substituted with 1-3 substituents independently selected from the group consisting of H, halo, $-CN$, $(C_1-C_3)$alkyl, $-NH_2$, $(C_1-C_3)$alkyl-(NH)—, $((C_1-C_3)$alkyl$)_2N-$, $-CF_3$, $-OCH_3$, and $-OCF_3$; and $R^6$ is independently H or ($C_1$-$C_3$) alkyl optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$)alkyl)$_2$N—, —$CF_3$, —$OCH_3$ and —$OCF_3$.

9. A compound according to claim 1, wherein $R^3$ is selected from the group consisting of H, halo, ($C_1$-$C_3$)alkyl, —$CF_3$, —$OCH_3$, —$OCF_3$, and $(R^7)_2$N—; and wherein $R^7$ is H or ($C_1$-$C_3$)alkyl.

10. A compound according to claim 1, wherein $R^1$ is selected from the group consisting of H, F, —$CH_3$, and —$OCH_3$.

11. A compound according to claim 1, wherein:

$R^2$ is selected from the group consisting of H, ($C_1$-$C_3$) alkyl, ($C_1$-$C_3$)alkoxy-, perfluoro($C_1$-$C_3$)alkyl, perfluoro($C_1$-$C_3$)alkoxy-, 3- to 10-membered cycloalkyl, 3- to 10-membered cycloalkyl-O—, 5- to 10-membered heterocycloalkyl, 6- to 10-membered aryl, $R^5$—(C$(R^4)_2)_n$—O— and $(R^6)_2$N—; wherein ($C_1$-$C_3$)alkyl, 3- to 10-membered cycloalkyl, 3- to 10-membered cycloalkyl-O—, 5- to 10-membered heterocycloalkyl, 6- to 10-membered aryl is optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$)alkyl)$_2$N—, —$CF_3$, —$OCH_3$, and —$OCF_3$;

each $R^4$ is independently H or ($C_1$-$C_3$) alkyl optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$) alkyl)$_2$N—, —$CF_3$, —$OCH_3$, and —$OCF_3$;

$R^5$ is selected from ($C_1$-$C_3$)alkyl, 3- to 10-membered cycloalkyl, 3- to 10-membered heterocycloalkyl, and 6- to 10-membered aryl; wherein ($C_1$-$C_3$) alkyl, 3- to 10-membered cycloalkyl, 3- to 10-membered heterocycloalkyl, and 6- to 10-membered aryl is optionally substituted with 1-3 substituents independently selected from the group consisting of H, halo, —CN, ($C_1$-$C_3$) alkyl, —$NH_2$, ($C_1$-$C_3$)alkyl-(NH)—, (($C_1$-$C_3$) alkyl)$_2$N—, —$CF_3$, —$OCH_3$, and —$OCF_3$; and $R^6$ is independently H or ($C_1$-$C_3$)alkyl optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$)alkyl)$_2$N—, —$CF_3$, —$OCH_3$, and —$OCF_3$.

12. A compound according to claim 1, wherein:

$R^2$ is selected from the group consisting of methoxy-, cyclopropoxy- and $R^5$-(C$(R^4)_2$)—O—; and each $R^4$ is H; wherein $R^5$ is selected from $C_1$-alkyl and tetrahydropyran, and wherein said $C_1$-alkyl is substituted with —$OCH_3$.

13. A compound according to claim 1, wherein $R^3$ is selected from the group consisting of H, F, —$CH_3$, —$OCH_3$, and $H_2$N—.

14. A compound according to claim 1, wherein:

$R^9$ is selected from the group consisting of H, halo, ($C_1$-$C_3$)alkyl, —$CF_3$, —$OCH_3$, —$OCF_3$, —CN, $R^{12}$O(($C_1$-$C_3$)alkyl)-($NR^{11}$)—, —$CO_2R^{12}$, and $(R^{11})_2$N—(C═O)—; and each $R^{11}$ is independently selected from the group consisting of H and ($C_1$-$C_3$)alkyl; and $R^{12}$ is H or ($C_1$-$C_3$) alkyl.

15. A compound according to claim 1, wherein at least one $R^9$ is selected from the group consisting of F, ($C_1$-$C_3$)alkyl, —$CF_3$, —$OCH_3$, —$OCF_3$, and —CN.

16. A compound according to claim 1, wherein at least one $R^{10}$ is H.

17. A compound according to claim 1, wherein Het is a ring of the formula iii

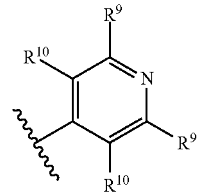

wherein:

one $R^9$ is H, and the other $R^9$ is —$CF_3$; and $R^{10}$ is H.

18. A compound according to claim 1, wherein $R^8$ is H.

19. A compound according to claim 1, wherein —X—Y—Z— is ═$CR^1$—$CR^2$═$CR^3$— or ═N—$CR^2$═$CR^3$—.

20. A compound of Formula IA or a pharmaceutically acceptable salt, ester, or prodrug thereof (IA)

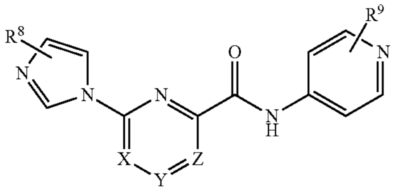

or the acceptable salt, ester, or prodrug thereof (I*A)

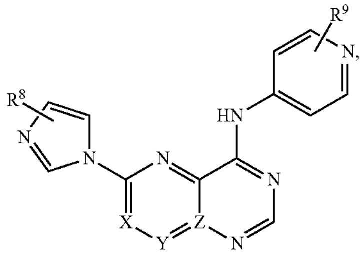

wherein:

—X—Y—Z— of the Formula IA is ═$CR^1$—$CR^2$═$CR^3$— or ═N—$CR^2$═$CR^3$—;

—X—Y—Z— of the Formula I*A is $CR^1$—$CR^2$═C or ═N—$CR^2$═C;

$R^1$ is selected from the group consisting of H, halo, —CN, ($C_1$-$C_3$)alkyl, —$OCH_3$, and —$OCF_3$;

$R^2$ is H, ($C_1$-$C_6$)alkyl, ($C_1$-$C_6$)alkoxy-, perfluoro($C_1$-$C_6$) alkyl, perfluoro($C_1$-$C_6$)alkoxy-, cycloalkyl, cycloalkyl-O—, heterocycloalkyl, aryl, $R^5$—(C$(R^4)_2)_n$—O—, or $(R^6)_2$N—; wherein ($C_1$-$C_6$) alkyl, cycloalkyl, cycloalkyl-O—, heterocycloalkyl and aryl are optionally substituted with 1-3 substituents independently selected from the group consisting of H, halo, —CN, ($C_1$-$C_3$) alkyl, —$NH_2$, ($C_1$-$C_3$)alkyl-(NH)—, (($C_1$-$C_3$)alkyl)$_2$N—, —$CF_3$, —$OCH_3$, and —$OCF_3$;

n is an integer from one to three;

each $R^4$ is independently H or ($C_1$-$C_3$)alkyl;

$R^5$ is selected from the group consisting of ($C_1$-$C_3$) alkyl, cycloalkyl, heterocycloalkyl, and aryl, wherein ($C_1$-$C_3$) alkyl, cycloalkyl, heterocycloalkyl and aryl are optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$) alkyl)$_2$N—, —$CF_3$, —$OCH_3$, and —$OCF_3$;

$R^6$ is independently H or ($C_1$-$C_3$)alkyl, wherein ($C_1$-$C_3$) alkyl is optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$)alkyl)$_2$N—, —$CF_3$, —$OCH_3$, and —$OCF_3$;

$R^3$ is H, halo, ($C_1$-$C_3$)alkyl, —$CF_3$, —$OCH_3$, —$OCF_3$, or ($R^7$)$_2$N—;

$R^7$ is H or ($C_1$-$C_3$)alkyl;

$R^8$ is H, —$CH_3$, or —$CF_3$;

$R^9$ is selected from H, halo, ($C_1$-$C_3$)alkyl, —$CF_3$, —$OCH_3$, —$OCF_3$, —CN, $R^{12}$O(($C_1$-$C_3$)alkyl)-($NR^{11}$)—, —$CO_2R^{12}$, and ($R^{11}$)$_2$N—(C═O)—;

each $R^{11}$ is independently selected from the group consisting of H and ($C_1$-$C_3$) alkyl; and $R^{12}$ is H or ($C_1$-$C_3$)alkyl.

21. A compound of Formula IB, or a pharmaceutically acceptable salt, ester, or prodrug thereof (IB)

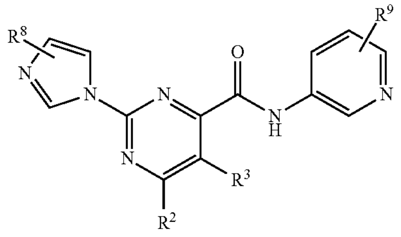

or the of Formula I*B, or a pharmaceutically acceptable salt, ester, or prodrug thereof (I*B)

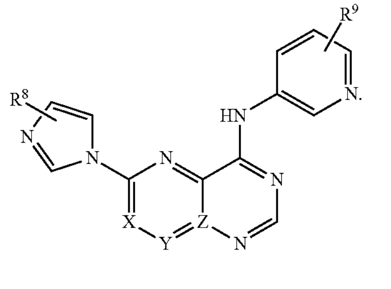

wherein:

—X—Y—Z— of the Formula I*B is CH—$CR^2$═C or ═N—$CR^2$═C;

$R^2$ is H, ($C_1$-$C_3$)alkyl, ($C_1$-$C_3$)alkoxy-, perfluoro($C_1$-$C_3$) alkyl, perfluoro($C_1$-$C_3$)alkoxy-, cycloalkyl, heterocycloalkyl, aryl, $R^5$—$(C(R^4)_2)_n$—O—, or ($R^6$)$_2$N—, wherein ($C_1$-$C_3$) alkyl is optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$)alkyl)$_2$N—, —$CF_3$, —$OCH_3$, and —$OCF_3$;

n is an integer from one to three;

each $R^4$ is independently H or ($C_1$-$C_3$)alkyl, wherein ($C_1$-$C_3$)alkyl is optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$)alkyl)$_2$N—, —$CF_3$, —$OCH_3$, and —$OCF_3$;

$R^5$ is selected from the group consisting of ($C_1$-$C_3$) alkyl, cycloalkyl, heterocycloalkyl, and aryl; wherein ($C_1$-$C_3$) alkyl, cycloalkyl, heterocycloalkyl and aryl is optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$) alkyl)$_2$N—, —$CF_3$, —$OCH_3$, and —$OCF_3$;

$R^6$ is independently H or ($C_1$-$C_3$)alkyl; wherein ($C_1$-$C_3$) alkyl is optionally substituted with 1-3 substituents independently selected from the group consisting of H, halo, —CN, ($C_1$-$C_3$)alkyl, —$NH_2$, ($C_1$-$C_3$)alkyl-(NH)—, (($C_1$-$C_3$)alkyl)$_2$N—, —$CF_3$, —$OCH_3$ and —$OCF_3$;

$R^3$ is H, halo, ($C_1$-$C_3$)alkyl, —$CF_3$, —$OCH_3$, —$OCF_3$ or ($R^7$)$_2$N—, wherein $R^7$ is H or ($C_1$-$C_3$)alkyl;

$R^8$ is H, —$CH_3$ or —$CF_3$; and $R^9$ is selected from the group consisting of H, halo, ($C_1$-$C_3$)alkyl, —$CF_3$, —$OCH_3$, —$OCF_3$, —CN, —($NR^{10}$)—(($C_1$-$C_3$)alkyl)-$OR^{11}$, —$CO_2R^{11}$, and —(C═O)—N($R^{10}$)$_2$; wherein $R^{10}$ is H or ($C_1$-$C_3$)alkyl; and $R^{11}$ is ($C_1$-$C_3$) alkyl.

22. A compound according to claim 1, selected from a) 6-(1H-imidazol-1-yl)-4-((tetrahydro-2H-pyran-4-yl)methoxy)-N-(2-(trifluoromethyl)pyridin-4-yl)picolinamide, b) 6-(1H-imidazol-1-yl)-4-methoxy-N-(2-(trifluoromethyl)pyridin-4-yl)picolinamide, c) 2-(1H-imidazol-1-yl)-6-(2-methoxyethoxy)-N-(2-(trifluoromethyl)pyridin-4-yl)pyrimidine-4-carboxamide, d) 6-(1H-imidazol-1-yl)-4-(2-methoxyethoxy)-N-(2-(trifluoromethyl)pyridin-4-yl)picolinamide, e) 4-cyclopropoxy-6-(1H-imidazol-1-yl)-N-(2-(trifluoromethyl)pyridin-4-yl)picolinamide, f) 6-(1H-imidazol-1-yl)-N-(pyridin-3-yl)pyrido [3,2-d] pyrimidin-4-amine, g) 6-(1H-imidazol-1-yl)-N-(pyridin-4-yl)pyrimido [5,4-d]pyrimidin-4-amine, h) 6-cyclopropyl-2-(1H-imidazol-1-yl)-N-(2-(trifluoromethyl)pyridin-4-yl)pyrimidine-4-carboxamide, i) 6-(1H-imidazol-1-yl)-4-((3-methyloxetan-3-yl)oxy)-N-(2-(trifluoromethyl)pyridin-4-yl)picolinamide, i) 2-(1-methyl-1H-imidazol-5-yl)-6-((3-methyloxetan-3-yl)oxy)-N-(2-(trifluoromethyl)pyridin-4-yl)pyrimidine-4-carboxamide, k) 2-(1-methyl-1H-imidazol-2-yl)-6-((3-methyloxetan-3-yl)oxy)-N-(2-(trifluoromethyl)pyridin-4-yl)pyrimidine-4-carboxamide, l) 2-(1-methyl-1H-imidazol-5-yl)-6-((tetrahydro-2H-pyran-4-yl)methoxy)-N-(2-(trifluoromethyl)pyridin-4-yl)pyrimidine-4-carboxamide, m) 2-(1-methyl-1H-imidazol-2-yl)-6-((tetrahydro-2H-pyran-4-yl)methoxy)-N-(2-(trifluoromethyl)pyridin-4-yl)pyrimidine-4-carboxamide, n) 6-(2-methoxyethoxy)-2-(1-methyl-1H-imidazol-5-yl)-N-(2-(trifluoromethyl)pyridin-4-yl)pyrimidine-4-carboxamide, o) 6-(2-methoxyethoxy)-2-(1-methyl-1H-imidazol-2-yl)-N-(2-(trifluoromethyl)pyridin-4-yl)pyrimidine-4-carboxamide, and p) 6-(2-hydroxy-2-methylpropoxy)-2-(1H-imidazol-1-yl)-N-(2-(trifluoromethyl)pyridin-4-yl)pyrimidine-4-carboxamide, or a pharmaceutically acceptable salt, ester, or prodrug thereof.

23. A pharmaceutical formulation comprising:

a compound of Formula I or I* according to claim 1; and a pharmaceutically acceptable carrier.

24. A method of treating a disease or disorder in a subject that benefits from modulation of the level of NAD+ or related metabolite thereof, comprising administering to the subject a therapeutically effective amount of the pharmaceutical formulation of claim 23.

* * * * *